United States Patent
Kang et al.

(10) Patent No.: US 9,997,723 B2
(45) Date of Patent: Jun. 12, 2018

(54) ORGANIC ELECTROLUMINESCENT COMPOUND AND AN ORGANIC ELECTROLUMINESCENT DEVICE COMPRISING THE SAME

(71) Applicant: Rohm and Haas Electronic Materials Korea Ltd., Cheonan (KR)

(72) Inventors: Hee-Ryong Kang, Seoul (KR); Hyun-Ju Kang, Gwangmyeong (KR); Jin-Ri Hong, Cheonan (KR); Doo-Hyeon Moon, Hwaseong (KR); Young-Mook Lim, Cheonan (KR); Bitnari Kim, Cheonan (KR); Nam-Kyun Kim, Yongin (KR); Mi-Ja Lee, Cheonan (KR)

(73) Assignee: Rohm and Haas Electronic Materials Korea Ltd, Chonan (KR)

(*) Notice: Subject to any disclaimer, the term of this patent is extended or adjusted under 35 U.S.C. 154(b) by 0 days. days.

(21) Appl. No.: 15/311,534

(22) PCT Filed: May 22, 2015

(86) PCT No.: PCT/KR2015/005193
§ 371 (c)(1),
(2) Date: Nov. 16, 2016

(87) PCT Pub. No.: WO2015/178731
PCT Pub. Date: Nov. 26, 2015

(65) Prior Publication Data
US 2017/0148998 A1 May 25, 2017

(30) Foreign Application Priority Data

| May 23, 2014 | (KR) | 10-2014-0062390 |
| Sep. 4, 2014 | (KR) | 10-2014-0117773 |
| Oct. 8, 2014 | (KR) | 10-2014-0136149 |
| May 19, 2015 | (KR) | 10-2015-0069705 |

(51) Int. Cl.
| *C07D 403/04* | (2006.01) |
| *C07D 401/04* | (2006.01) |
| *C07D 405/10* | (2006.01) |
| *C07D 409/10* | (2006.01) |
| *C09K 11/06* | (2006.01) |
| *H01L 51/50* | (2006.01) |
| *H01L 51/00* | (2006.01) |
| *C09K 11/02* | (2006.01) |
| *C07D 403/14* | (2006.01) |
| *C07D 409/14* | (2006.01) |
| *C07D 403/10* | (2006.01) |

(52) U.S. Cl.
CPC ........ *H01L 51/0072* (2013.01); *C07D 403/04* (2013.01); *C07D 403/10* (2013.01); *C07D 403/14* (2013.01); *C07D 409/14* (2013.01); *C09K 11/02* (2013.01); *C09K 11/06* (2013.01); *H01L 51/0052* (2013.01); *H01L 51/0074* (2013.01); *C09K 2211/1007* (2013.01); *C09K 2211/1044* (2013.01); *C09K 2211/1092* (2013.01); *H01L 51/5016* (2013.01)

(58) Field of Classification Search
CPC .. C07D 403/04; C07D 403/10; C07D 401/04; C07D 401/10; C07D 405/10; C09K 11/06; H01L 51/5032; H01L 5/5032
USPC .................................. 544/284, 353; 546/152
See application file for complete search history.

(56) References Cited

U.S. PATENT DOCUMENTS

| 8,227,798 B2 | 7/2012 | Kai et al. |
| 8,986,857 B2 | 3/2015 | Suzuki et al. |
| 2012/0133274 A1 | 5/2012 | Kawakami et al. |
| 2014/0100367 A1 | 4/2014 | Yoon et al. |

FOREIGN PATENT DOCUMENTS

| KR | 10-1074193 B1 | 10/2011 | |
| KR | 10-2014-0079594 | 6/2014 | |
| WO | 2010114264 A2 | 10/2010 | |
| WO | 2010126234 A1 | 11/2010 | |
| WO | WO 2012165844 A1 * | 12/2012 | ........... C07D 401/14 |
| WO | 2014098455 A1 | 6/2014 | |

OTHER PUBLICATIONS

Atzrodt et al. Angew. Chem. Int. Ed. 2007, 46, 7744-7765.*
Sajiki, et al., "Aromatic ring favorable and efficient H-D exchange reaction catalyzed by Pt/C", Tetrahedron Letters, vol. 46, pp. 6995-6998 (2005).
Verbeeck, et al., "ONSH: Optimization of Oxidative Alkylamination Reactions through Study of the Reaction Mechanism", J. Org. Chem., vol. 75, pp. 5126-5133 (2010).

* cited by examiner

*Primary Examiner* — Venkataraman Balasubramanian
(74) *Attorney, Agent, or Firm* — S. Matthew Cairns

(57) ABSTRACT

The present invention relates to an organic electroluminescent compound and an organic electroluminescent device comprising the same. By using the organic electroluminescent compound according to the present invention, it is possible to produce an organic electroluminescent device having low driving voltage, excellent current and power efficiencies, and noticeably improved driving lifespan.

7 Claims, No Drawings

ORGANIC ELECTROLUMINESCENT COMPOUND AND AN ORGANIC ELECTROLUMINESCENT DEVICE COMPRISING THE SAME

TECHNICAL FIELD

The present invention relates to organic electroluminescent compounds and organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak, by using small aromatic diamine molecules, and aluminum complexes as materials for forming a light-emitting layer [Appl. Phys. Lett. 51, 913, 1987].

The most important factor determining luminous efficiency in an organic EL device is light-emitting materials. Until now, fluorescent materials have been widely used as light-emitting material. However, in view of electroluminescent mechanisms, since phosphorescent materials theoretically enhance luminous efficiency by four (4) times compared to fluorescent materials, development of phosphorescent light-emitting materials are widely being researched. Iridium(III) complexes have been widely known as phosphorescent materials, including bis(2-(2'-benzothienyl)-pyridinato-N,C3')iridium(acetylacetonate) ((acac)Ir(btp)$_2$), tris(2-phenylpyridine)iridium (Ir(ppy)$_3$) and bis(4,6-difluorophenylpyridinato-N,C2)picolinate iridium (Firpic) as red, green and blue materials, respectively.

At present, 4,4'-N,N'-dicarbazol-biphenyl (CBP) is the most widely known phosphorescent host material. Recently, Pioneer (Japan) et al. developed a high performance organic EL device using bathocuproine (BCP) and aluminum(III)bis(2-methyl-8-quinolinate)(4-phenylphenolate) (BAlq) etc., as host materials, which were known as hole blocking layer materials.

Although these materials provide good light-emitting characteristics, they have the following disadvantages: (1) Due to their low glass transition temperature and poor thermal stability, their degradation may occur during a high-temperature deposition process in a vacuum, and the lifespan of the device decreases. (2) The power efficiency of an organic EL device is given by [(π/voltage)×current efficiency], and the power efficiency is inversely proportional to the voltage. Although an organic EL device comprising phosphorescent host materials provides higher current efficiency (cd/A) than one comprising fluorescent materials, a significantly high driving voltage is necessary. Thus, there is no merit in terms of power efficiency (lm/W). (3) Further, the operational lifespan of an organic EL device is short and luminous efficiency is still required to be improved.

Meanwhile, in order to enhance its efficiency and stability, an organic EL device has a structure of a multilayer comprising a hole injection layer, a hole transport layer, a light-emitting layer, an electron transport layer, and an electron injection layer. The selection of a compound comprised in the hole transport layer is known as a method for improving the characteristics of a device such as hole transport efficiency to the light-emitting layer, luminous efficiency, lifespan, etc.

In this regard, copper phthalocyanine (CuPc), 4,4'-bis[N-(1-naphthyl)-N-phenylamino]biphenyl (NPB), N,N'-diphenyl-N,N'-bis(3-methylphenyl)-(1,1'-biphenyl)-4,4'-diamine (TPD), 4,4',4"-tris(3-methylphenylphenylamino)triphenylamine (MTDATA), etc. were used as a hole injection and transport material. However, an organic EL device using these materials is problematic in quantum efficiency and operational lifespan. It is because, when an organic EL device is driven under high current, thermal stress occurs between an anode and the hole injection layer. Thermal stress significantly reduces the operational lifespan of the device. Further, since the organic material used in the hole injection layer has very high hole mobility, the hole-electron charge balance may be broken and quantum yield (cd/A) may decrease.

Therefore, a hole transport layer for improving durability of an organic EL device still needs to be developed.

U.S. Pat. No. 8,227,798 B2 and Korean Patent Appln. Laying-Open No. 10-2010-0108924 disclose a compound wherein a nitrogen-containing heteroaryl such as triazine is bonded to a nitrogen atom of a dibenzocarbazole as an organic electroluminescent compound; Korean Patent No. 10-1074193 discloses a compound wherein a nitrogen-containing heteroaryl such as triazine is bonded to a nitrogen atom of a benzocarbazole as an organic electroluminescent compound; and Korean Patent Appln. Laying-Open No. 10-2014-0015259 discloses a compound wherein an aryl including anthracene is bonded to a nitrogen atom of a dibenzocarbazole as an organic electroluminescent compound. However, the above references do not specifically disclose an organic electroluminescent compound in which a quinazoline or quinoxaline is bonded to a nitrogen atom of a dibenzocarbazole directly or via a linker.

DISCLOSURE OF THE INVENTION

Problems to be Solved

The objective of the present invention is to provide i) an organic electroluminescent compound which can produce an organic electroluminescent device having long operational lifespan, low driving voltage, and excellent luminous efficiency, i.e. current and power efficiencies, and ii) an organic electroluminescent device comprising the compound.

Solution to Problems

The present inventors found that the above objective can be achieved by an organic electroluminescent compound represented by the following formula 1:

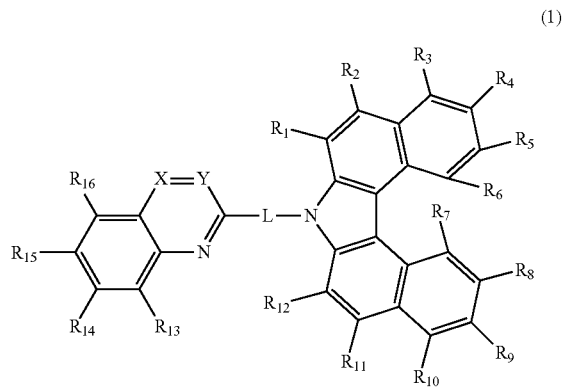

wherein

L represents a single bond, a substituted or unsubstituted (C6-C30)arylene, or a substituted or unsubstituted 3- to 30-membered heteroarylene;

X and Y each independently represent N or $CR_{17}$;

$R_1$ to $R_{17}$ each independently represent hydrogen, deuterium, a substituted or unsubstituted (C3-C30)cycloalkyl, a substituted or unsubstituted (C6-C30)aryl, a substituted or unsubstituted 3- to 30-membered heteroaryl, a substituted or unsubstituted mono- or di-(C6-C30)arylamino, a substituted or unsubstituted (C1-C30)alkyl(C6-C30)arylamino, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted (C1-C30)alkyldi(C6-C30)arylsilyl; or are linked to an adjacent substituent(s) to form a substituted or unsubstituted, mono- or polycyclic (C3-C30) alicyclic or aromatic ring, whose carbon atom(s) may be replaced with at least one hetero atom selected from nitrogen, oxygen, and sulfur; and the heteroaryl contains at least one hetero atom selected from B, N, O, S, P(=O), Si, and P.

Effects of the Invention

By using the organic electroluminescent compound according to the present invention, it is possible to manufacture an organic electroluminescent device having low driving voltage, excellent current and power efficiencies, and remarkably improved operational lifespan.

EMBODIMENTS OF THE INVENTION

Hereinafter, the present invention will be described in detail. However, the following description is intended to explain the invention, and is not meant in any way to restrict the scope of the invention.

The present invention relates to an organic electroluminescent compound of formula 1, an organic electroluminescent material comprising the compound, and an organic electroluminescent device comprising the material.

The organic electroluminescent compound of the present invention has a novel structure, and it is possible to manufacture an organic electroluminescent device having good device performance by using it. Compounds having a structure of carbazole, a-benzocarbazole, and c-benzocarbazole have been disclosed. However, these compounds have an imbalance in electron and hole mobilities, so that performances such as efficiency, lifespan, driving voltage, etc., were subpar when producing an organic electroluminescent device comprising them. In the present invention, compounds having a structure of di-c-benzocarbazole, in which a ring is additionally fused to c-benzocarbazole, improve the injections and mobilities of the holes and electrons. Hence, an organic electroluminescent device having high efficiency, long lifespan, and low driving voltage can be provided. In the structural aspect, unlike carbazole and c-benzocarbazole, two additionally fused rings form naphthyl, and the dihedral angle is slightly distorted to have completely different structural characteristics, and the glass transition temperature rises to improve thermal stability.

The organic electroluminescent compound represented by the above formula 1 will be described in detail.

The compound of formula 1 may be represented by the following formula 2 or 3.

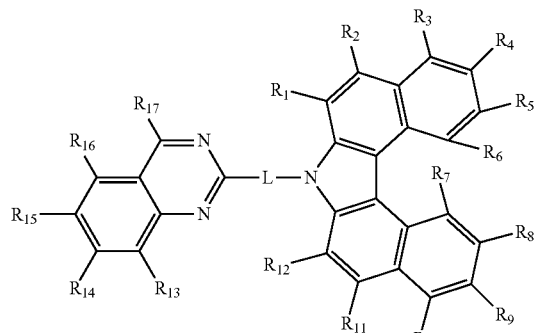

(2)

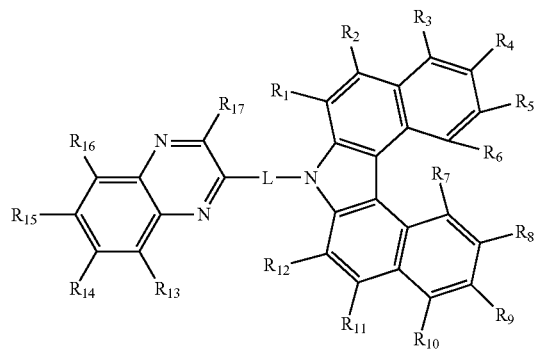

(3)

wherein

L, and $R_1$ to $R_{17}$ are as defined in formula 1.

Herein, "(C1-C30)alkyl" is meant to be a linear or branched alkyl having 1 to 30 carbon atoms, in which the number of carbon atoms is preferably 1 to 10, more preferably 1 to 6, and includes methyl, ethyl, n-propyl, isopropyl, n-butyl, isobutyl, tert-butyl, etc.; "(C2-C30)alkenyl" is meant to be a linear or branched alkenyl having 2 to 30 carbon atoms, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc.; "(C2-C30)alkynyl" is meant to be a linear or branched alkynyl having 2 to 30 carbon atoms, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc.; "(C3-C30)cycloalkyl" is a mono- or polycyclic hydrocarbon having 3 to 30 carbon atoms, in which the number of carbon atoms is preferably 3 to 20, more preferably 3 to 7, and includes cyclopropyl, cyclobutyl, cyclopentyl, cyclohexyl, etc.; "3- to 7-membered heterocycloalkyl" is a cycloalkyl having 3 to 7 ring backbone atoms, including at least one heteroatom selected from B, N, O, S, P(=O), Si, and P, preferably O, S, and N, and includes tetrahydrofuran, pyrrolidine, thiolan, tetrahydropyran, etc.; "(C6-C30)aryl(ene)" is a monocyclic or fused ring derived from an aromatic hydrocarbon having 6 to 30 carbon atoms, in which the number of carbon atoms is preferably 6 to 20, more preferably 6 to 15, and includes phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc.; "3- to 30-membered heteroaryl" is an aryl having 3 to 30 ring backbone atoms, including at least one, preferably 1 to 4 heteroatoms selected from the group consisting of B, N, O, S, P(=O), Si, and P; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. Further, "halogen" includes F, Cl, Br, and I.

Herein, "substituted" in the expression "substituted or unsubstituted" means that a hydrogen atom in a certain functional group is replaced with another atom or group, i.e. a substituent. The substituents of the substituted (C3-C30) cycloalkyl, the substituted (C6-C30)aryl(ene), the substituted 3- to 30-membered heteroaryl(ene), the substituted tri(C1-C30)alkylsilyl, the substituted tri(C6-C30)arylsilyl, the substituted di(C1-C30)alkyl(C6-C30)arylsilyl, the substituted (C1-C30)alkyldi(C6-C30)arylsilyl, the substituted mono- or di-(C6-C30)arylamino, the substituted (C1-C30)alkyl(C6-C30)arylamino, and the substituted mono- or polycyclic (C3-C30) alicyclic or aromatic ring in L, and $R_1$ to $R_{17}$ in formula 1 each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 5- to 30-membered heteroaryl unsubstituted or substituted with a (C6-C30)aryl, a (C6-C30)aryl unsubstituted or substituted with a 5- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30) arylamino, a (C1-C30)alkyl(C6-C30)arylamino, a (C1-C30) alkylcarbonyl, a (C1-C30)alkoxycarbonyl, a (C6-C30)arylcarbonyl, a di(C6-C30)arylboronyl, a di(C1-C30) alkylboronyl, a (C1-C30)alkyl(C6-C30)arylboronyl, a (C6-C30)aryl(C1-C30)alkyl, and a (C1-C30)alkyl(C6-C30)aryl, and preferably each independently are at least one selected from the group consisting of a (C6-C25)aryl or a (C6-C20) aryl(C1-C6)alkyl.

In formula 1 above, L represents a single bond, a substituted or unsubstituted (C6-C30)arylene, or a substituted or unsubstituted 3- to 30-membered heteroarylene, preferably represents a single bond, a substituted or unsubstituted (C6-C12)arylene, or a substituted or unsubstituted 3- to 20-membered heteroarylene, and more preferably represents a single bond, an unsubstituted (C6-C12)arylene or a 3- to 20-membered heteroarylene unsubstituted or substituted with a (C6-C12)aryl.

According to one embodiment of the present invention, L represents a single bond, a substituted or unsubstituted phenyl, a substituted or unsubstituted biphenyl, a substituted or unsubstituted terphenyl, a substituted or unsubstituted naphthyl, a substituted or unsubstituted fluorenyl, a substituted or unsubstituted phenanthrenyl, a substituted or unsubstituted anthracenyl, a substituted or unsubstituted indenyl, a substituted or unsubstituted triphenylenyl, a substituted or unsubstituted pyrenyl, a substituted or unsubstituted tetracenyl, a substituted or unsubstituted perylenyl, a substituted or unsubstituted chrysenyl, a substituted or unsubstituted naphthacenyl, a substituted or unsubstituted fluoranthenyl, a substituted or unsubstituted carbazole, or a substituted or unsubstituted benzocarbazole.

X and Y each independently represent N or $CR_{17}$.

$R_1$ to $R_{17}$ each independently represent hydrogen, deuterium, a substituted or unsubstituted (C3-C30)cycloalkyl, a substituted or unsubstituted (C6-C30)aryl, a substituted or unsubstituted 3- to 30-membered heteroaryl, a substituted or unsubstituted mono- or di-(C6-C30)arylamino, a substituted or unsubstituted (C1-C30)alkyl(C6-C30)arylamino, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted (C1-C30)alkyldi(C6-C30)arylsilyl; or are linked to an adjacent substituent(s) to form a substituted or unsubstituted, mono- or polycyclic (C3-C30) alicyclic or aromatic ring, whose carbon atom(s) may be replaced with at least one hetero atom selected from nitrogen, oxygen, and sulfur, preferably each independently represent hydrogen, a substituted or unsubstituted (C6-C25)aryl, or a substituted or unsubstituted 3- to 20-membered heteroaryl; or are linked to an adjacent substituent(s) to form a substituted or unsubstituted, mono- or polycyclic (C3-C20) alicyclic or aromatic ring, and more preferably each independently represent hydrogen, a (C6-C25)aryl unsubstituted or substituted with a (C6-C20)aryl(C1-C6)alkyl or a (C6-C25)aryl, or a 3- to 20-membered heteroaryl unsubstituted or substituted with a (C6-C12)aryl; or are linked to an adjacent substituent(s) to form a mono- or polycyclic (C3-C20) aromatic ring unsubstituted or substituted with a (C6-C12)aryl.

According to one embodiment of the present invention, in formula 1 above, L represents a single bond, a substituted or unsubstituted (C6-C12)arylene, or a substituted or unsubstituted 3- to 20-membered heteroarylene; X and Y each independently represent N or $CR_{17}$; and $R_1$ to $R_{17}$ each independently represent hydrogen, a substituted or unsubstituted (C6-C25)aryl, or a substituted or unsubstituted 3- to 20-membered heteroaryl, or are linked to an adjacent substituent(s) to form a substituted or unsubstituted, mono- or polycyclic (C3-C20) alicyclic or aromatic ring, whose carbon atom(s) may be replaced with at least one hetero atom selected from nitrogen, oxygen, and sulfur.

According to another embodiment of the present invention, in formula 1 above, L represents a single bond, an unsubstituted (C6-C12)arylene or a 3- to 20-membered heteroarylene unsubstituted or substituted with a (C6-C12) aryl; X and Y each independently represent N or $CR_{17}$; and $R_1$ to $R_{17}$ each independently represent hydrogen, a (C6-C25)aryl unsubstituted or substituted with a (C6-C20)aryl (C1-C6)alkyl or a (C6-C25)aryl, or a 3- to 20-membered heteroaryl unsubstituted or substituted with a (C6-C12)aryl, or are linked to an adjacent substituent(s) to form a mono- or polycyclic (C3-C20) aromatic ring unsubstituted or substituted with a (C6-C12)aryl, whose carbon atom(s) may be replaced with at least one hetero atom selected from nitrogen, oxygen, and sulfur.

The specific compounds of the present invention include the following compounds, but are not limited thereto:

A-1
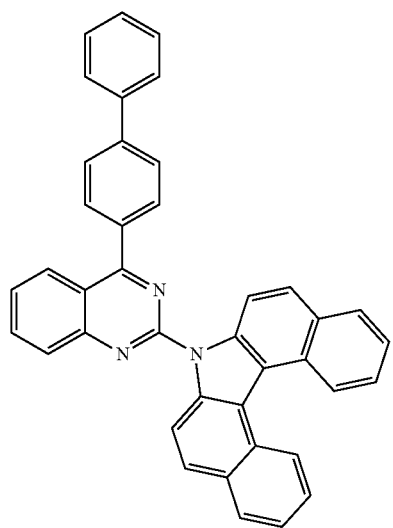
A-2
A-3
A-4
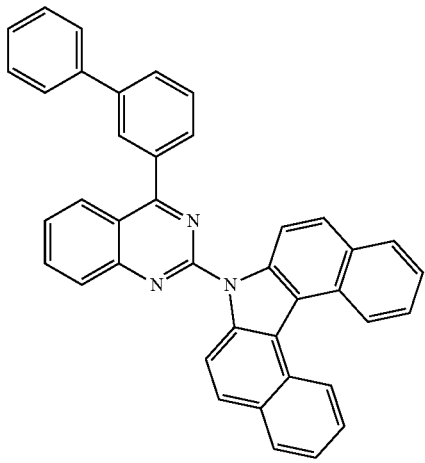
A-5
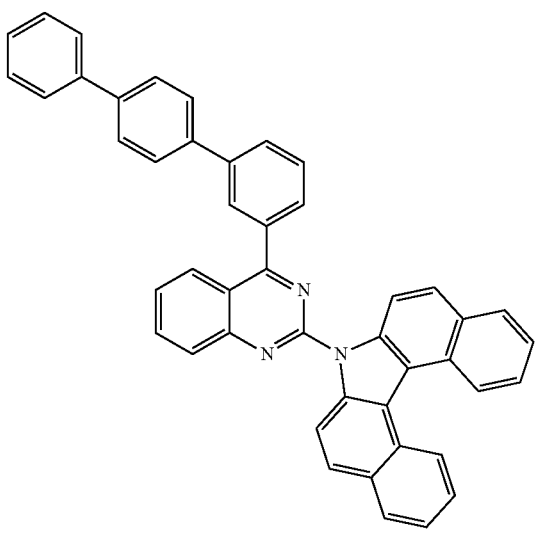
A-6
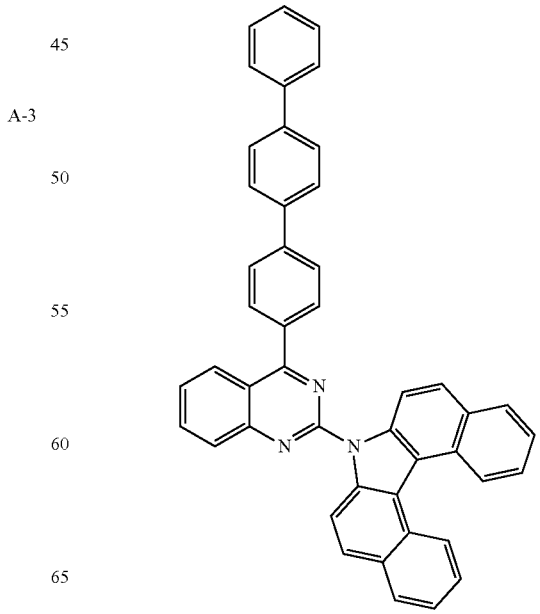

A-7
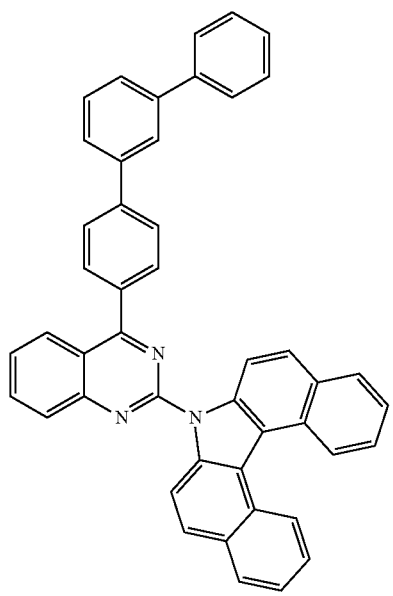
A-8
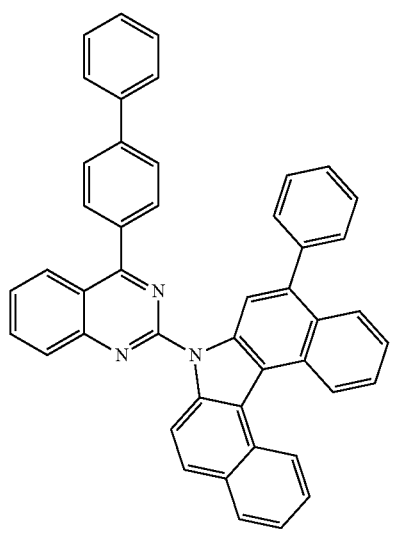
A-9
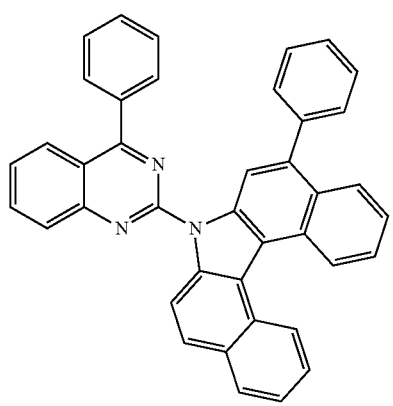
A-10
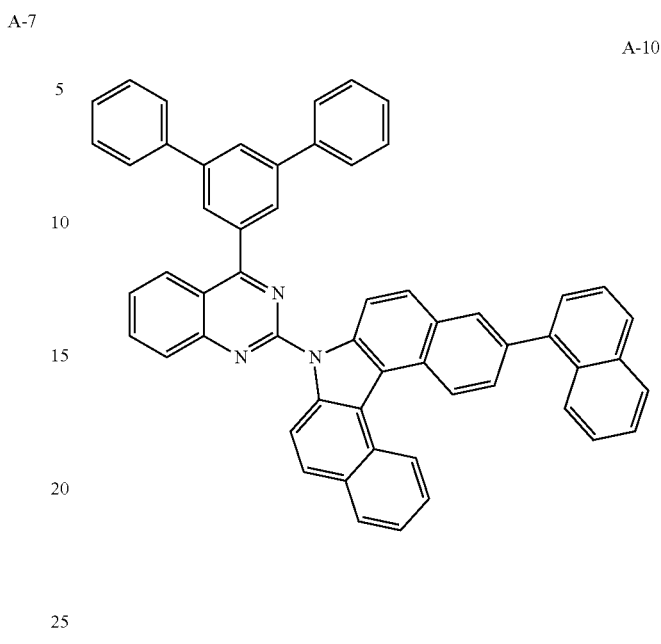
A-11
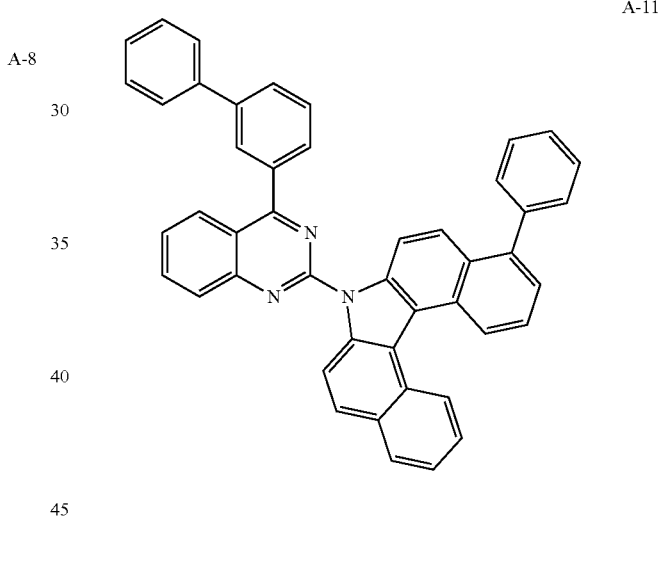
A-12
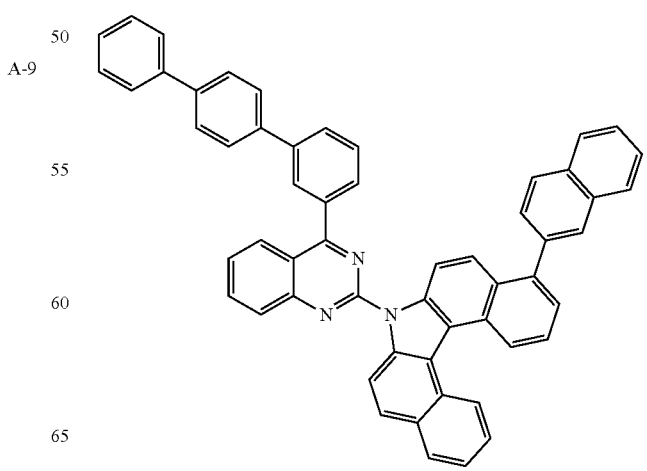

A-13
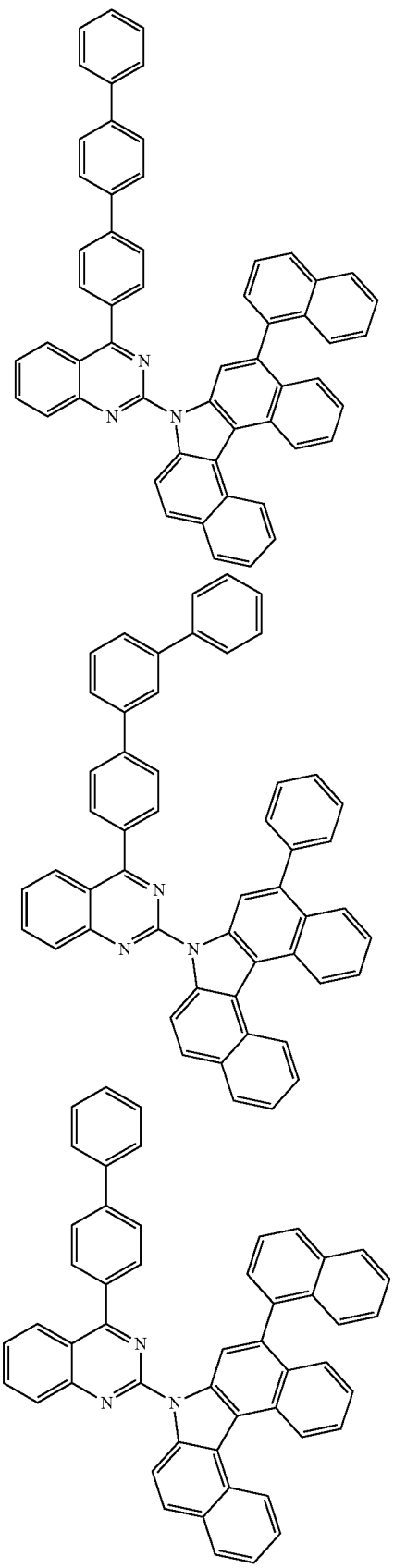
A-14
A-15
A-16
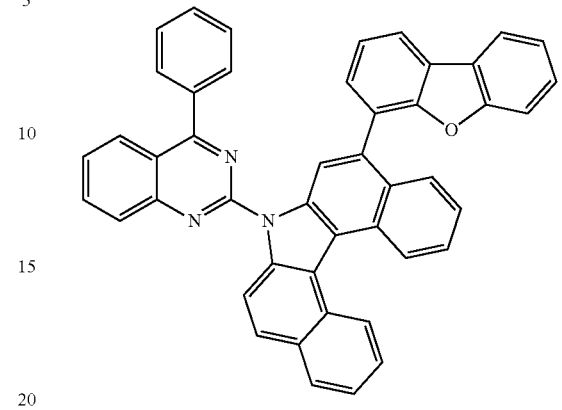
A-17
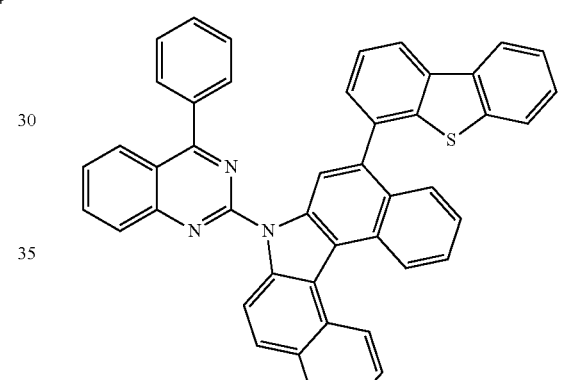
A-18
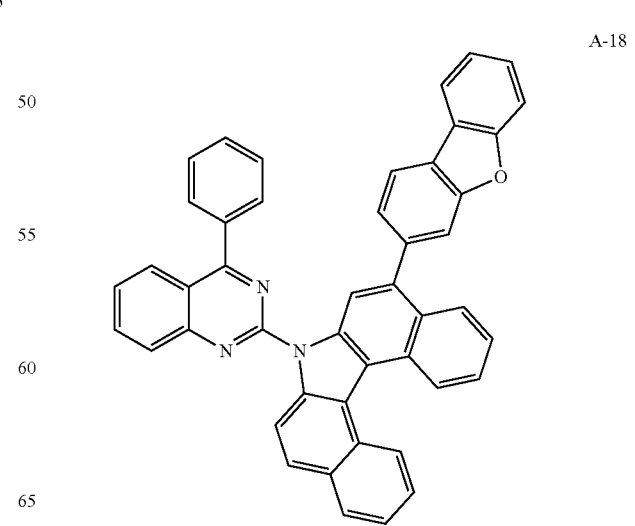

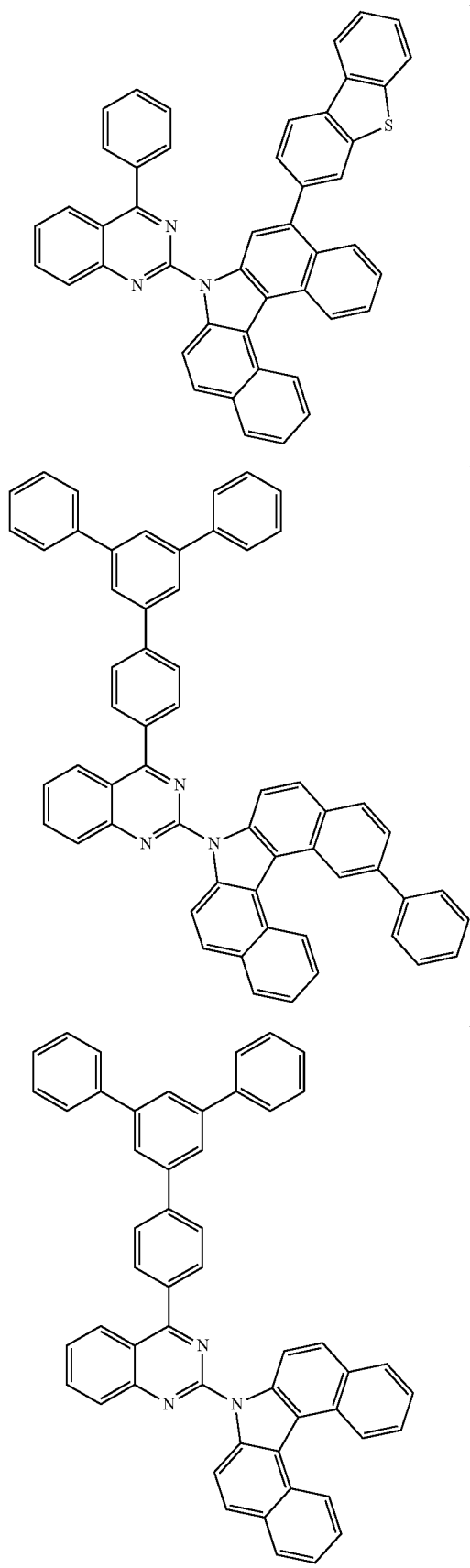
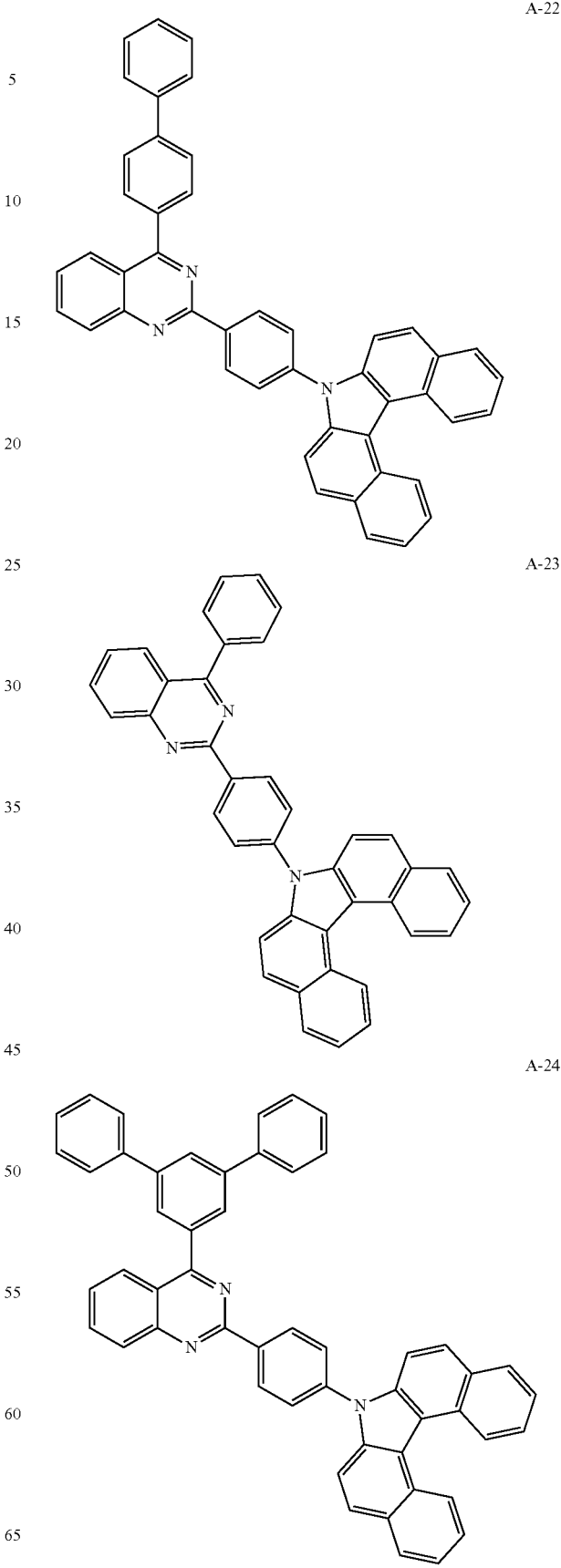

A-25
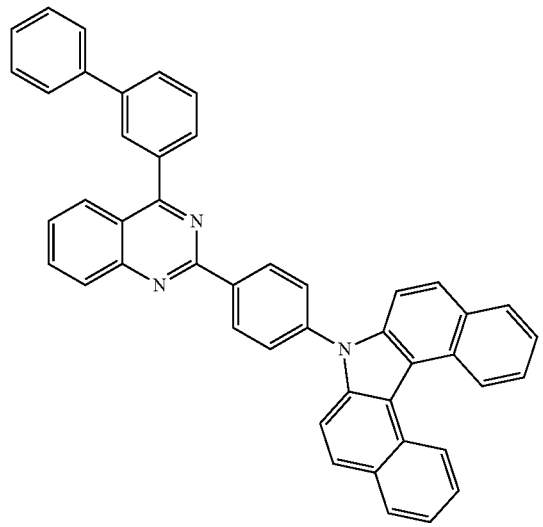
A-26
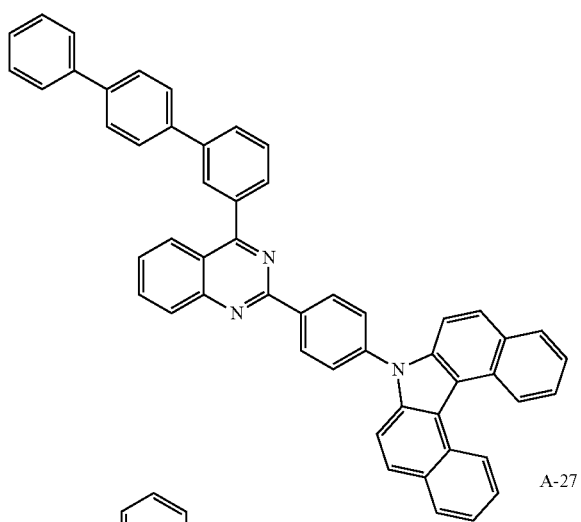
A-27
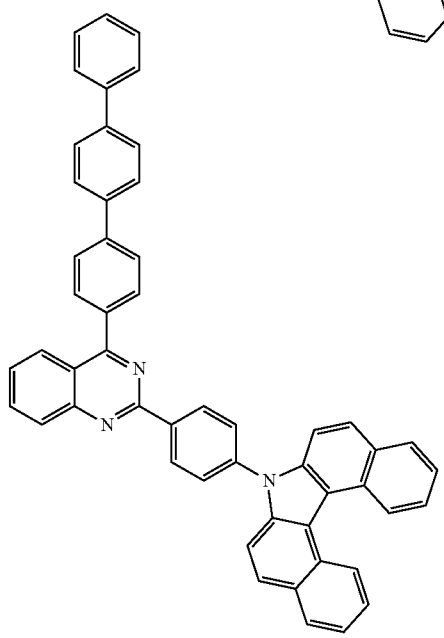
A-28
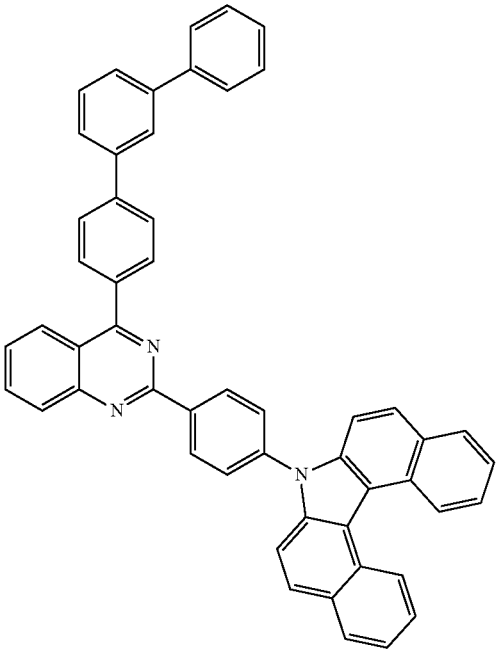
A-29
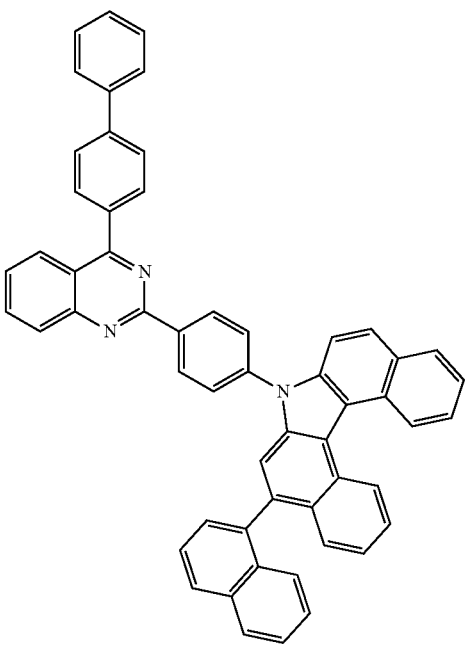

A-30
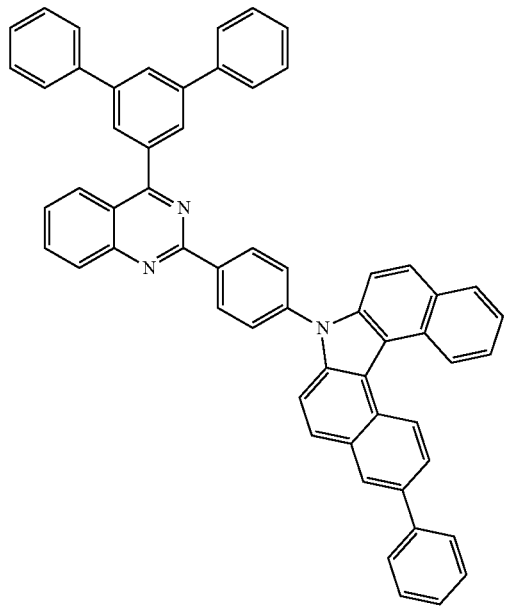
A-31
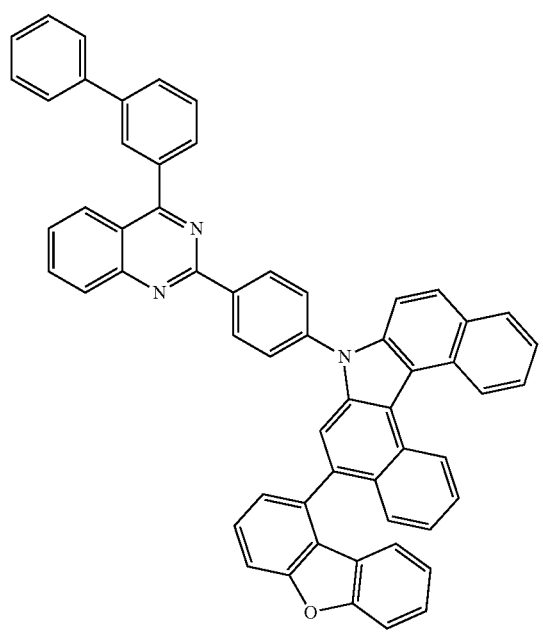
A-32
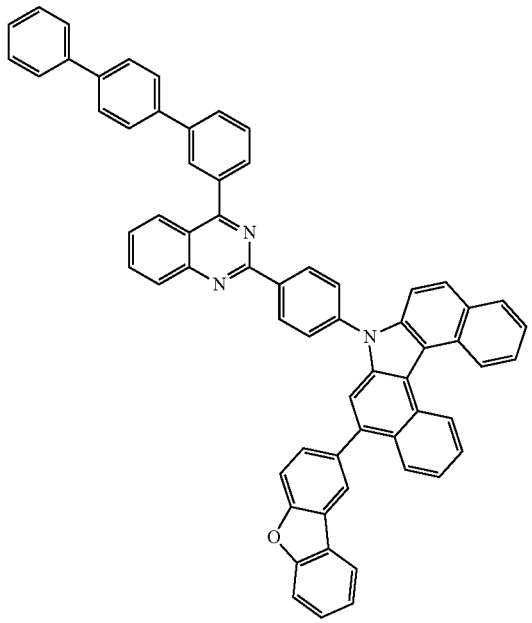
A-33
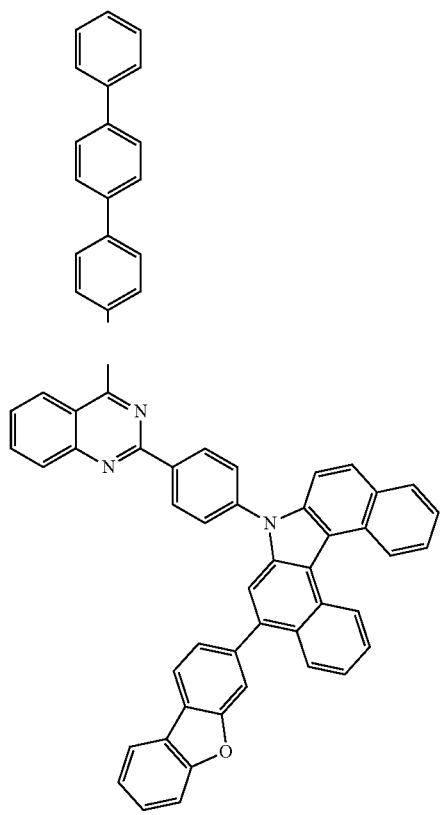

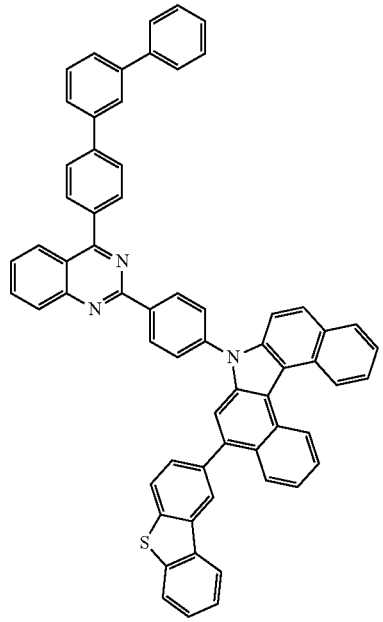
A-34
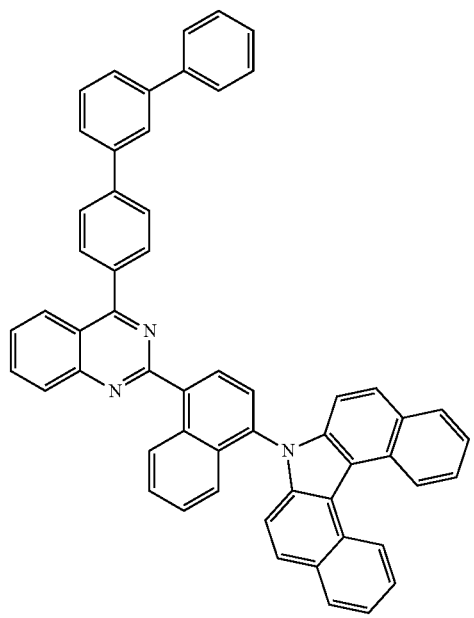
A-36
A-35
A-37

A-38
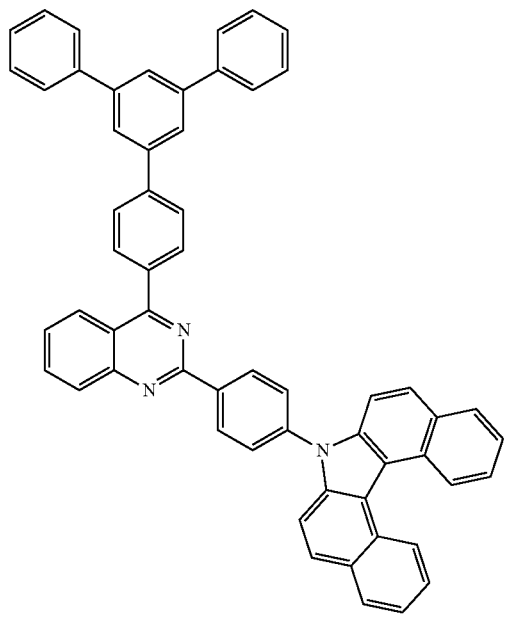
A-39
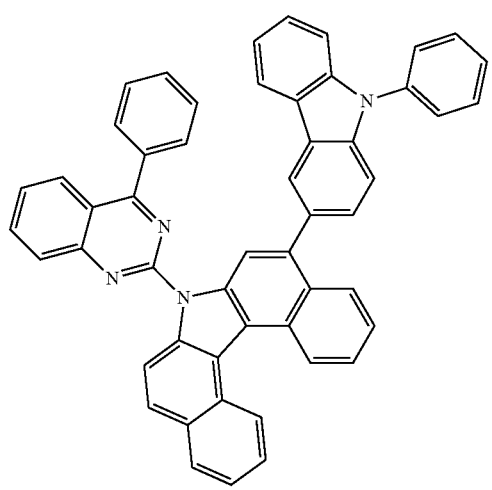
A-40
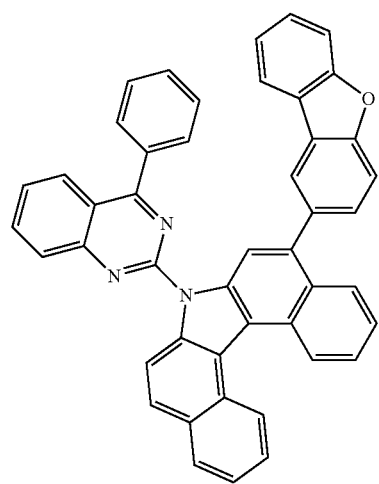
A-41
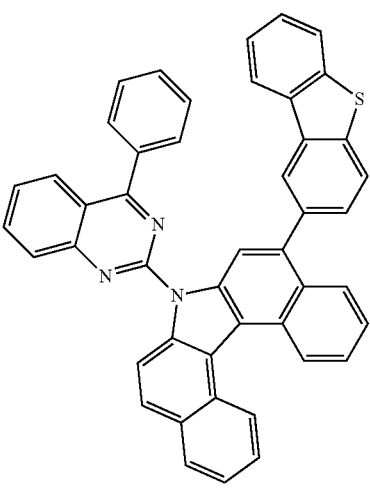
A-42
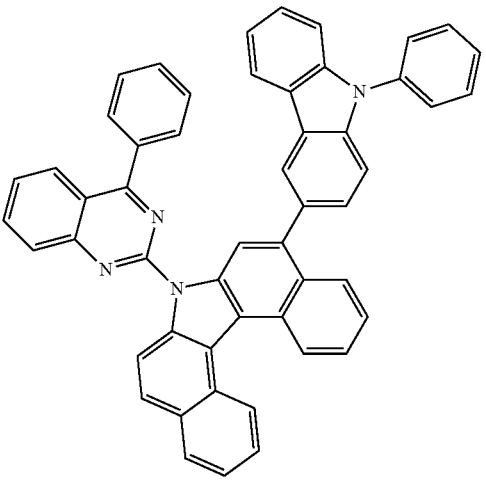
A-43
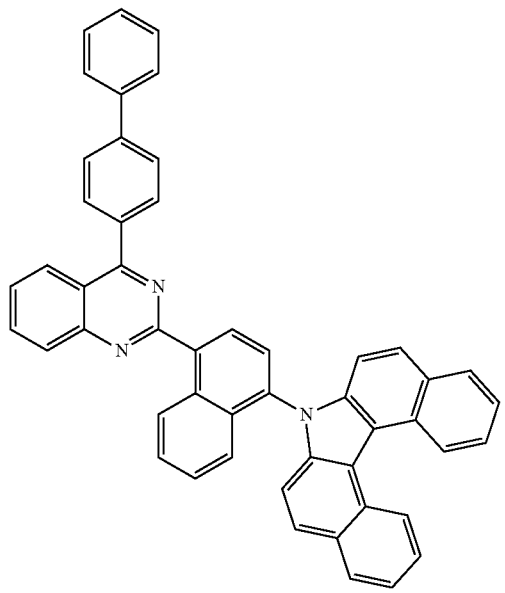

A-44
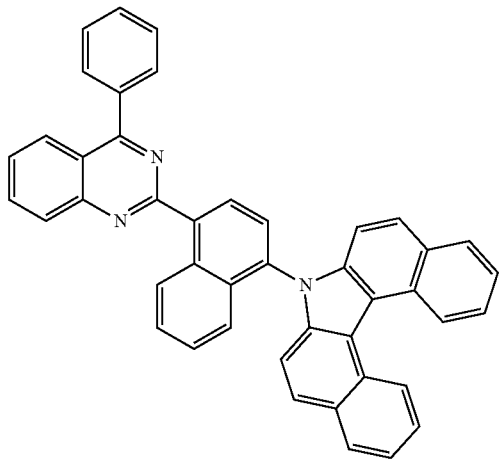
A-45
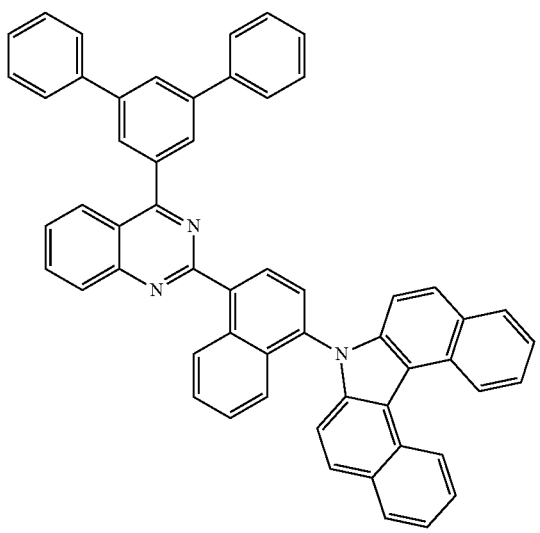
A-46
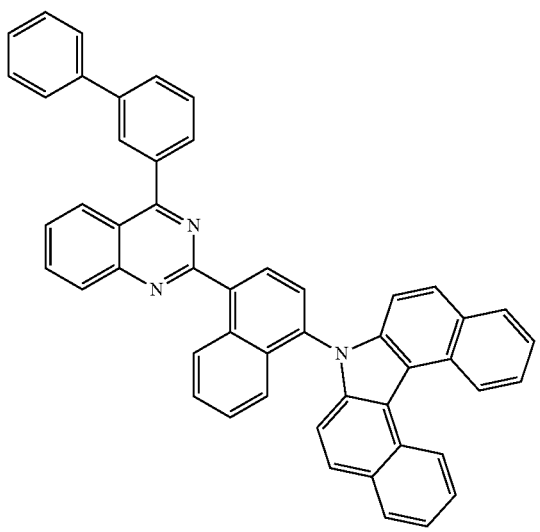
A-47
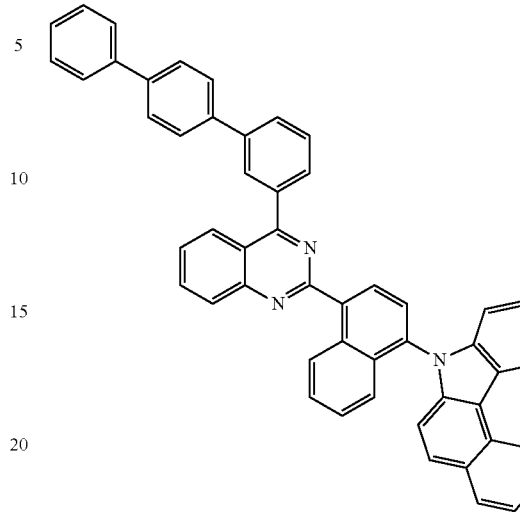
A-48
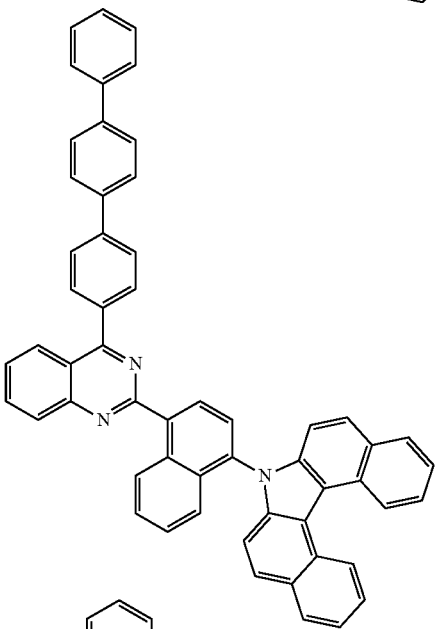
A-49
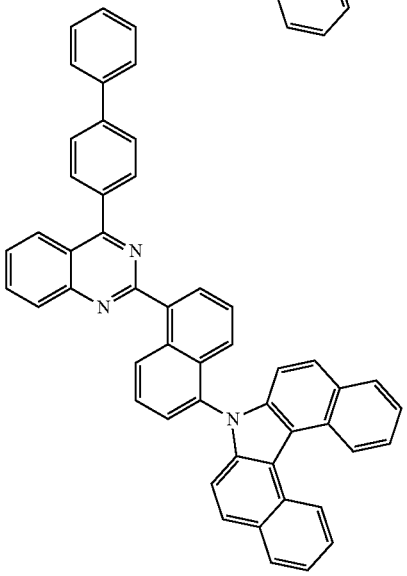

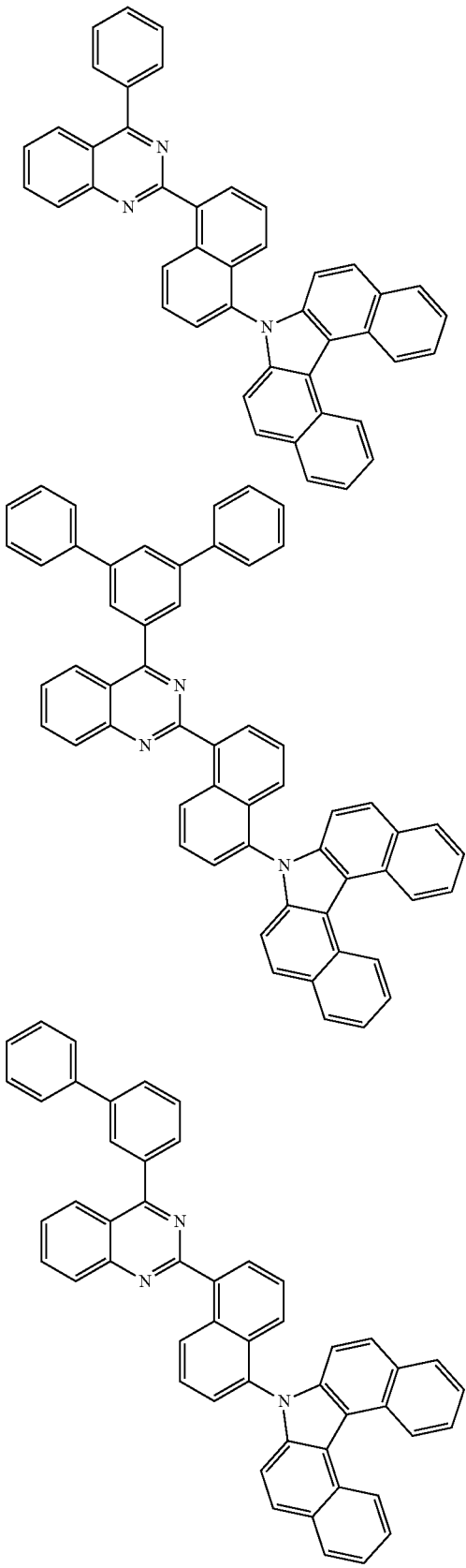

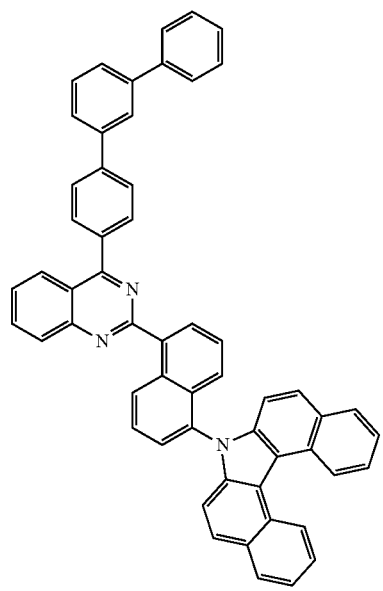
A-55
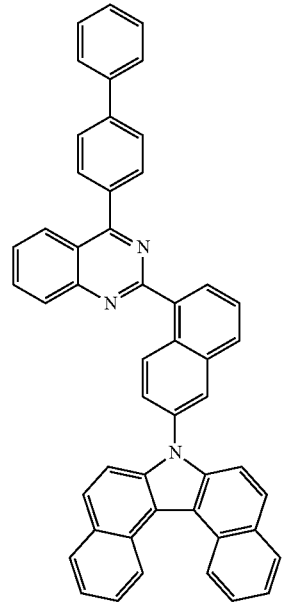
A-57
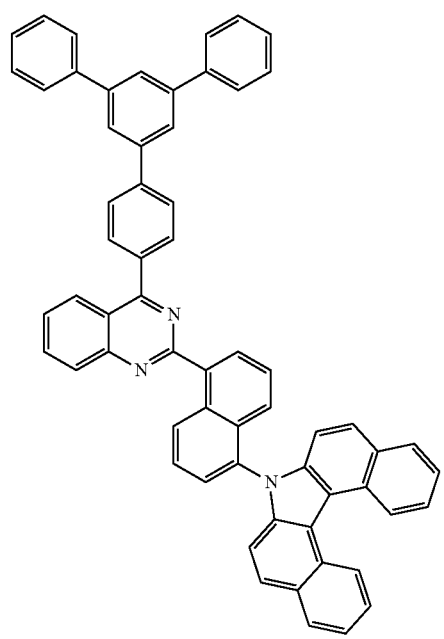
A-56
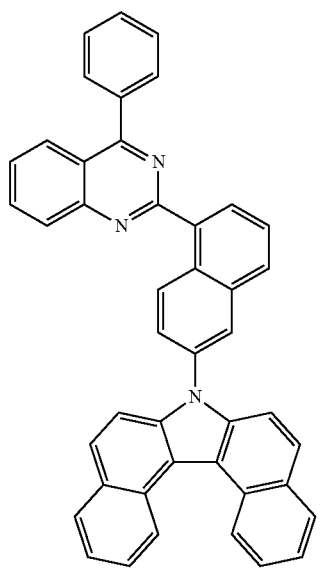
A-58

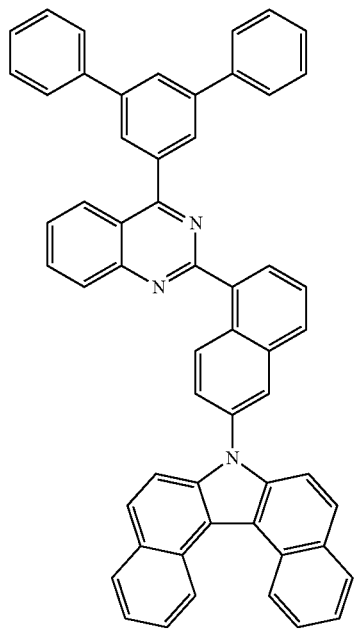
A-59
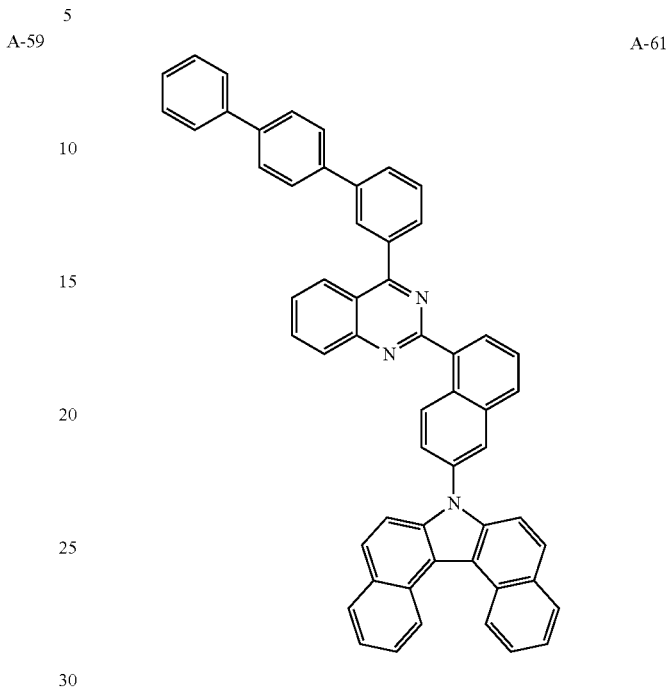
A-61
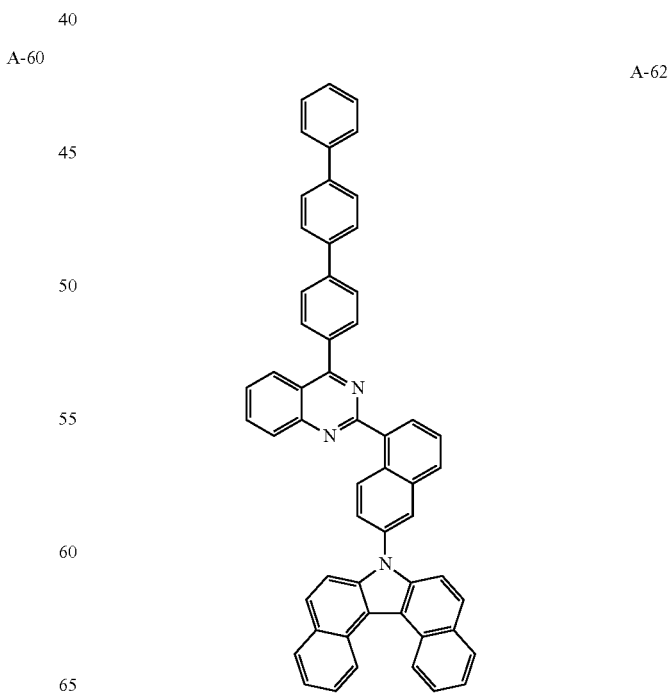
A-60
A-62

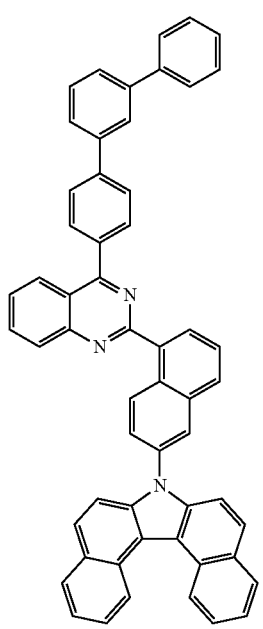
A-63
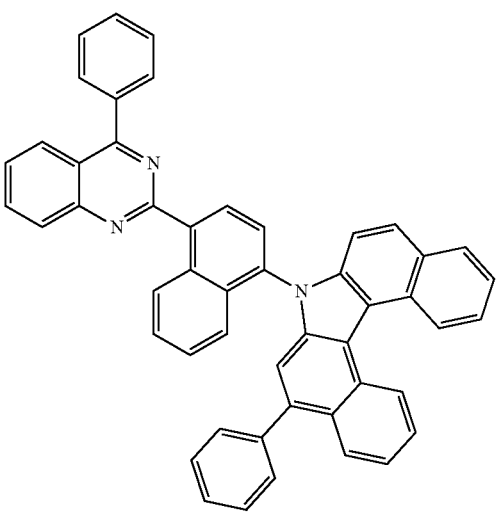
A-65
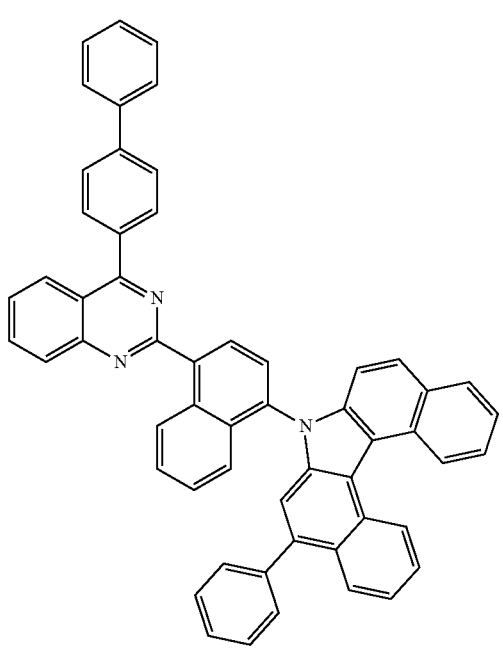
A-64
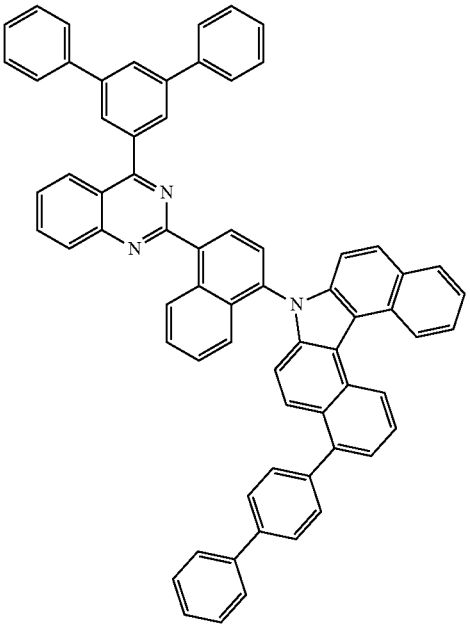
A-66

-continued
A-67
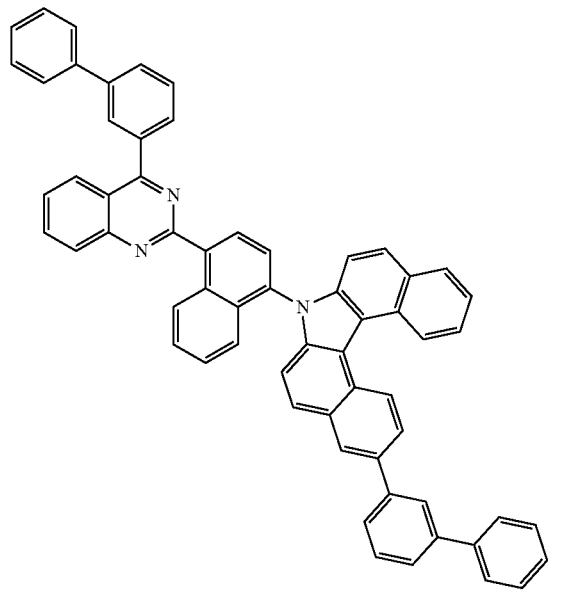
A-68
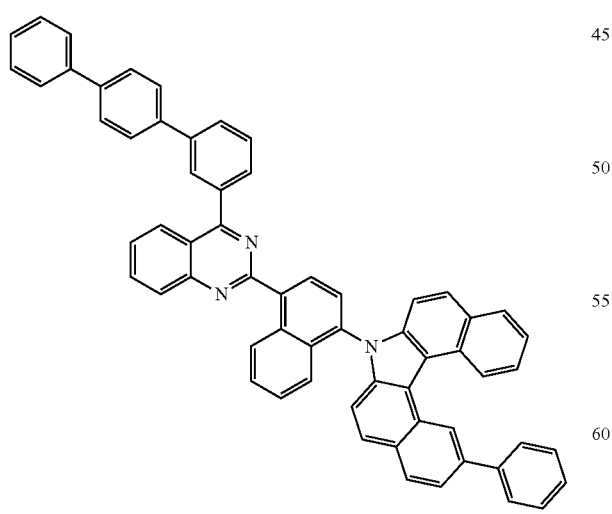
A-69
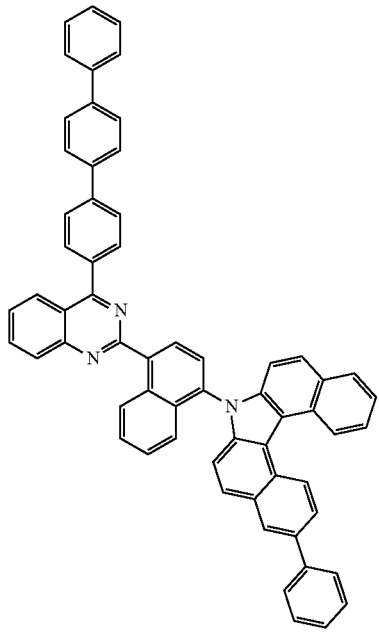
A-70
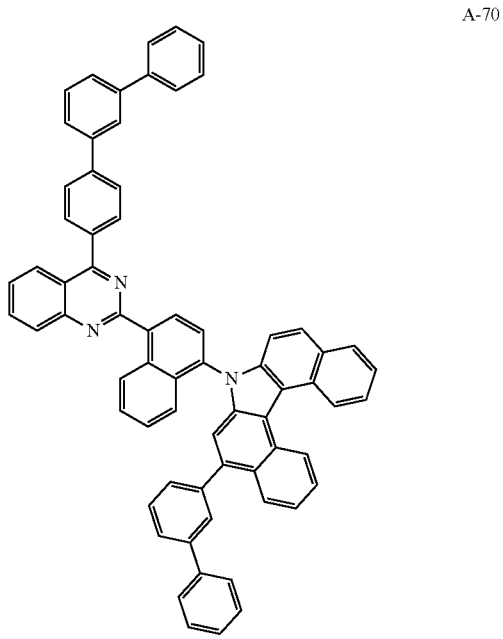

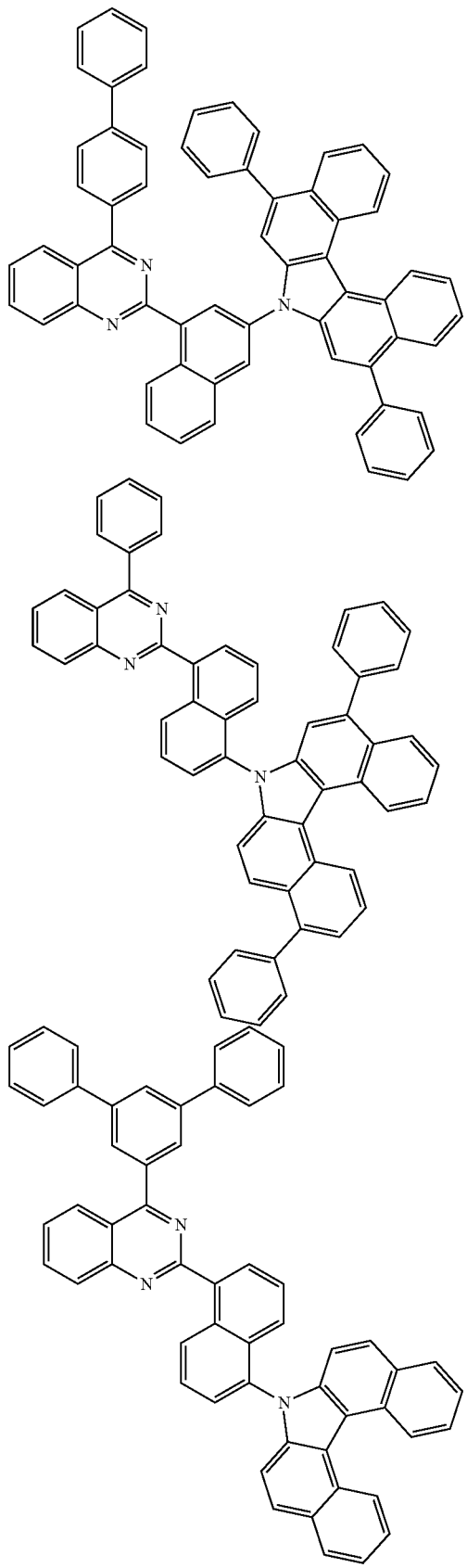
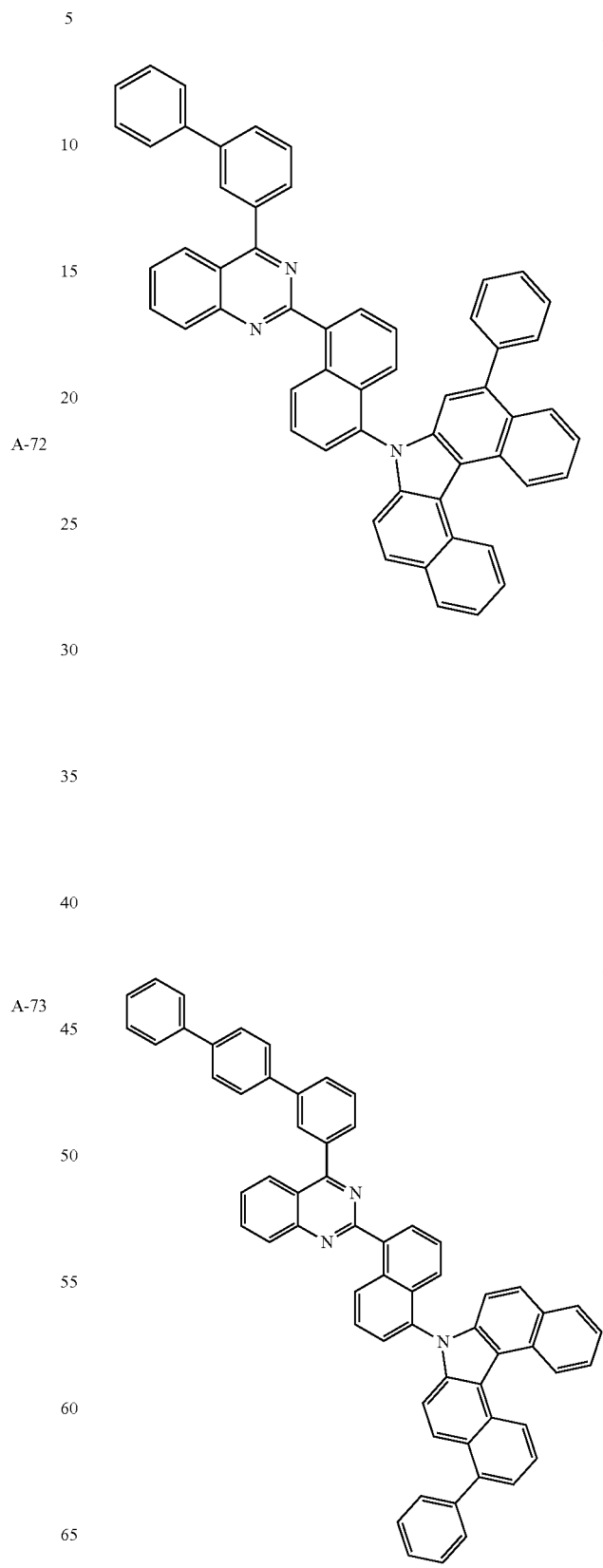

A-76
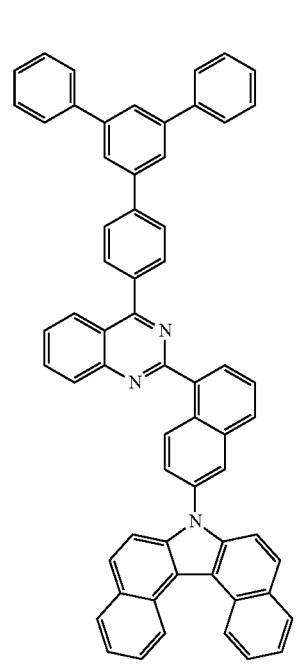
A-77
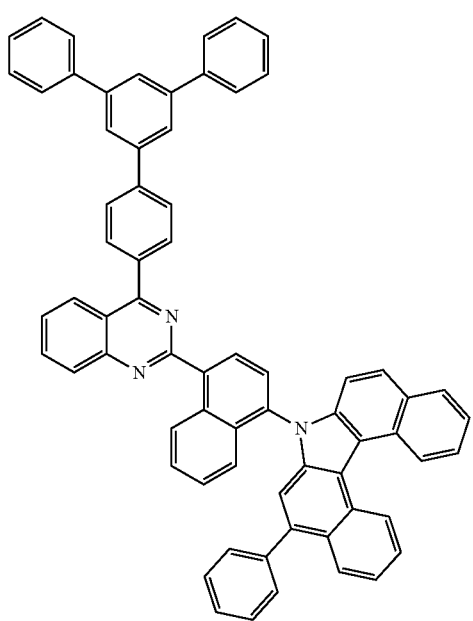
A-78
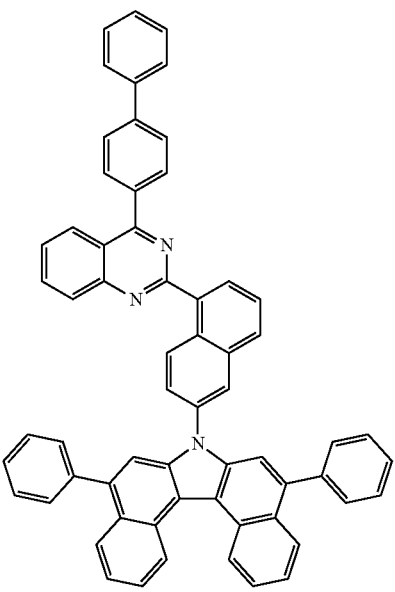
A-79
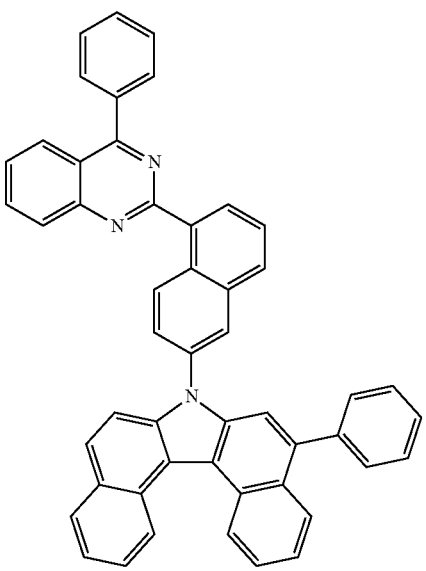

A-80
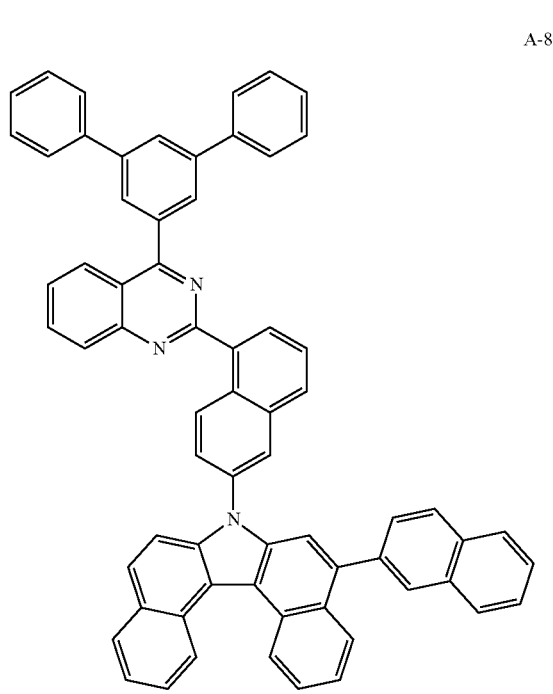
A-82
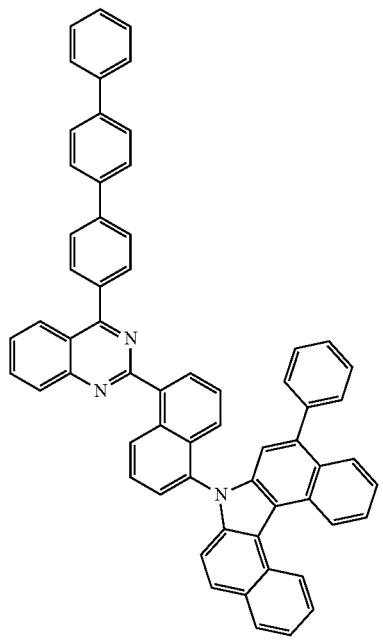
A-81
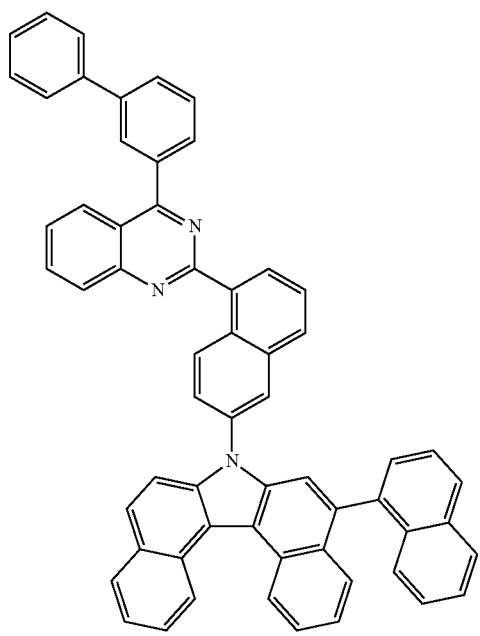
A-83
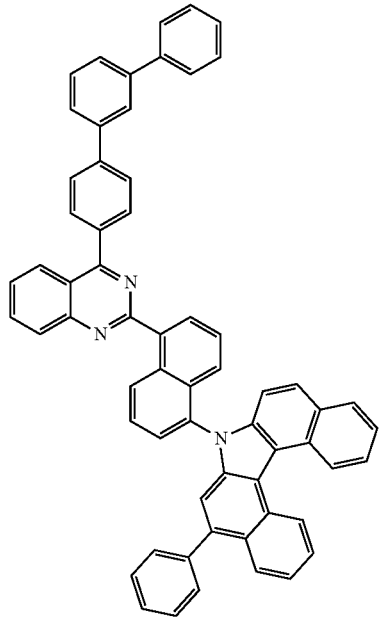

-continued
A-84
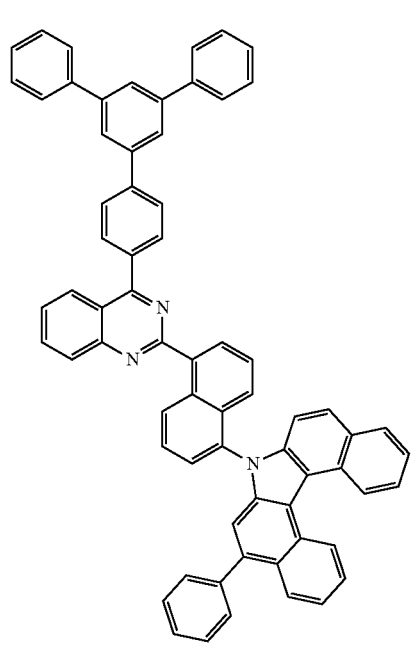
A-85
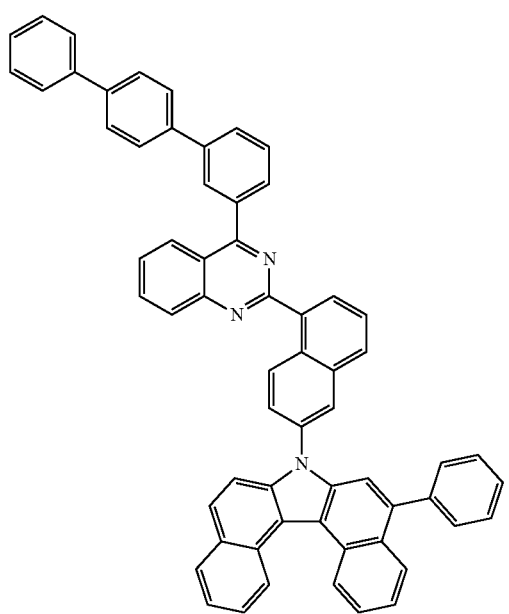
A-86
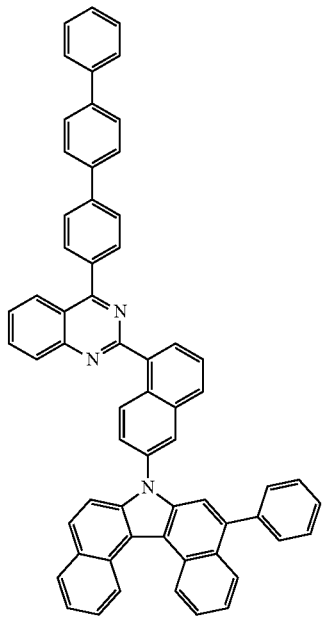
A-87
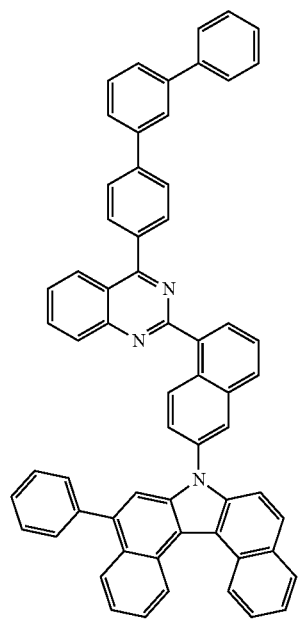

-continued
A-88
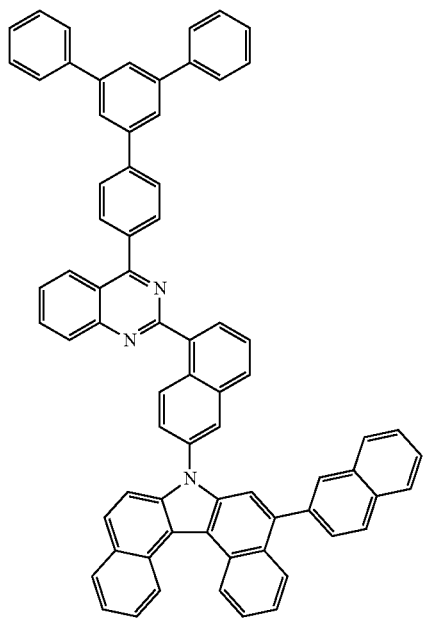
A-89
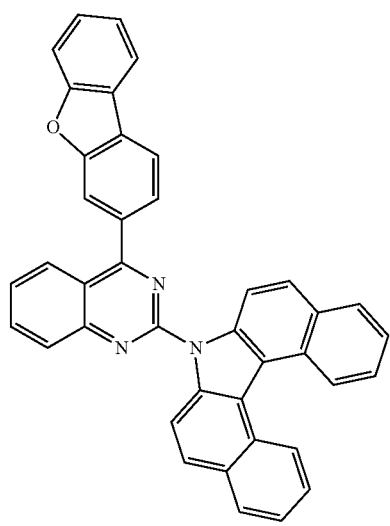
A-90
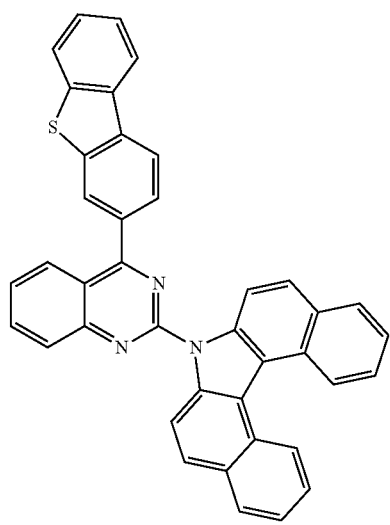
A-91
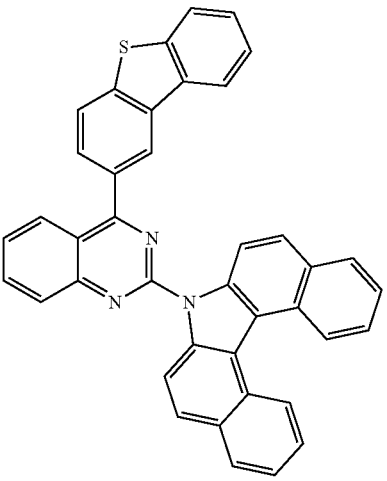
A-92
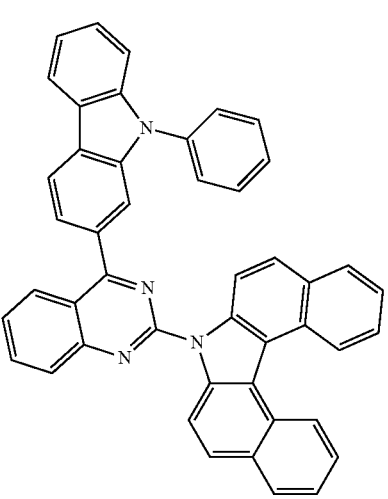
A-93
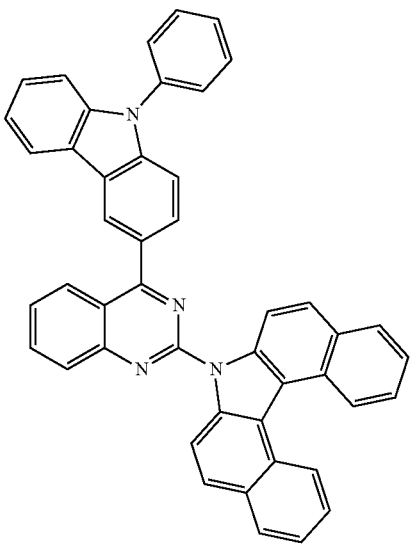

A-94
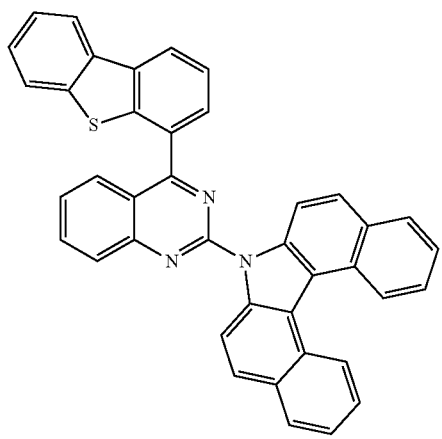
A-95
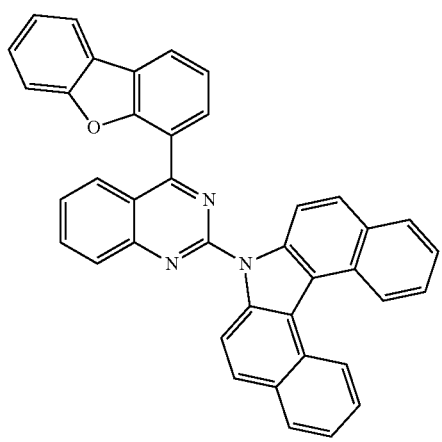
A-96
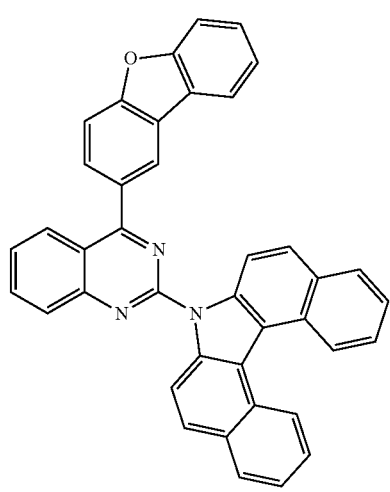
A-97
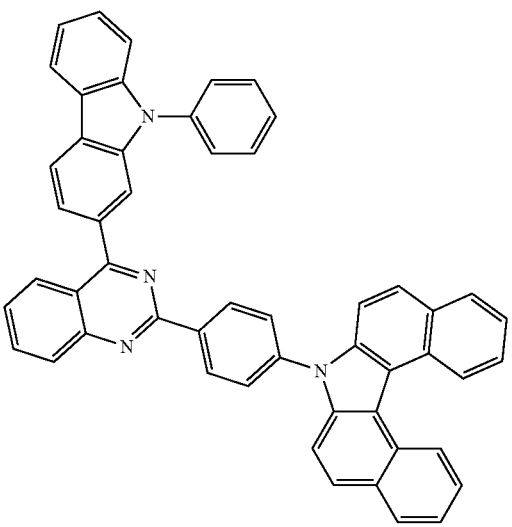
A-98
A-99
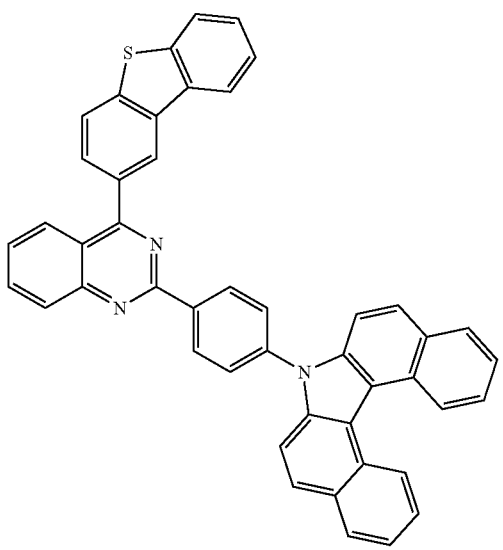

A-100
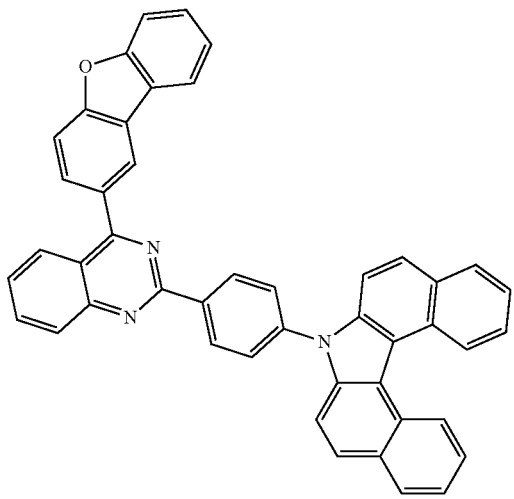
A-101
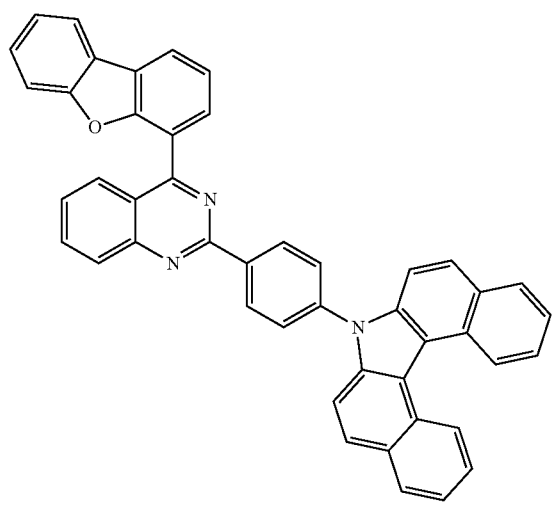
A-102
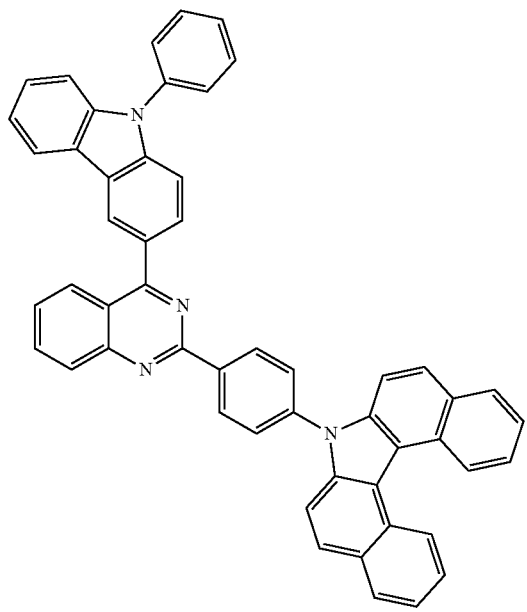
A-103
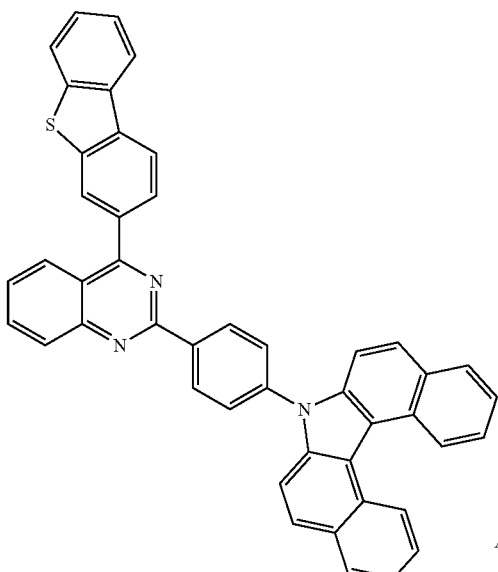
A-104
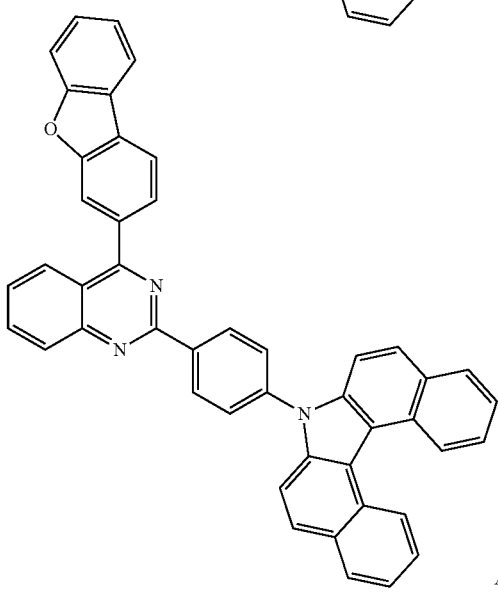
A-105
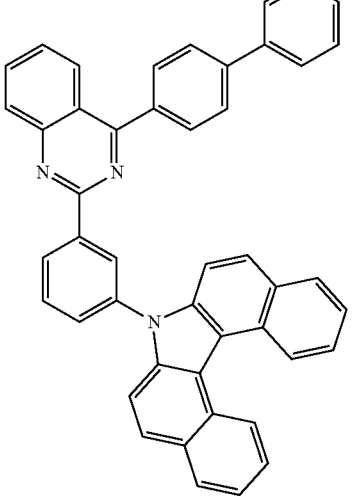

A-106
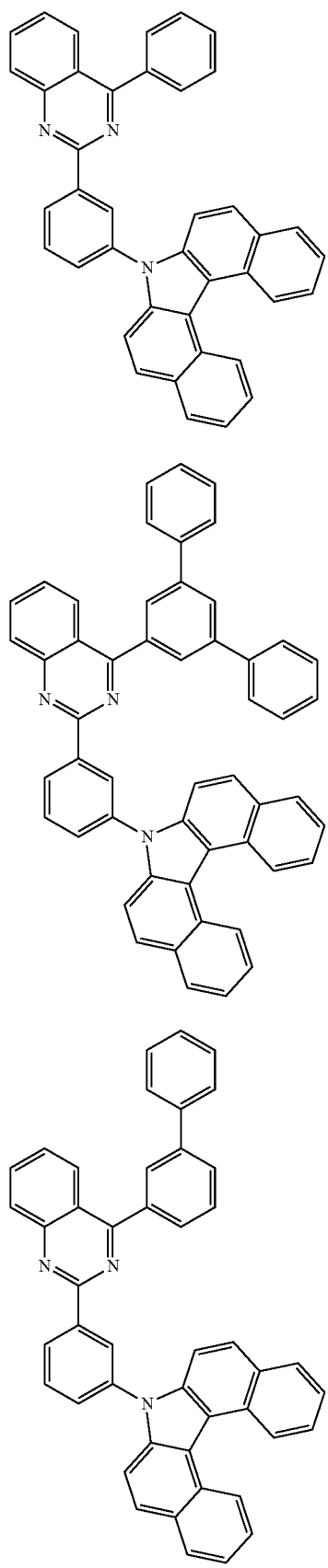
A-107
A-108
A-109
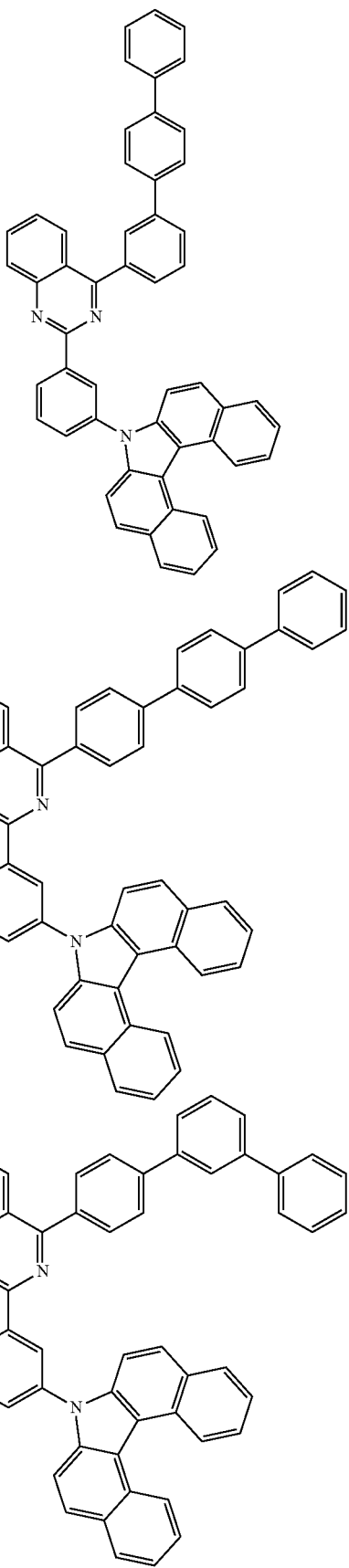
A-110
A-111

A-112
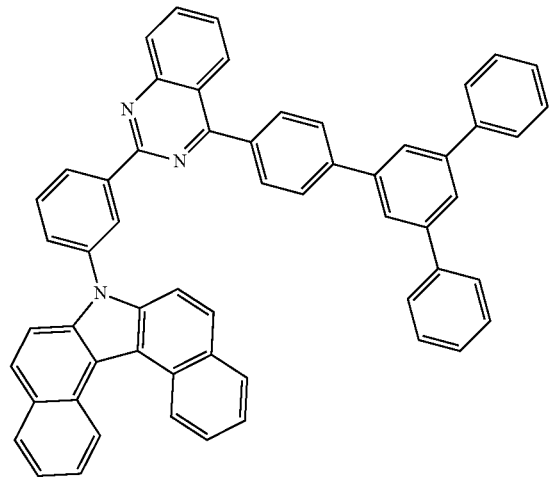
A-115
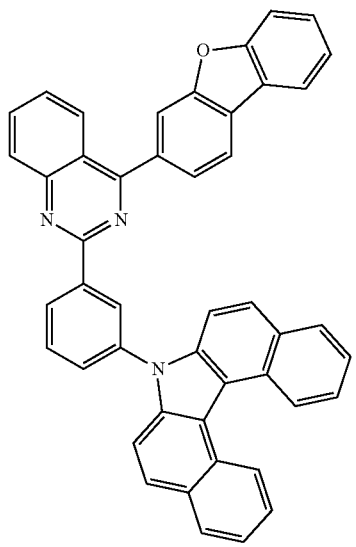
A-113
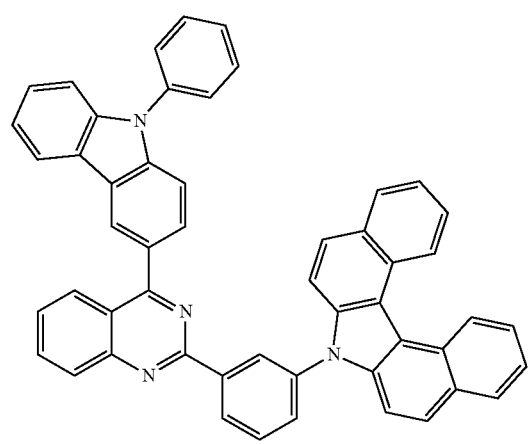
A-116
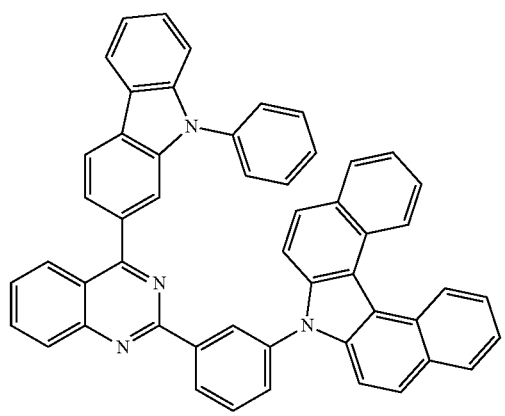
A-114
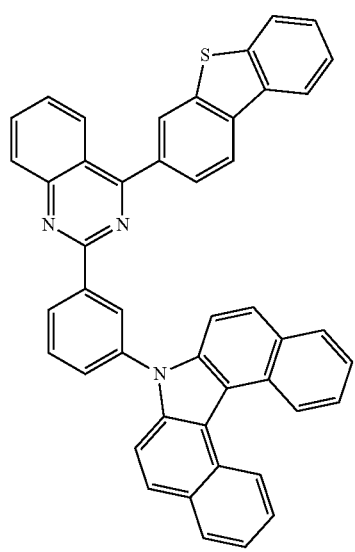
A-117
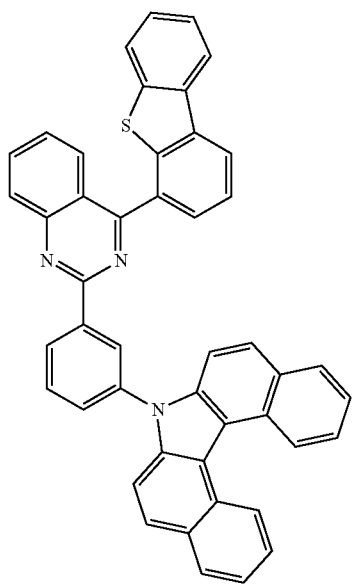

A-118
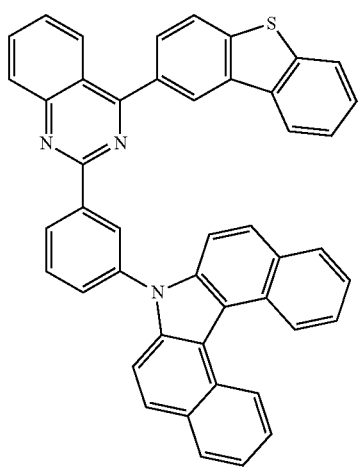
A-119
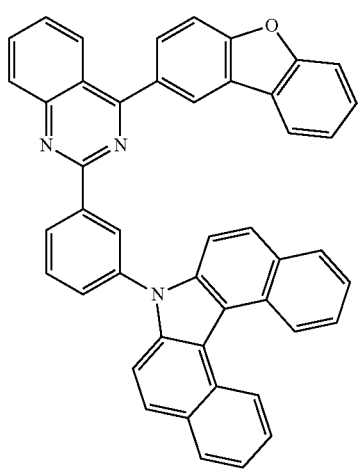
A-120
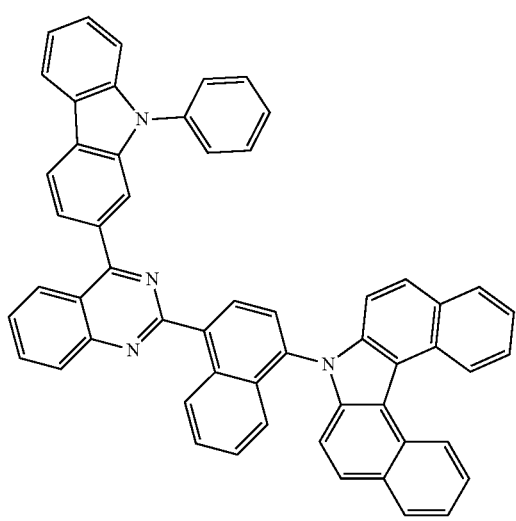
A-121
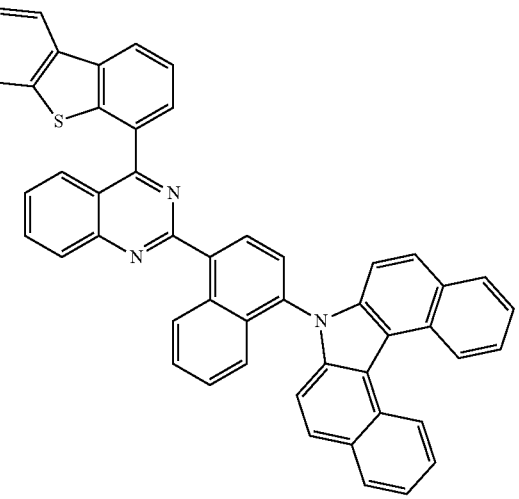
A-122
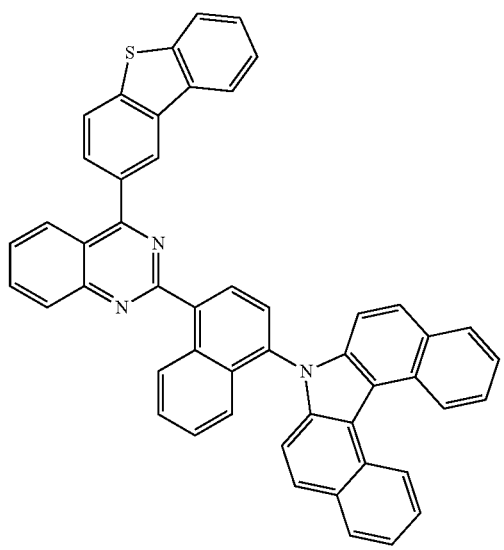
A-123
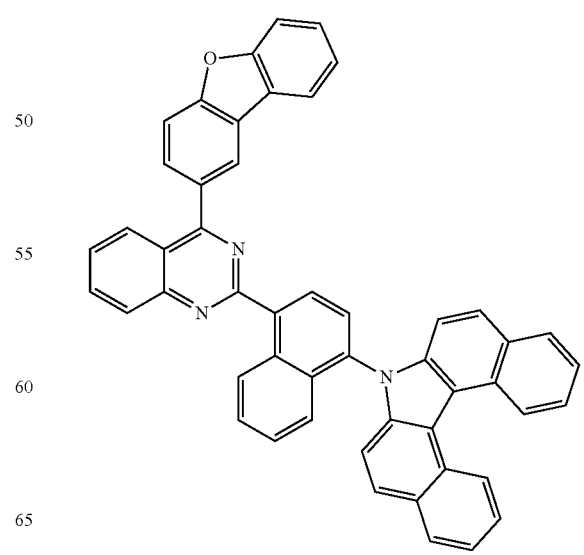

A-124
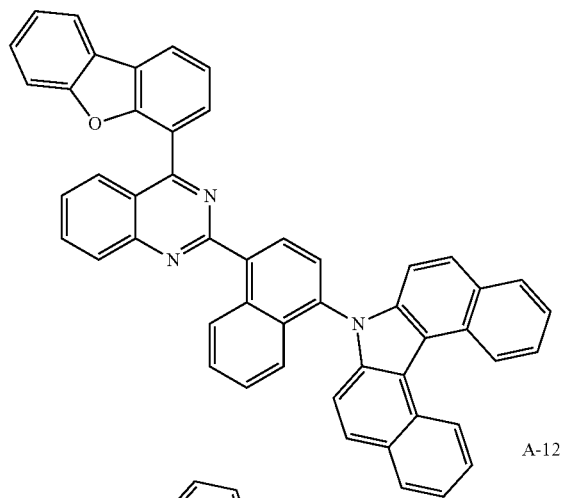
A-125
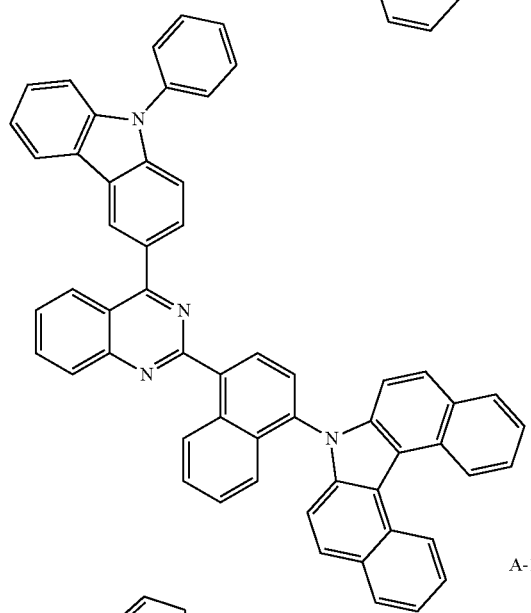
A-126
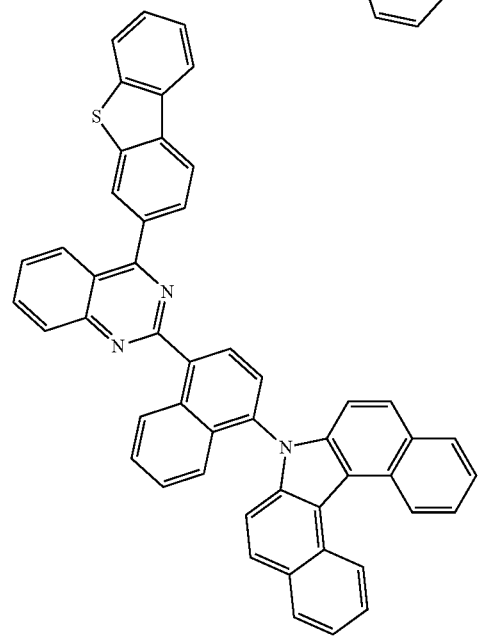
A-127
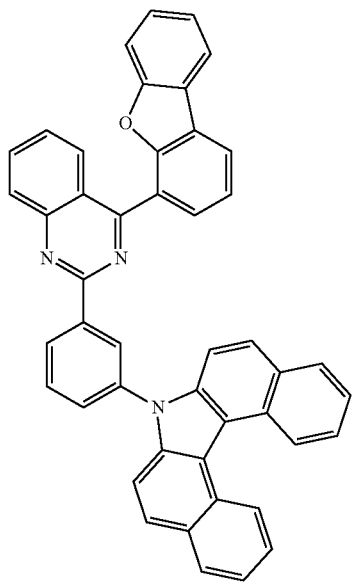
A-128
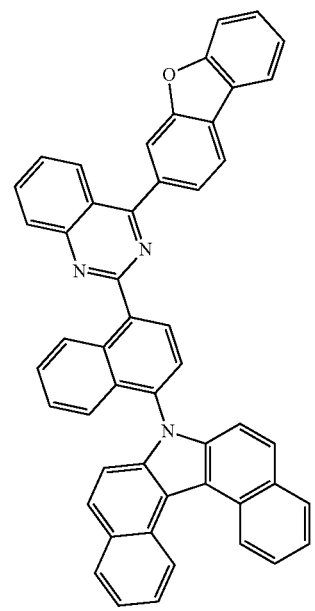
A-129
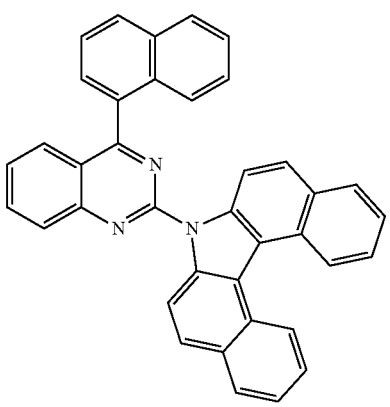

A-130
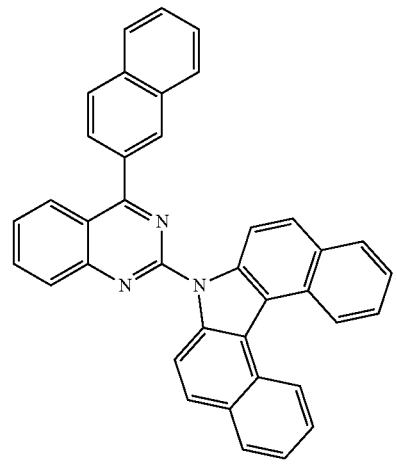
A-131
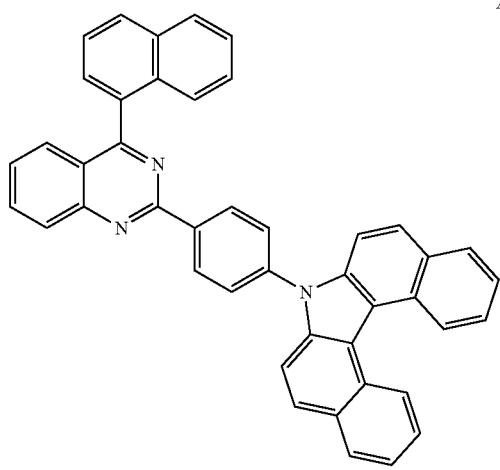
A-132
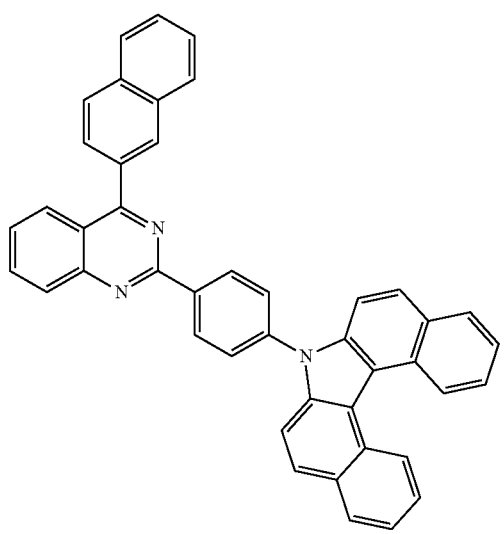
A-133
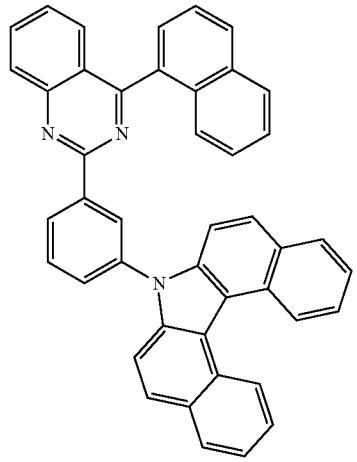
A-134
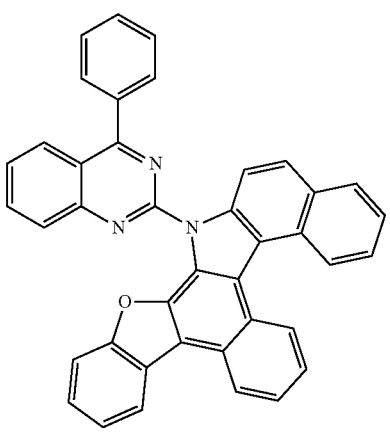
A-135
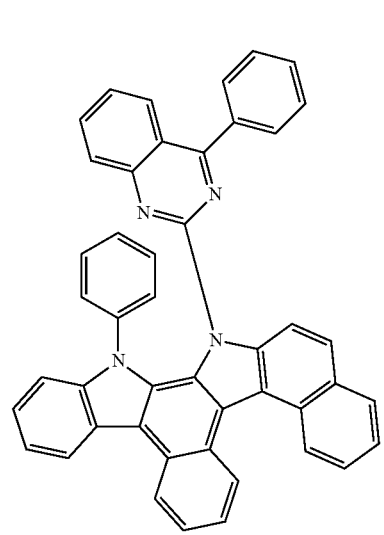

A-136
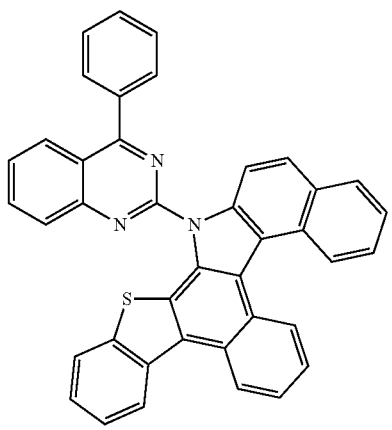
A-137
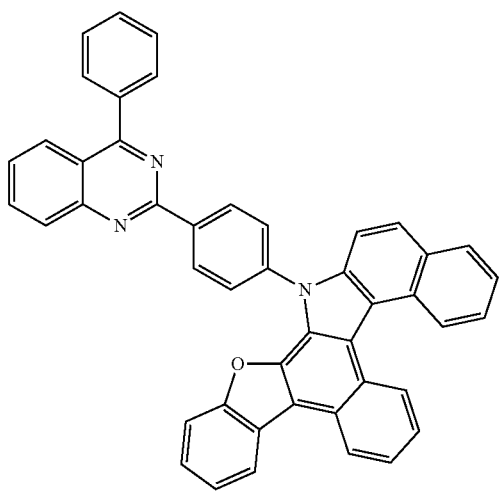
A-138
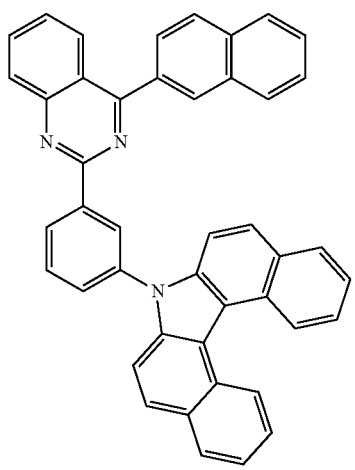
A-139
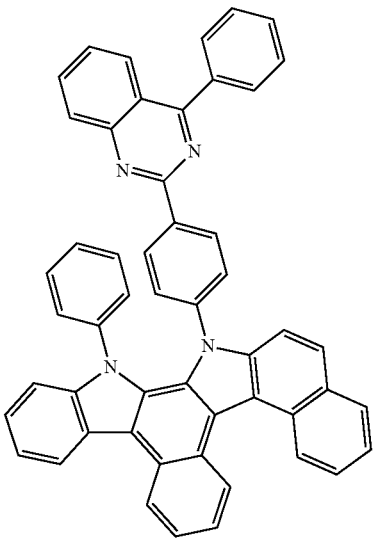
A-140
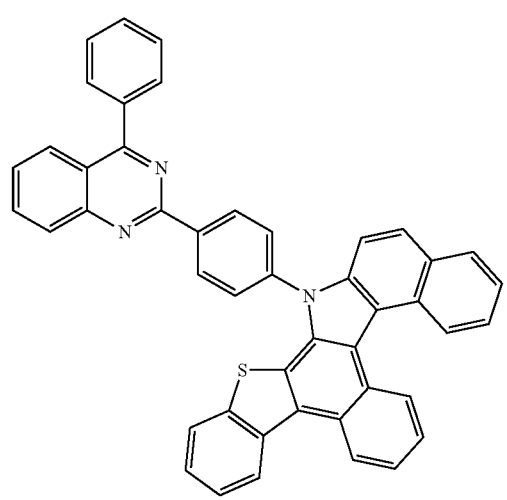
A-141
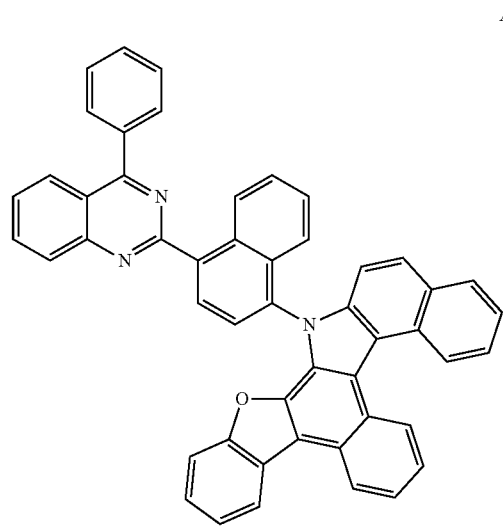

A-142
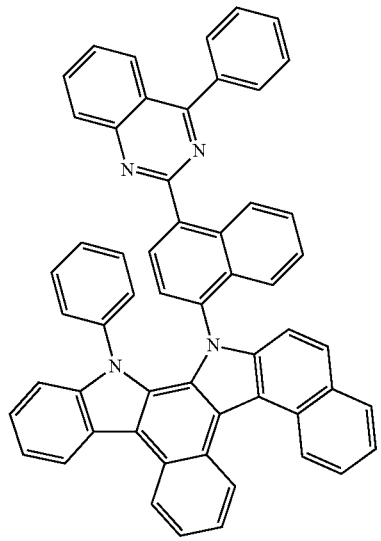
A-145
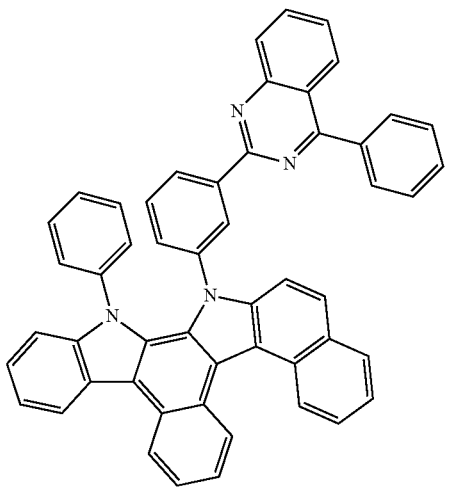
A-143
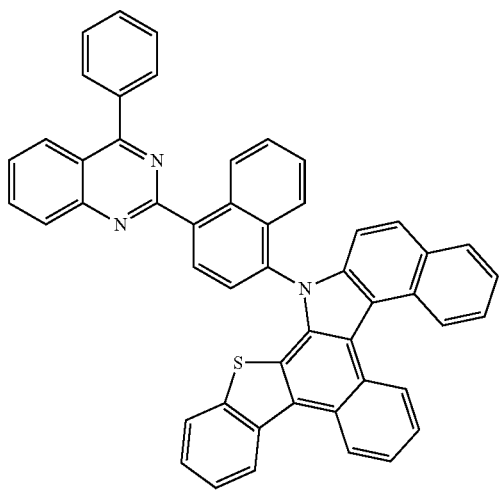
A-146
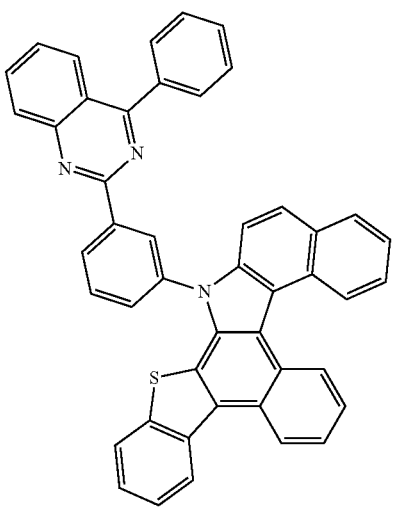
A-144
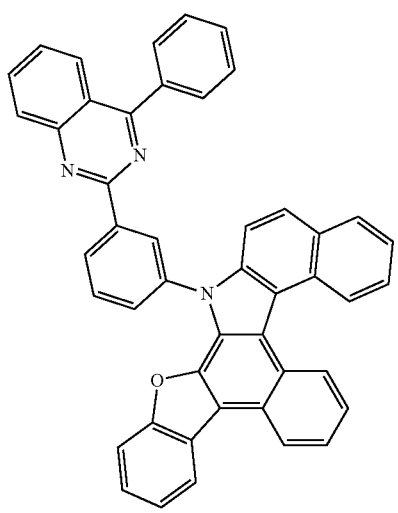
A-147
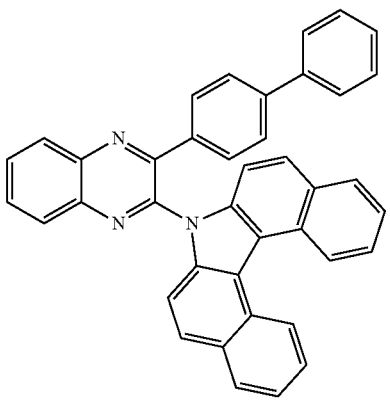

A-148
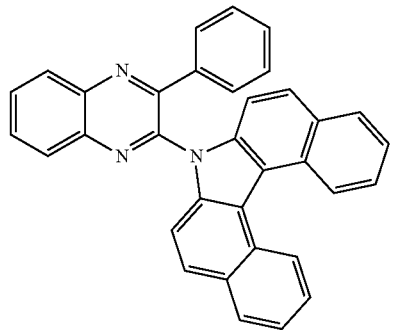
A-149
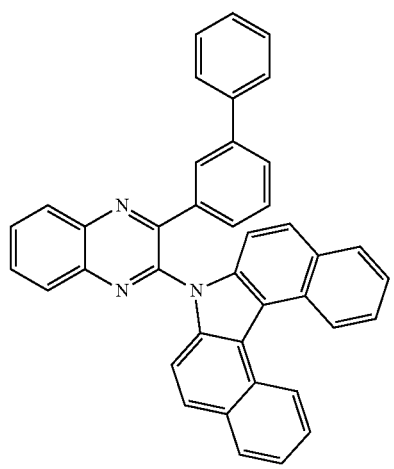
A-150
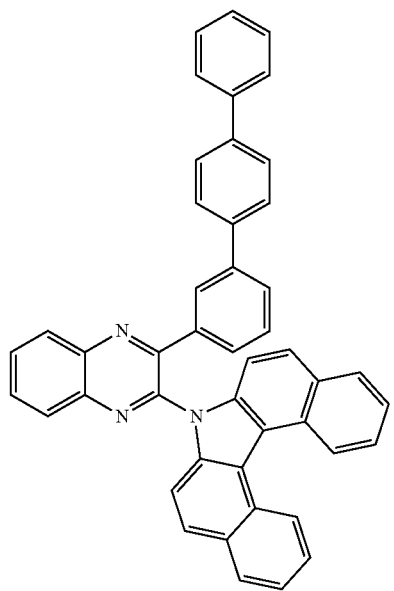
A-151
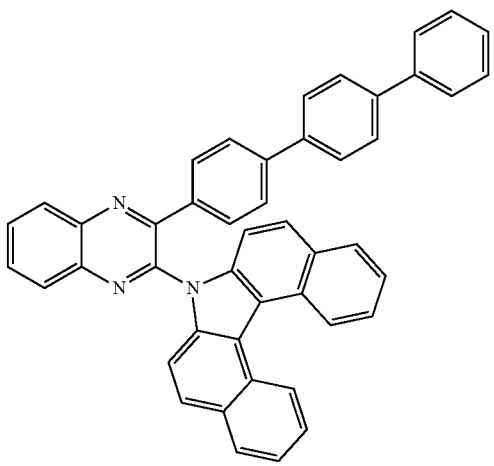
A-152
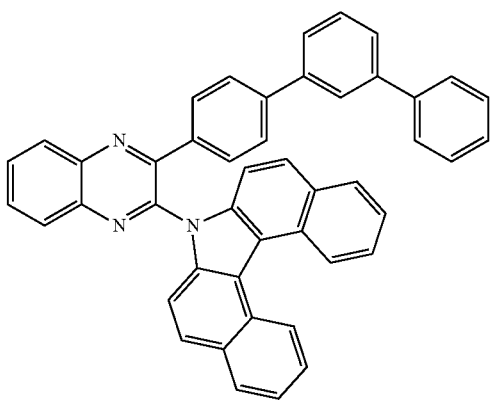
A-153
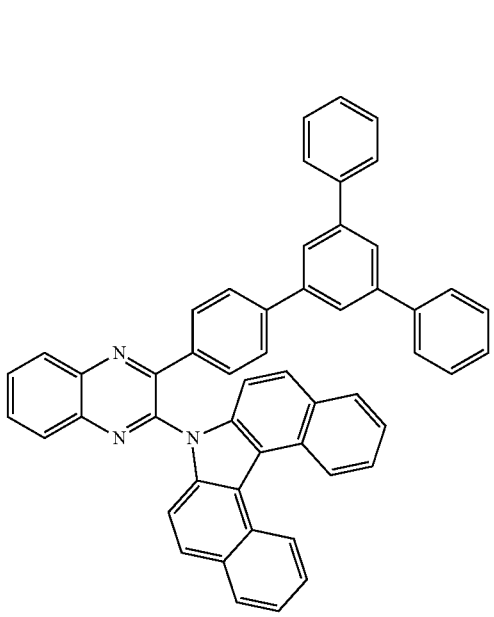

-continued
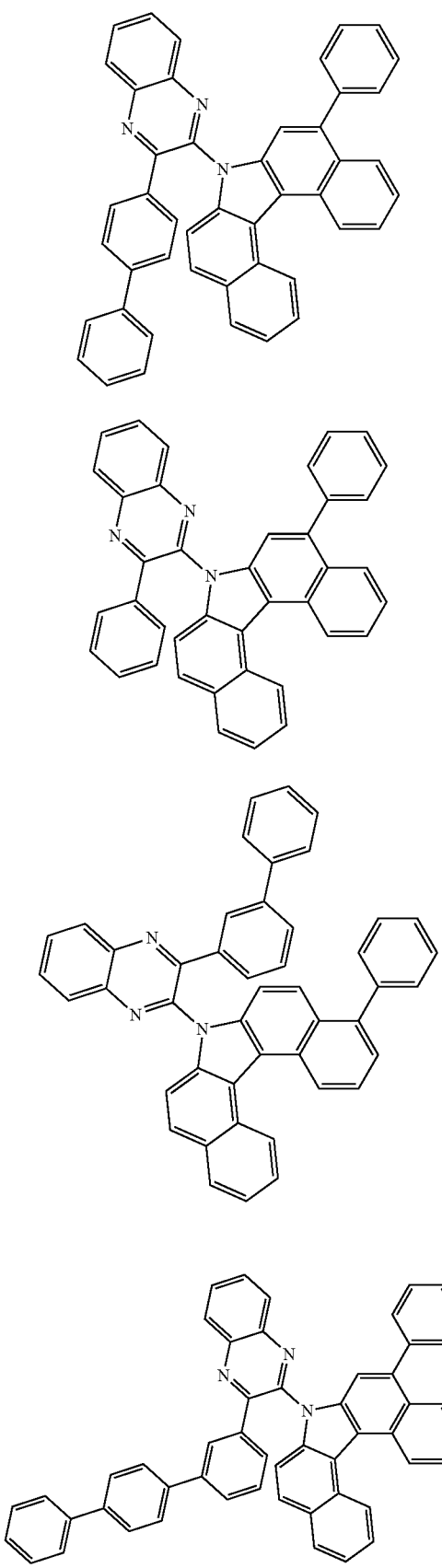
A-154
A-155
A-156
A-157
-continued
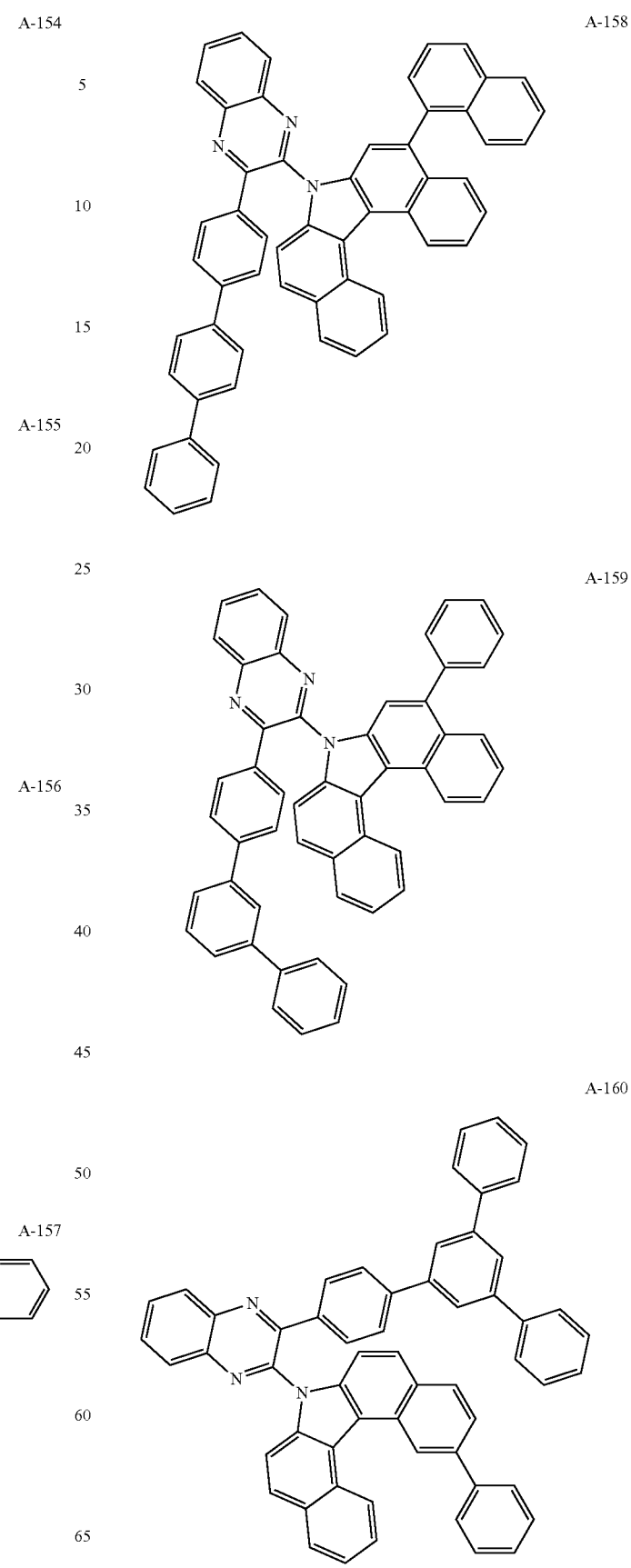
A-158
A-159
A-160

A-161
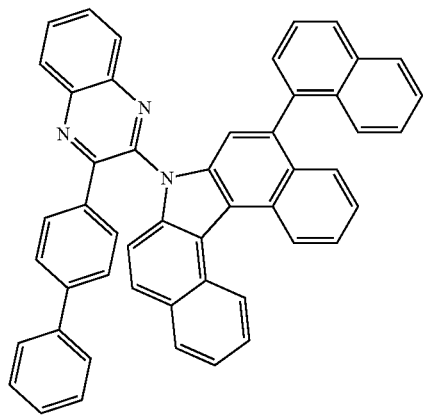
A-162
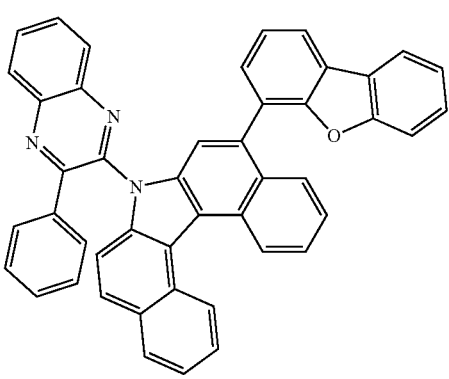
A-163
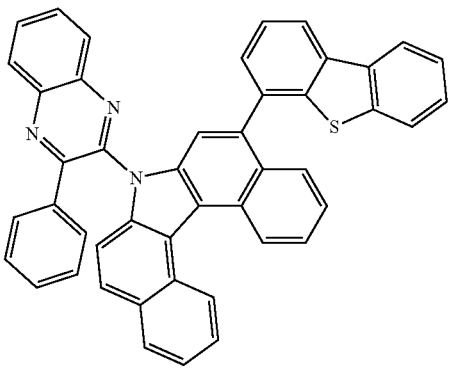
A-164
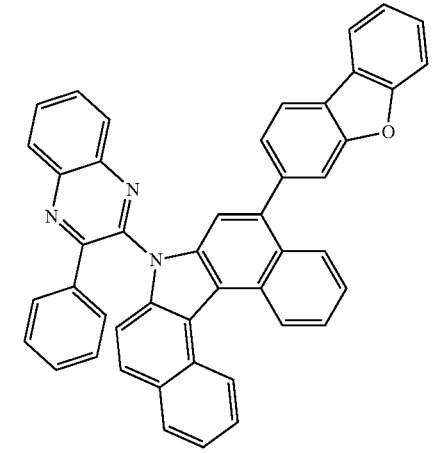
A-165
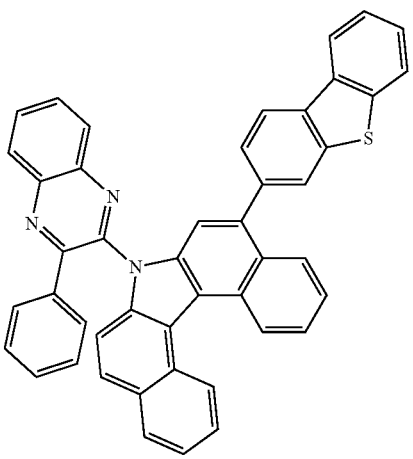
A-166
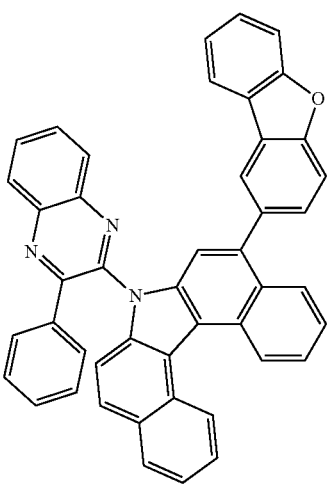
A-167
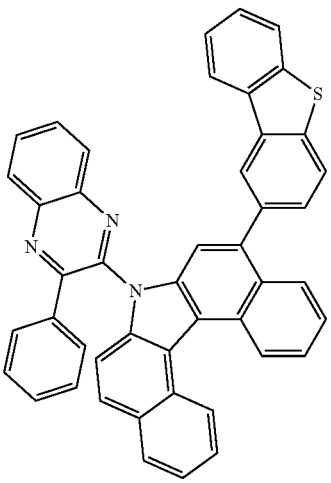

-continued
A-168
A-169
A-170
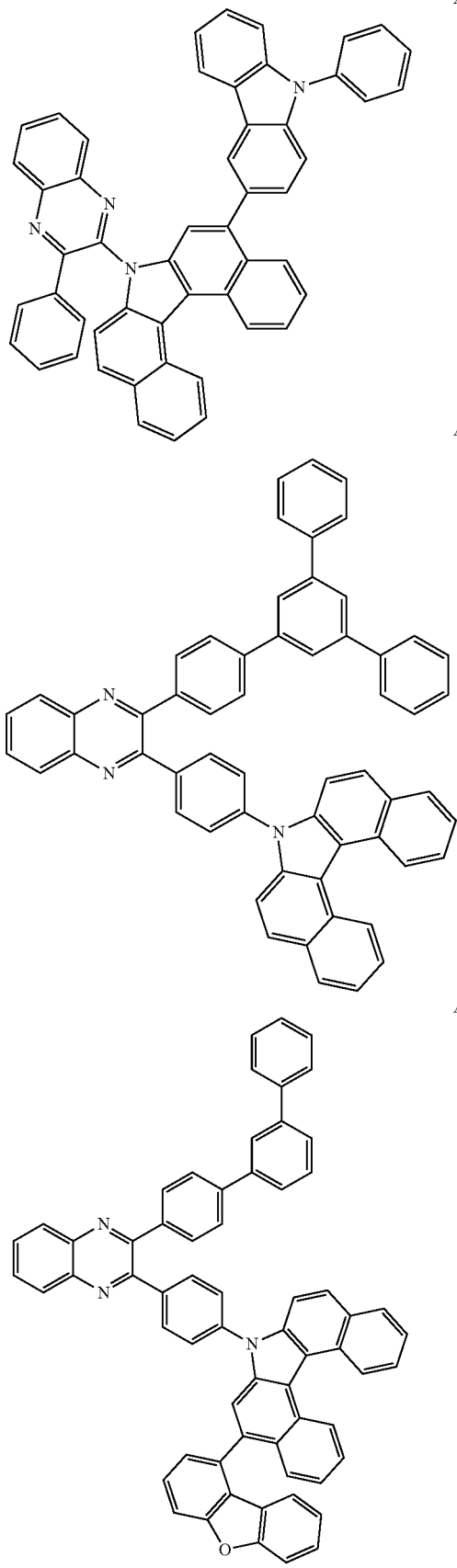
-continued
A-171
A-172

A-173
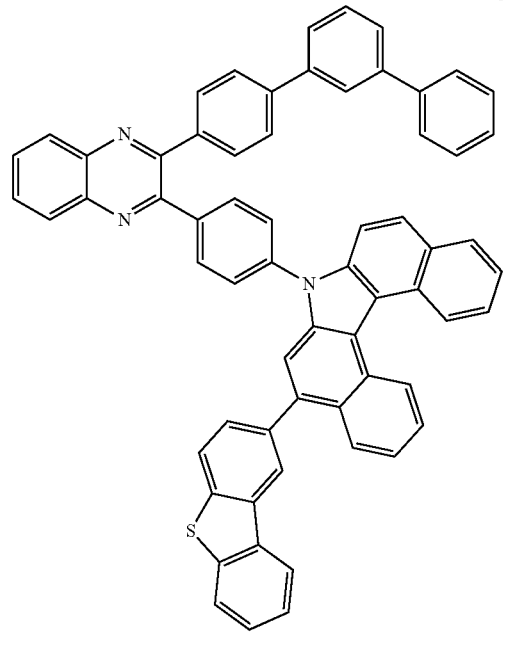
A-174
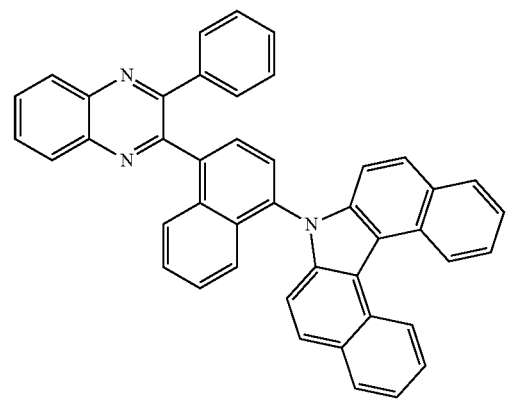
A-175
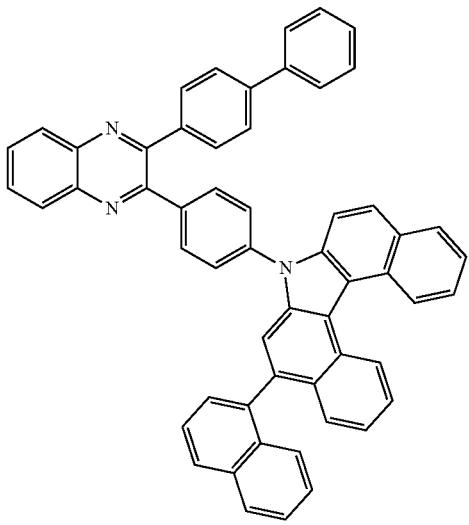
A-176
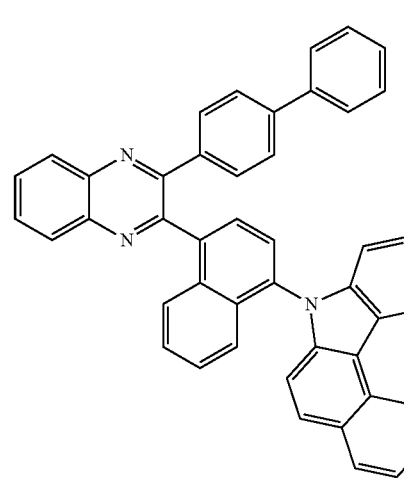
A-177
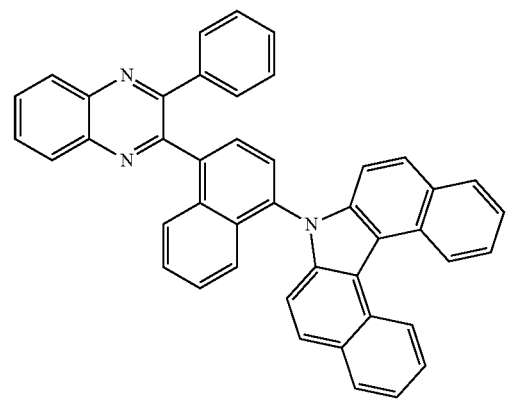

A-178
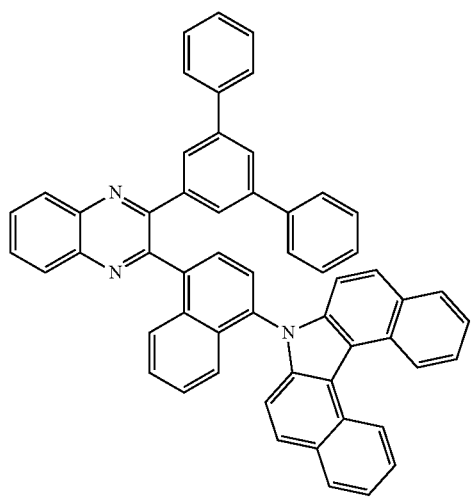
A-179
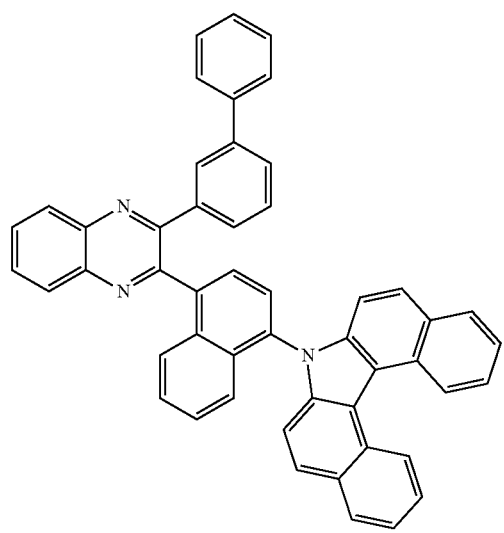
A-180
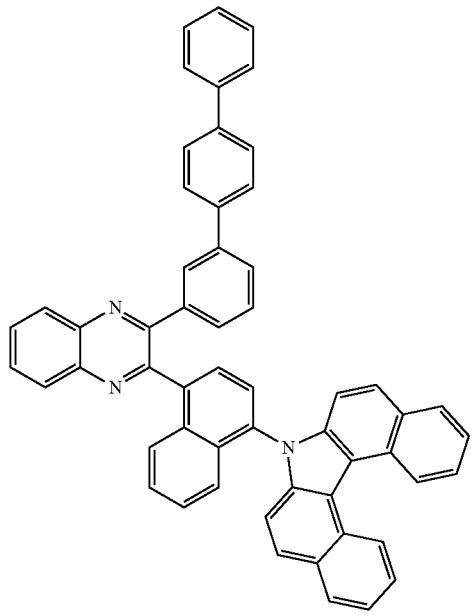
A-181
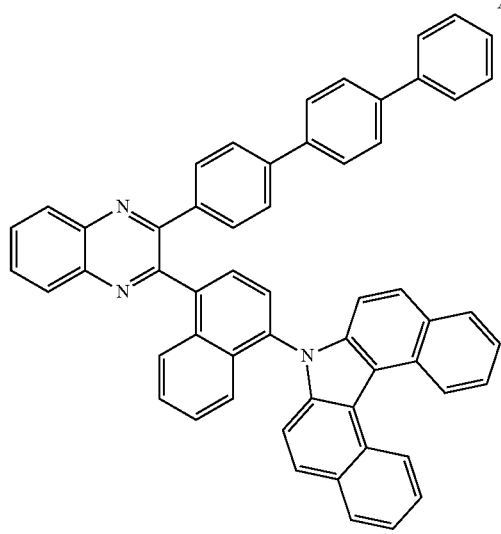
A-182
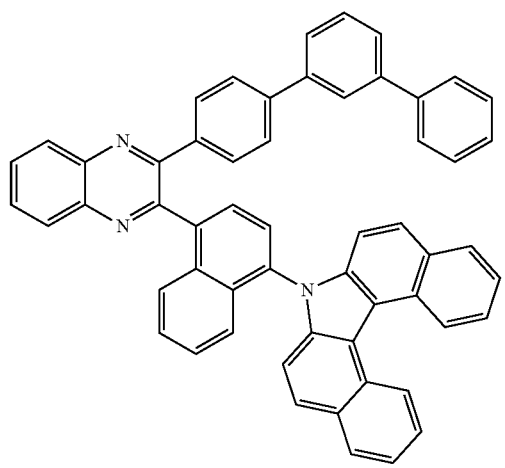
A-183
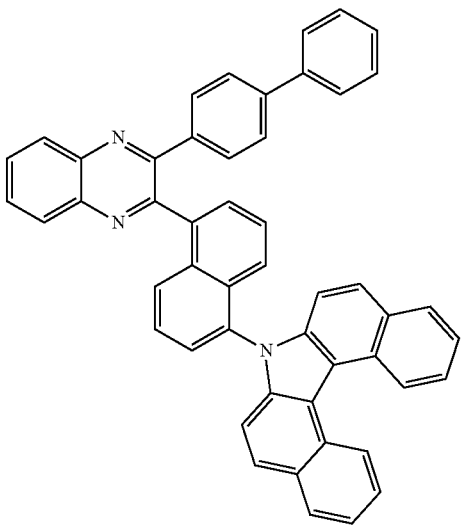

A-184
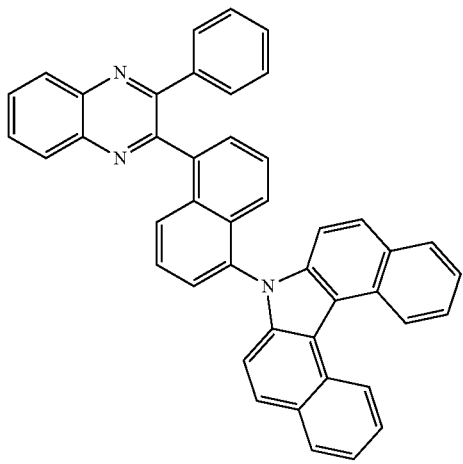
A-185
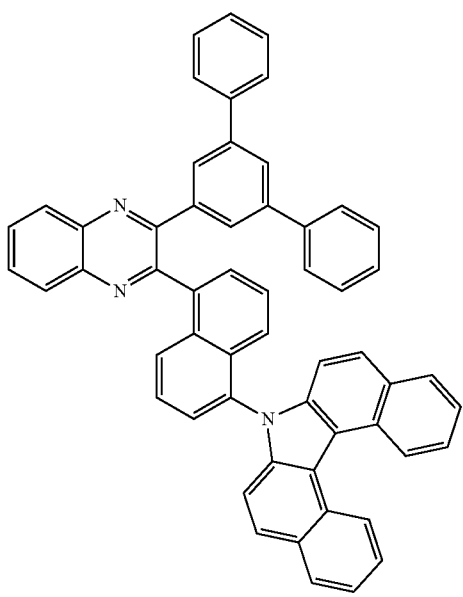
A-186
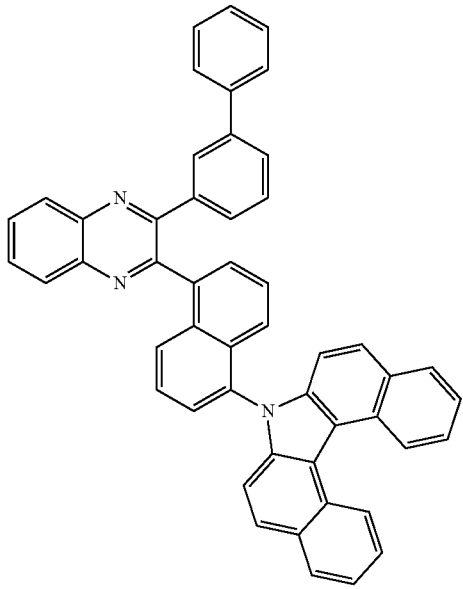
A-187
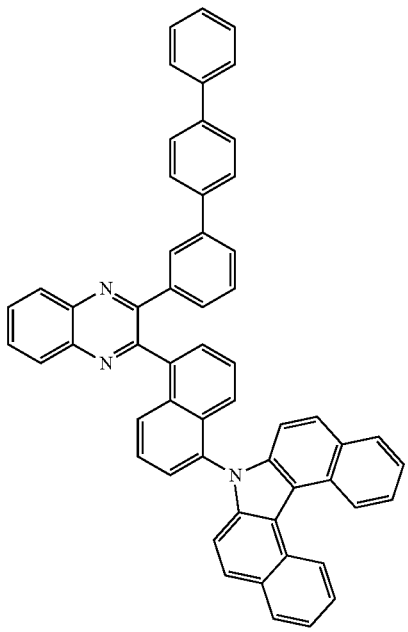
A-188
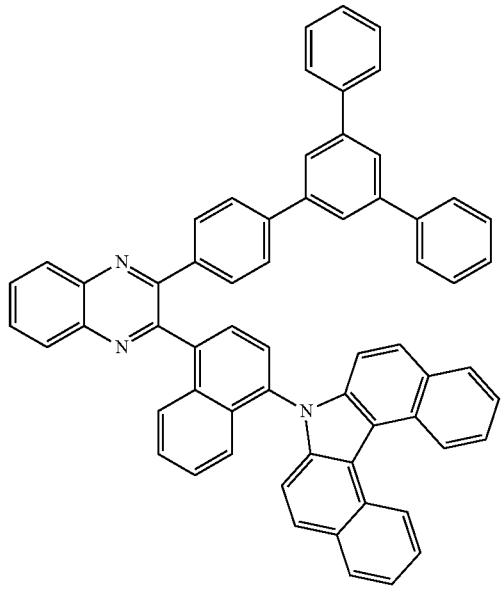

-continued
A-189
A-190
A-191
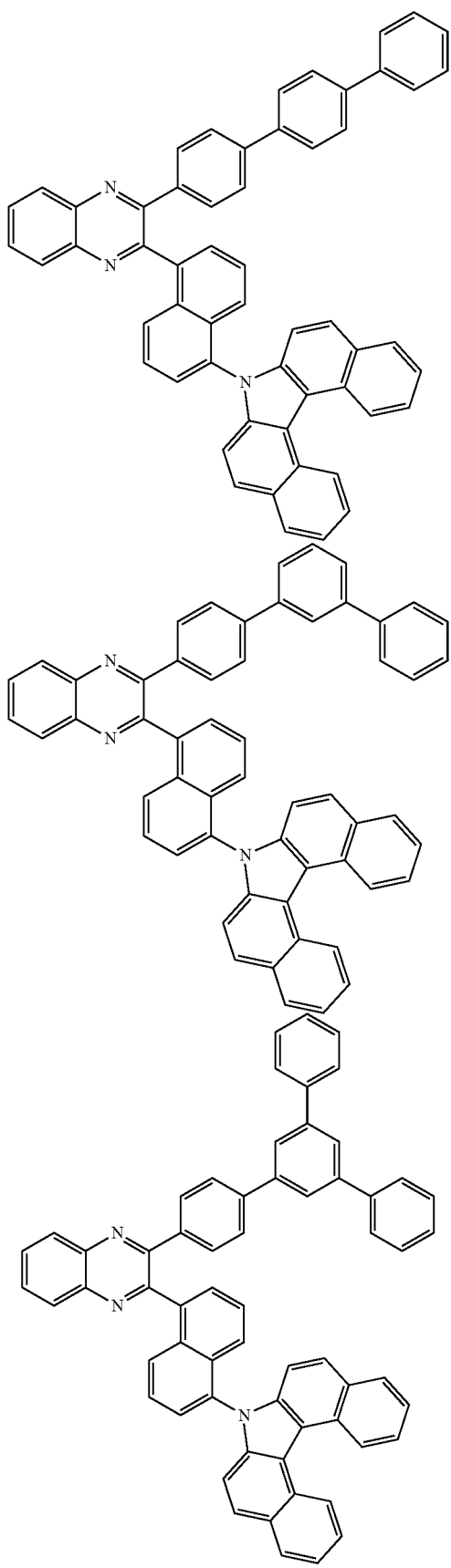
-continued
A-192
A-193
A-194
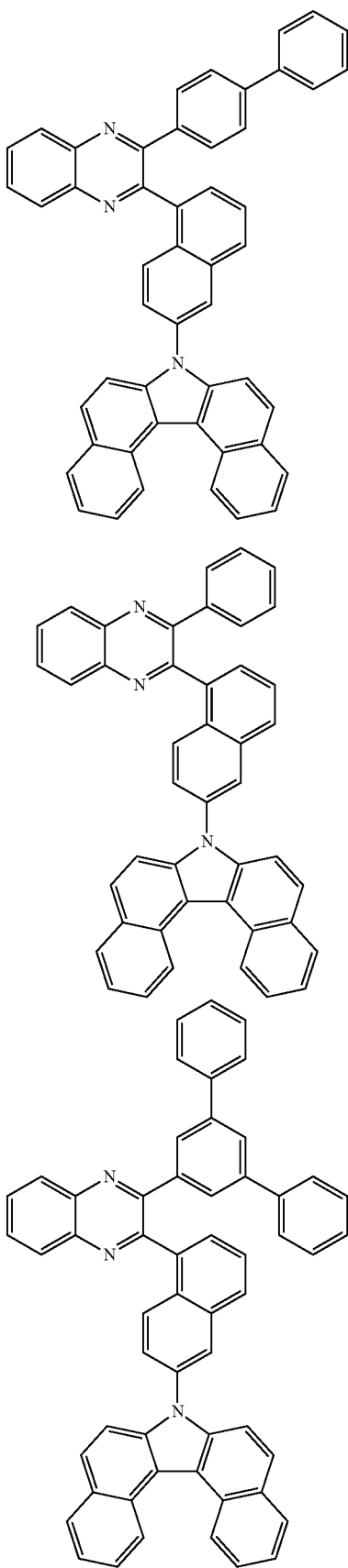

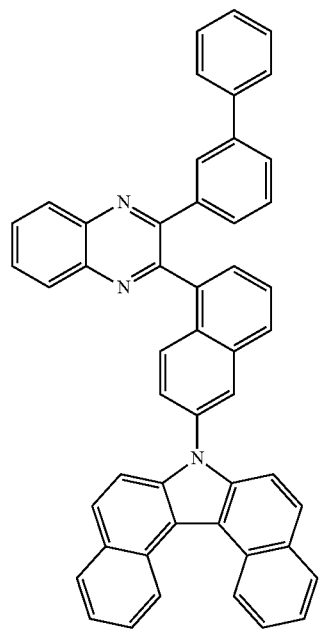
A-195
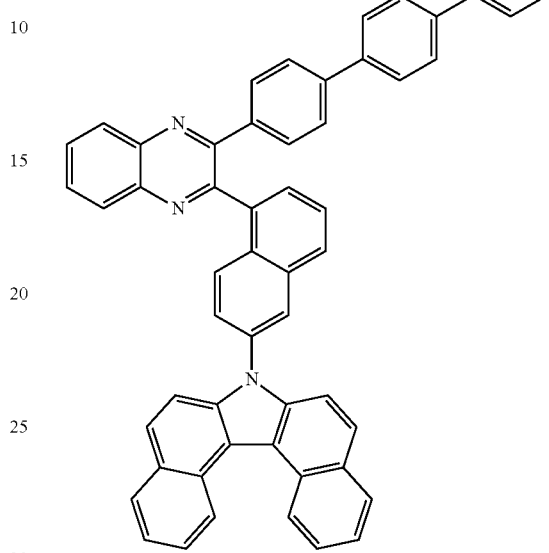
A-197
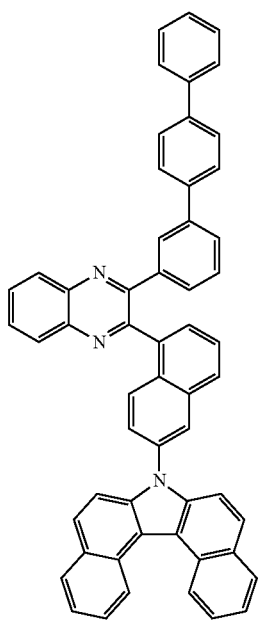
A-196
A-198

A-199
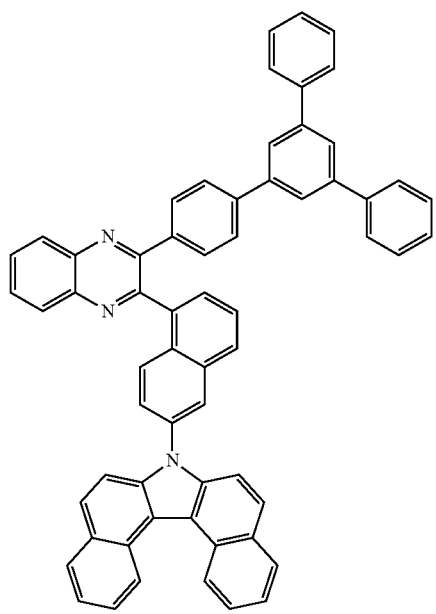
A-200
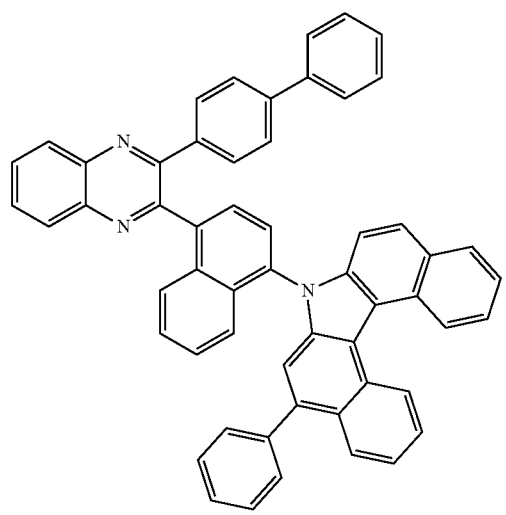
A-201
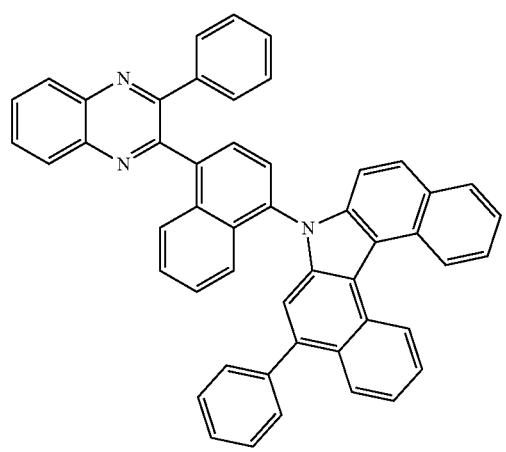
A-202
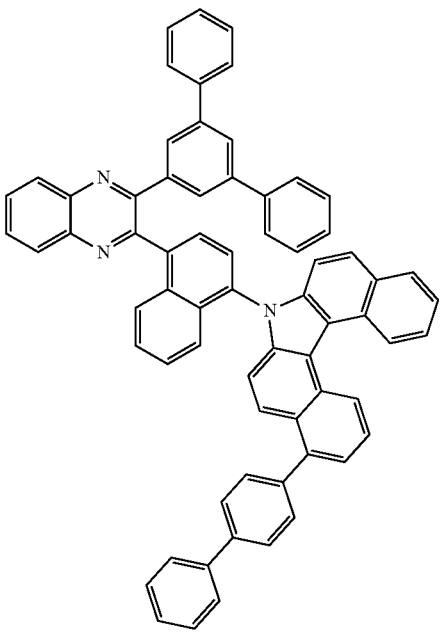
A-203
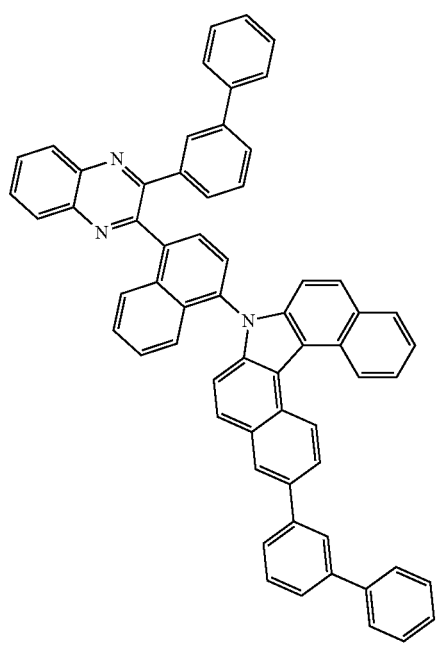

A-204
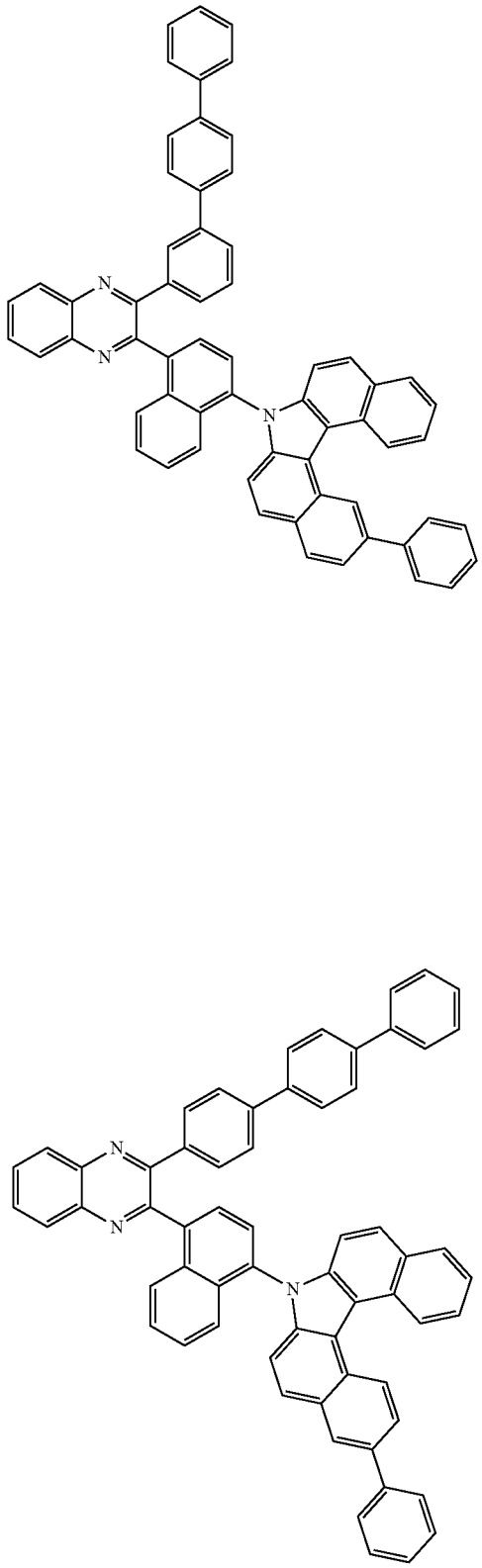
A-205
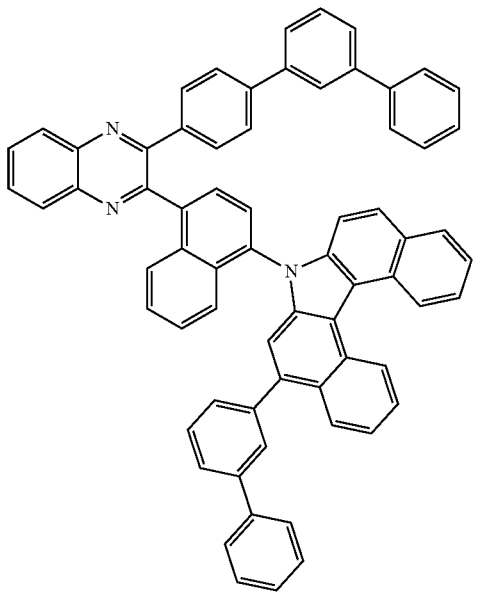
A-206
A-207
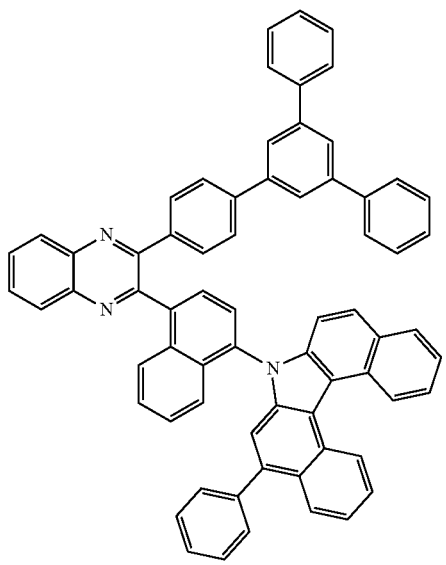
A-208
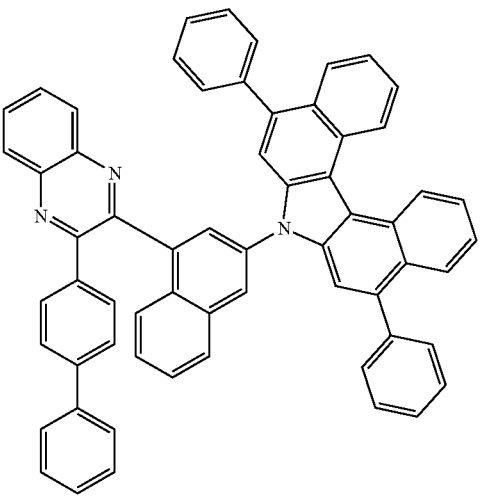

A-209
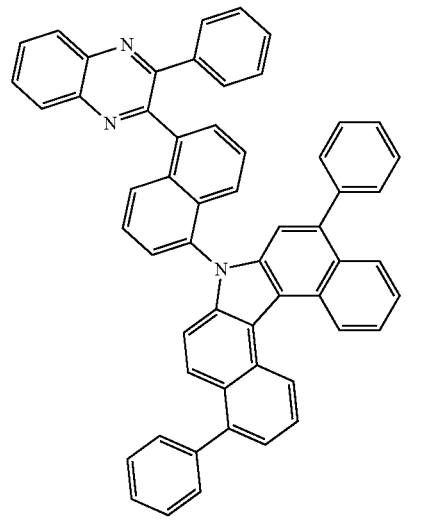
A-210
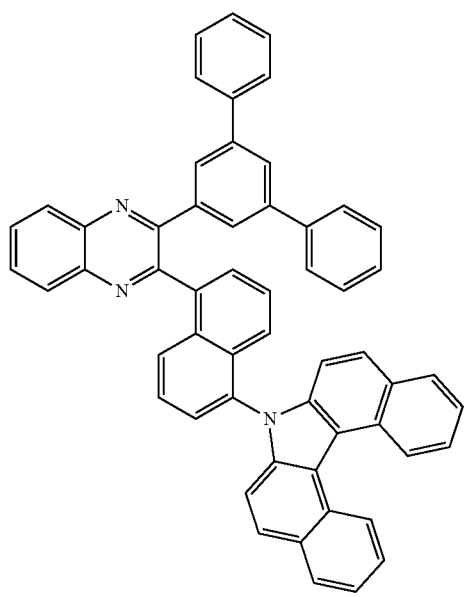
A-211
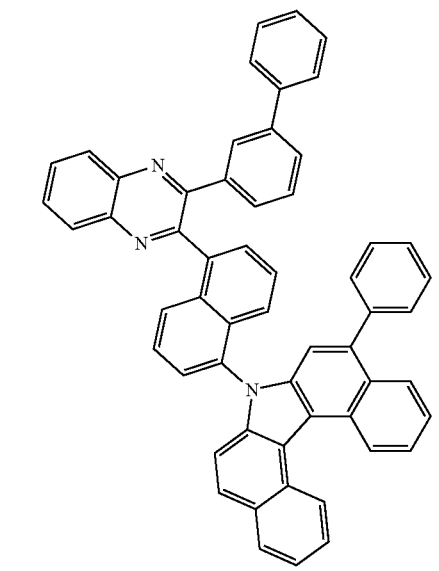
A-212
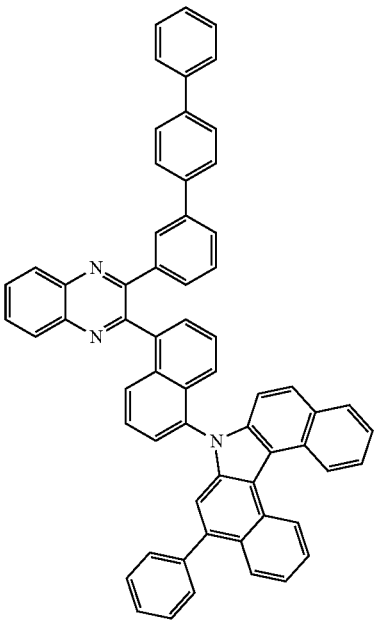
A-213
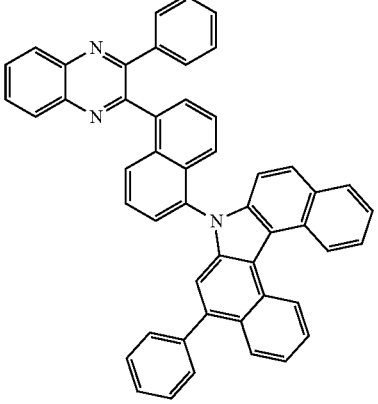
A-214
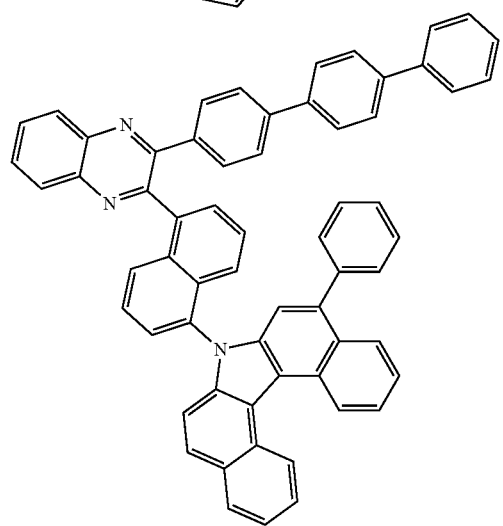

-continued
A-215
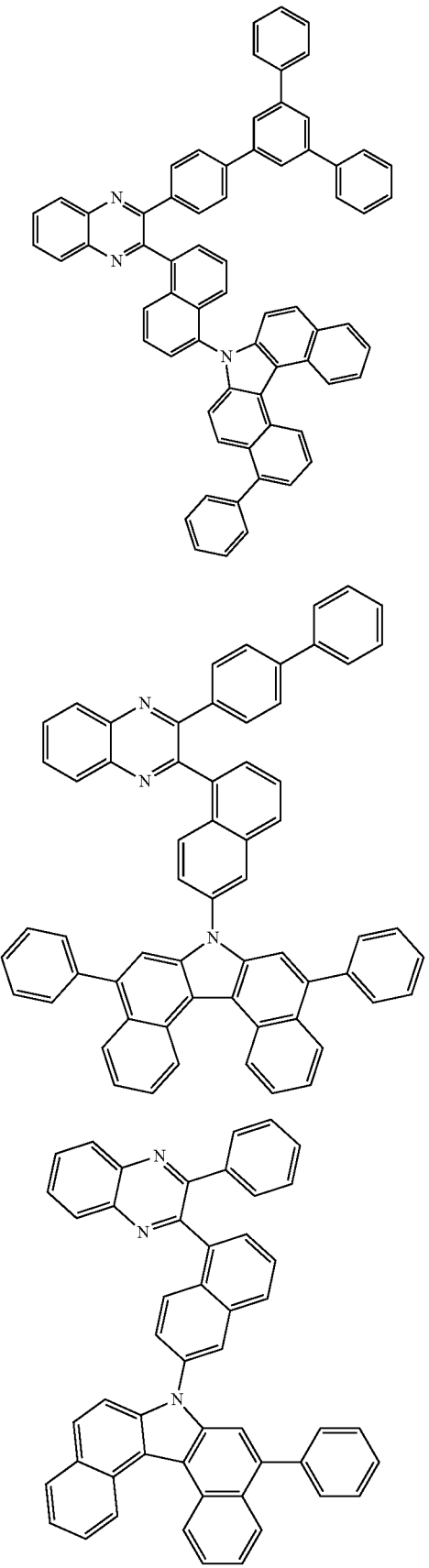
A-216
A-217
-continued
A-218
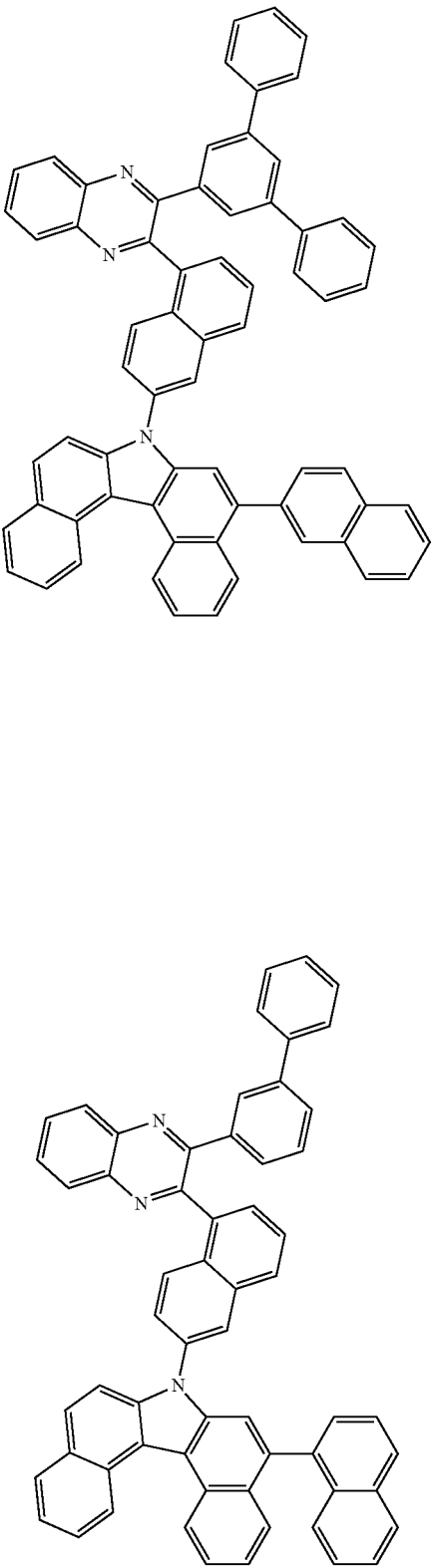
A-219

A-220
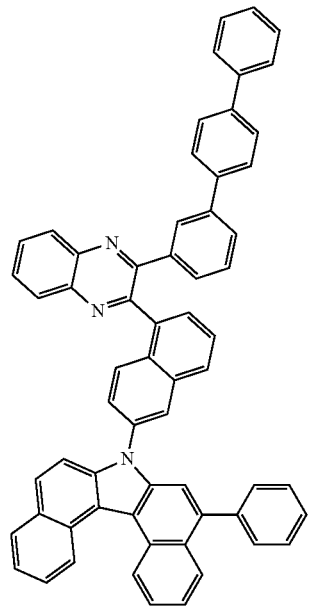
A-221
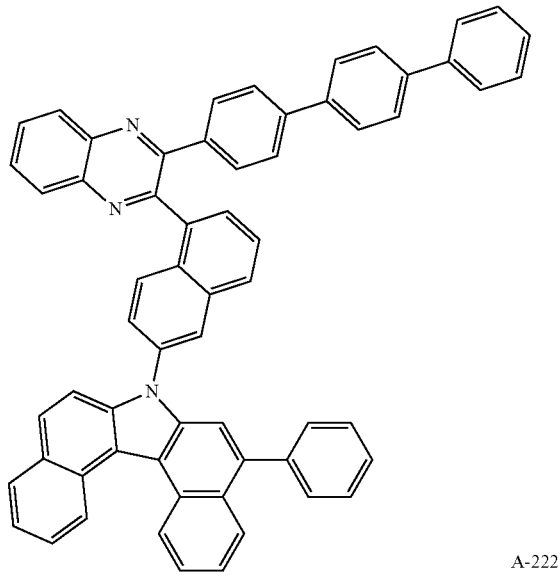
A-222
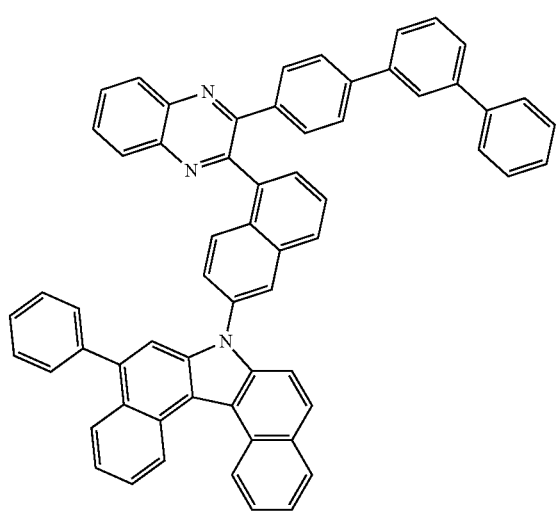
A-223
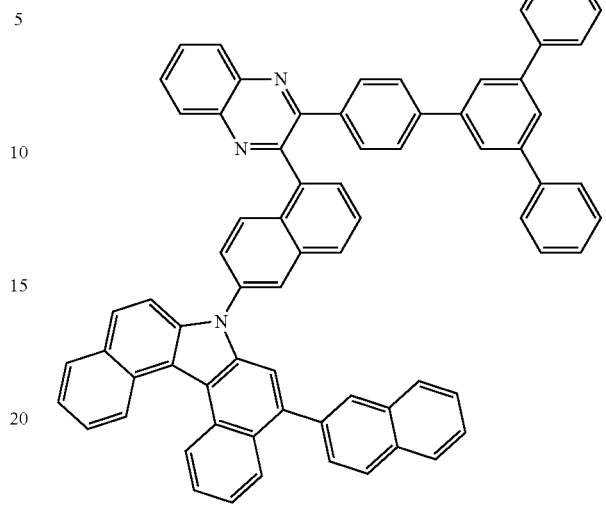
A-224
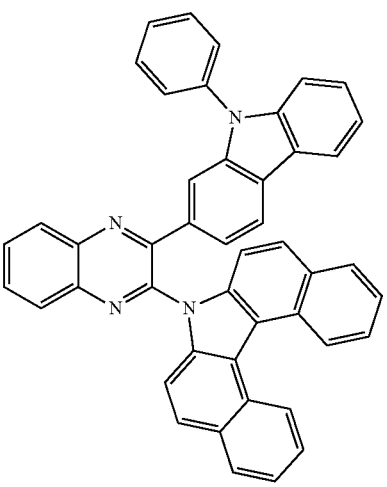
A-225
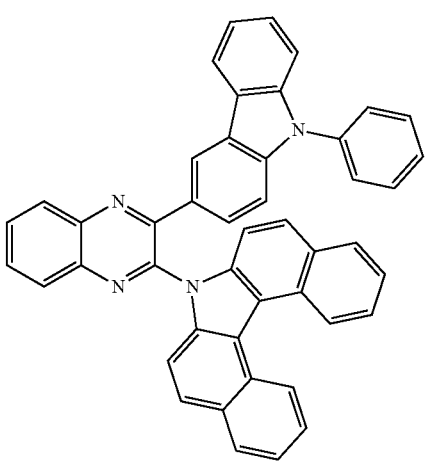

A-226
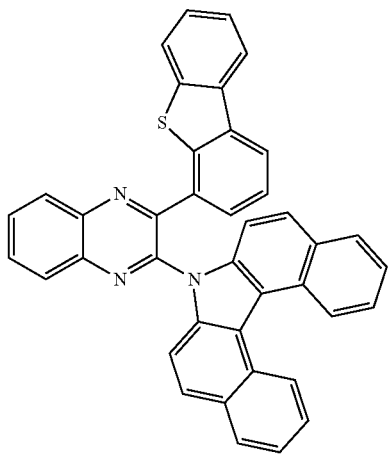
A-227
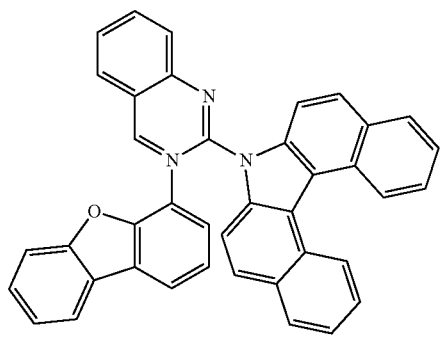
A-228
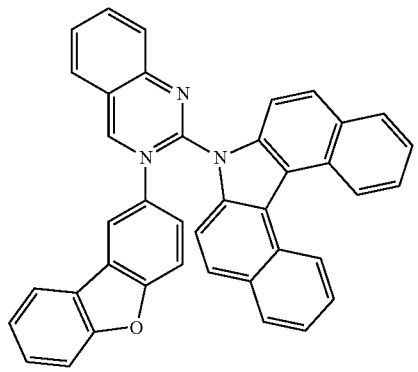
A-229
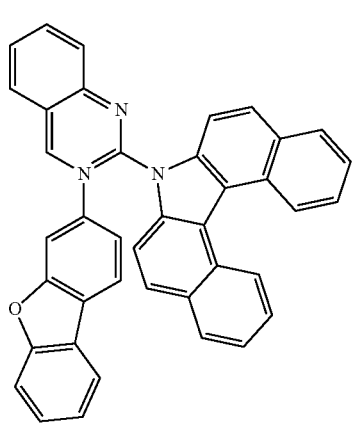
A-230
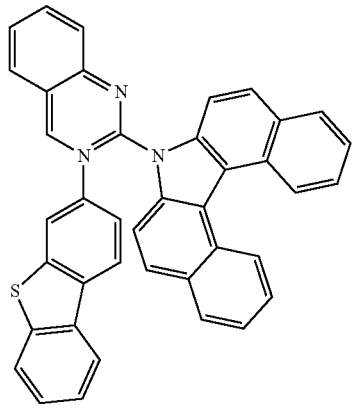
A-231
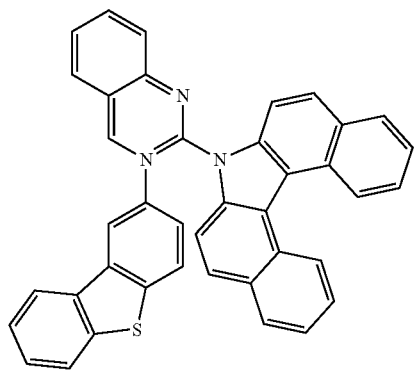
A-232
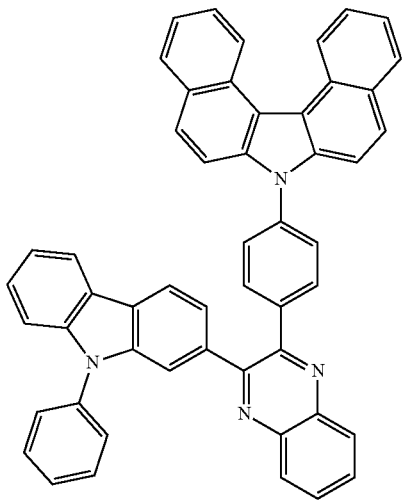

A-233
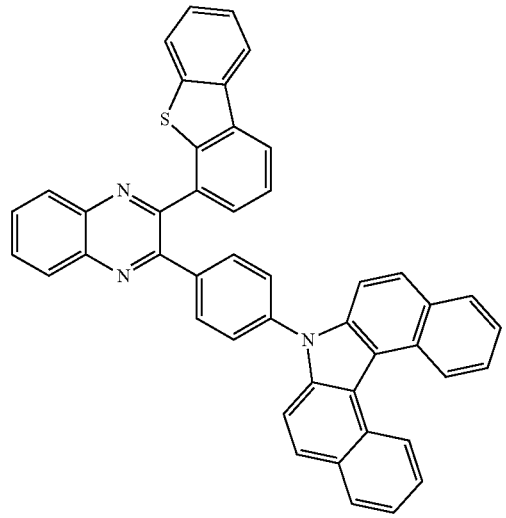
A-234
A-235
A-236
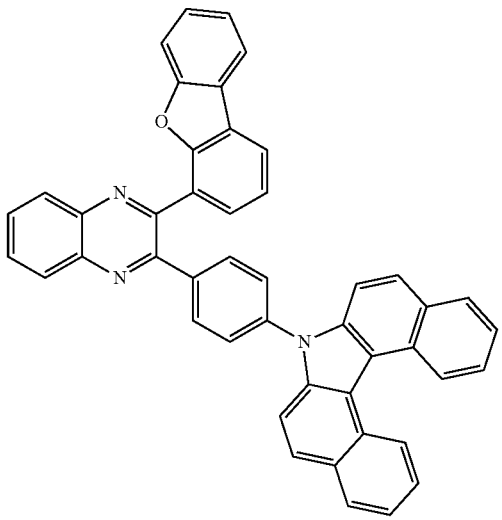
A-237
A-238
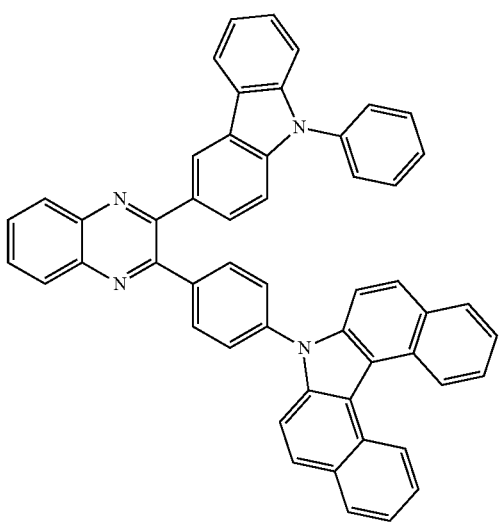
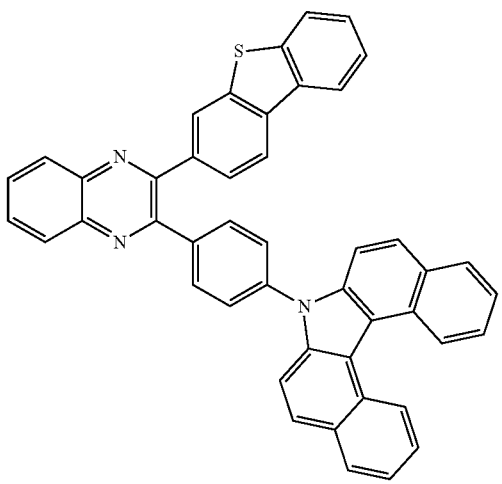

A-239
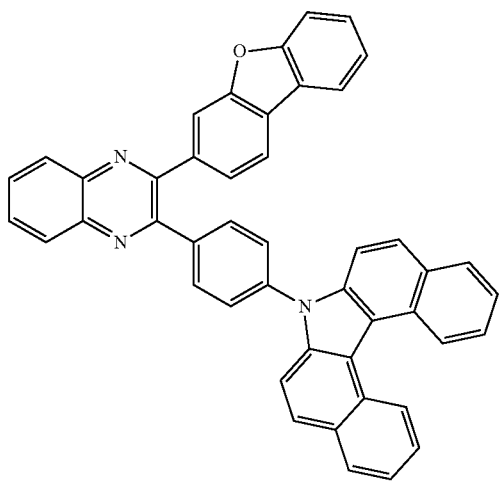
A-240
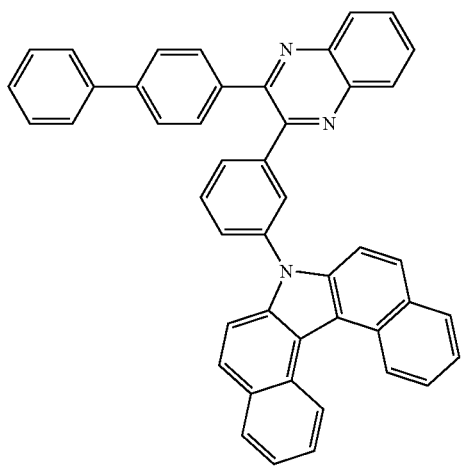
A-241
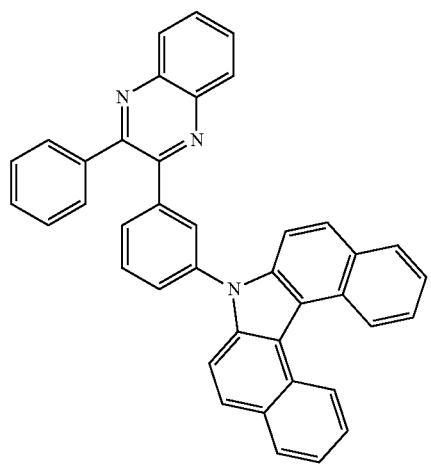
A-242
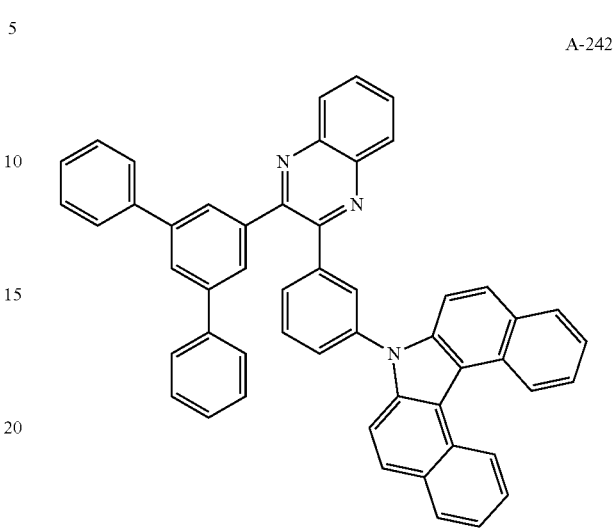
A-243
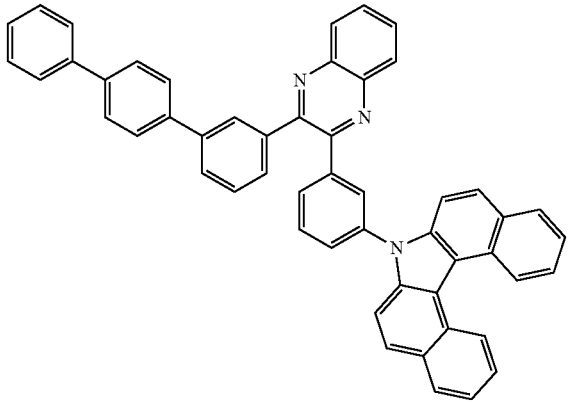
A-244

-continued
A-245
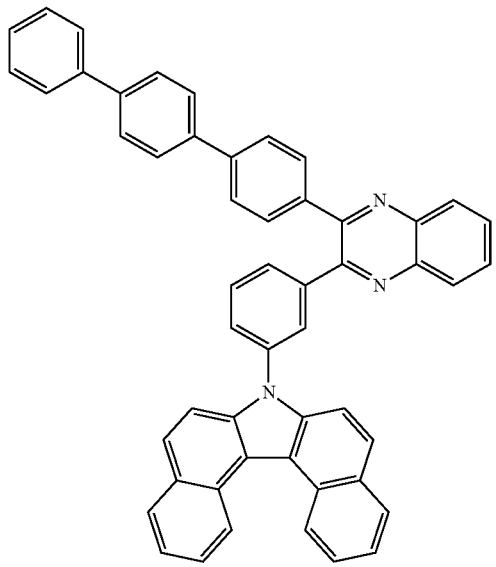
A-246
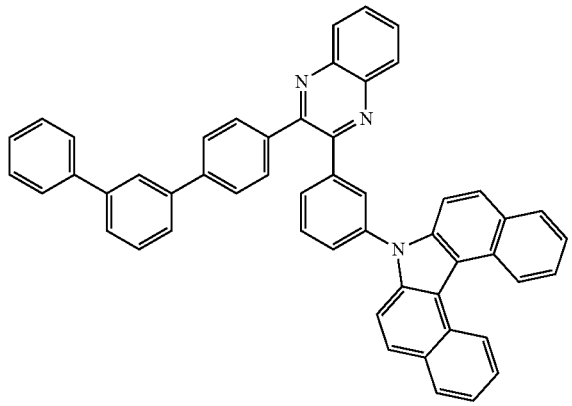
A-247
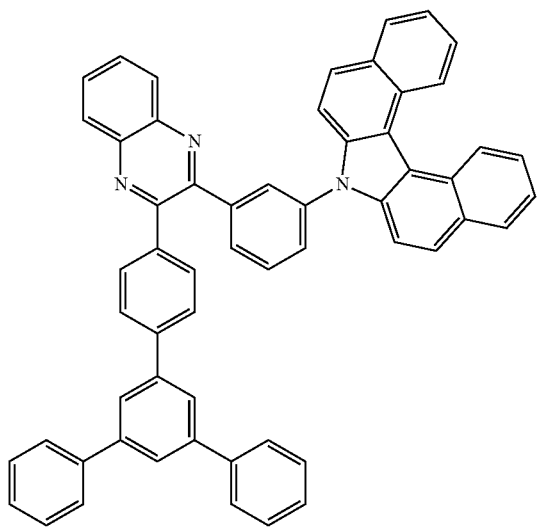
-continued
A-248
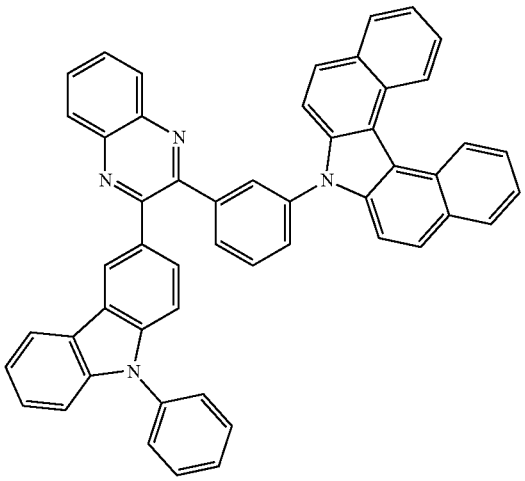
A-249
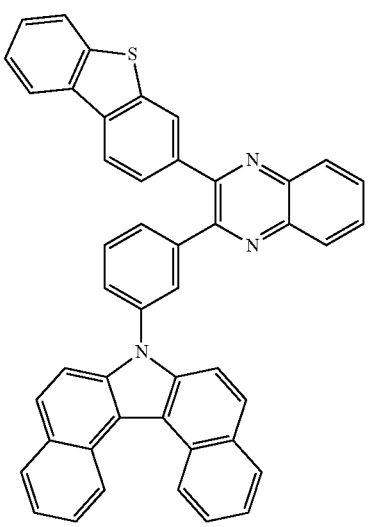
A-250
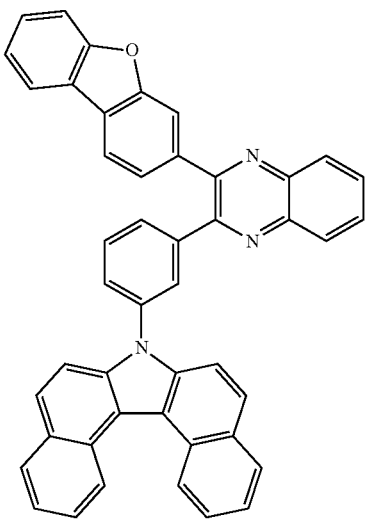

A-251
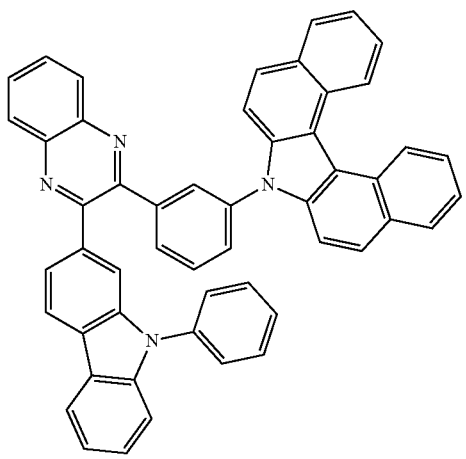
A-254
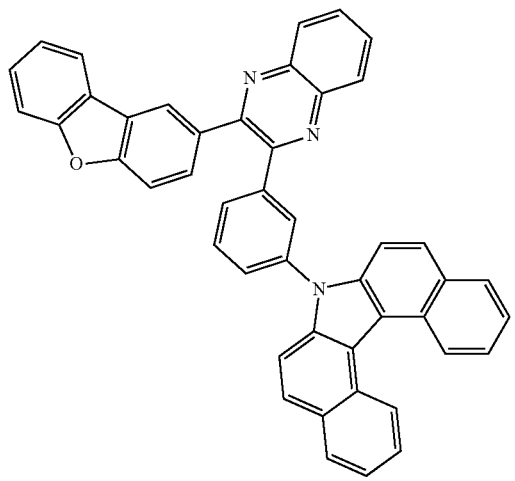
A-252
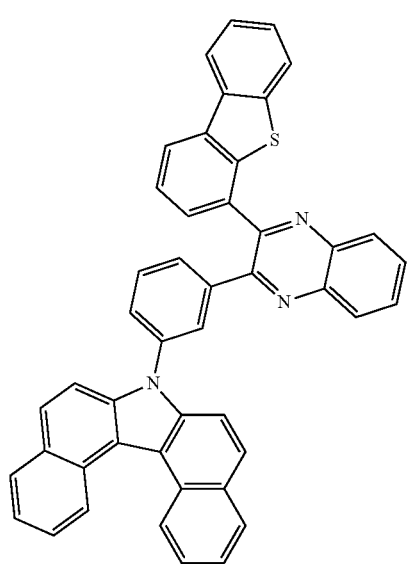
A-255
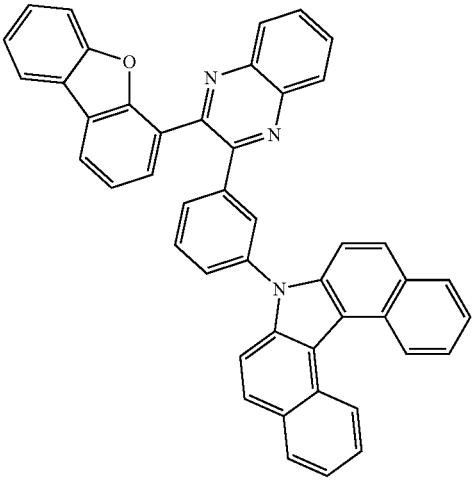
A-253
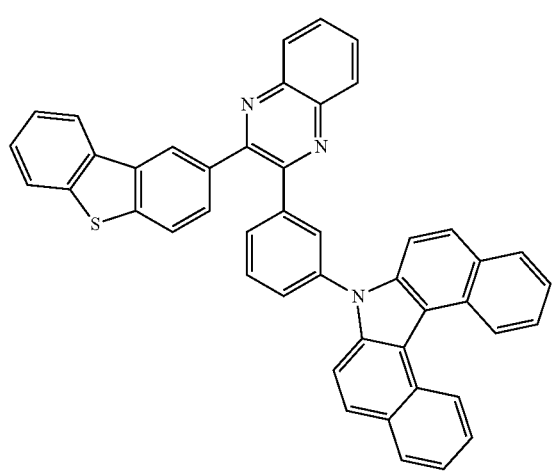
A-256
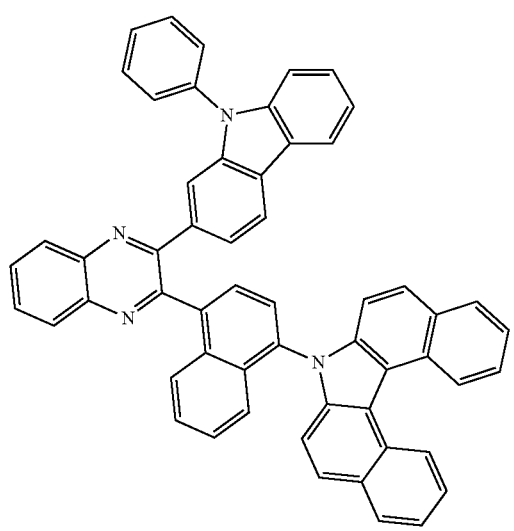

-continued
A-257
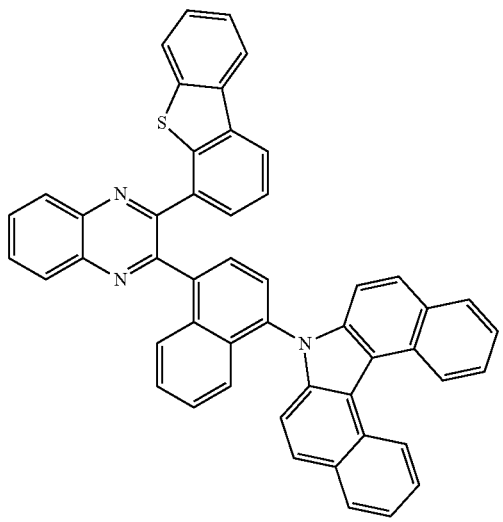
A-258
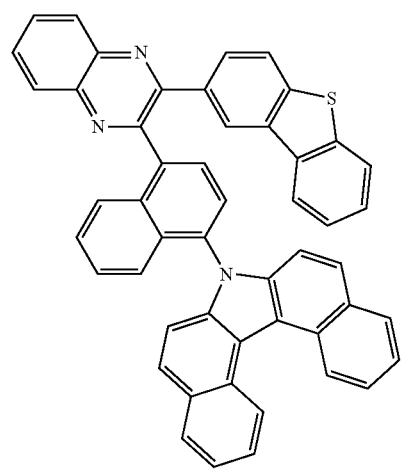
A-259
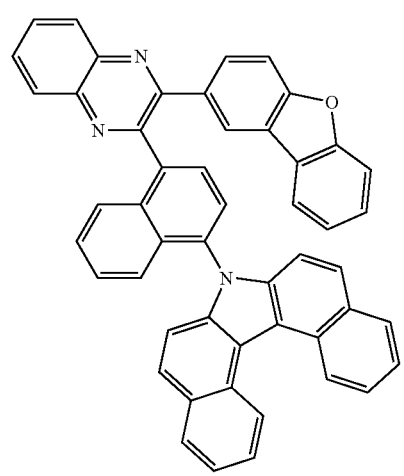
-continued
A-260
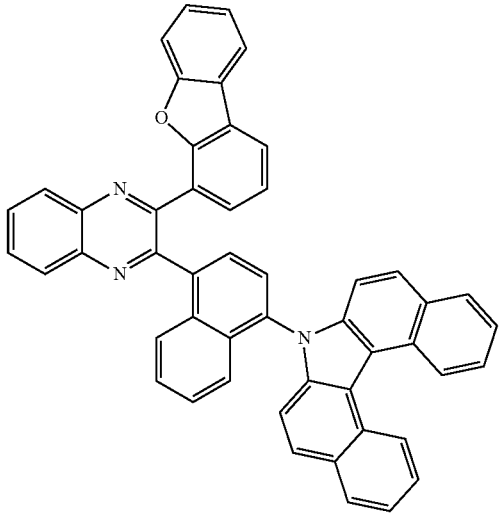
A-261
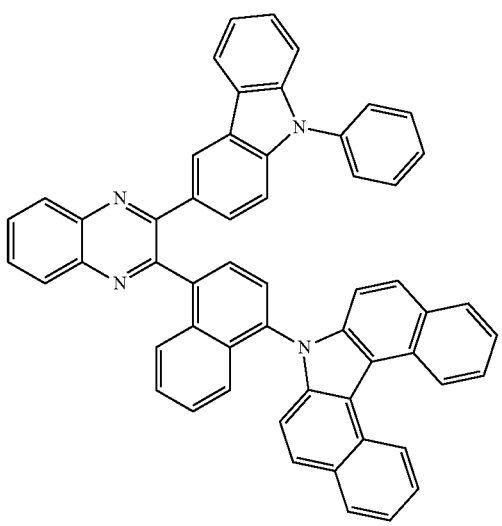
A-262
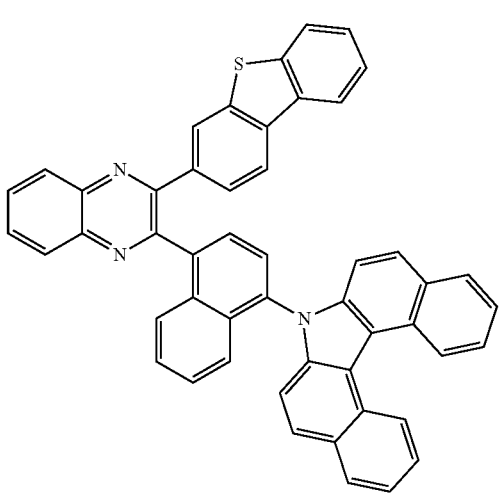

-continued
A-263
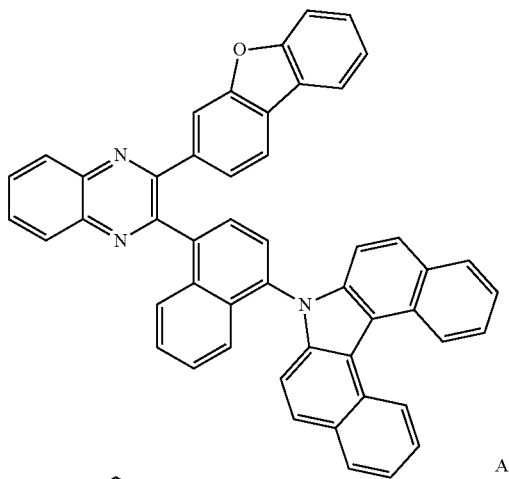
A-264
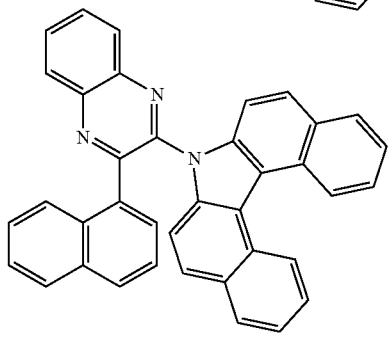
A-265
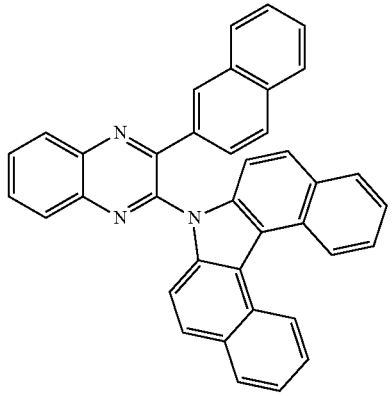
A-266
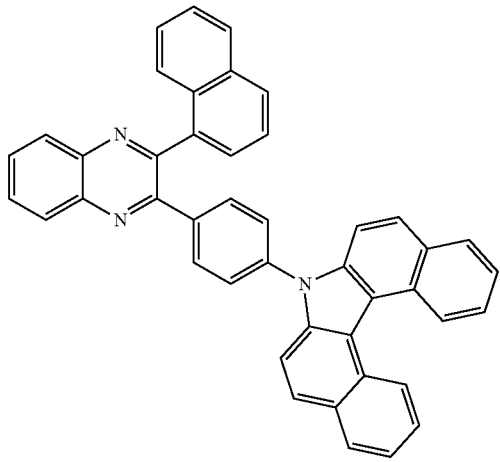
-continued
A-267
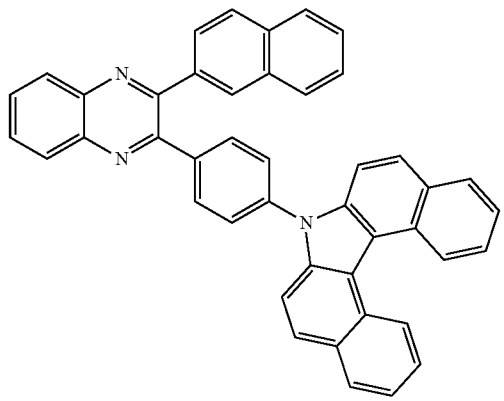
A-268
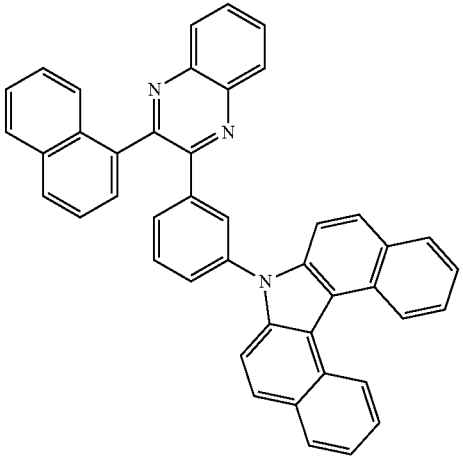
A-269
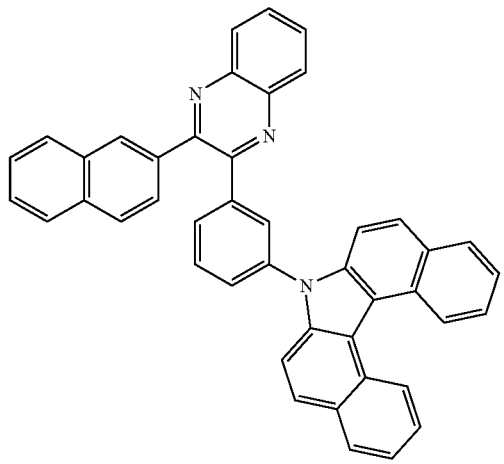

A-270
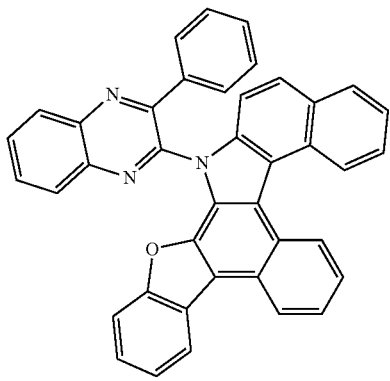
A-271
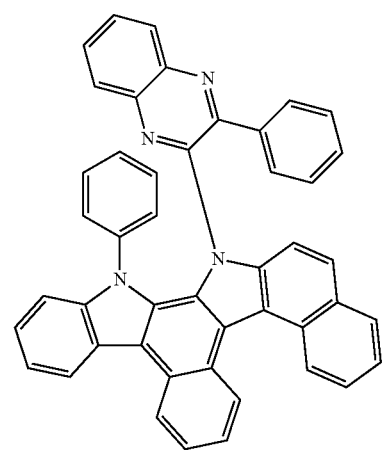
A-272
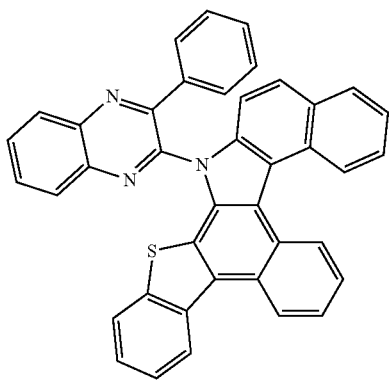
A-273
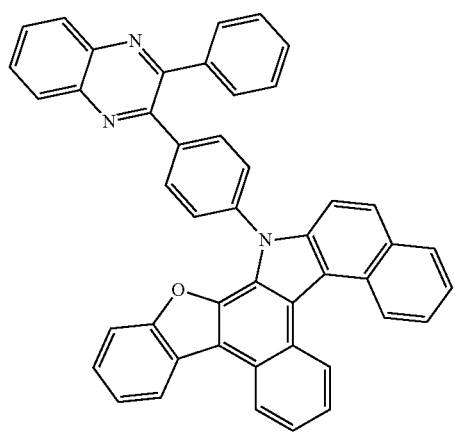
A-274
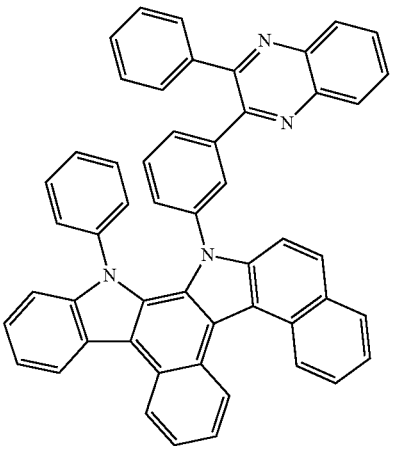
A-275
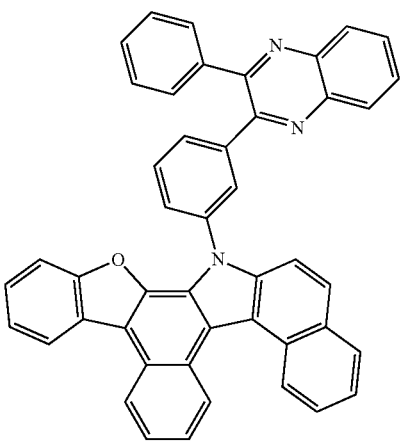
A-276
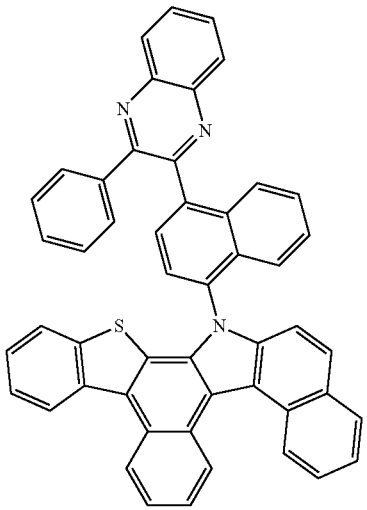

A-277
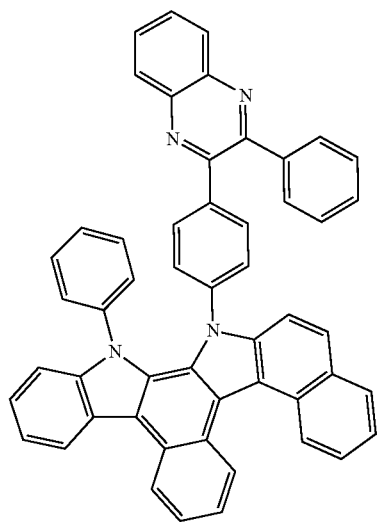
A-278
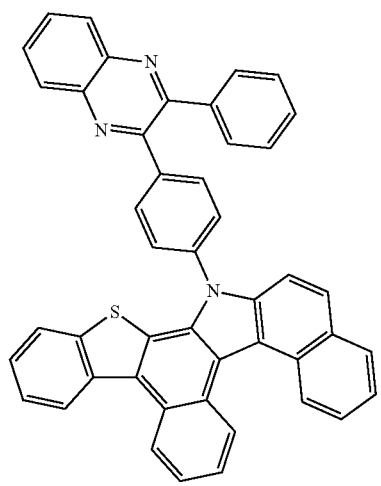
A-279
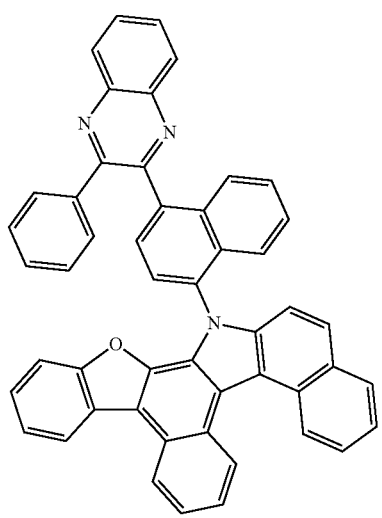
A-280
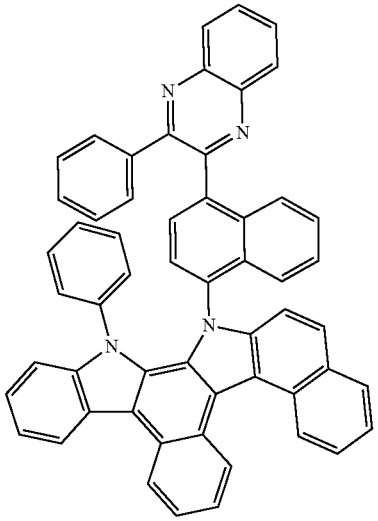
A-281
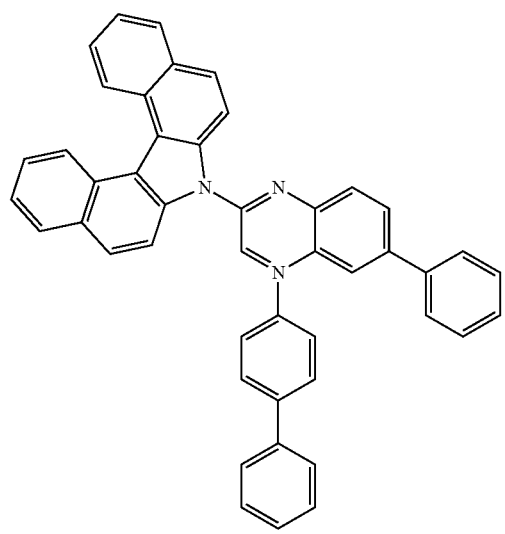
A-282
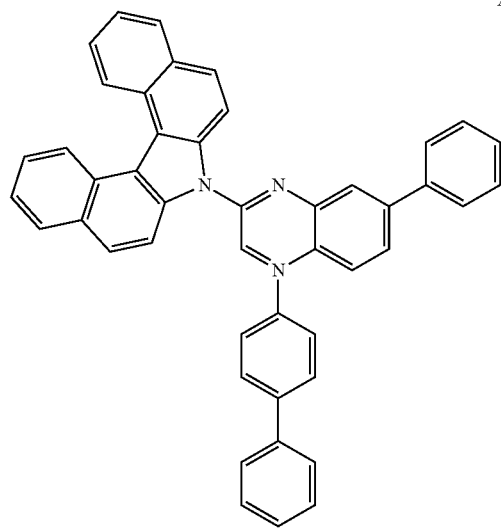

A-283
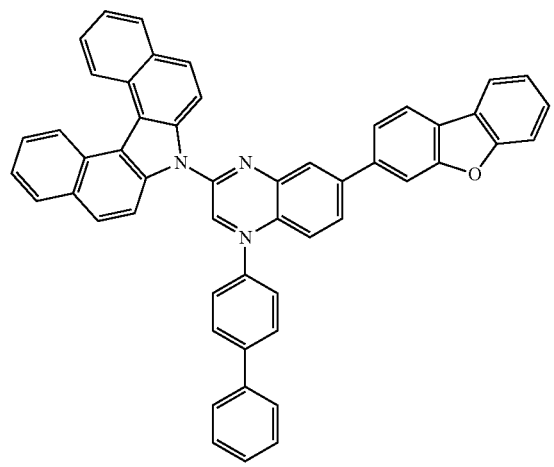
A-284
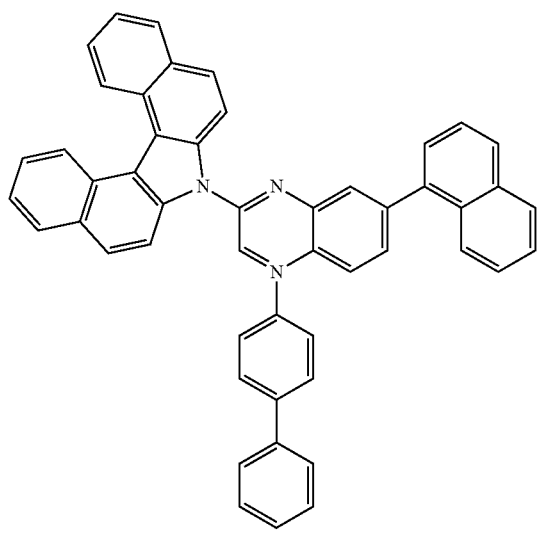
A-285
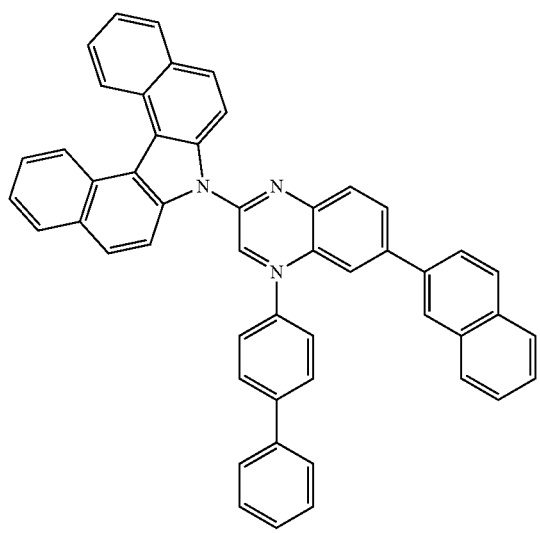
A-286
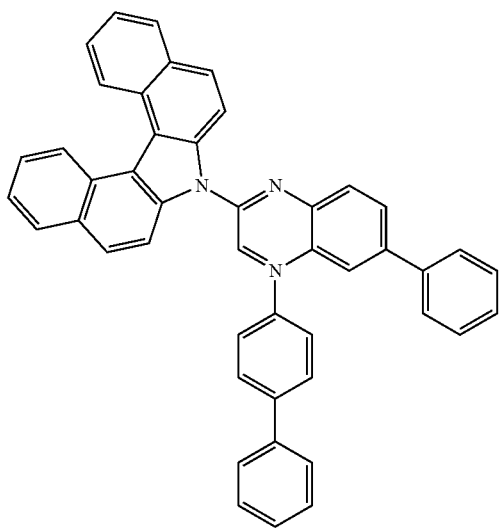
A-287
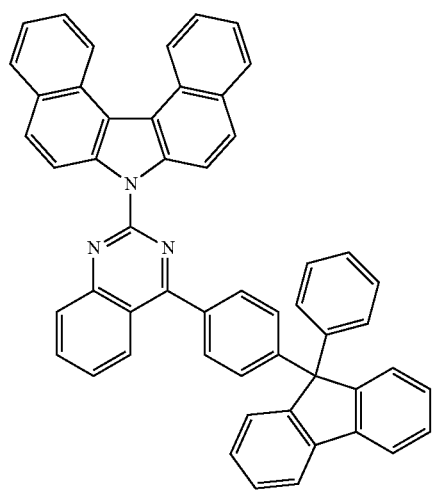
A-288
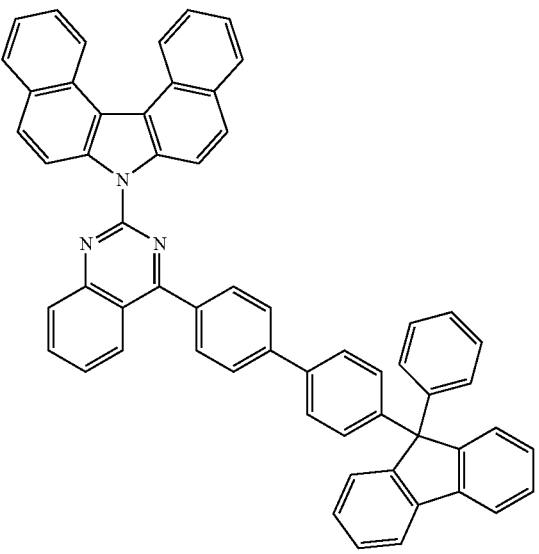

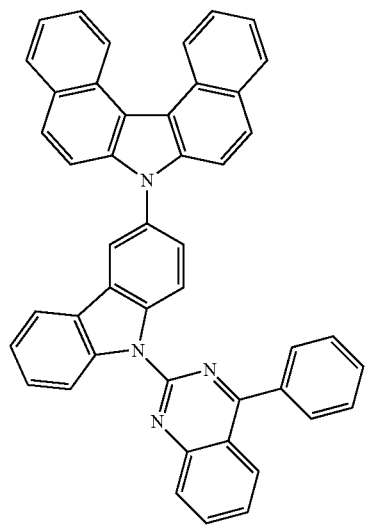
A-289
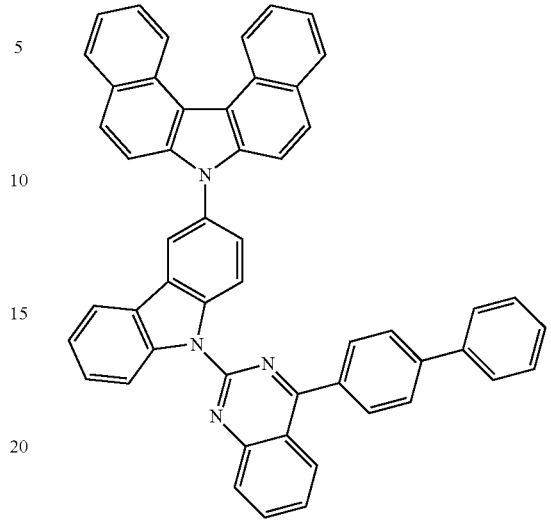
A-292
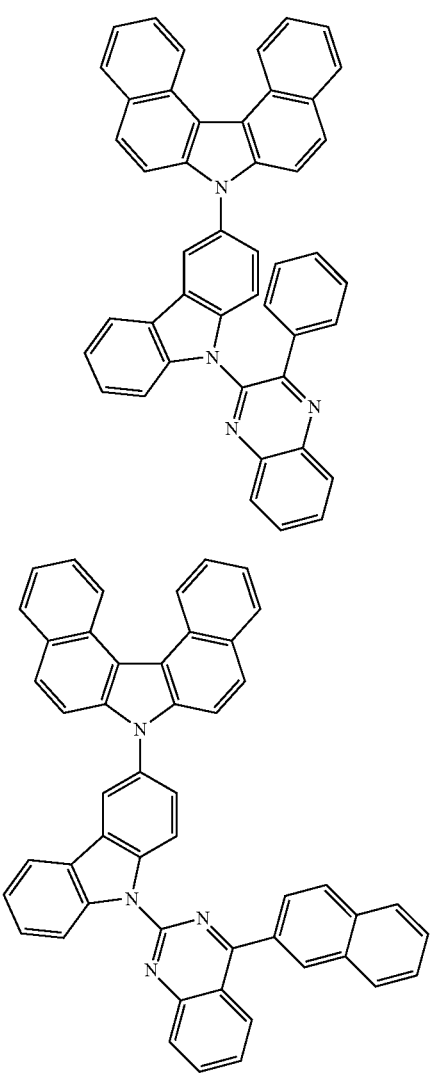
A-290
A-291
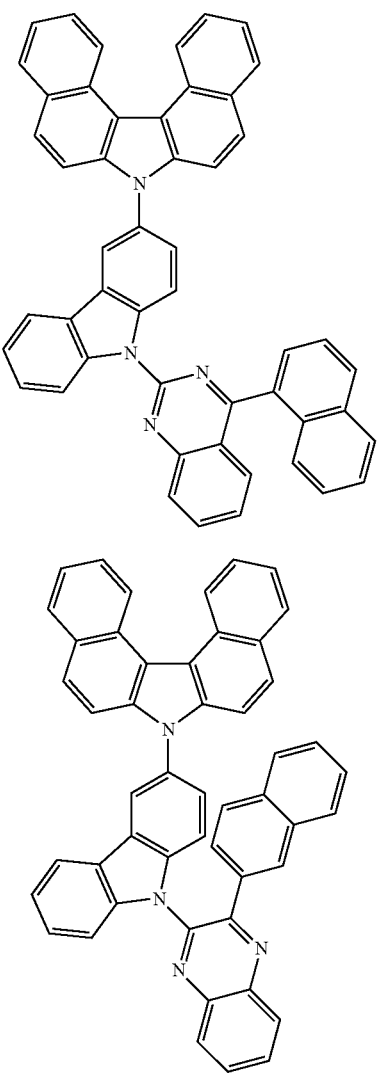
A-293
A-294

A-295
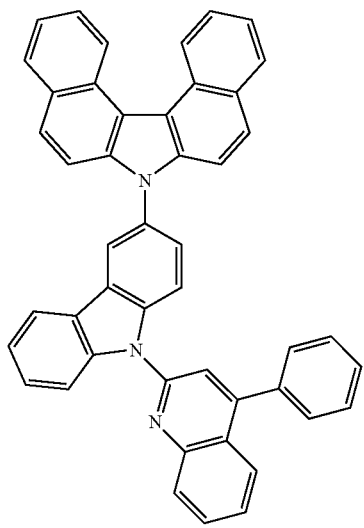
A-296
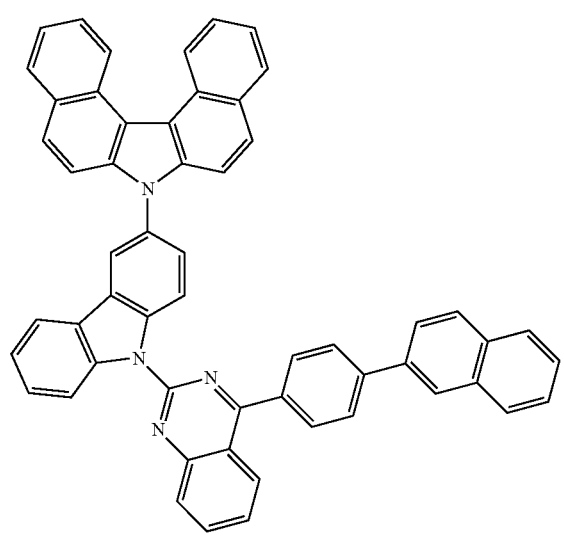
A-297
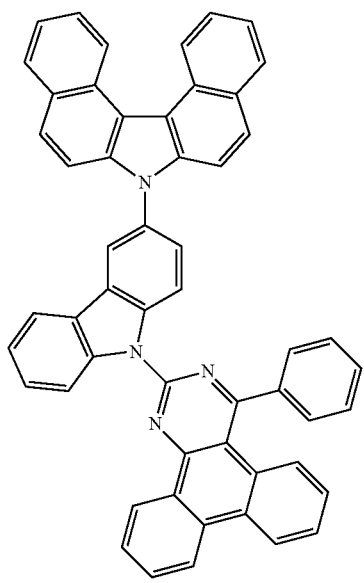
A-298
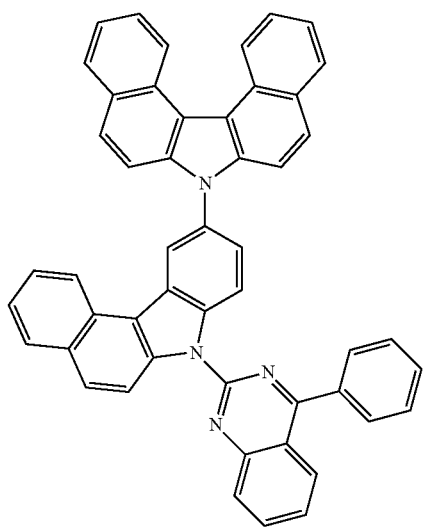
A-299
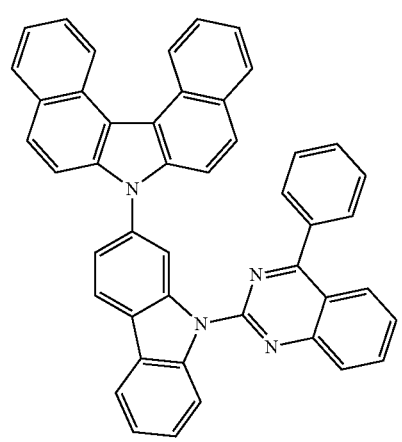
A-300
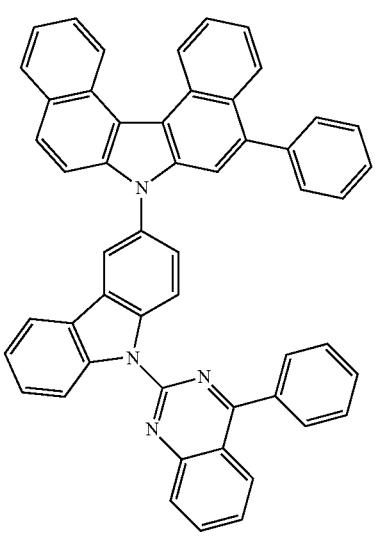

A-301
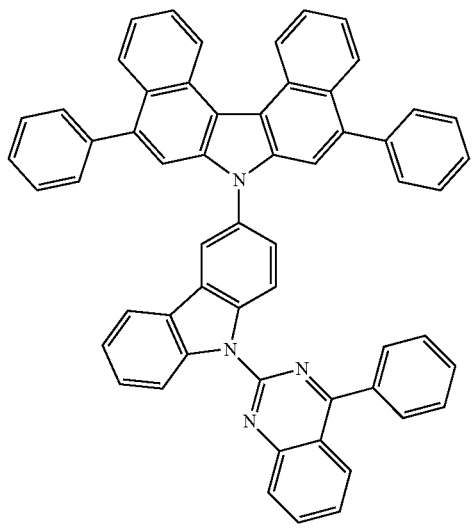
A-302
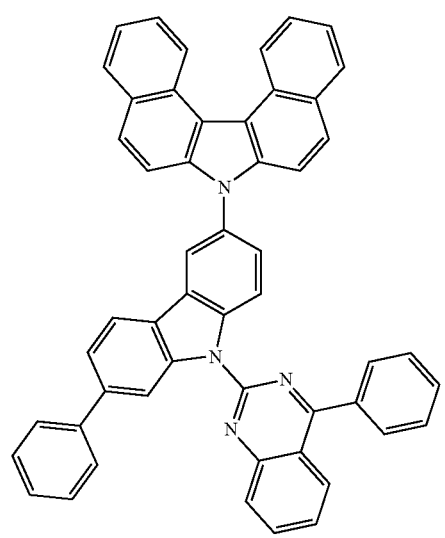
A-303
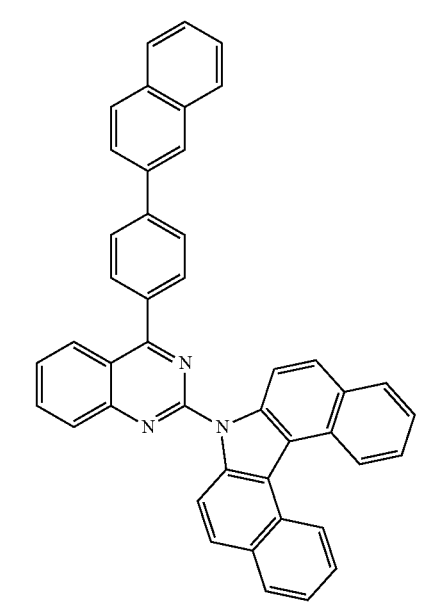
A-304
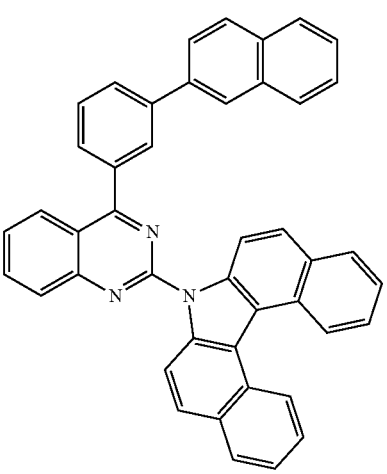
A-305
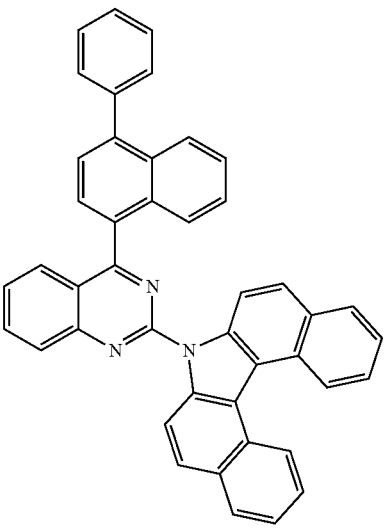
A-306
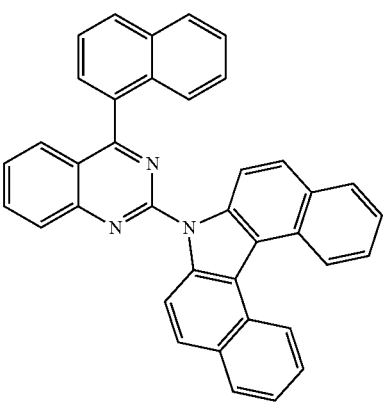

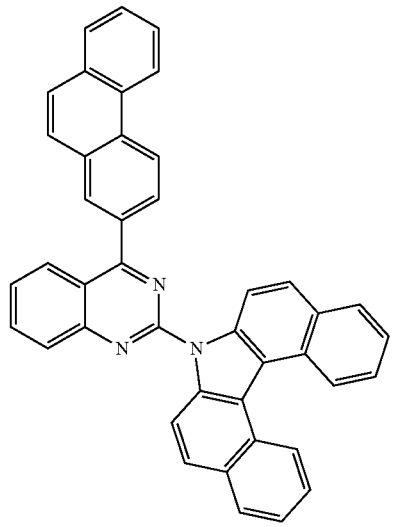
A-307
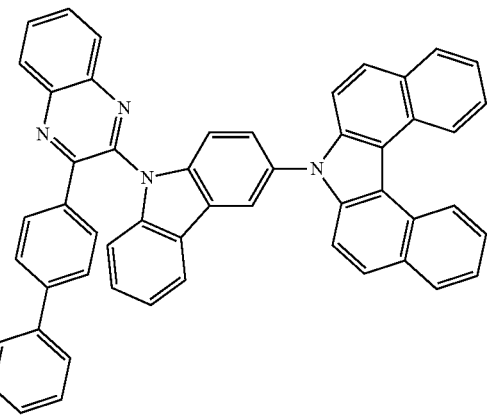
A-310
The organic electroluminescent compounds of the present invention can be prepared by a synthetic method known to a person skilled in the art. For example, they can be prepared according to the following reaction scheme.
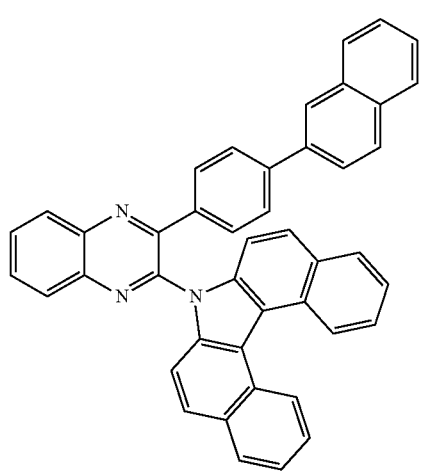
A-308
[Reaction Scheme 1]
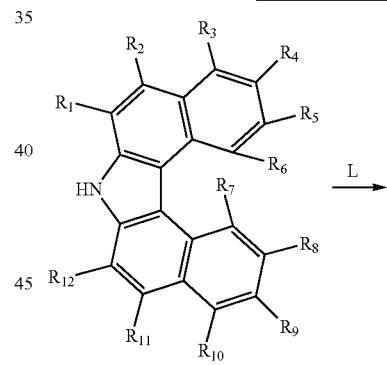
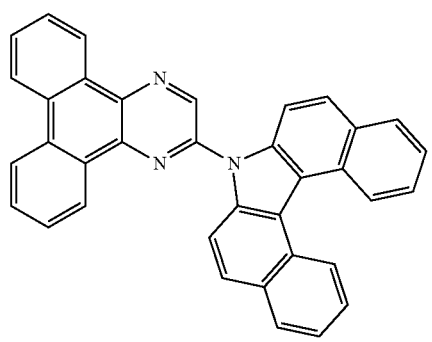
A-309
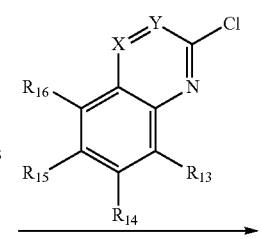

-continued

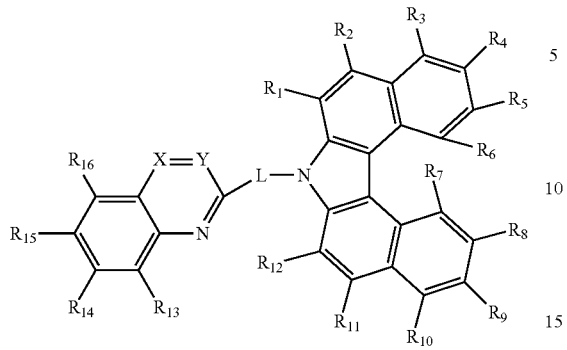

wherein L, X, Y, and $R_1$ to $R_{16}$ are as defined in formula 1.

The present invention provides an organic electroluminescent material comprising the organic electroluminescent compound of formula 1, and an organic electroluminescent device comprising the material.

The above material can be comprised of the organic electroluminescent compound according to the present invention alone, or can further include conventional materials generally used in organic electroluminescent materials.

The organic electroluminescent device comprises a first electrode; a second electrode; and at least one organic layer between the first and second electrodes. The organic layer may comprise at least one organic electroluminescent compound of formula 1.

One of the first and second electrodes can be an anode, and the other can be a cathode. The organic layer comprises a light-emitting layer, and may further comprise at least one layer selected from the group consisting of a hole injection layer, a hole transport layer, an electron transport layer, an electron injection layer, an interlayer, a hole blocking layer, and an electron blocking layer.

The compound of formula 1 according to the present invention can be comprised in the light-emitting layer. Where used in the light-emitting layer, the compound of formula 1 according to the present invention can be comprised as a phosphorescent host material. Preferably, the light-emitting layer can further comprise one or more dopants. If necessary, a compound other than the compound of formula 1 according to the present invention can be additionally comprised as a second host material. Herein, the weight ratio of the first host material to the second host material is in the range of 1:99 to 99:1.

The second host material can be from any of the known phosphorescent hosts. Specifically, the phosphorescent host selected from the group consisting of the compounds of formulae 11 to 15 below is preferable in terms of luminous efficiency.

 (11)

 (12)

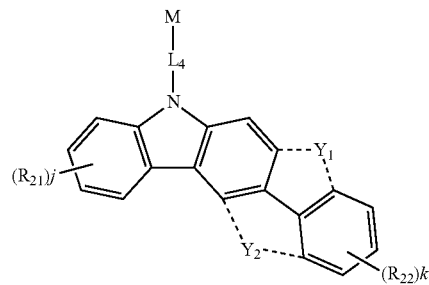 (13)

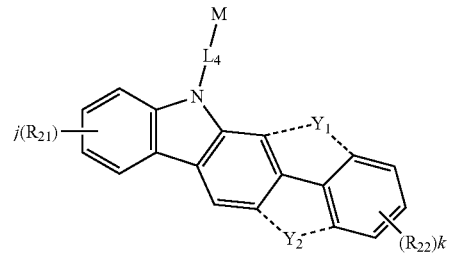 (14)

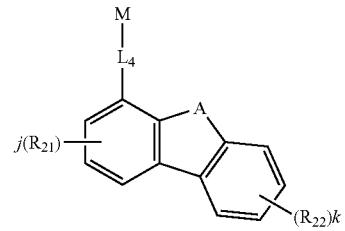 (15)

wherein Cz represents the following structure;

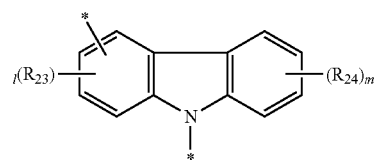

A represents —O— or —S—;

$R_{21}$ to $R_{24}$ each independently represent hydrogen, deuterium, a halogen, a substituted or unsubstituted (C1-C30) alkyl, a substituted of unsubstituted (C6-C30)aryl, a substituted or unsubstituted 5- to 30-membered heteroaryl, or —$SiR_{25}R_{26}R_{27}$;

$R_{25}$ to $R_{27}$ each independently represent a substituted or unsubstituted (C1-C30)alkyl, or a substituted or unsubstituted (C6-C30)aryl;

$L_4$ represents a single bond, a substituted or unsubstituted (C6-C30)arylene, or a substituted or unsubstituted 5- to 30-membered heteroarylene;

M represents a substituted or unsubstituted (C6-C30)aryl, or a substituted or unsubstituted 5- to 30-membered heteroaryl;

$Y_1$ and $Y_2$ each independently represent —O—, —S—, —N($R_{31}$)—, or —C($R_{32}$)($R_{33}$)—, provided that $Y_1$ and $Y_2$ do not simultaneously exist;

$R_{31}$ to $R_{33}$ each independently represent a substituted or unsubstituted (C1-C30)alkyl, a substituted or unsubstituted (C6-C30)aryl, or a substituted or unsubstituted 5- to 30-membered heteroaryl, and $R_{32}$ and $R_{33}$ may be the same or different;

h and i each independently represent an integer of 1 to 3;
j, k, l, and m each independently represent an integer of 0 to 4; and
where h, i, j, k, l, or m is an integer of 2 or more, each of (Cz-$L_4$), each of (Cz), each of $R_{21}$, each of $R_{22}$, each of $R_{23}$, or each of $R_{24}$ may be the same or different.
Specifically, preferable examples of the second host material are as follows:
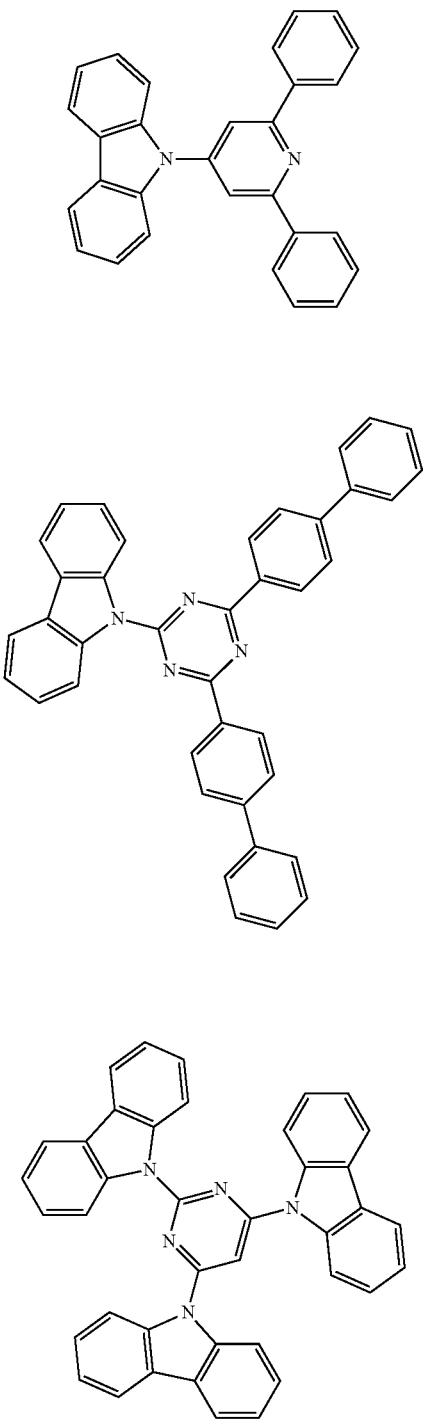
-continued
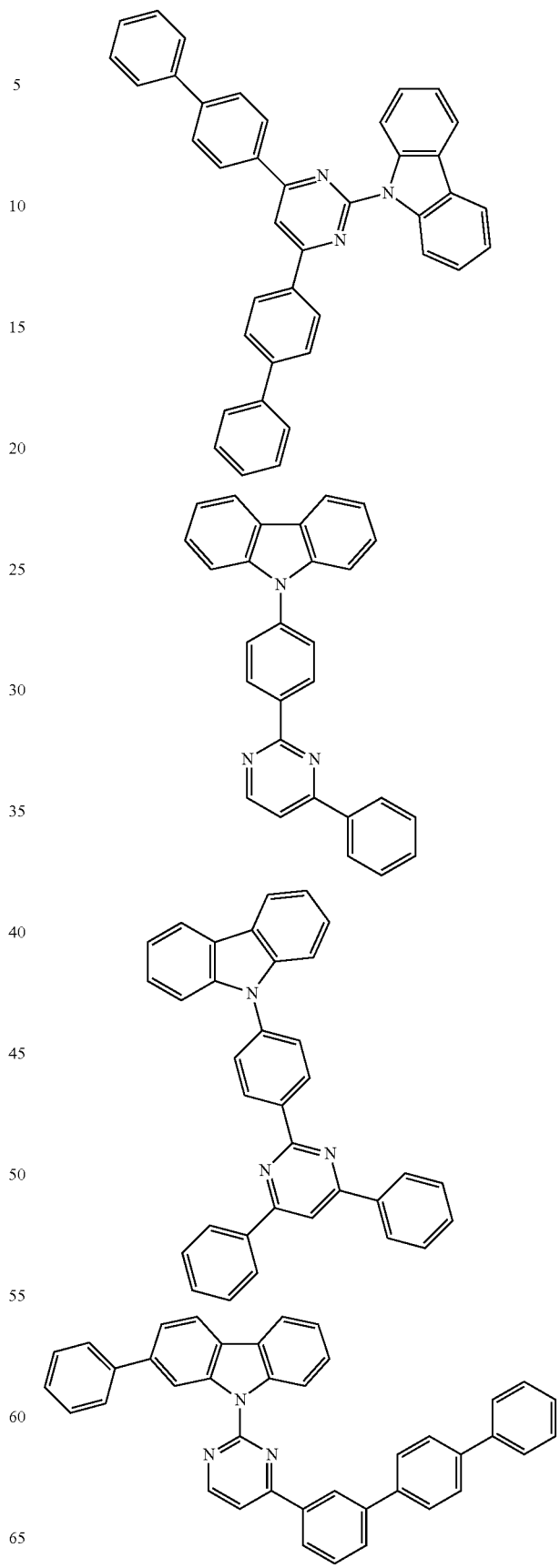

123
-continued
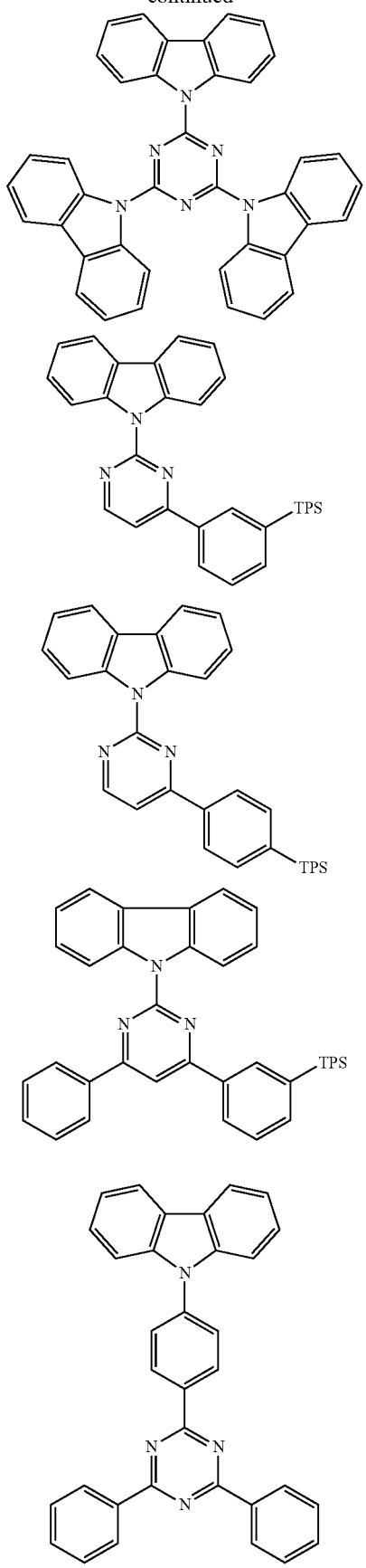
124
-continued
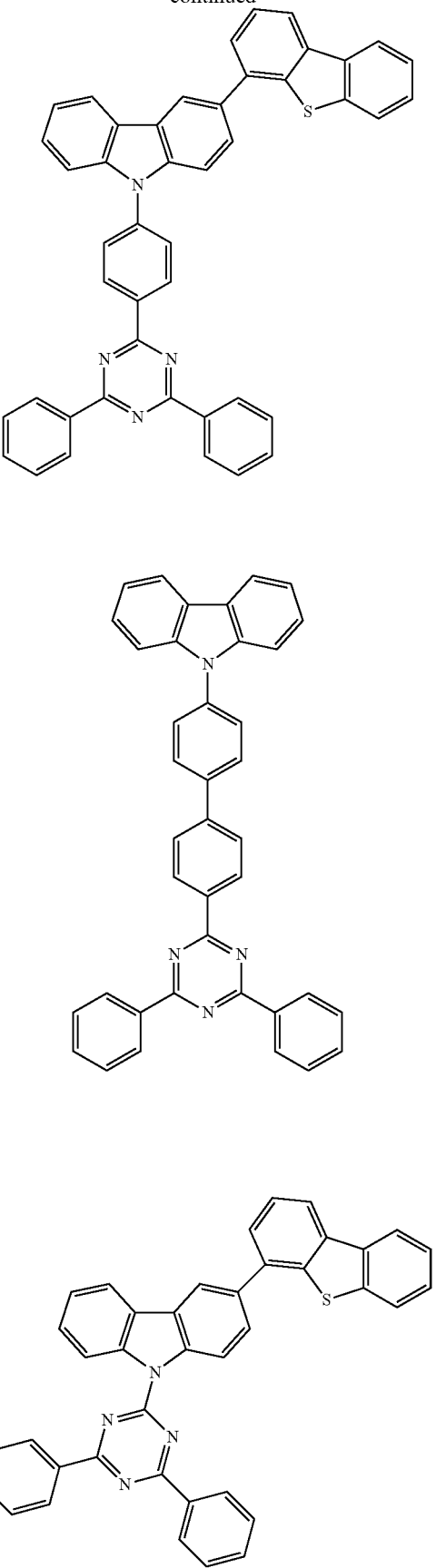

125
-continued
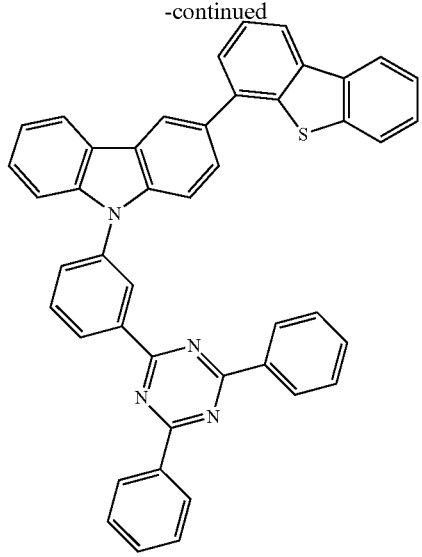
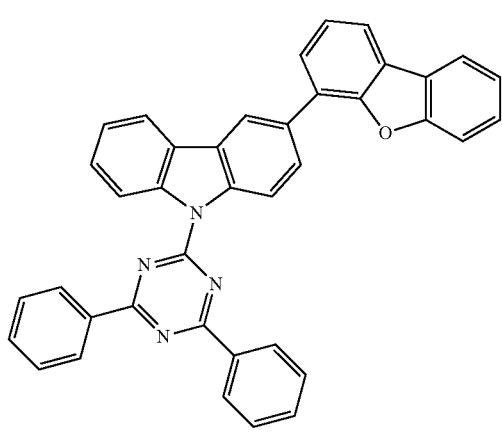
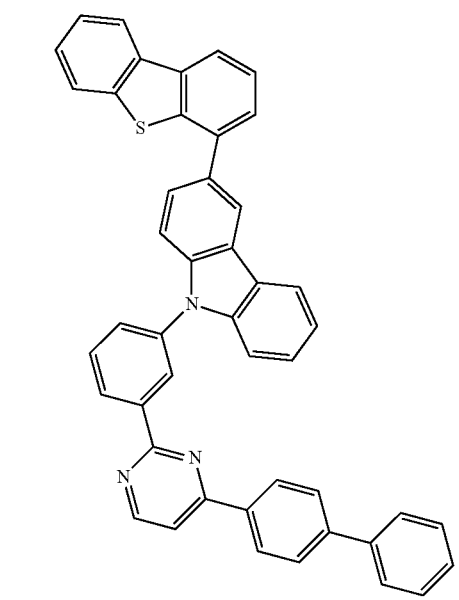
126
-continued
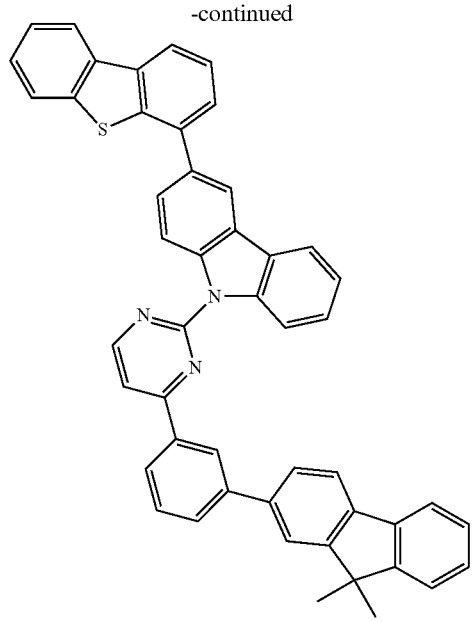
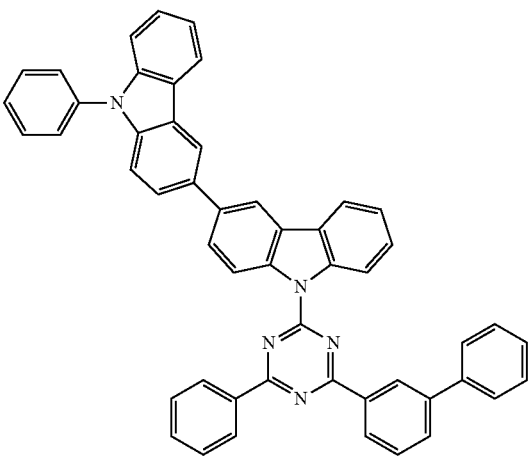
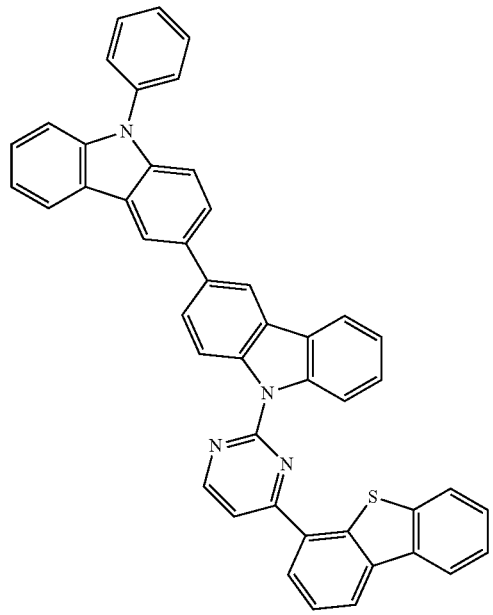

127
-continued
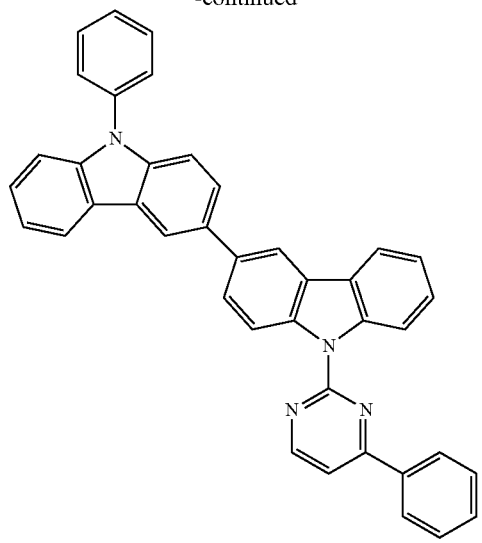
128
-continued
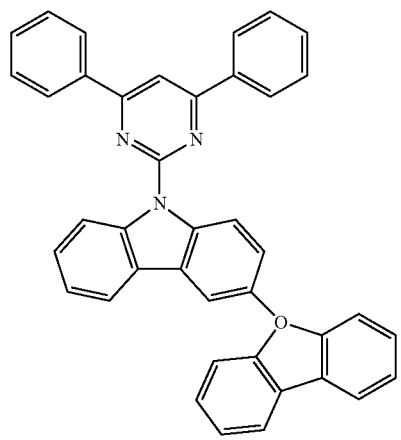
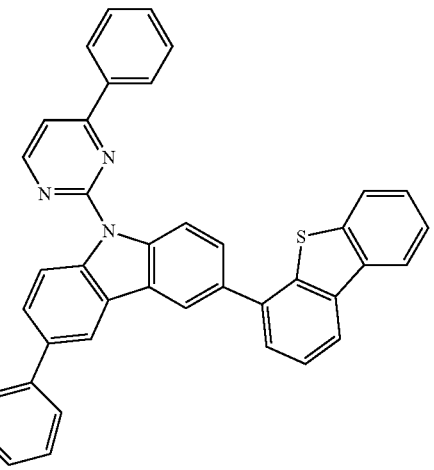
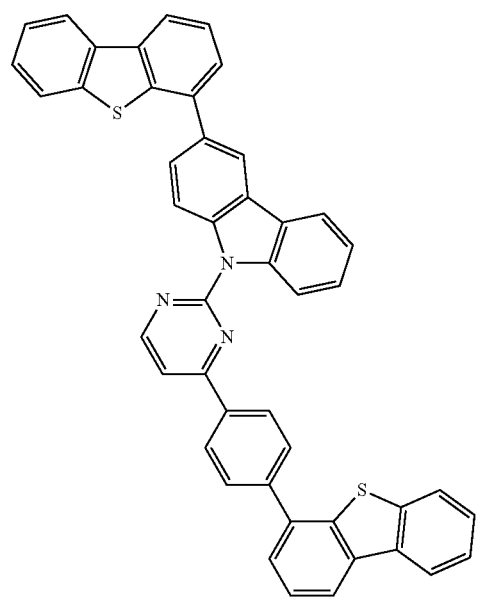
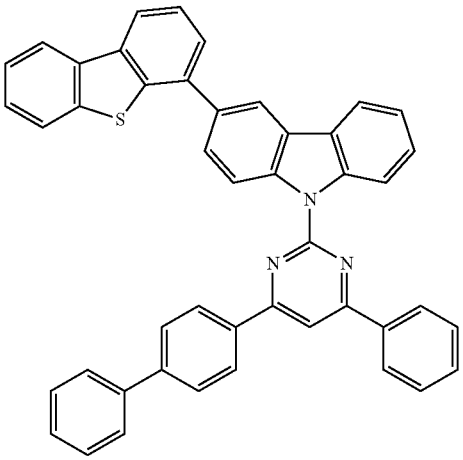

129
-continued
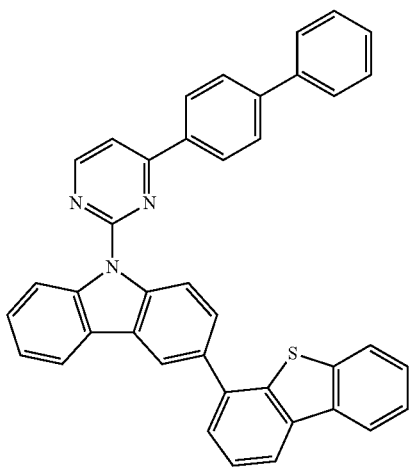
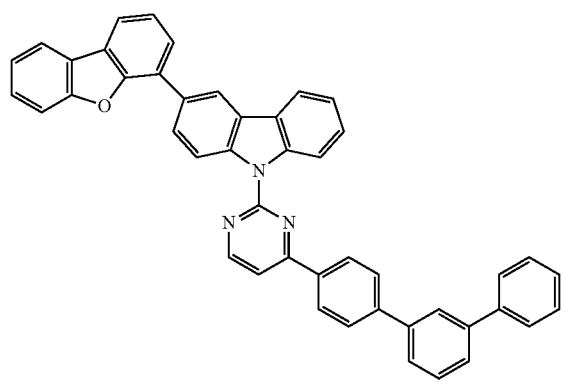
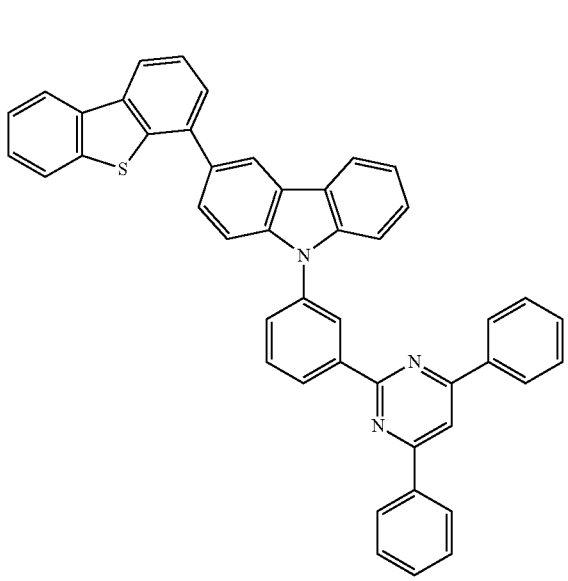
130
-continued
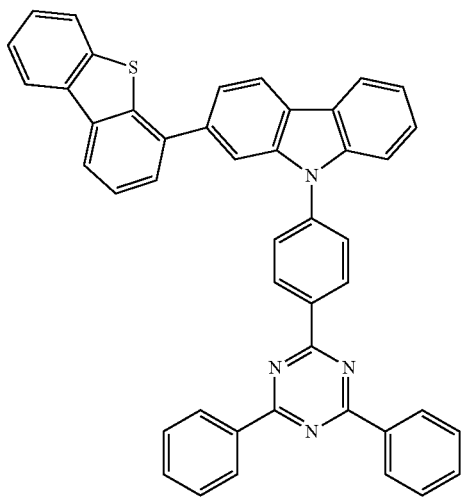
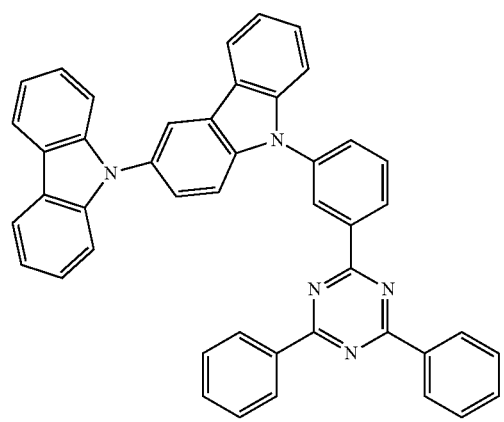
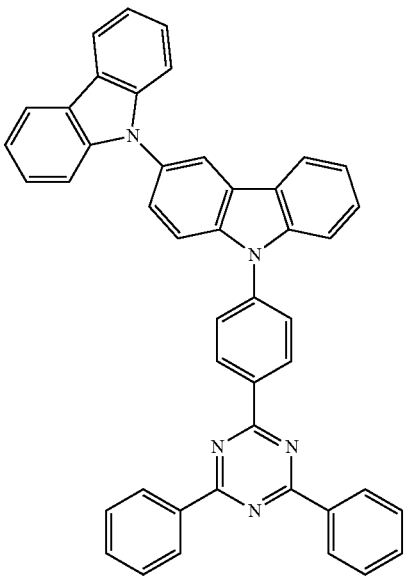

131
-continued
132
-continued
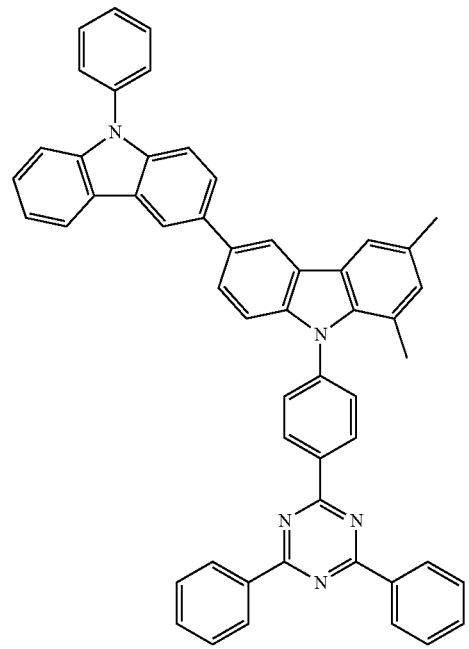
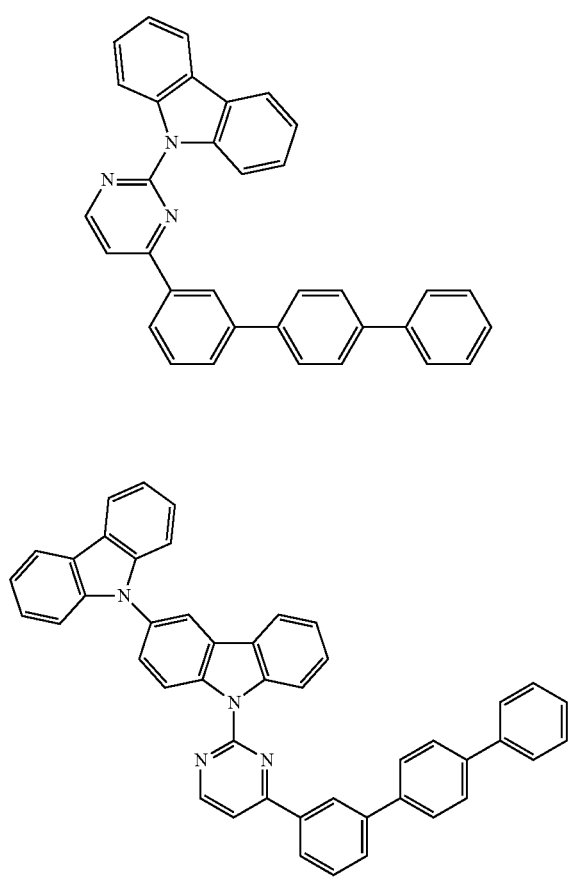
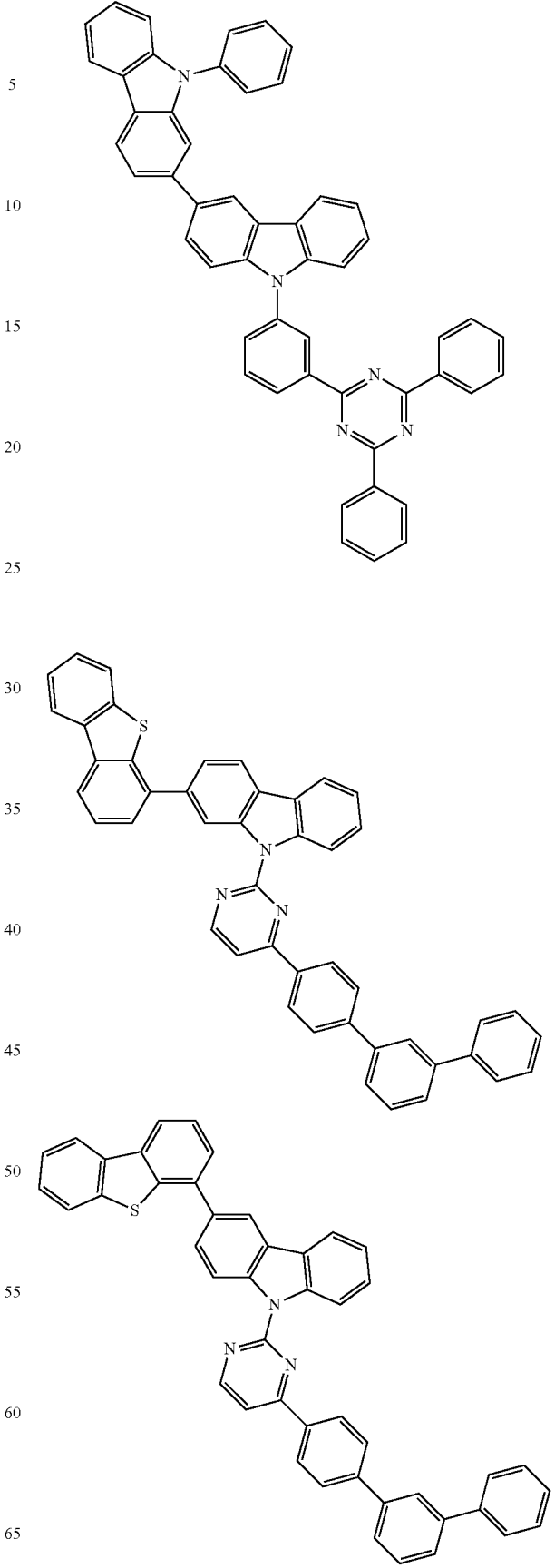

133
-continued
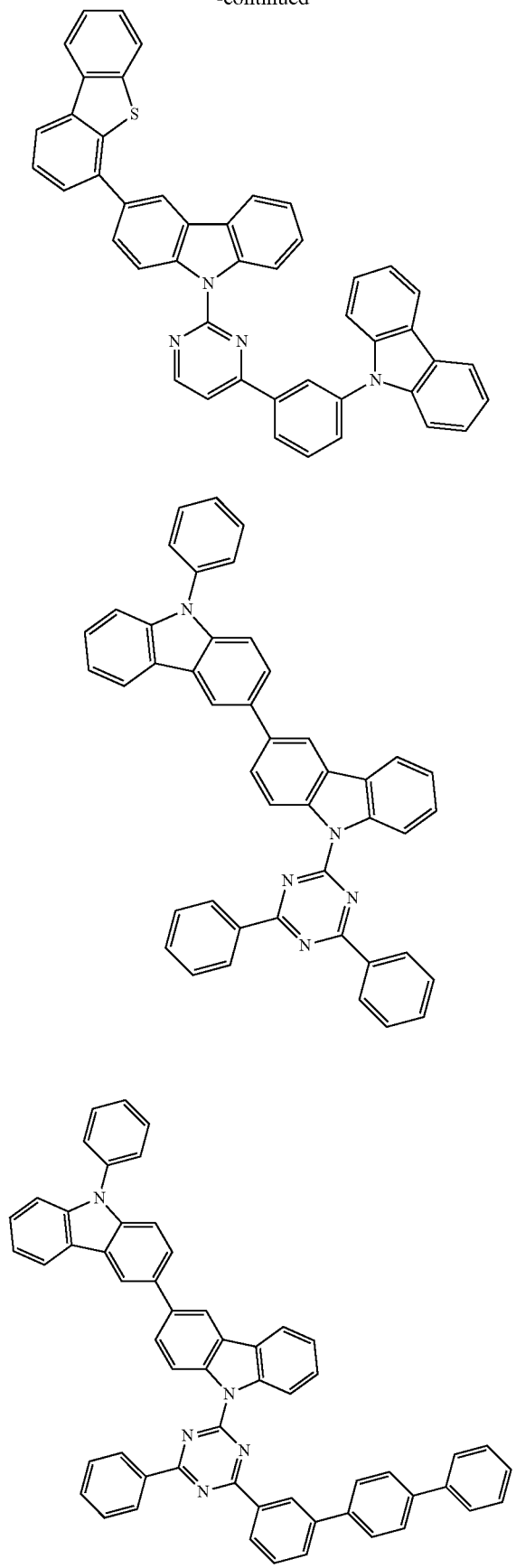
134
-continued
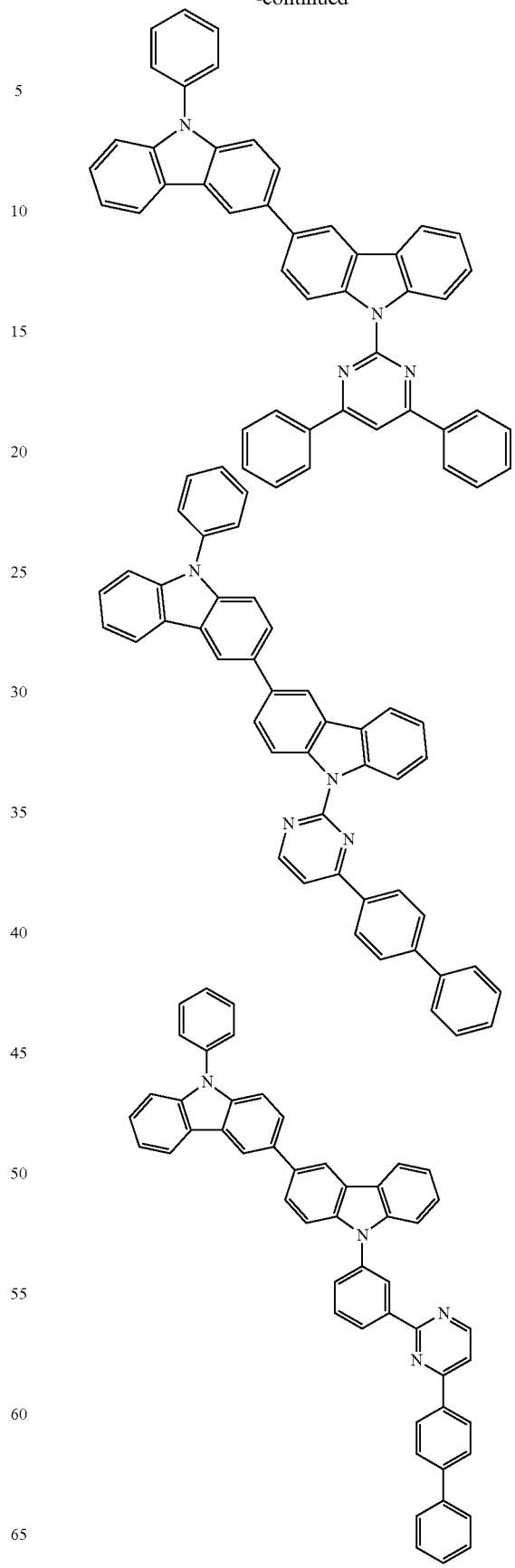

135
-continued
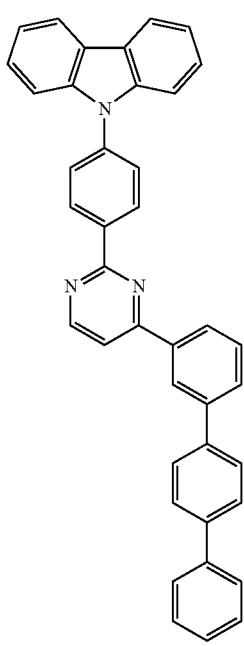
136
-continued
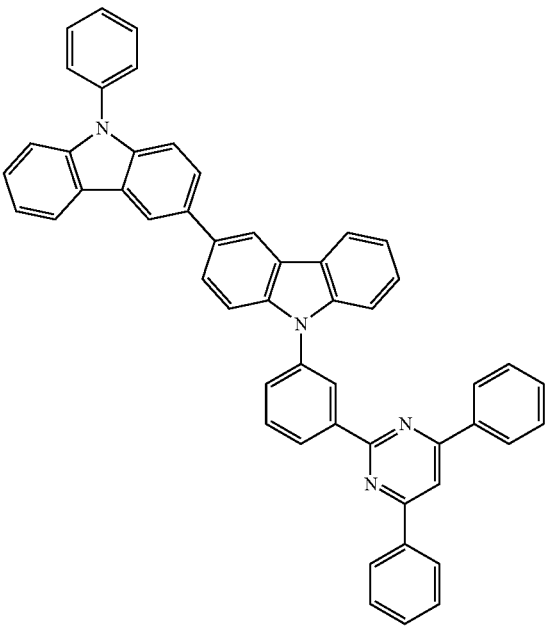
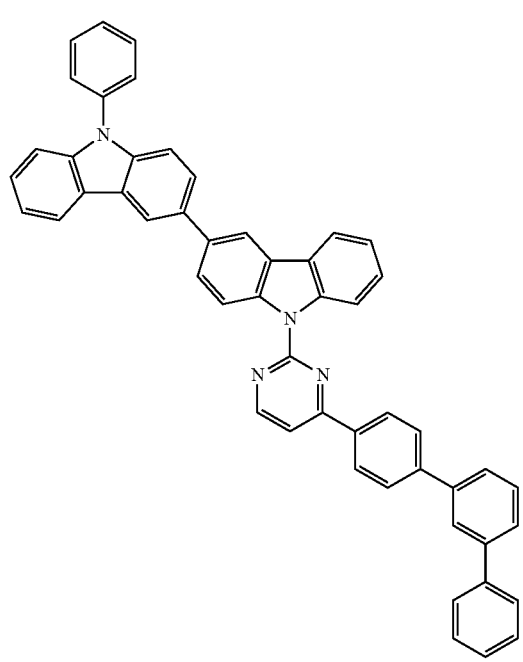
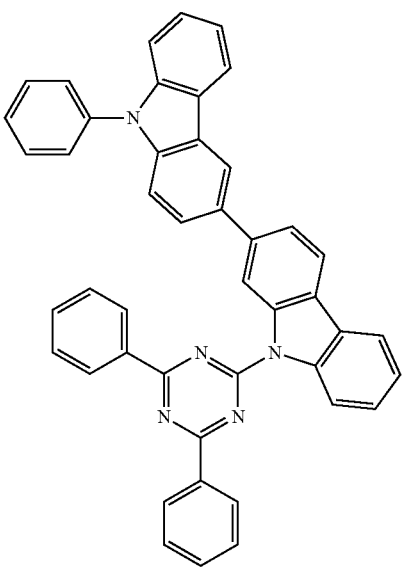

137
-continued
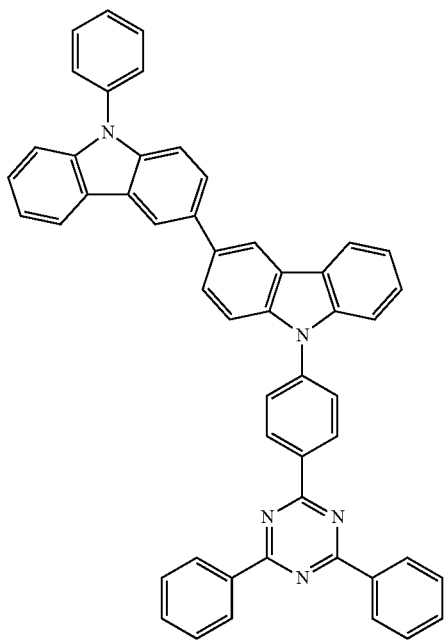
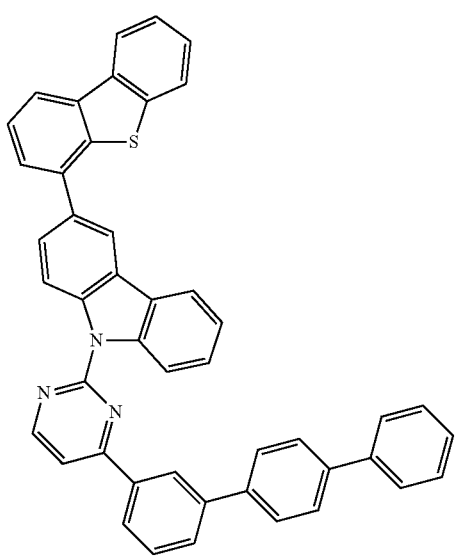
138
-continued
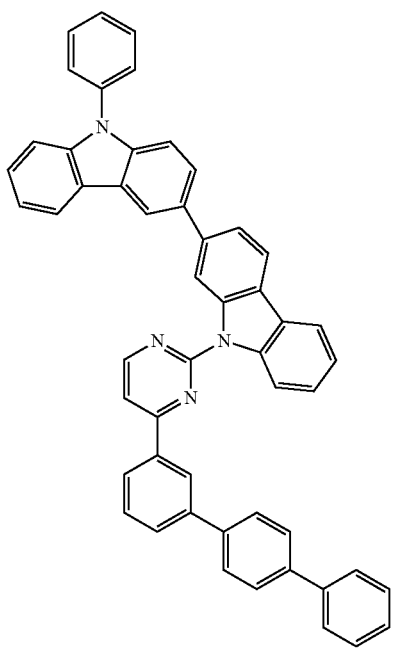

139
-continued
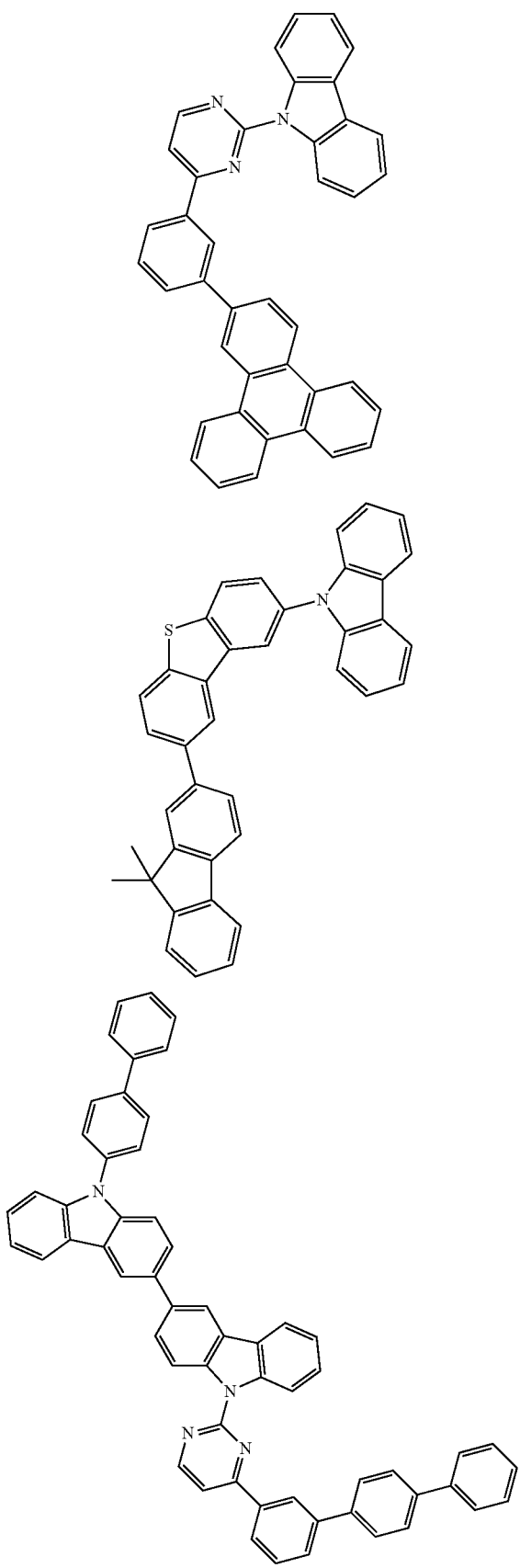
140
-continued
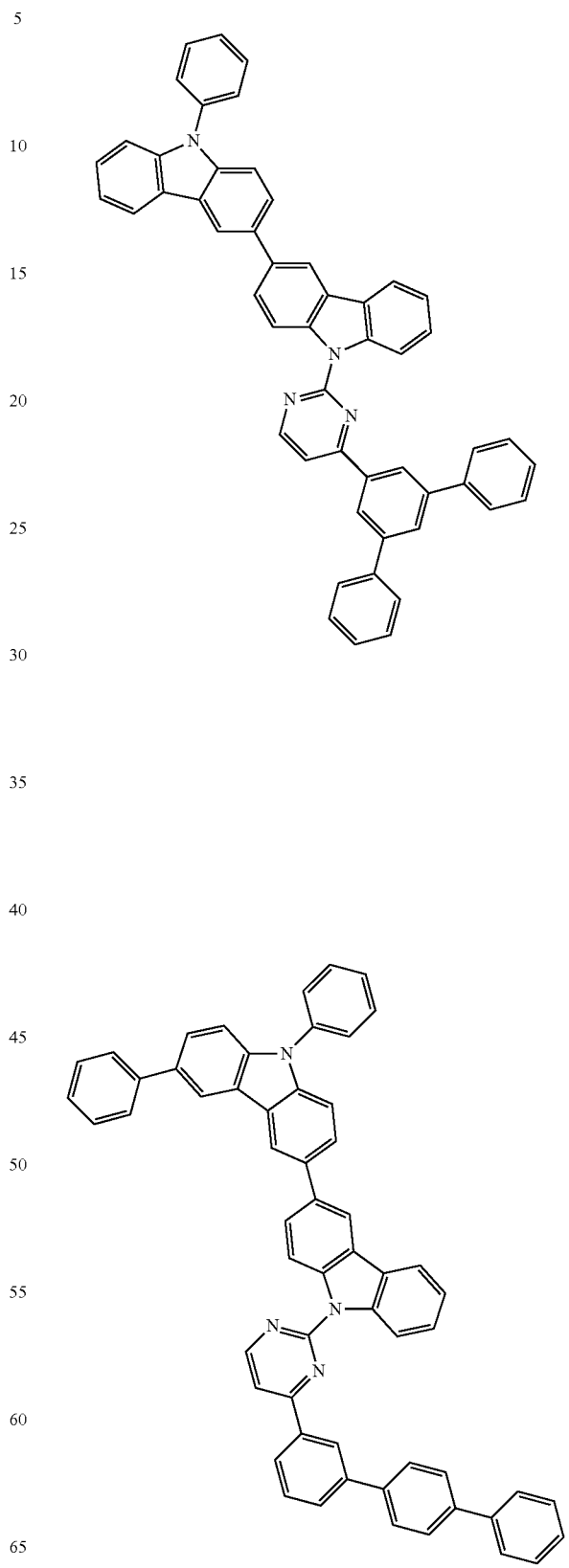

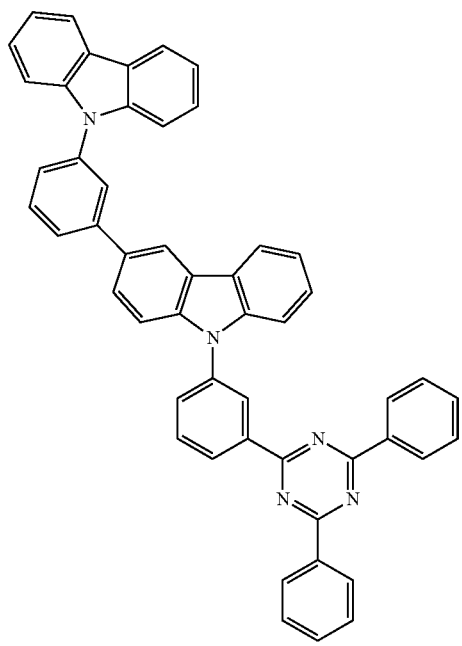
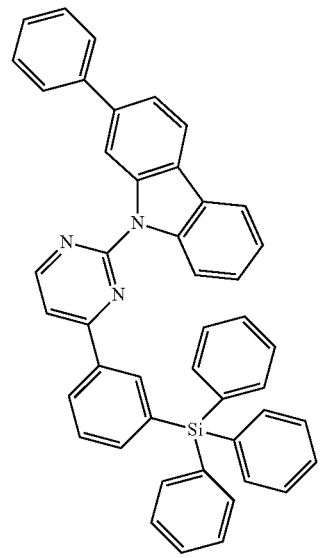
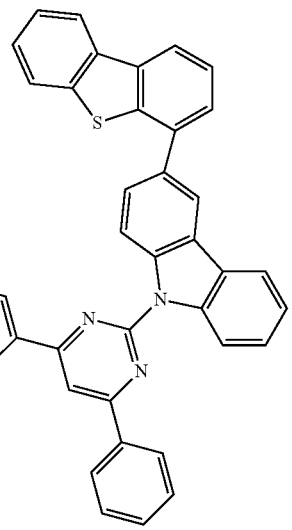
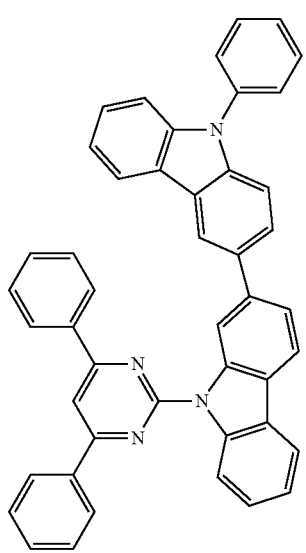

143
-continued
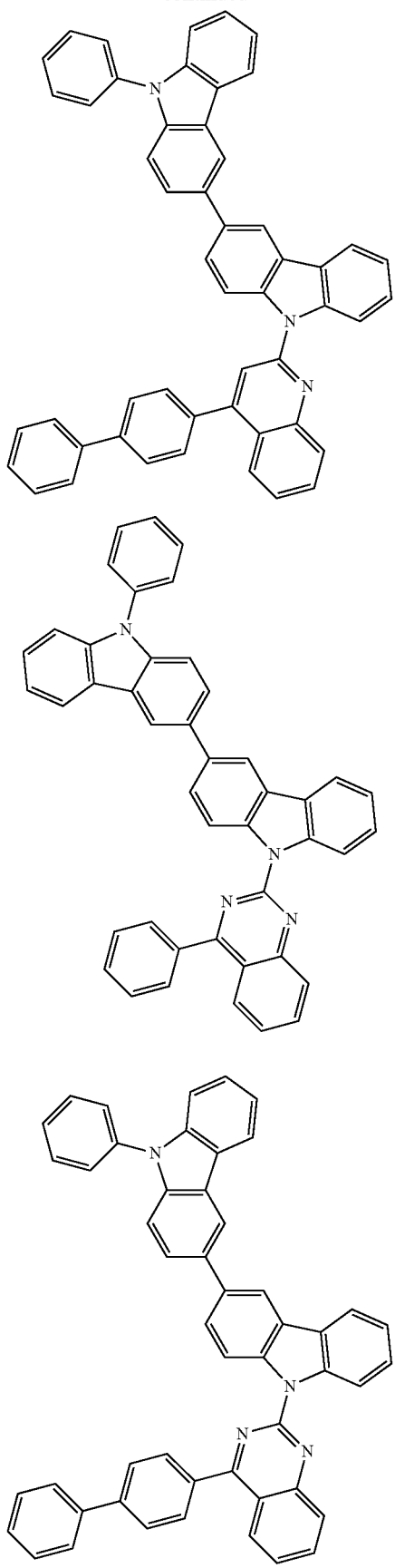
144
-continued
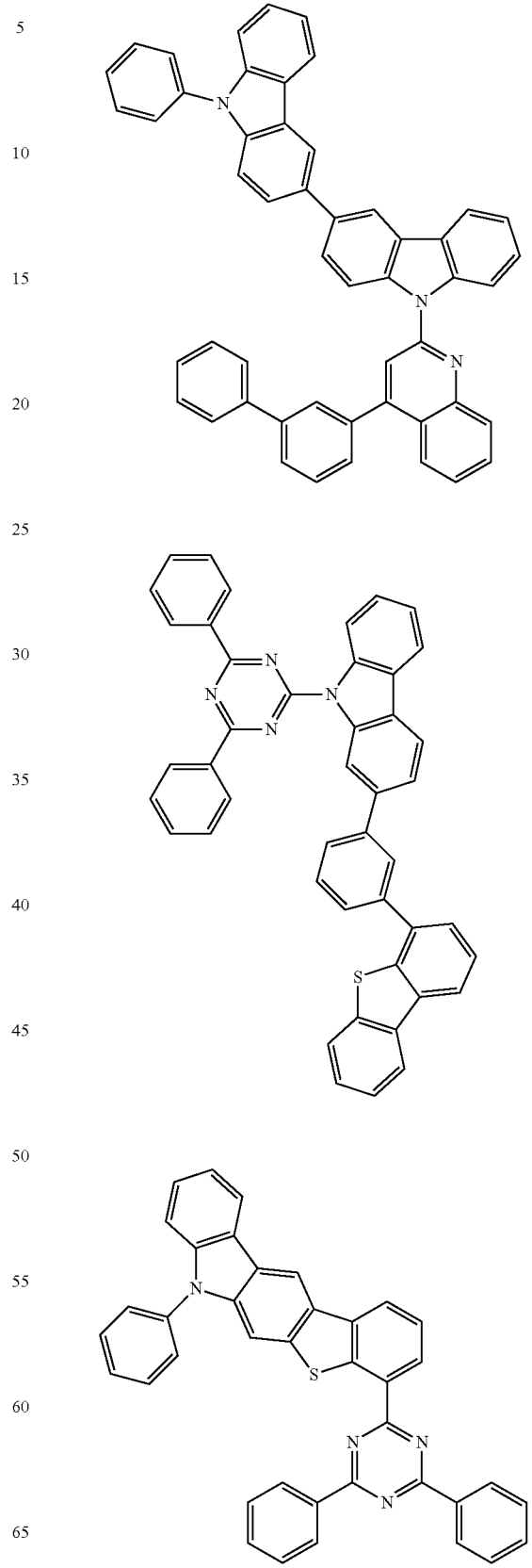

145
-continued
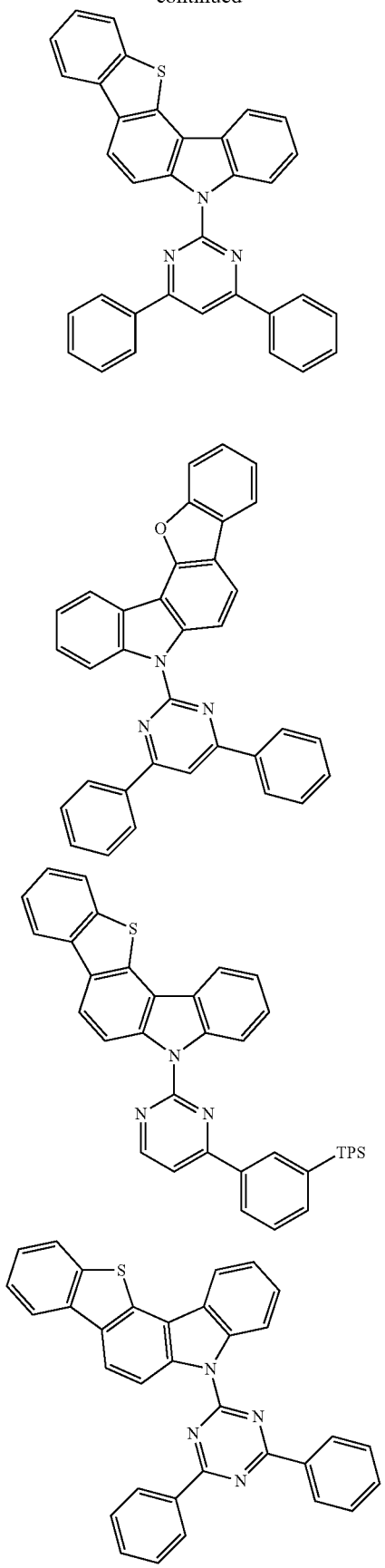
146
-continued
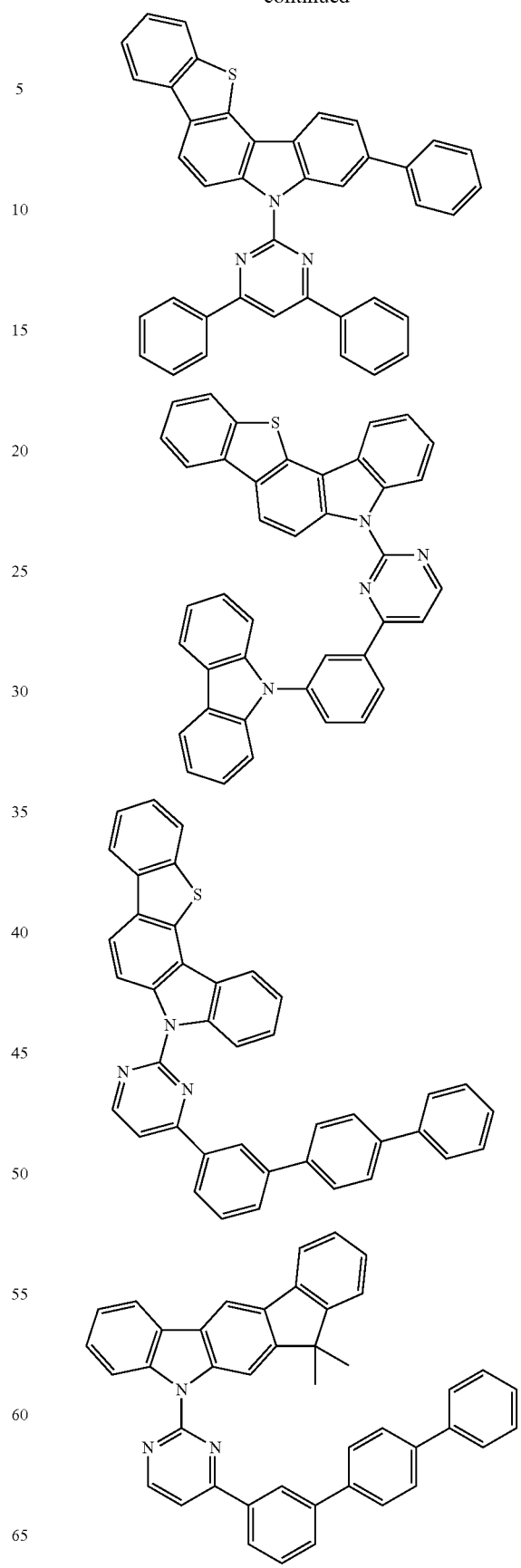

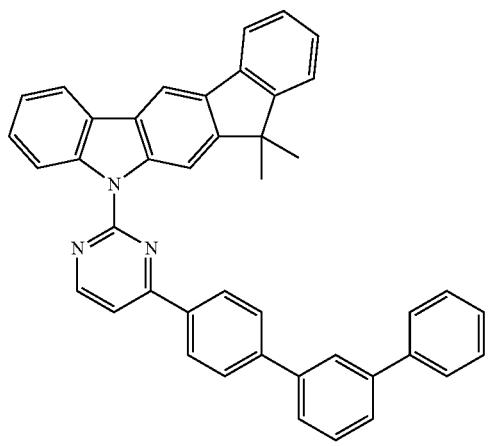
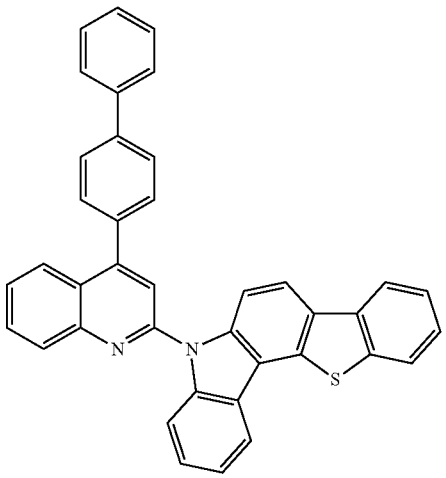
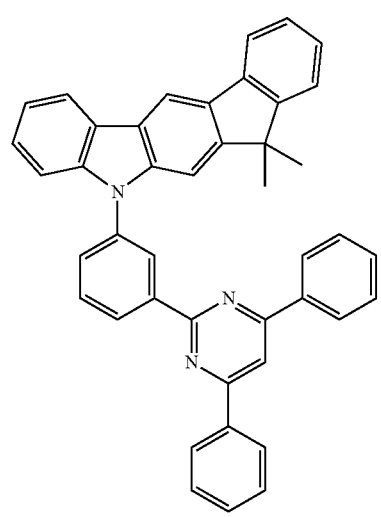
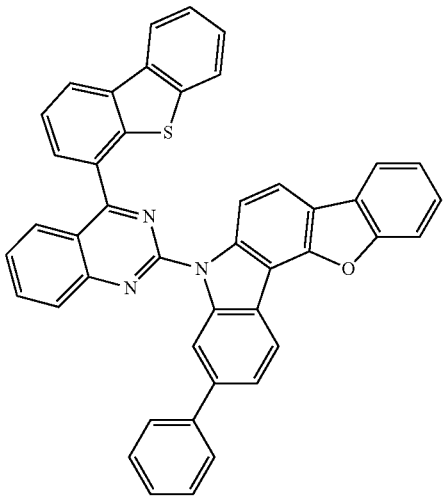
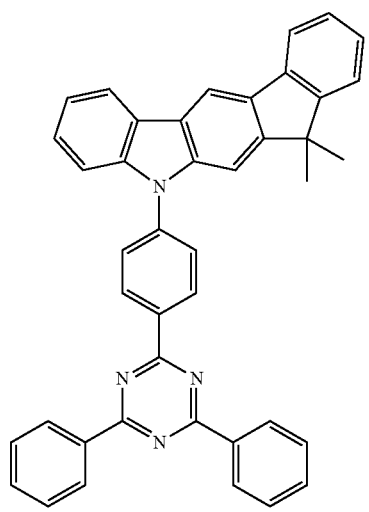
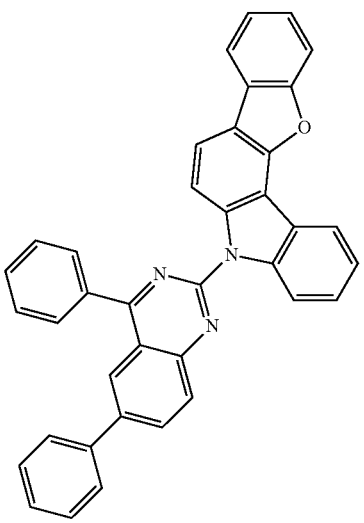

149
-continued
150
-continued
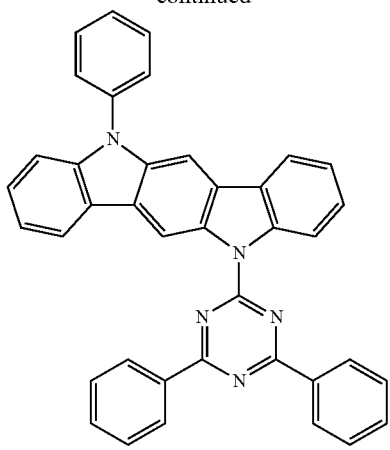
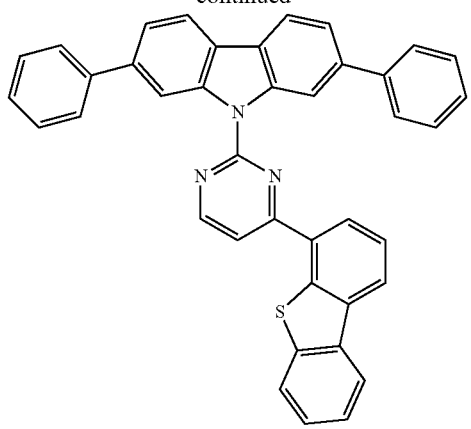
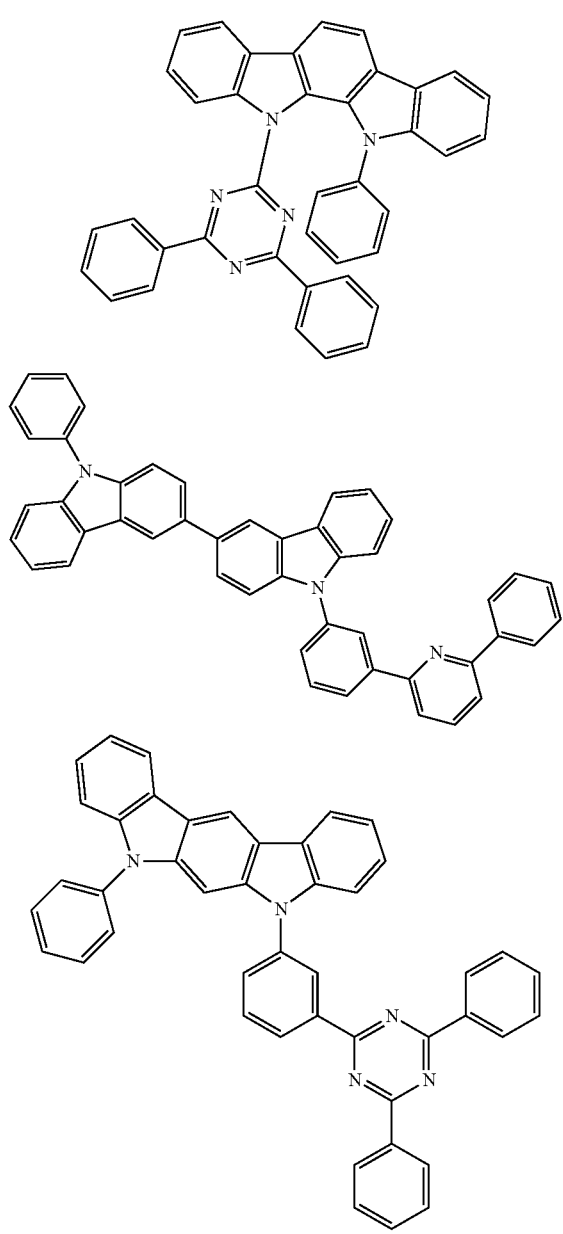
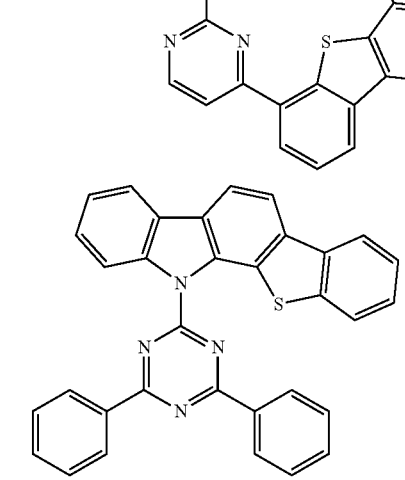

151
-continued

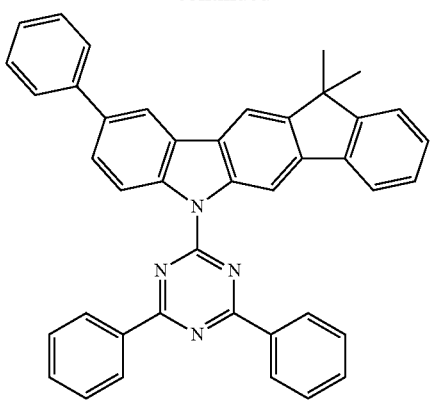

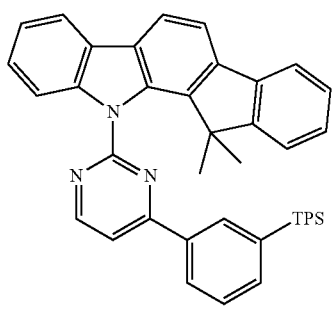

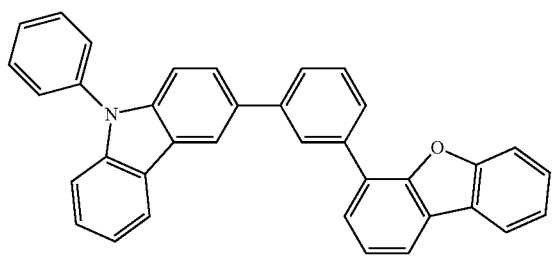

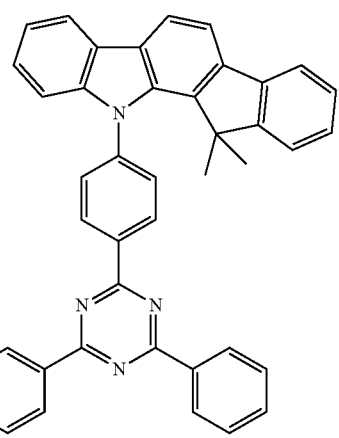

152
-continued

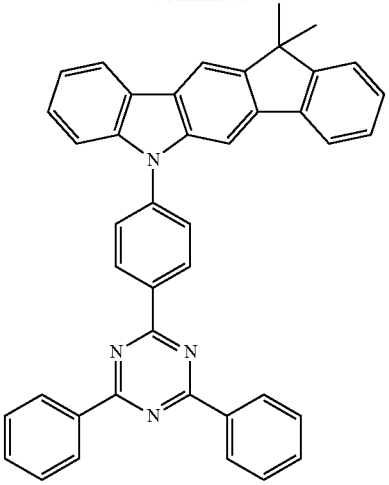

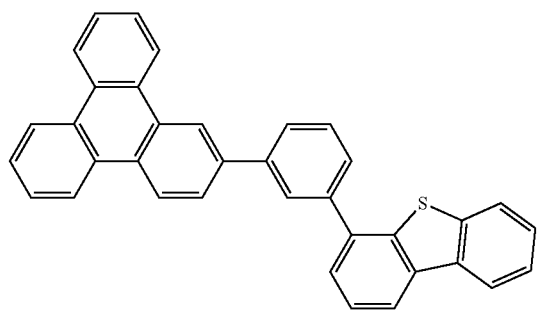

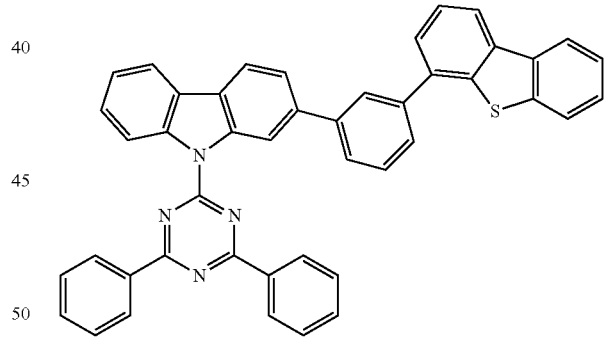

[wherein TPS represents triphenylsilyl]

The dopant comprised in the organic electroluminescent device according to the present invention is preferably at least one phosphorescent dopant. The dopant materials applied to the organic electroluminescent device according to the present invention are not limited, but may be preferably selected from metallated complex compounds of iridium, osmium, copper and platinum, more preferably selected from ortho-metallated complex compounds of iridium, osmium, copper and platinum, and even more preferably ortho-metallated iridium complex compounds.

The dopants comprised in the organic electroluminescent device of the present invention may be preferably selected from compounds represented by the following formulae 101 to 103.

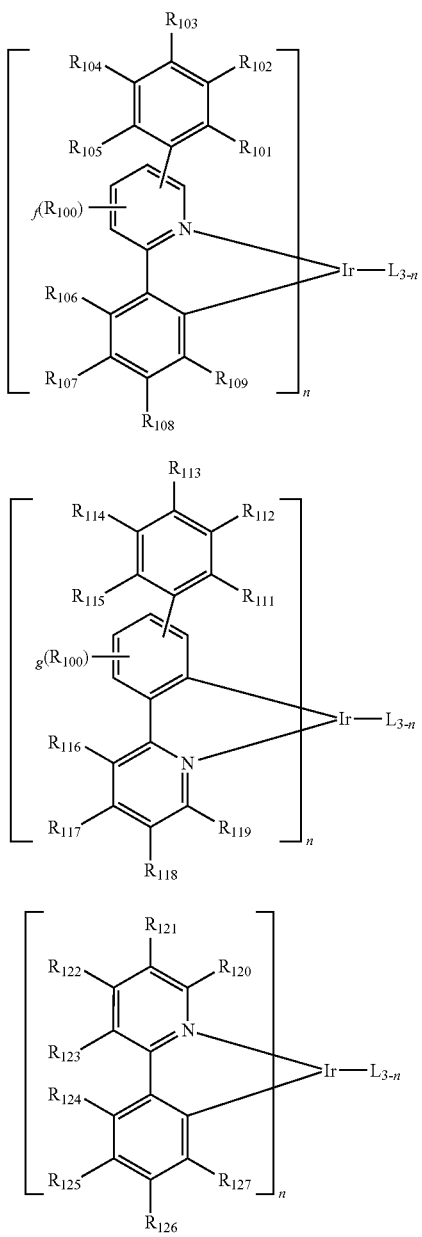

(101)

(102)

(103)

wherein L is selected from the following structures:

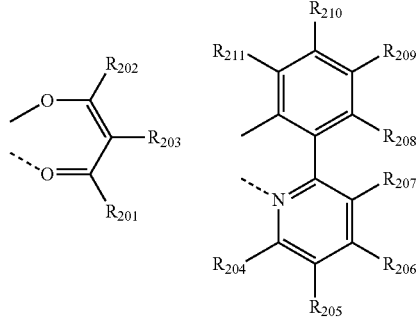

$R_{100}$ represents hydrogen, a substituted or unsubstituted (C1-C30)alkyl, or a substituted or unsubstituted (C3-C30)cycloalkyl;

$R_{101}$ to $R_{109}$, and $R_{111}$ to $R_{123}$ each independently represent hydrogen, deuterium, a halogen, a (C1-C30)alkyl unsubstituted or substituted with deuterium or a halogen(s), a substituted or unsubstituted (C3-C30)cycloalkyl, a substituted or unsubstituted (C6-C30)aryl, a cyano, or a substituted or unsubstituted (C1-C30)alkoxy; adjacent substituents of $R_{106}$ to $R_{109}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl; and adjacent substituents of $R_{120}$ to $R_{123}$ may be linked to each other to form a substituted or unsubstituted fused ring, e.g., quinoline unsubstituted or substituted with a halogen, alkyl, or aryl;

$R_{124}$ to $R_{127}$ each independently represent hydrogen, deuterium, a halogen, a substituted or unsubstituted (C1-C30)alkyl, or a substituted or unsubstituted (C6-C30)aryl; and adjacent substituents of $R_{124}$ to $R_{127}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

$R_{201}$ to $R_{211}$ each independently represent hydrogen, deuterium, a halogen, a (C1-C30)alkyl unsubstituted or substituted with deuterium or a halogen(s), a substituted or unsubstituted (C3-C30)cycloalkyl, or a substituted or unsubstituted (C6-C30)aryl, and adjacent substituents of $R_{208}$ to $R_{211}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

f and g each independently represent an integer of 1 to 3; where f or g is an integer of 2 or more, each of $R_{100}$ may be the same or different; and n represents an integer of 1 to 3.

Specifically, the dopant compounds include the following:

D-1

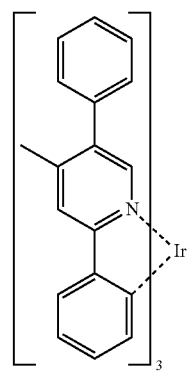

D-2
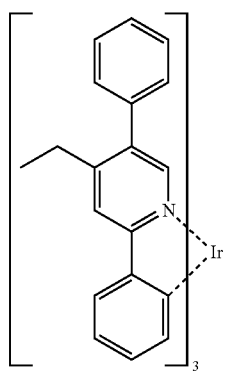
D-3
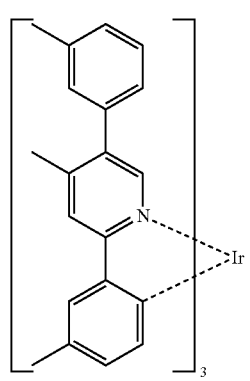
D-4
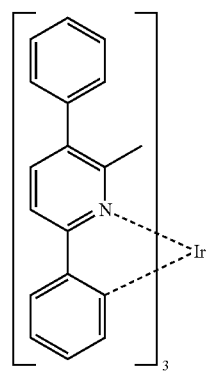
D-5
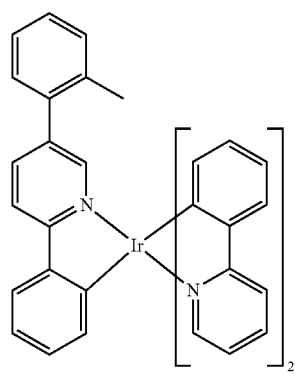
D-6
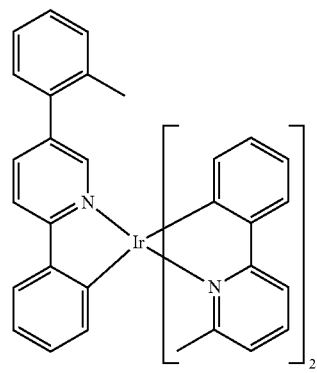
D-7
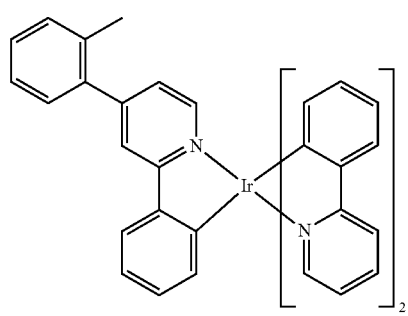
D-8
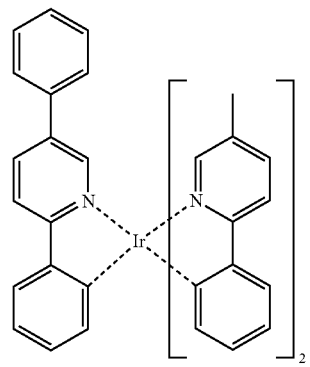
D-9
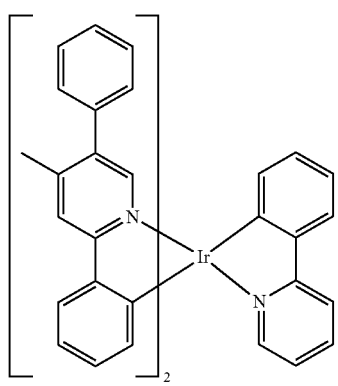

-continued
D-10
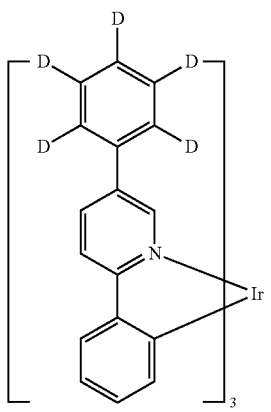
D-11
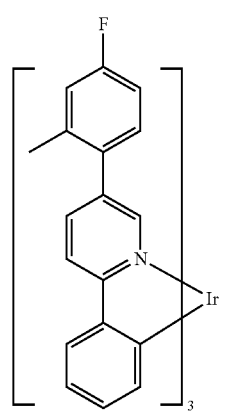
D-12
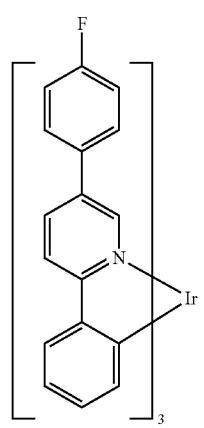
D-13
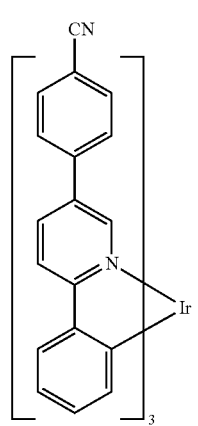
-continued
D-14
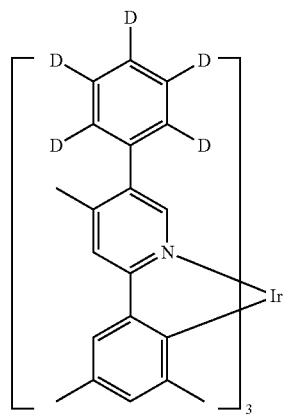
D-15
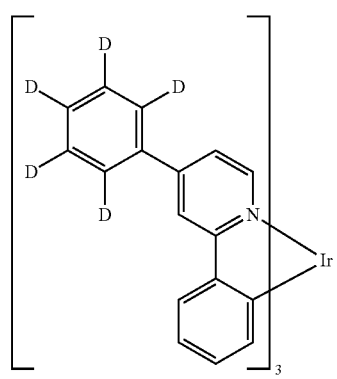
D-16
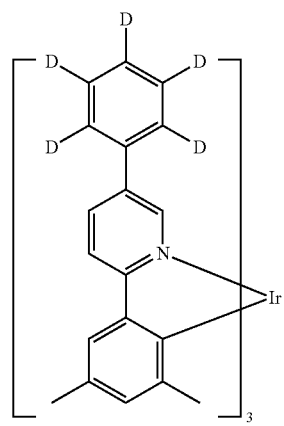
D-17
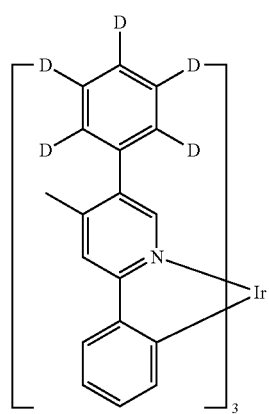

-continued
D-18
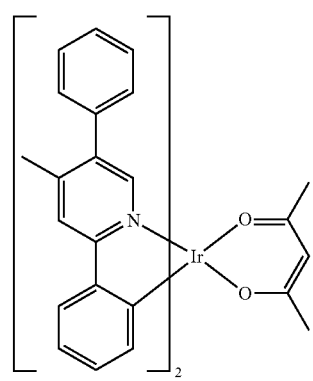
D-19
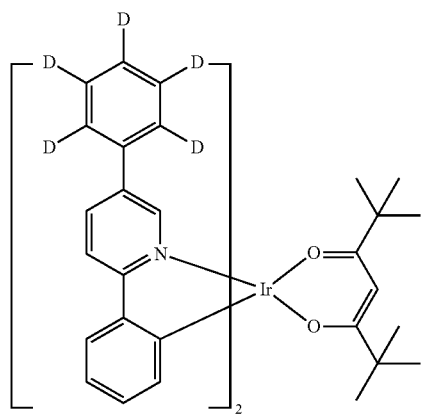
D-20
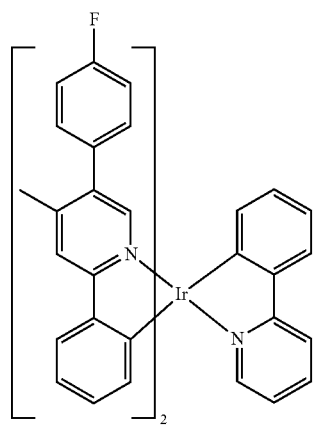
D-21
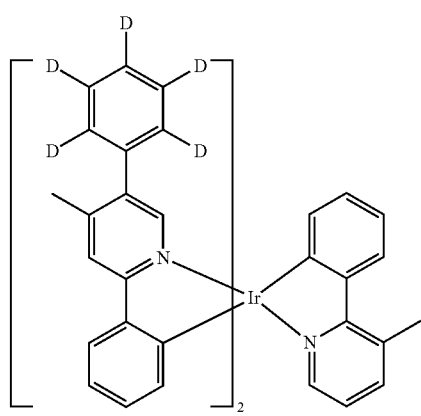
-continued
D-22
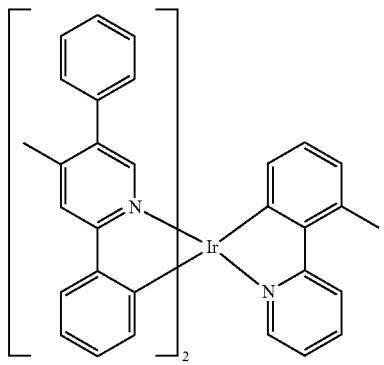
D-23
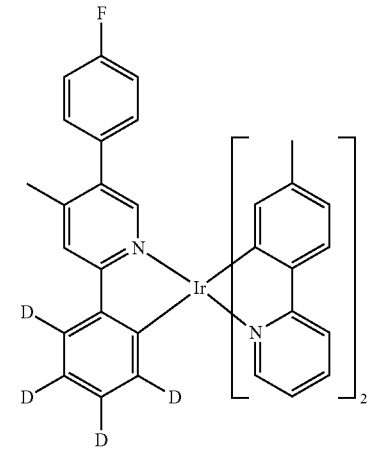
D-24
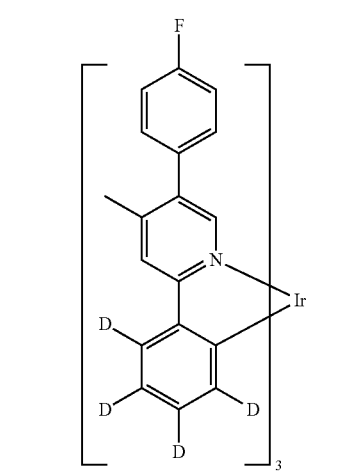
D-25
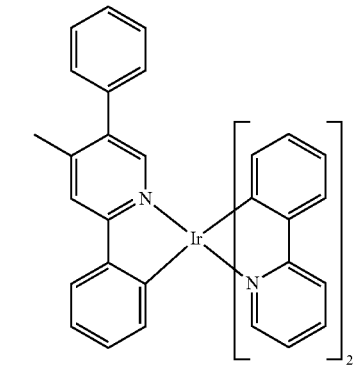

D-26
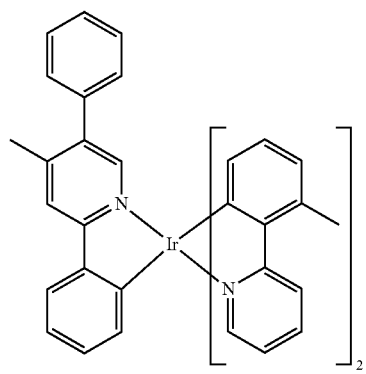
D-27
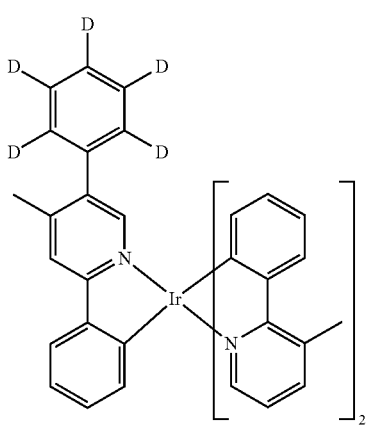
D-28
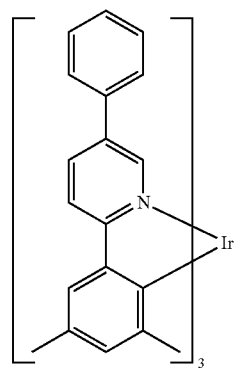
D-29
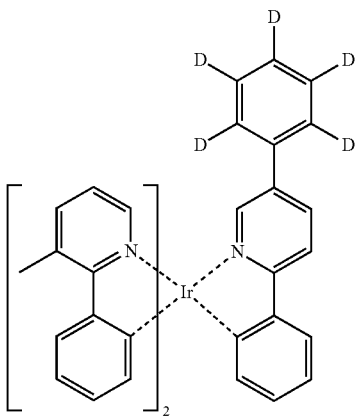
D-30
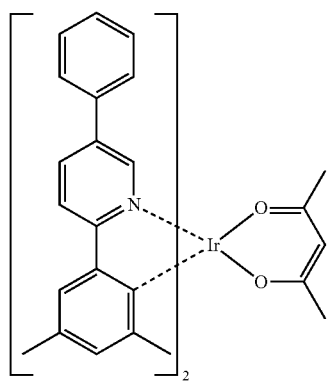
D-31
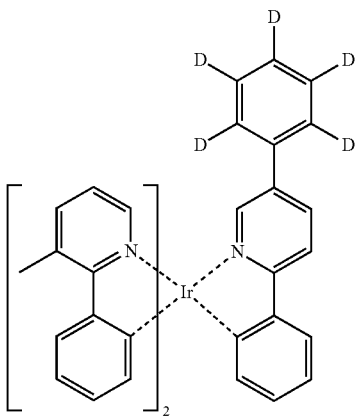
D-32
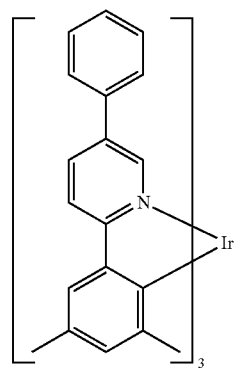
D-33
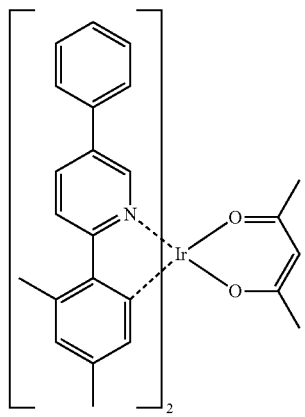

-continued
D-34
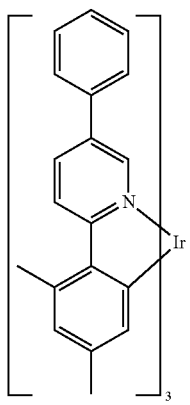
D-35
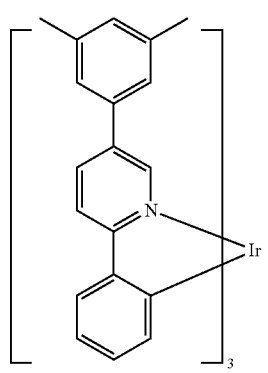
D-36
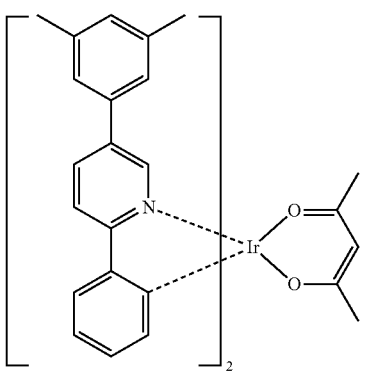
D-37
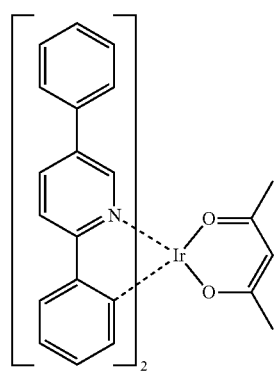
-continued
D-38
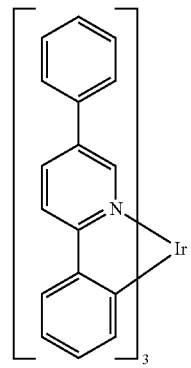
D-39
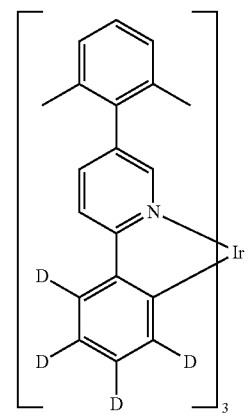
D-40
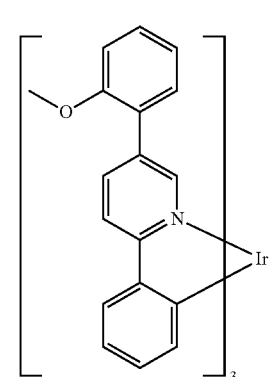
D-41
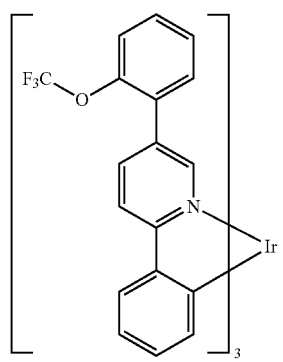

-continued
D-42
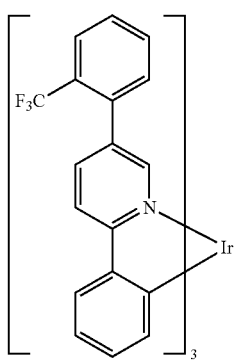
D-43
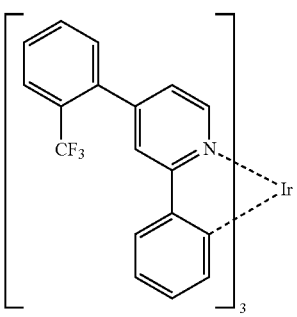
D-44
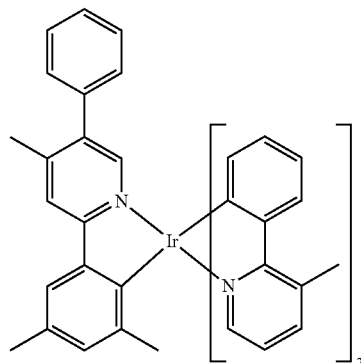
D-45
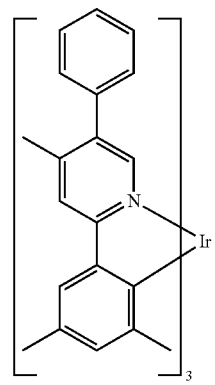
-continued
D-46
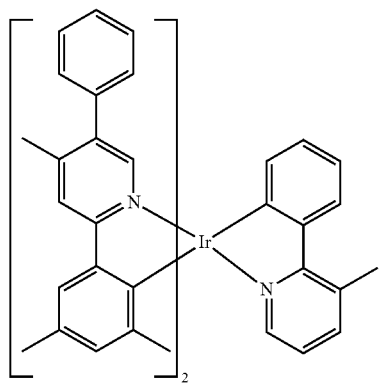
D-47
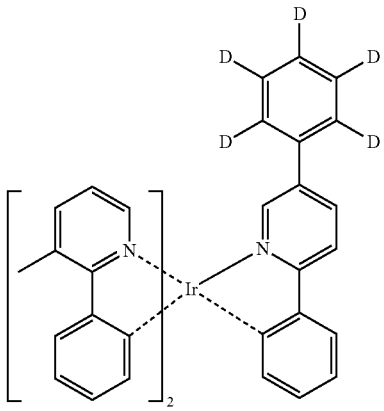
D-48
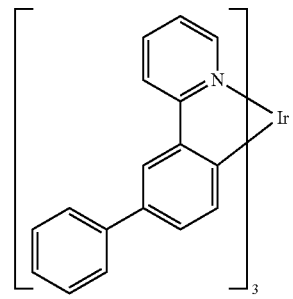
D-49
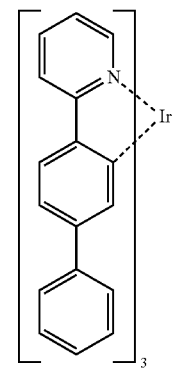

-continued
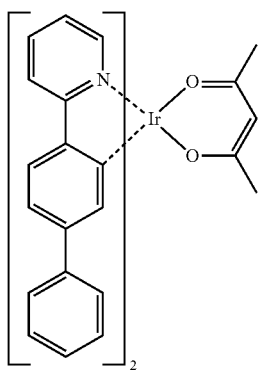
D-50
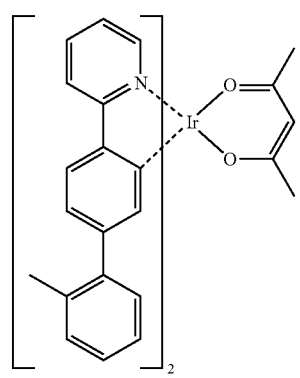
D-51
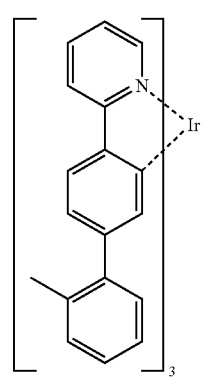
D-52
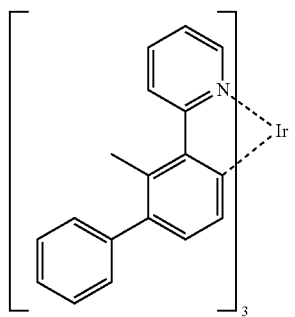
D-53
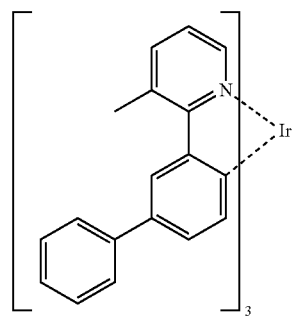
D-54
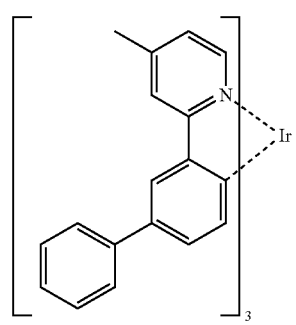
D-55
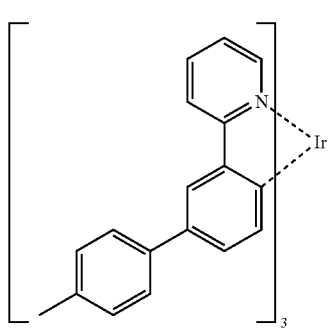
D-56
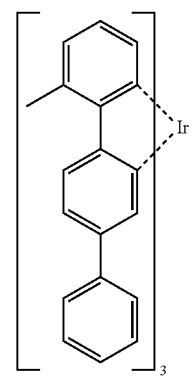
D-57

D-58
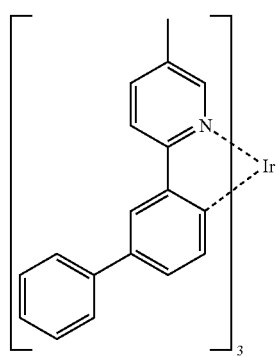
D-59
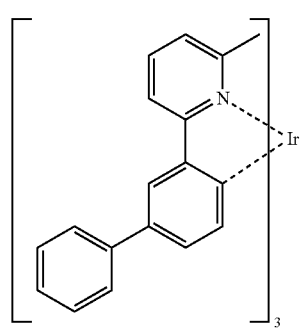
D-60
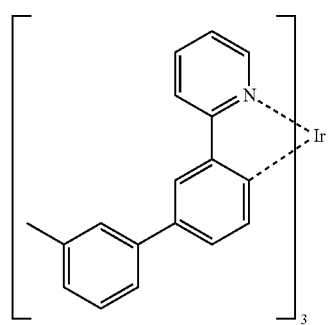
D-61
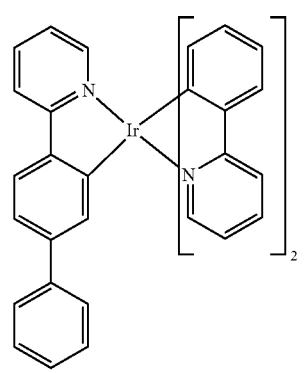
D-62
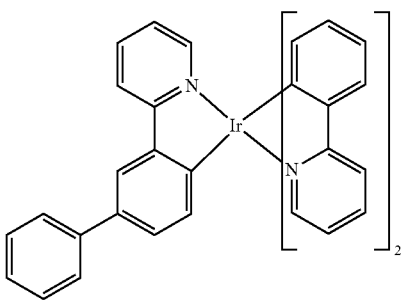
D-63
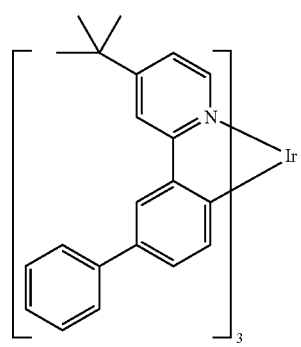
D-64
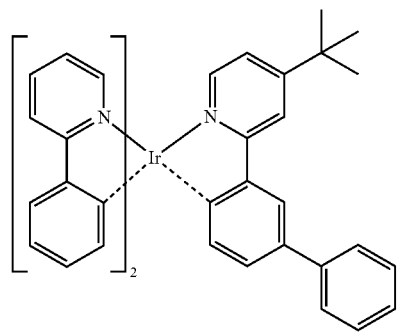
D-65
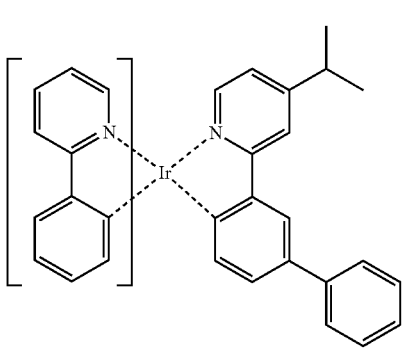

D-66
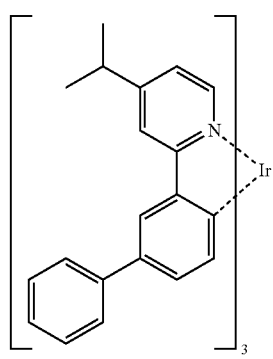
D-67
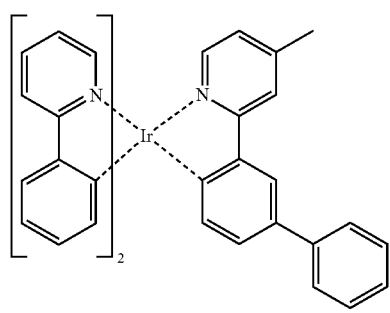
D-68
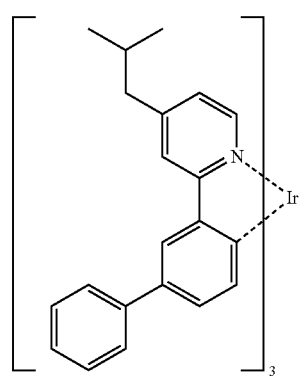
D-69
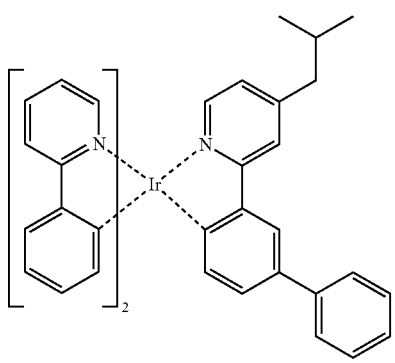
D-70
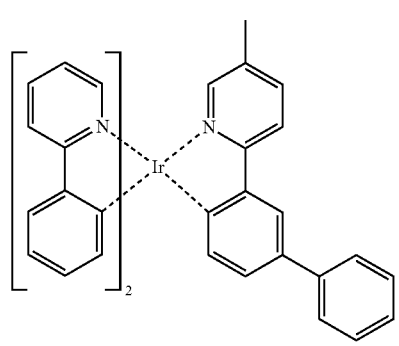
D-71
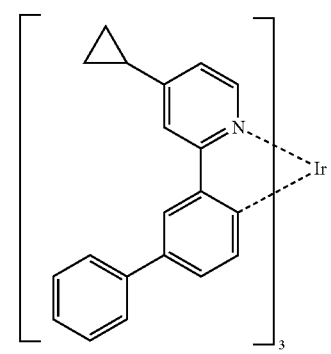
D-72
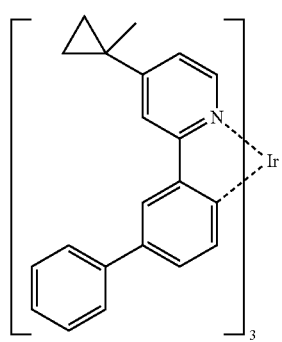
D-73

-continued
D-74
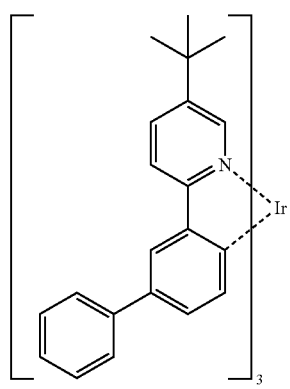
D-75
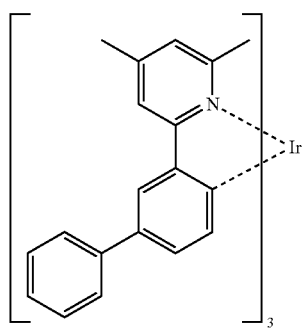
D-76
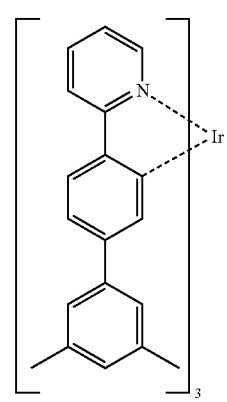
D-77
-continued
D-78
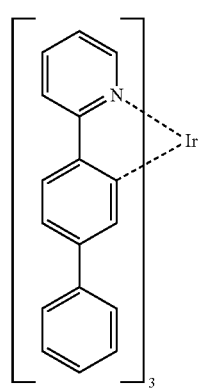
D-79
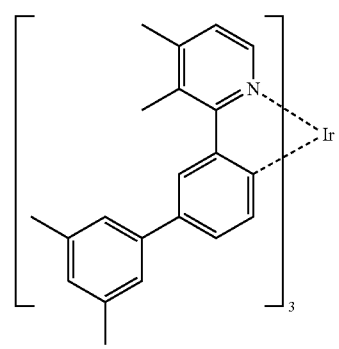
D-80
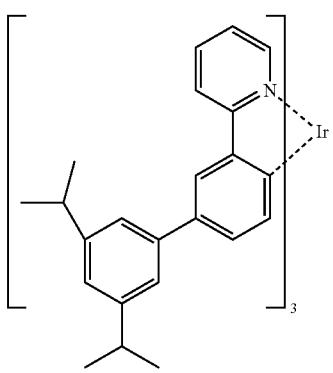
D-81

D-82 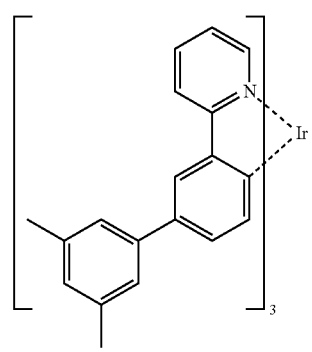
D-83 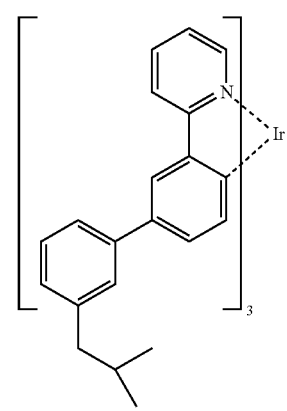
D-84 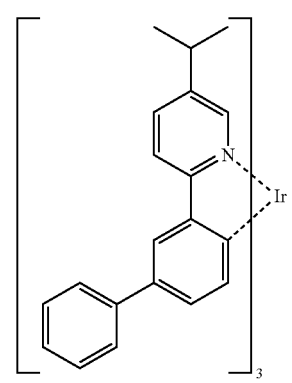
D-85 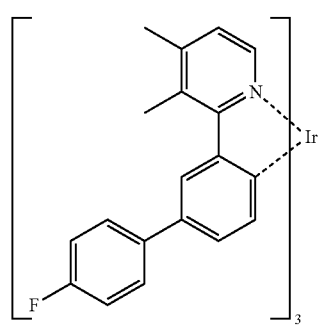
D-86 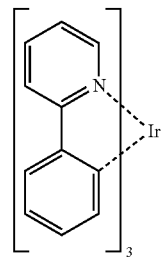
D-87 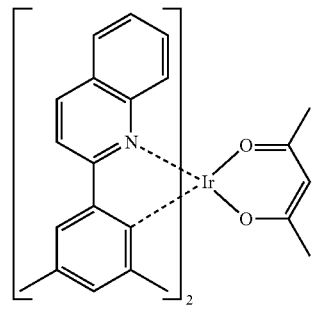
D-88 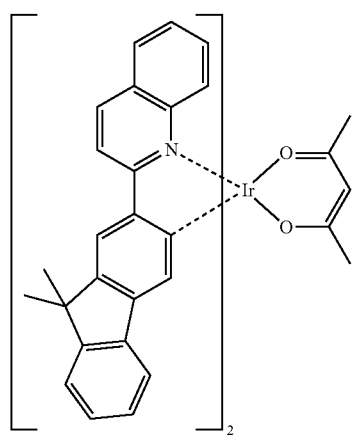
D-89 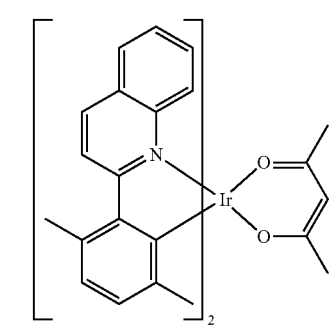
D-90 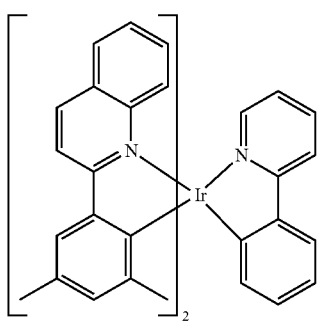

-continued
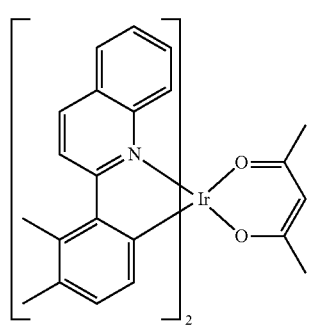
D-91
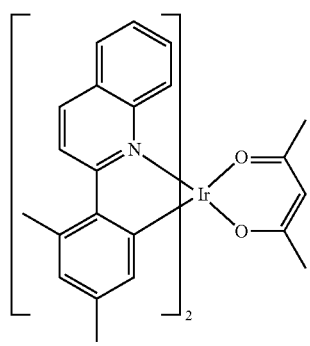
D-92
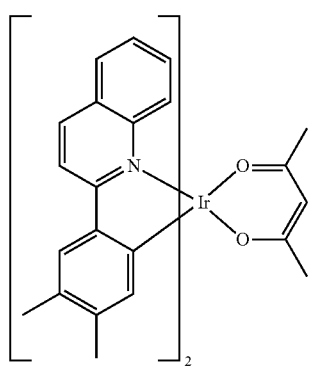
D-93
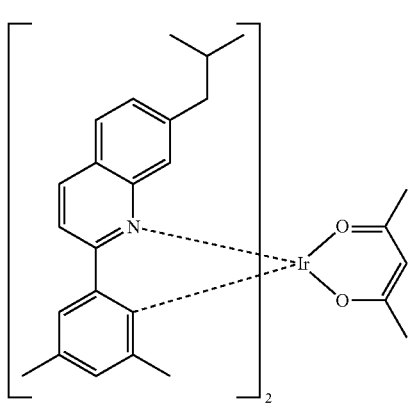
D-94
-continued
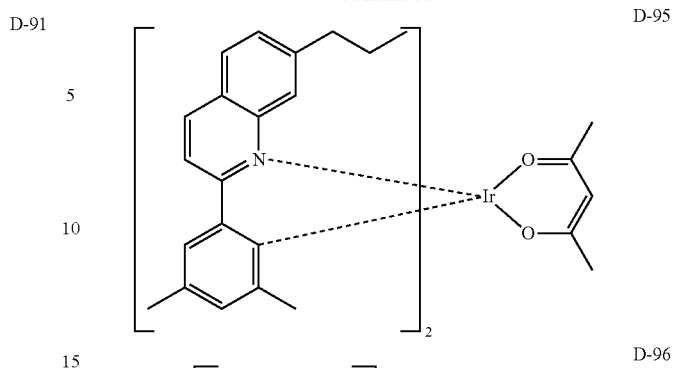
D-95

D-100 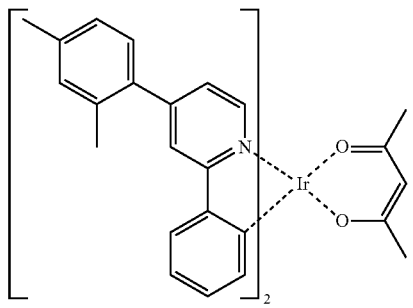
D-101 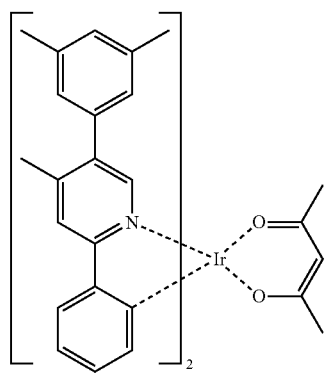
D-102 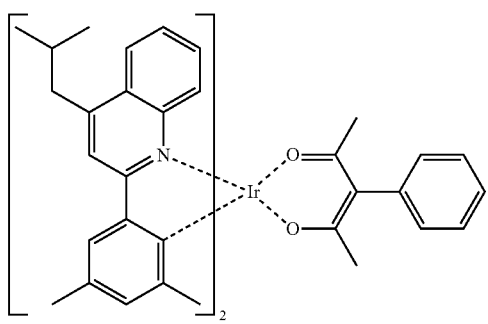
D-103 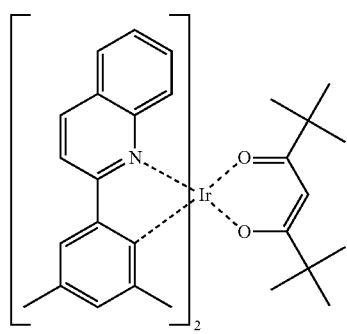
D-104 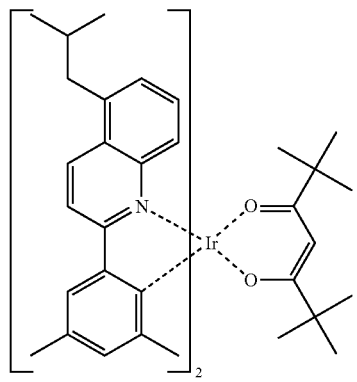
D-105 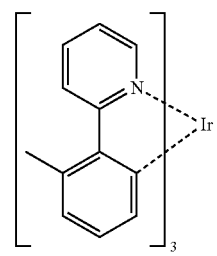
D-106 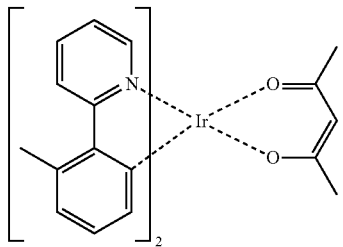
D-107 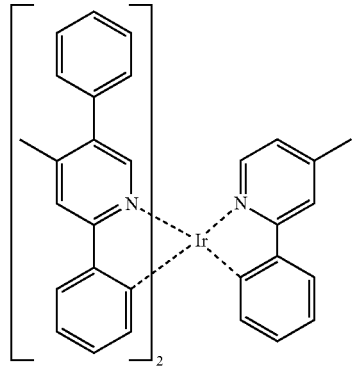
D-108 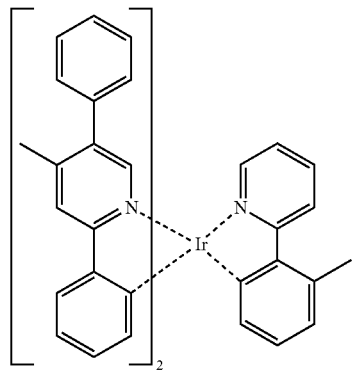

D-109
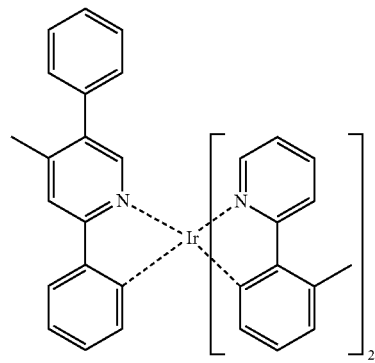
D-110
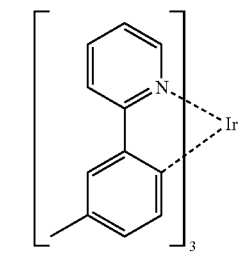
D-111
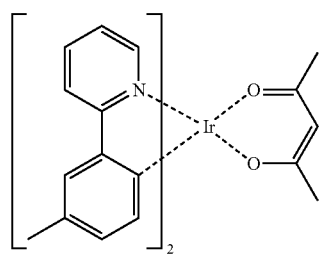
D-112
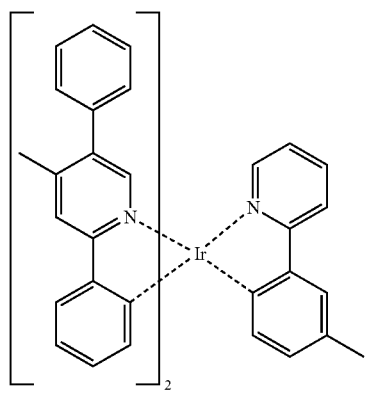
D-113
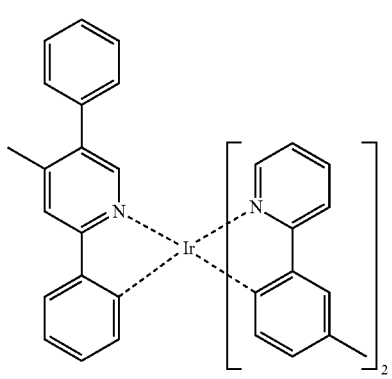
D-114
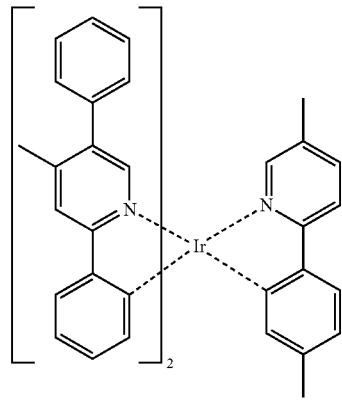
D-115
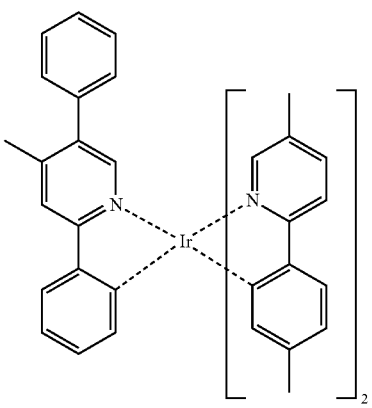
D-116
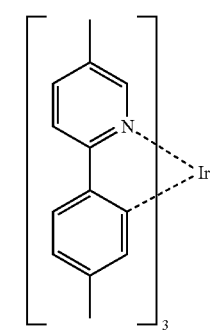
D-117
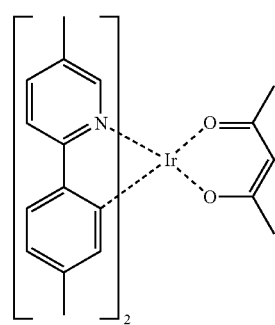

D-118
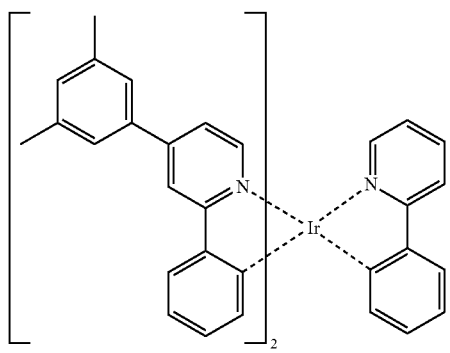
D-119
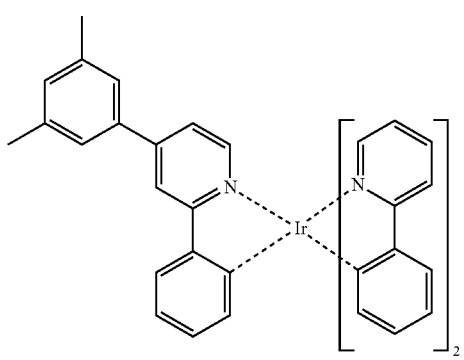
D-120
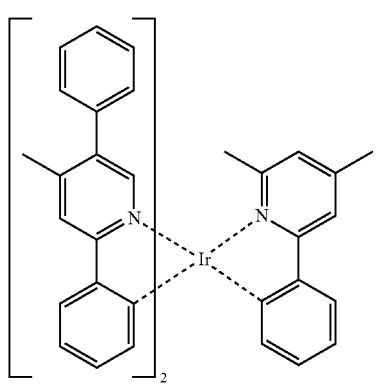
D-121
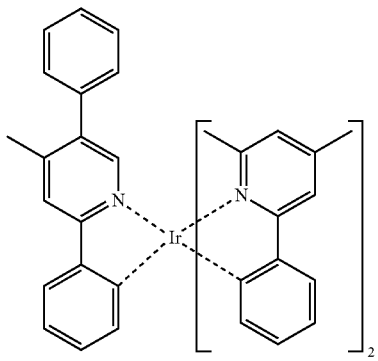
D-122
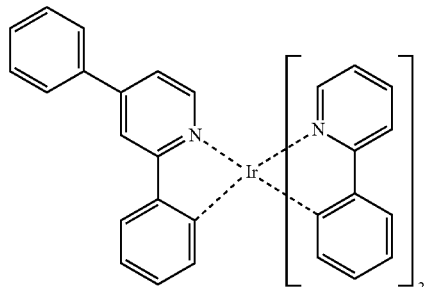
D-123
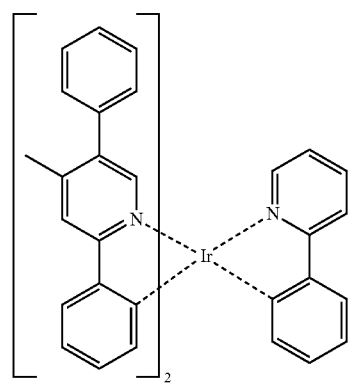
D-124
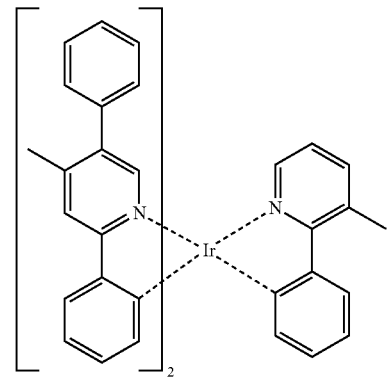
D-125
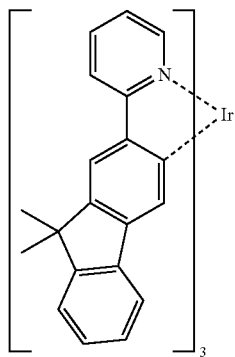

D-126 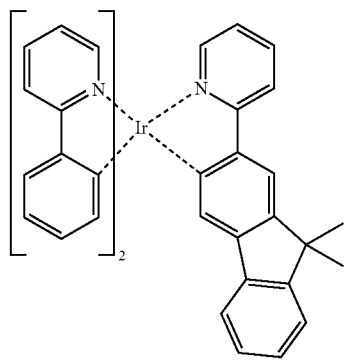
D-127 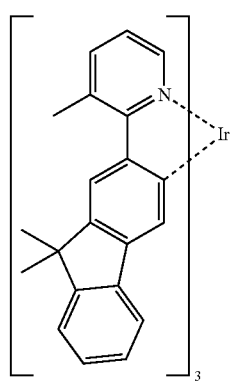
D-128 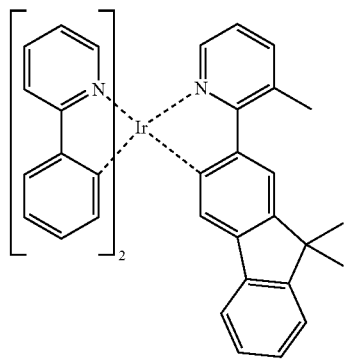
D-129 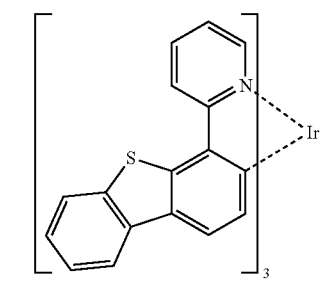
D-130 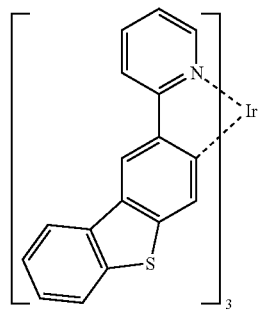
D-131 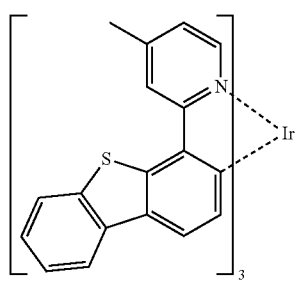
D-132 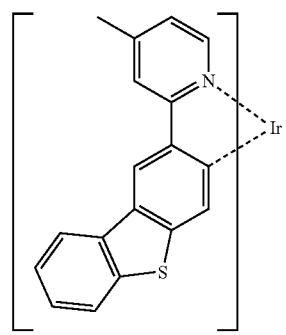
D-133 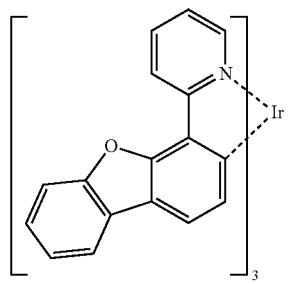
D-134 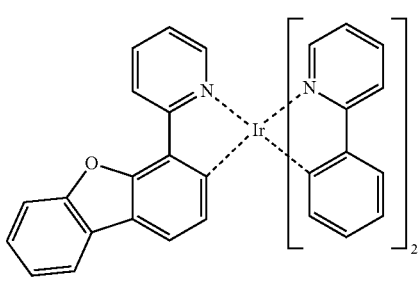

D-135
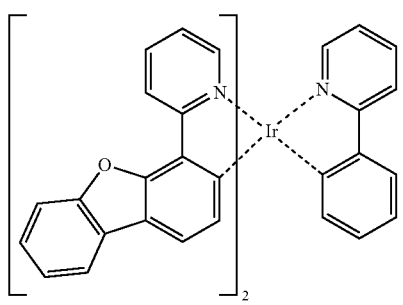
D-136
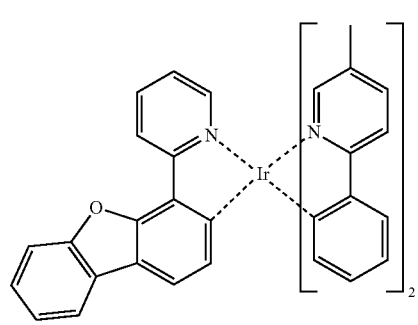
D-137
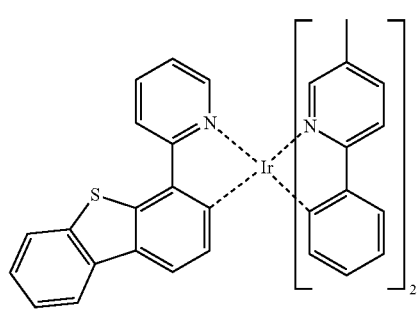
D-138
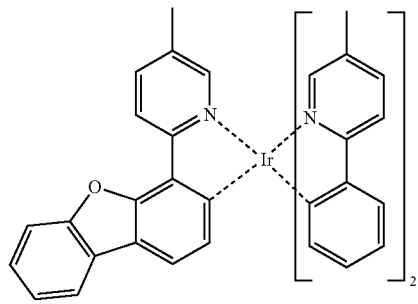
D-139
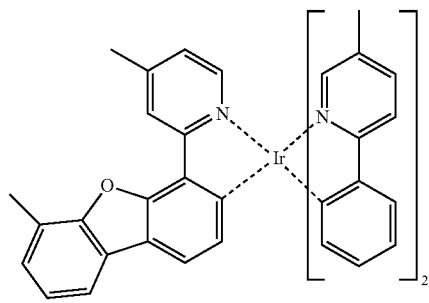
D-140
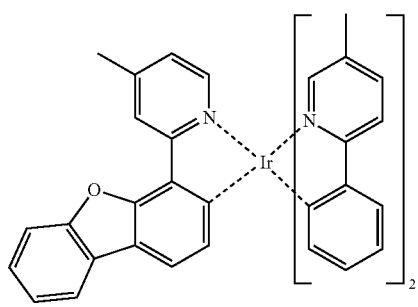
D-141
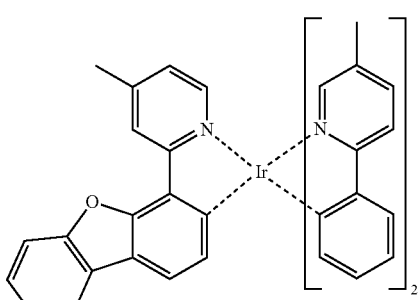
D-142
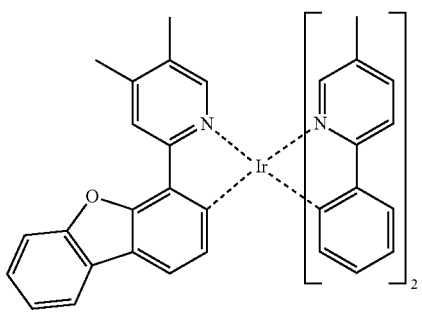
D-143
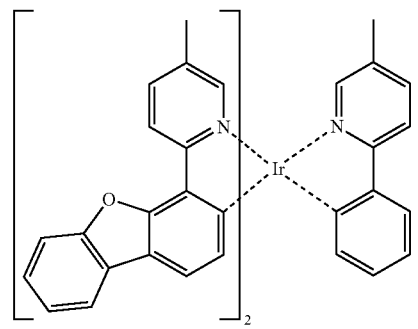
D-144
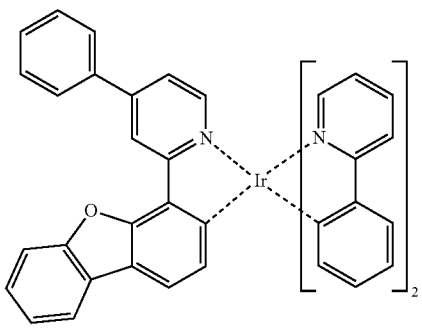

-continued
D-145
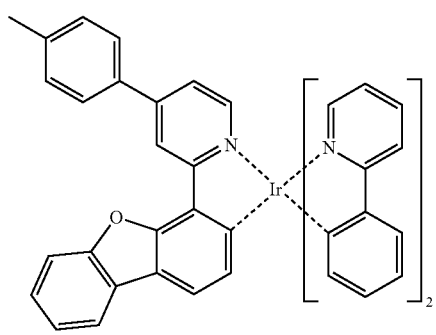
D-146
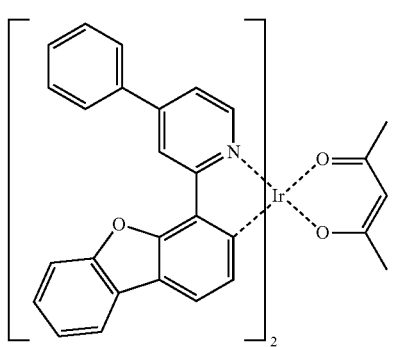
D-147
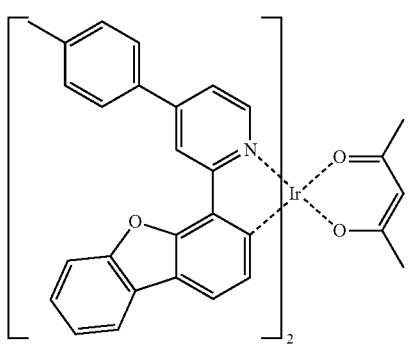
D-148
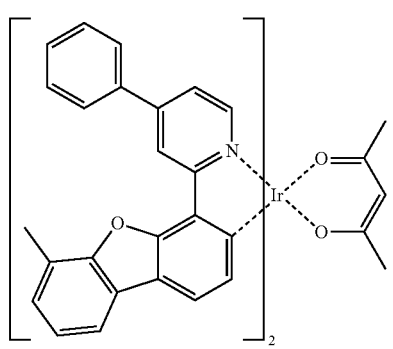
-continued
D-149
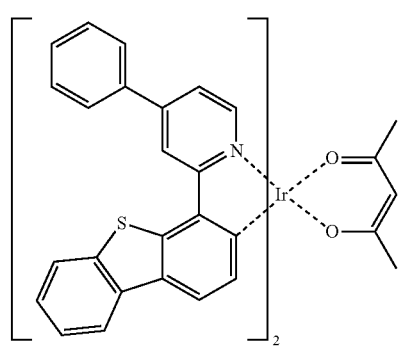
D-150
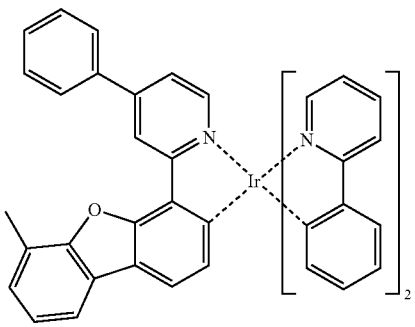
D-151
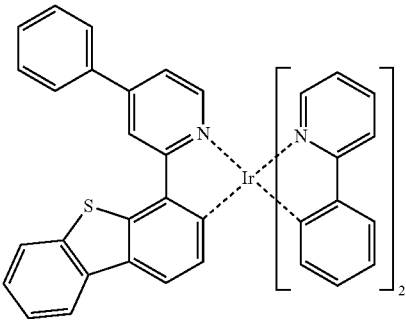
D-152
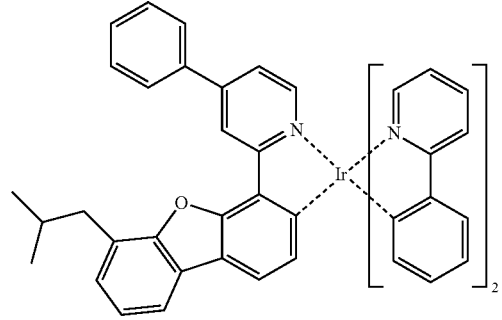
D-153
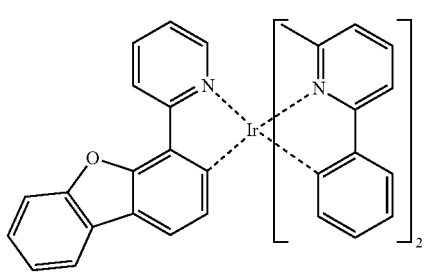

D-154 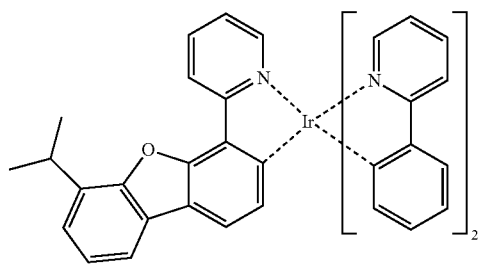
D-155 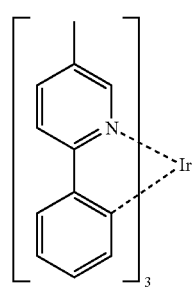
D-156 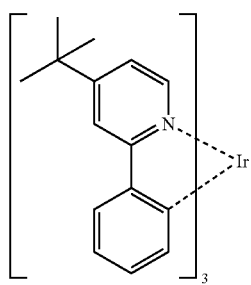
D-157 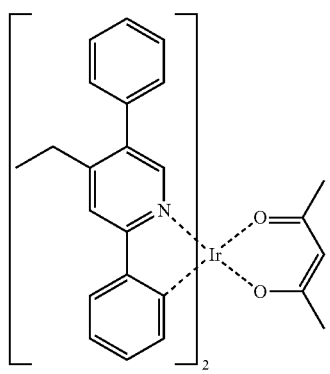
D-158 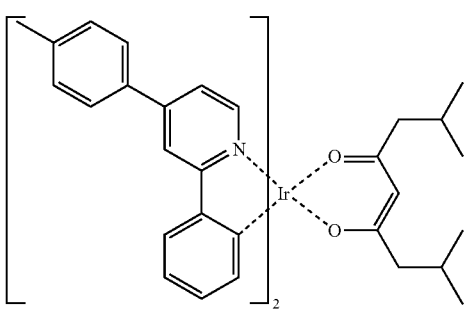
D-159 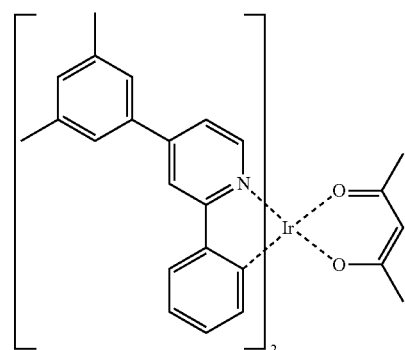
D-160 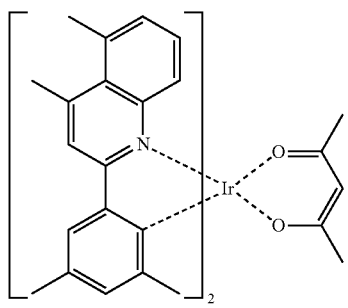
D-161 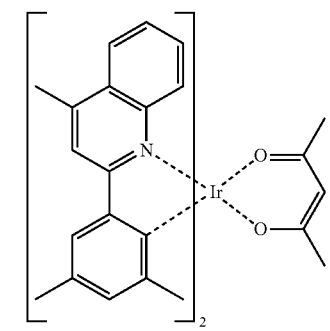
D-162 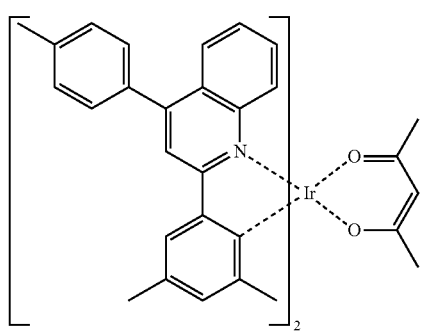
D-163 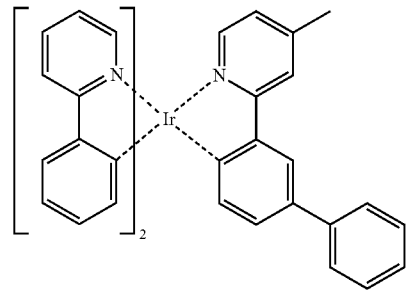

D-164
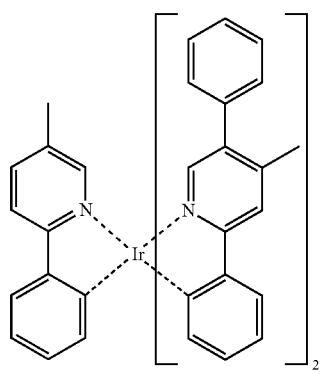
D-165
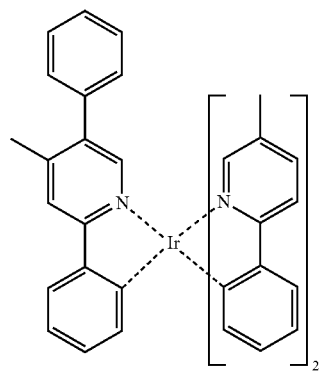
D-166
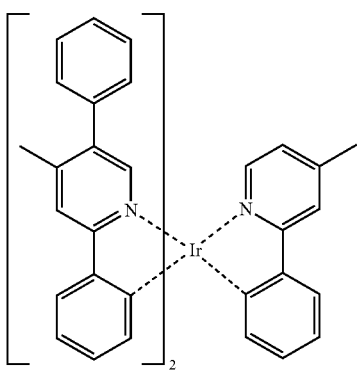
D-167
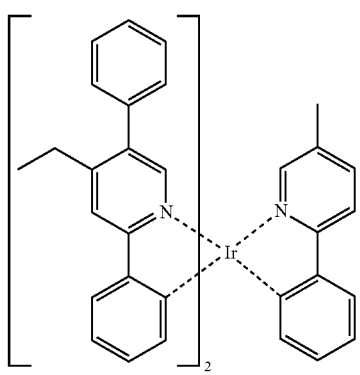
D-168
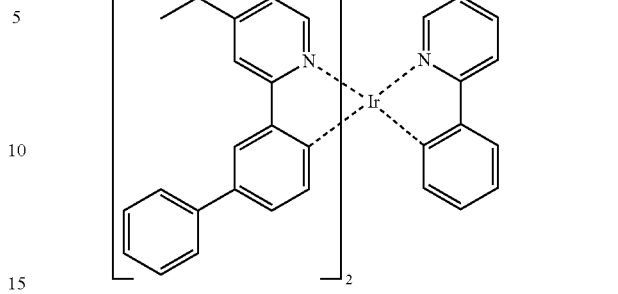
D-169
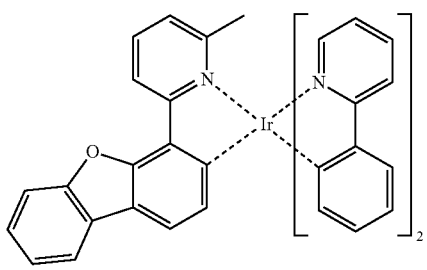
D-170
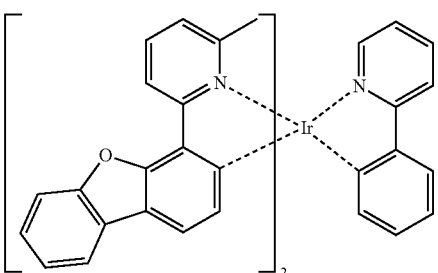
D-171
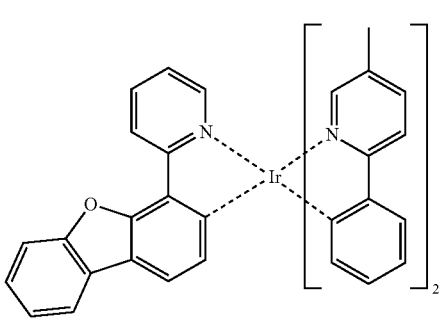
D-172
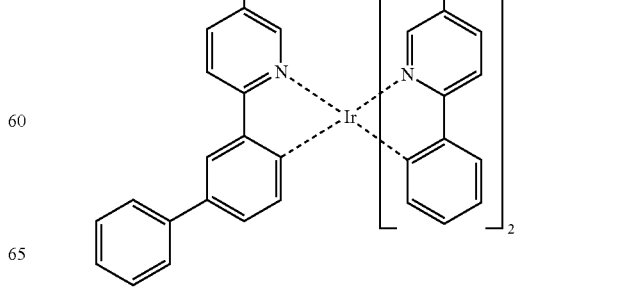

D-173
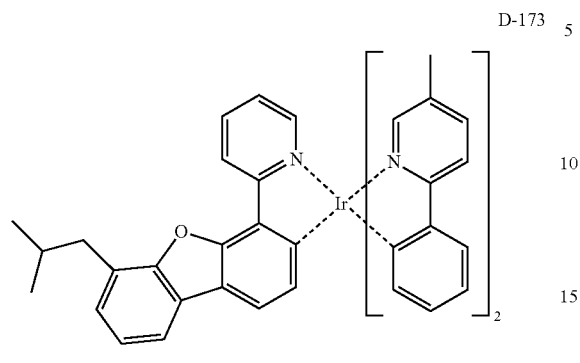
D-177
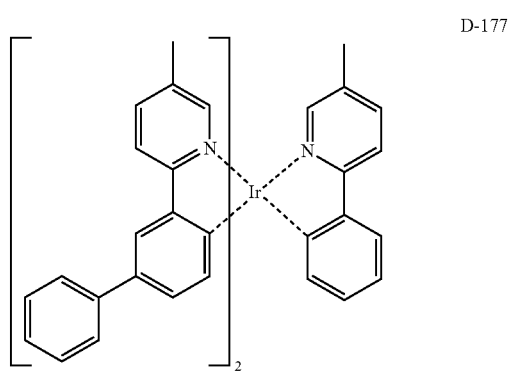
D-174
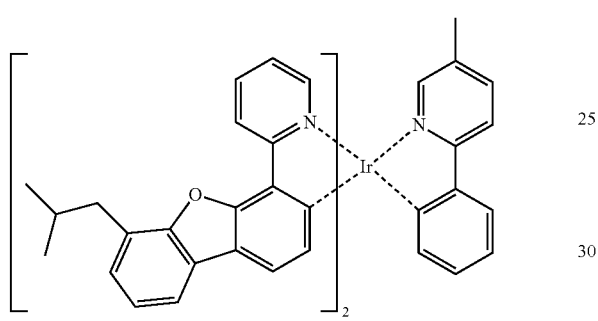
D-178
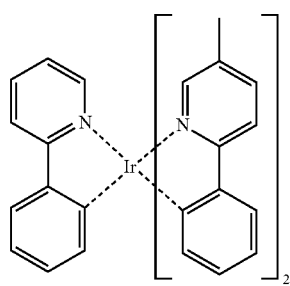
D-175
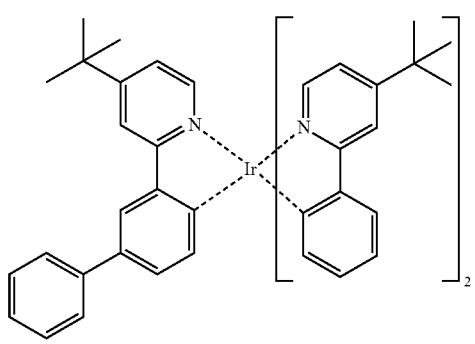
D-179
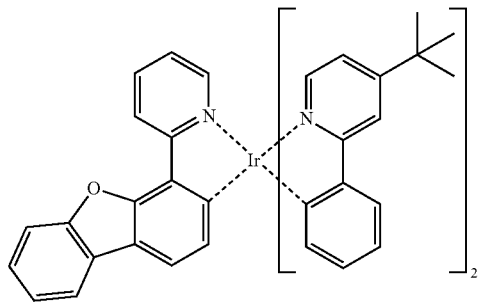
D-176
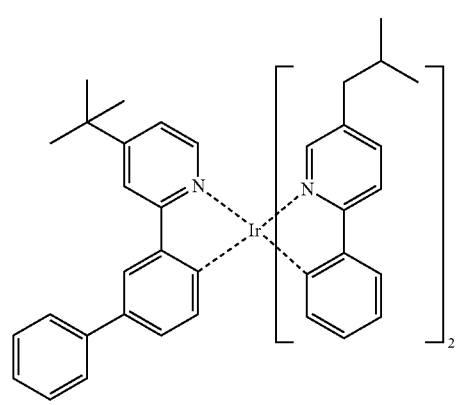
D-180
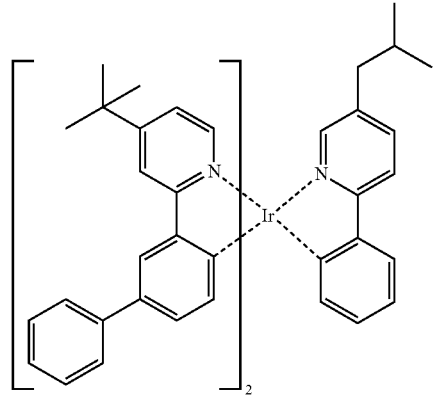

-continued
D-181
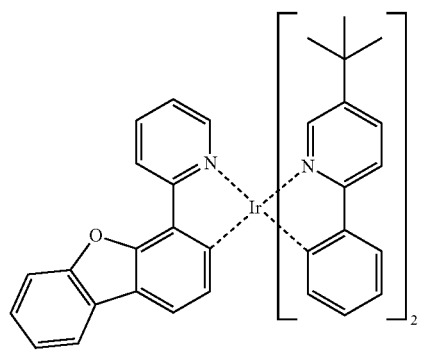
D-182
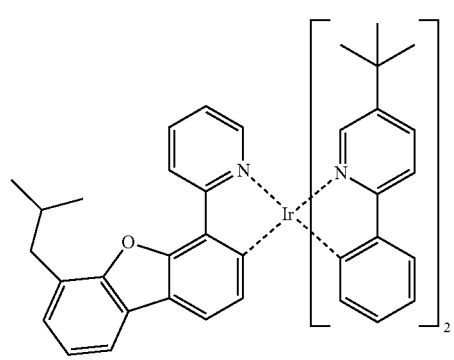
D-183
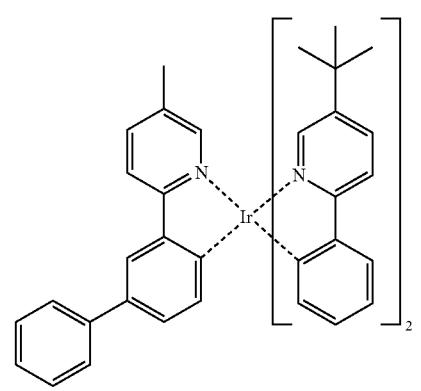
D-184
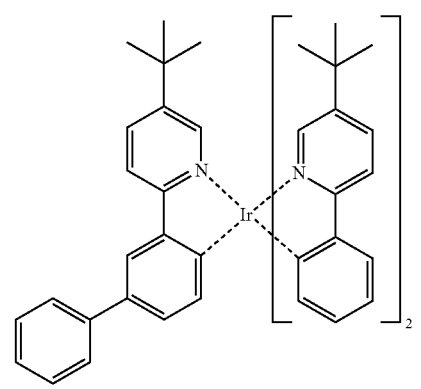
-continued
D-185
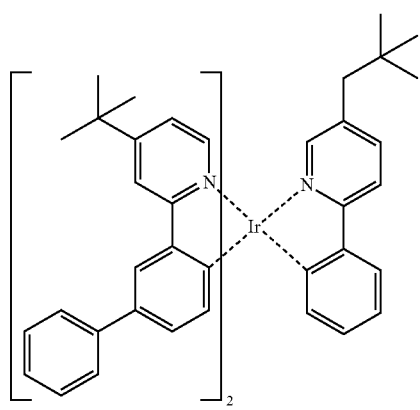
D-186
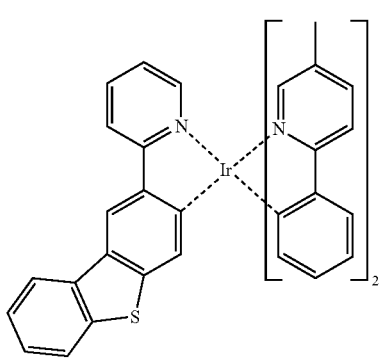
D-187
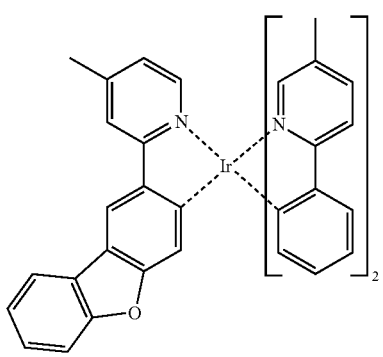
D-188
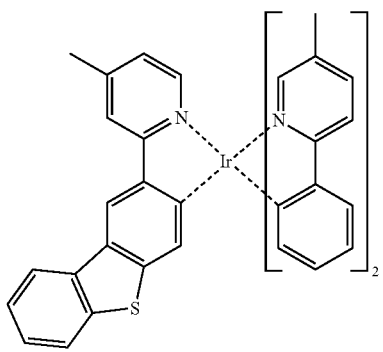

-continued
D-189
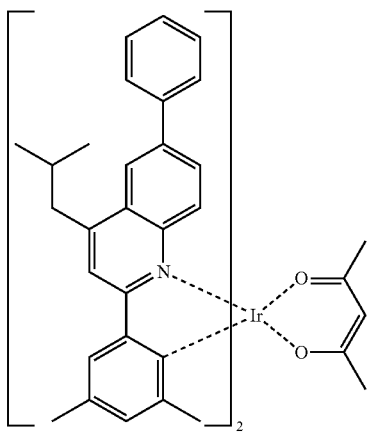
D-190
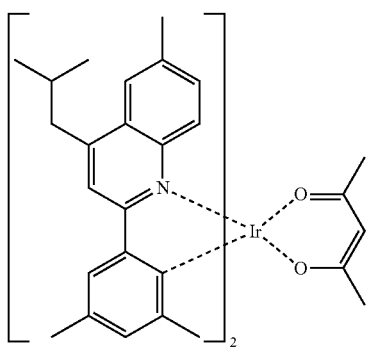
D-191
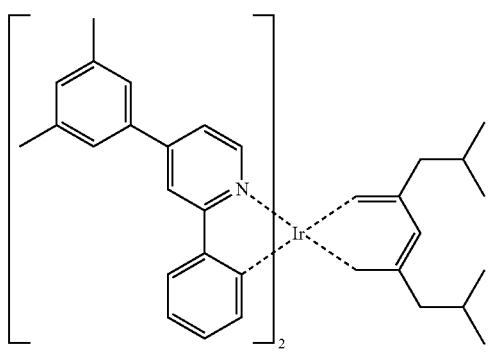
D-192
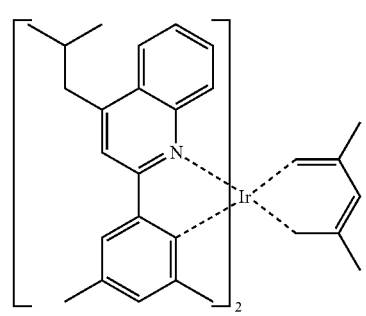
-continued
D-193
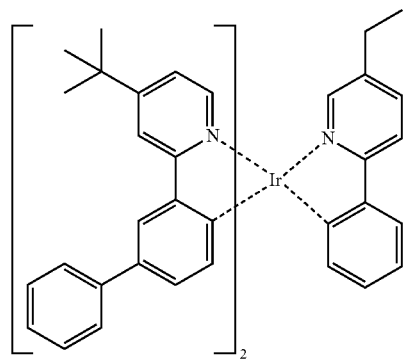
D-194
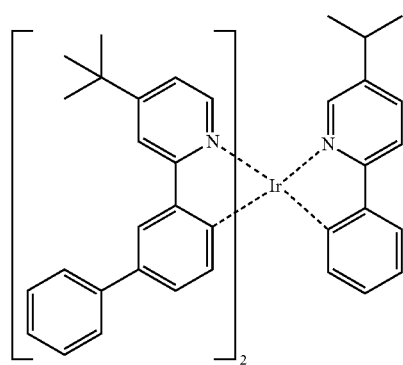
D-195
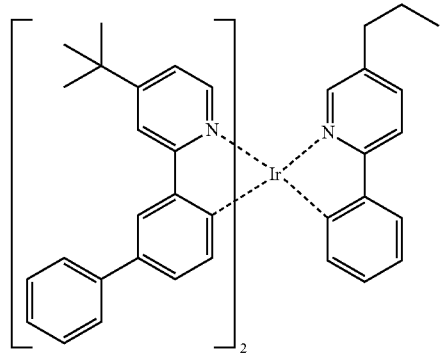
D-196
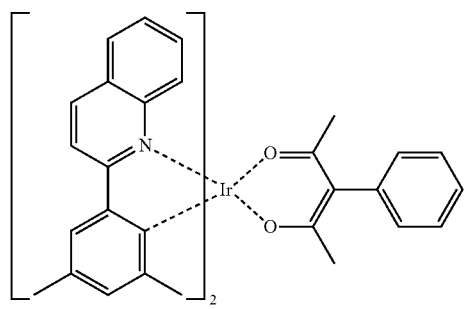

-continued
D-197
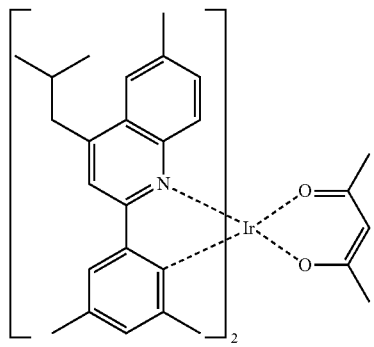
D-198
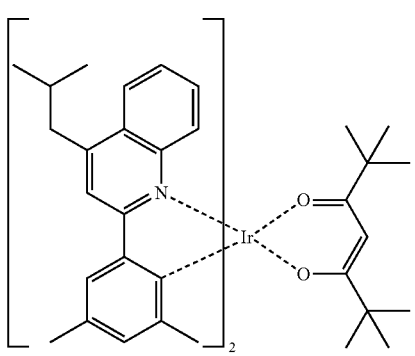
D-199
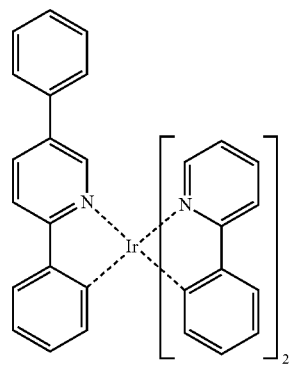
D-200
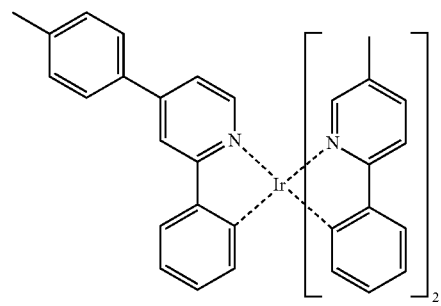
-continued
D-201
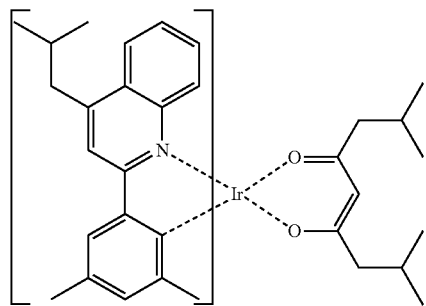
D-202
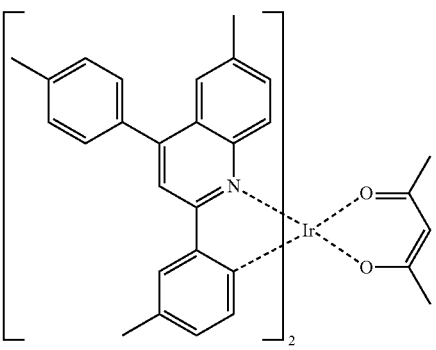
D-203
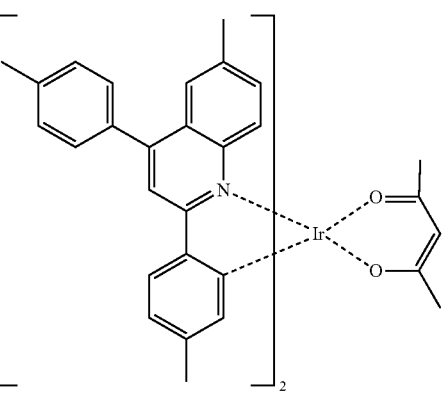
D-204
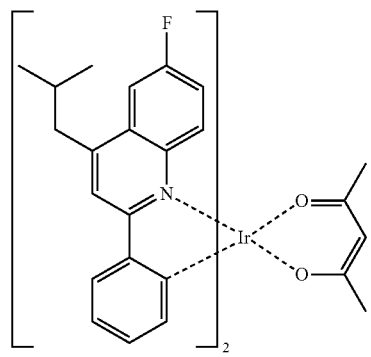

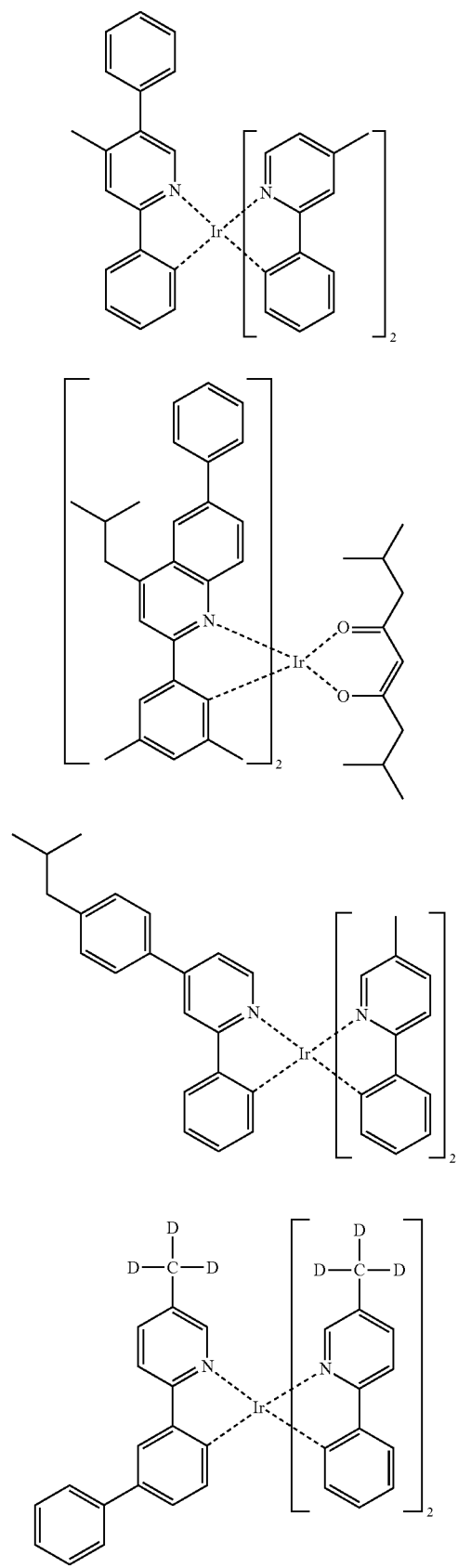

D-212

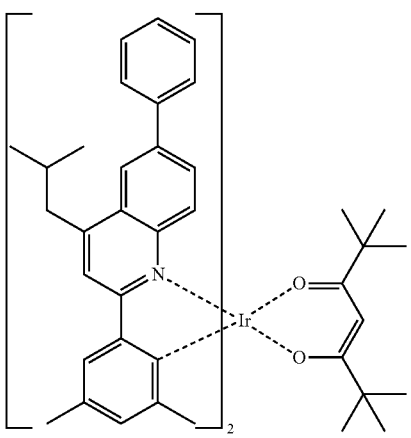

In another embodiment of the present invention, a composition for preparing an organic electroluminescent device is provided. The composition comprises the compound according to the present invention as a host material or a hole transport material.

In addition, the organic electroluminescent device according to the present invention comprises a first electrode; a second electrode; and at least one organic layer between the first and second electrodes. The organic layer comprises a light-emitting layer, and the light-emitting layer may comprise the composition for preparing the organic electroluminescent device according to the present invention.

The organic electroluminescent device according to the present invention may further comprise, in addition to the organic electroluminescent compound represented by formula 1, at least one compound selected from the group consisting of arylamine-based compounds and styrylarylamine-based compounds.

In the organic electroluminescent device according to the present invention, the organic layer may further comprise at least one metal selected from the group consisting of metals of Group 1, metals of Group 2, transition metals of the 4$^{th}$ period, transition metals of the 5$^{th}$ period, lanthanides and organic metals of d-transition elements of the Periodic Table, or at least one complex compound comprising said metal. The organic layer may further comprise a light-emitting layer and a charge generating layer.

In addition, the organic electroluminescent device according to the present invention may emit white light by further comprising at least one light-emitting layer which comprises a blue electroluminescent compound, a red electroluminescent compound or a green electroluminescent compound known in the field, besides the compound according to the present invention. Also, if necessary, a yellow or orange light-emitting layer can be comprised in the device.

According to the present invention, at least one layer (hereinafter, "a surface layer") is preferably placed on an inner surface(s) of one or both electrode(s); selected from a chalcogenide layer, a metal halide layer and a metal oxide layer. Specifically, a chalcogenide(includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, said chalcogenide includes $SiO_X(1 \leq X \leq 2)$, $AlO_X(1 \leq X \leq 1.5)$, SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

In the organic electroluminescent device according to the present invention, a mixed region of an electron transport compound and an reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge generating layer to prepare an electroluminescent device having two or more electroluminescent layers and emitting white light.

In order to form each layer of the organic electroluminescent device according to the present invention, dry film-forming methods such as vacuum evaporation, sputtering, plasma and ion plating methods, or wet film-forming methods such as spin coating, dip coating, and flow coating methods can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the organic electroluminescent compound, the preparation method of the compound, and the luminescent properties of the device will be explained in detail with reference to the following examples.

EXAMPLE 1: PREPARATION OF COMPOUND A-92

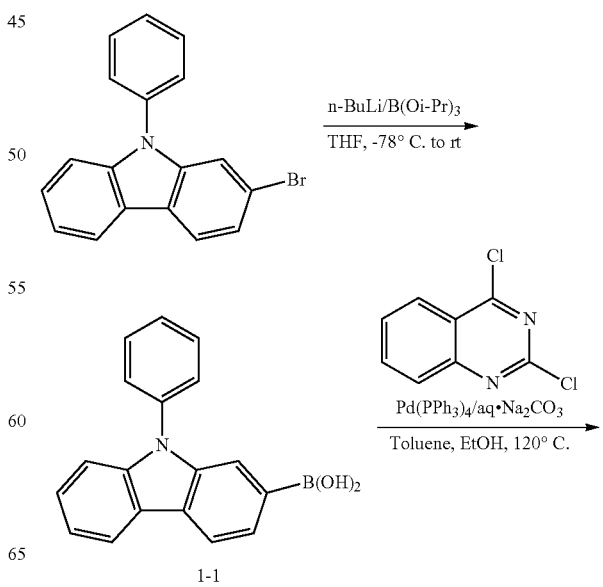

-continued

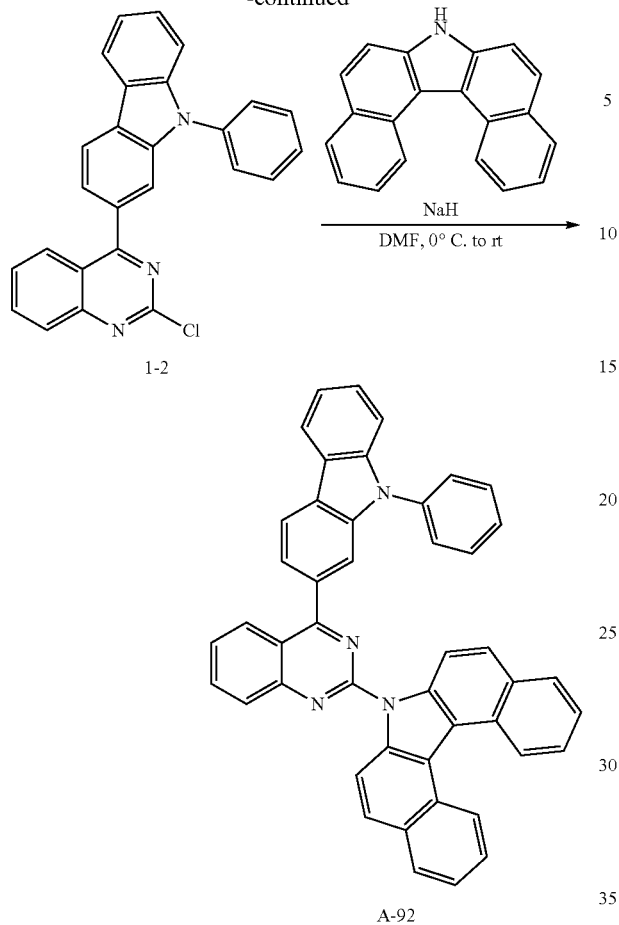

1-2

A-92

Preparation of Compound 1-1

After dissolving 2-bromo-9-phenyl-9H-carbazole (25 g, 77.59 mmol) in tetrahydrofuran (THF) 400 mL in a flask, n-BuLi (2.5 M) was slowly added dropwise to the mixture at −78° C. After stirring the mixture for 1 hour, triisopropyl borate was added dropwise to the mixture. After completing the reaction, an organic layer was extracted with ethyl acetate, and the remaining moisture was removed using magnesium sulfate. The residue was dried using a rotary evaporator to obtain compound 1-1 (15.5 g, 70%).

Preparation of Compound 1-2

After dissolving compound 1-1 (15.5 g, 53.98 mmol), 2,4-dichloroquinazoline (10.7 g, 53.98 mmol), and Pd(PPh₃)₄ (1.9 g, 1.62 mmol) in a mixture solvent of 2 M Na₂CO₃ 67 mL, toluene 270 mL, and ethanol 67 mL in a flask, the mixture was stirred under reflux at 120° C. for 5 hours. After completing the reaction, an organic layer was extracted with ethyl acetate, and the remaining moisture was removed using magnesium sulfate. The residue was dried and separated with column chromatography to obtain compound 1-2 (13.5 g, 61%).

Preparation of Compound A-92

After dissolving compound 1-2 (13.5 g, 33.26 mmol) and 7H-dibenzo[c,g]carbazole (8.1 g, 30.24 mmol) in N,N-dimethylformamide (DMF) 500 mL in a flask, NaH (1.8 g, 45.36 mmol, 60% in mineral oil) was added to the mixture. The mixture was stirred for 3 hours at room temperature, and methanol and distilled water were then added to the mixture. The obtained solid was filtered under reduced pressure and separated with column chromatography to obtain compound A-92 (11 g, 55%).

|  | MW | UV | PL | M.P |
|---|---|---|---|---|
| A-92 | 636.74 | 408 nm | 545 nm | 263° C. |

EXAMPLE 2: PREPARATION OF COMPOUND A-148

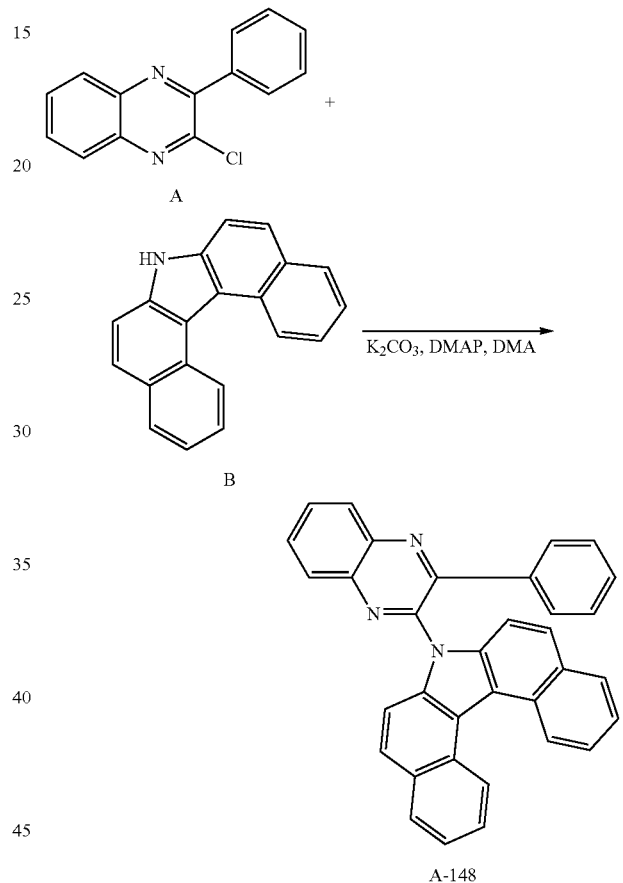

A-148

Preparation of Compound A-148

After dissolving compound A (11 g, 44.89 mmol), 7H-dibenzo[c,g]carbazole (10 g, 37.40 mmol), K₂CO₃ (5.1 g, 37.40 mmol), and dimethylaminopyridine (DMAP) (2.2 g, 18.70 mmol) in N,N-dimethylacetamide (DMA) 200 mL in a flask, the mixture was stirred under reflux at 220° C. for 5 hours. After completing the reaction, an organic layer was extracted with ethyl acetate, and the remaining moisture was removed using magnesium sulfate. The residue was dried and separated with column chromatography to obtain compound A-148 (3.2 g, 18%).

|  | MW | UV | PL | M.P |
|---|---|---|---|---|
| A-148 | 471.55 | 413 nm | 539 nm | 255.6° C. |

EXAMPLE 3: PREPARATION OF COMPOUND A-94

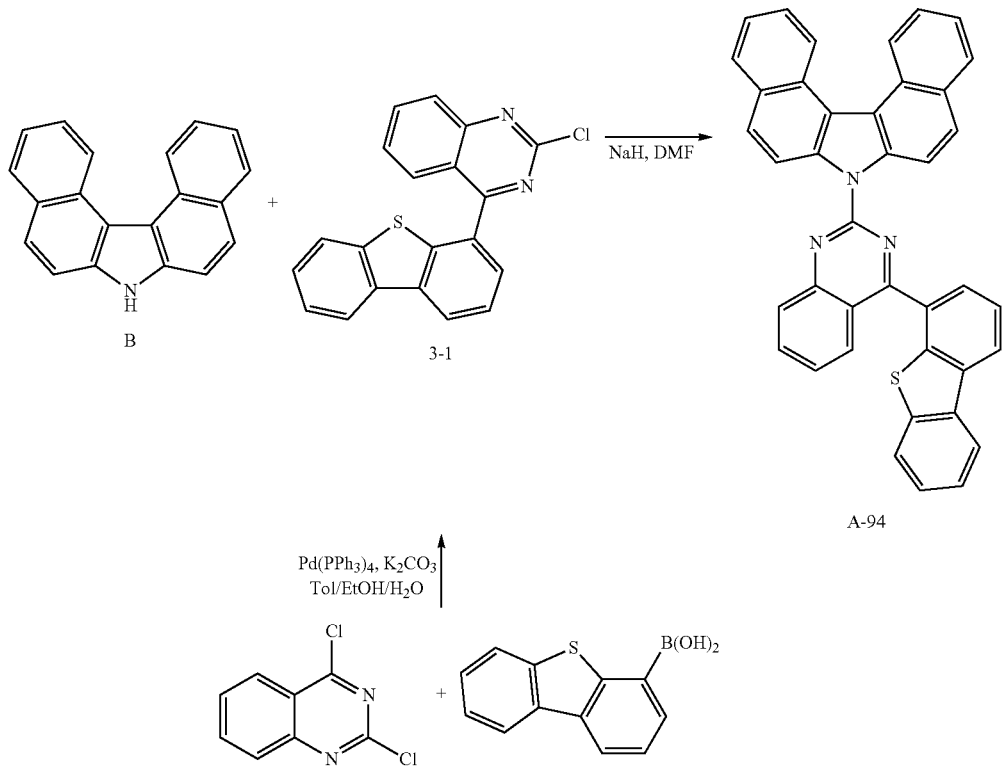

Preparation of Compound 3-1

After dissolving 2,4-chloroquinazoline (70 g, 306.9 mmol), dibenzothiophen-4-yl boronic acid (61 g, 306.9 mmol), and Pd(PPh$_3$)$_4$ (17.7 g, 15.34 mmol) in a mixture solvent of 2 M K$_2$CO$_3$ aqueous solution 300 mL, toluene 1000 mL, and ethanol 300 mL in a flask, the mixture was stirred under reflux at 120° C. for 5 hours. After completing the reaction, an organic layer was extracted with ethyl acetate, and the remaining moisture was removed using magnesium sulfate. The residue was dried and separated with column chromatography to obtain compound 3-1 (77.7 g, 73%).

Preparation of Compound A-94

After dissolving compound B (7H-dibenzo[c,g]carbazole) (10 g, 37.4 mmol) and compound 3-1 (14.3 g, 41.15 mmol) in DMF 200 mL in a flask, NaH (1.8 g, 44.88 mmol, 60% in mineral oil) was added to the mixture. The mixture was stirred at 150° C. for 4 hours, and methanol and distilled water were then added to the mixture. The obtained solid was filtered under reduced pressure and separated with column chromatography to obtain compound A-94 (13.3 g, 56%).

|  | MW | UV | PL | M.P |
| --- | --- | --- | --- | --- |
| A-94 | 577.7 | 418 nm | 577 nm | 272.3° C. |

EXAMPLE 4: PREPARATION OF COMPOUND A-23

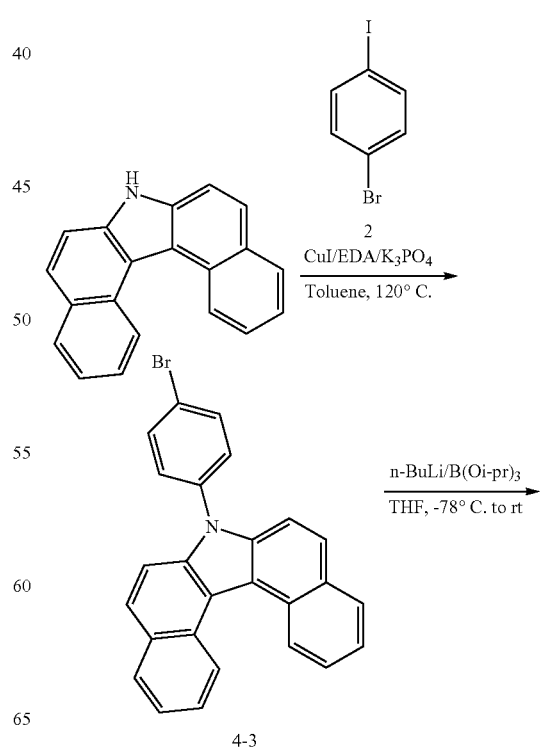

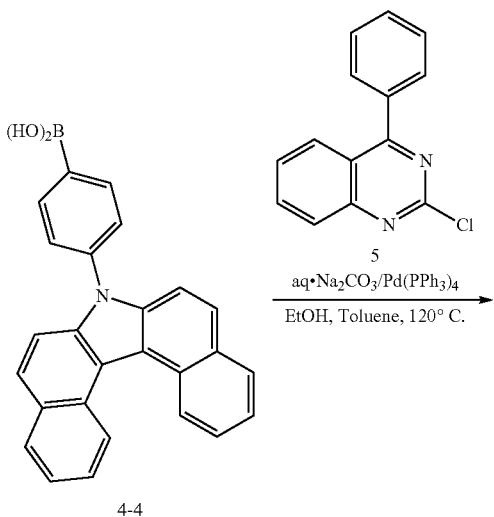

4-4

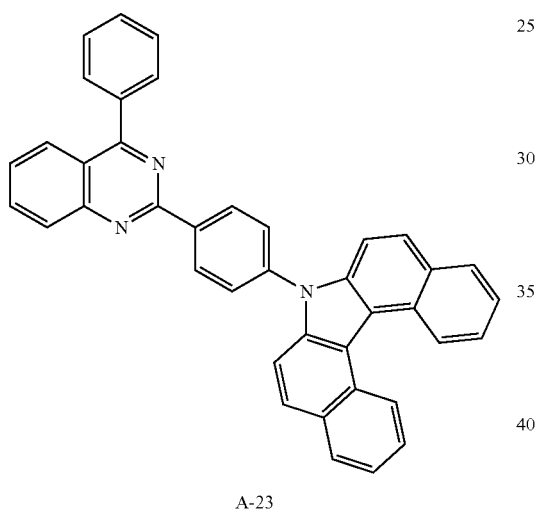

A-23

Preparation of Compound 4-3

After introducing 7H-dibenzo[c,g]carbazole (10 g, 37.41 mmol), 1-bromo-4-iodobenzene (21 g, 74.82 mmol), copper (I) iodide (3.6 g, 18.71 mmol), potassium phosphate (20 g, 93.53 mmol), ethylenediamine (2.5 mL, 37.41 mmol), and toluene 200 mL in a reaction container, the mixture was stirred under reflux for 5 hours. After completing the reaction, the mixture was washed with distilled water and extracted with ethyl acetate. The obtained organic layer was dried with magnesium sulfate, the solvent was removed using a rotary evaporator, and the residue was purified with column chromatography to obtain compound 4-3 (11.4 g, 72%).

Preparation of Compound 4-4

After introducing compound 4-3 (11.4 g, 26.99 mmol) and tetrahydrofuran 210 mL in a reaction container, the mixture was subjected to nitrogen atmosphere and cooled to −78° C. N-BuLi (16 mL, 2.5 M, 40.49 mmol) was slowly added dropwise to the mixture. After stirring the mixture for 1 hour at −78° C., triisopropyl borate (9.3 mL, 40.49 mmol) was slowly added dropwise to the mixture. After completing the reaction, ammonium chloride aqueous solution was added to the mixture. Next, the mixture was washed with distilled water and extracted with ethyl acetate. The obtained organic layer was dried with magnesium sulfate, the solvent was removed using a rotary evaporator, and the residue was purified with column chromatography to obtain compound 4-4 (8.3 g, 79%).

Preparation of Compound A-23

After introducing compound 4-4 (8.3 g, 21.43 mmol), 2-chloro-4-phenylquinazoline (4.3 g, 17.86 mmol), tetrakistriphenylphosphine palladium (0.6 g, 0.54 mmol), sodium carbonate (4.7 g, 44.65 mmol), and a mixture solvent of toluene 90 mL, ethanol 22 mL, and distilled water 22 mL in a reaction container, the mixture was stirred at 120° C. for 5 hours. After completing the reaction, the mixture was washed with distilled water and extracted with ethyl acetate. The obtained organic layer was dried with magnesium sulfate, the solvent was removed using a rotary evaporator, and the residue was purified with column chromatography to obtain compound A-23 (4.5 g, 46%).

|      | MW     | UV     | PL     | M.P    |
|------|--------|--------|--------|--------|
| A-23 | 547.65 | 390 nm | 437 nm | 232° C. |

EXAMPLE 5: PREPARATION OF COMPOUND A-1

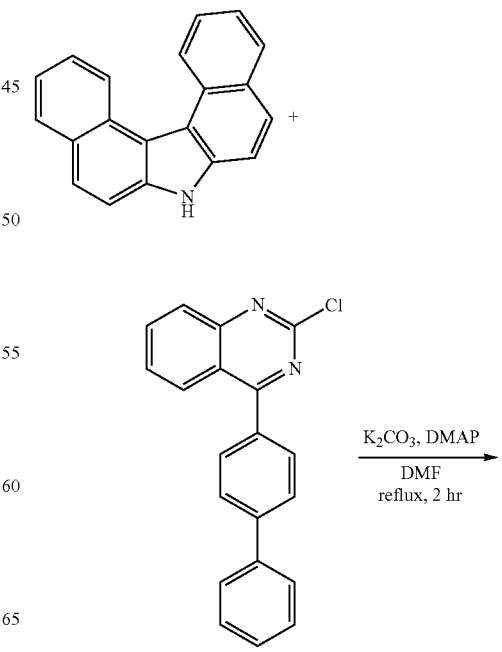

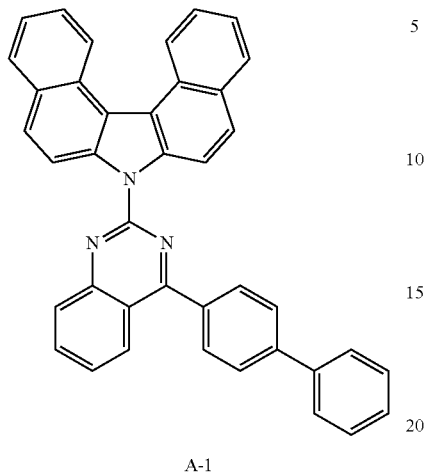

A-1

Preparation of Compound A-148

After introducing 7H-dibenzo[c,g]carbazole (5.00 g, 18.70 mmol), 4-([1,1'-biphenyl]-4-yl)-2-chloroquinazoline (7.11 g, 22.45 mmol), K$_2$CO$_3$ (2.58 g, 18.70 mmol), and DMAP (1.14 g, 9.35 mmol) in DMF 100 mL, the mixture was stirred under reflux for 2 hours. The mixture was then cooled to room temperature, reversely added dropwise to MeOH 400 mL, and filtered under reduced pressure to obtain an ocherous solid. The solid was was dissolved in CHCl$_3$ 140 mL under heat and filtered with silica. The filtrate was distilled under reduced pressure, solidified by adding methanol, and filtered under reduced pressure to obtain a lemon-colored solid. The solid was recrystallized with DMF to obtain compound A-1 (4.8 g, 46.9%).

|  | MW | UV | PL | M.P |
|---|---|---|---|---|
| A-1 | 547.65 | 431 nm | 558 nm | 231° C. |

EXAMPLE 6: PREPARATION OF COMPOUND A-6

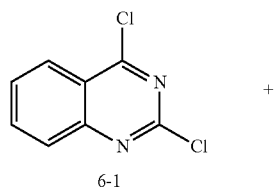

6-1

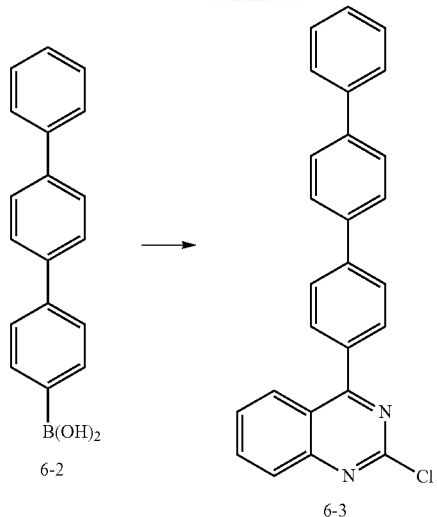

6-2

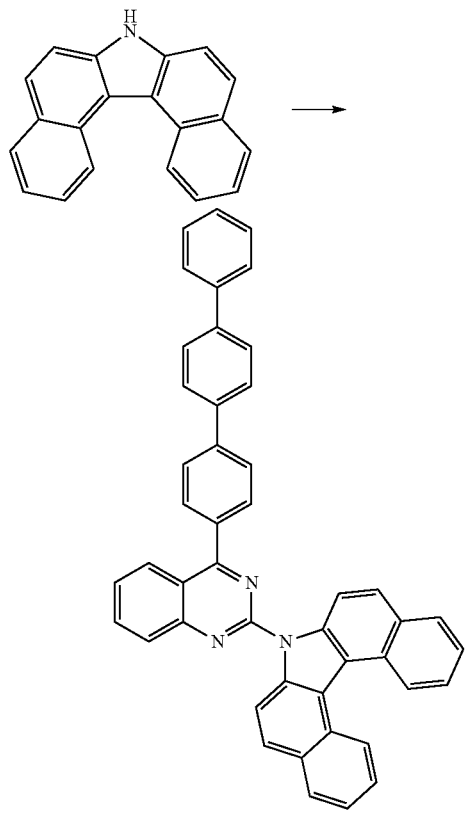

A-6

Preparation of Compound 6-3

After dissolving compound 6-1 (9.4 g, 47.42 mmol), compound 6-2 (13 g, 47.42 mmol), and Pd(PPh$_3$)$_4$ (1.6 g, 1.422 mmol) in a mixture solvent of 2 M Na$_2$CO$_3$ 120 mL, toluene 250 mL, and ethanol 120 mL in a flask, the mixture was stirred under reflux at 120° C. for 5 hours. After completing the reaction, an organic layer was extracted with ethyl acetate, and the remaining moisture was removed using magnesium sulfate. The residue was dried and separated with column chromatography to obtain compound 6-3 (7.5 g, 42%).

Preparation of Compound A-6

After dissolving compound 6-3 (7.5 g, 19.80 mmol), 7H-dibenzo[c,g]carbazole (4.3 g, 15.90 mmol), K$_2$CO$_3$ (2.2 g, 15.90 mmol), and DMAP (0.9 g, 7.950 mmol) in DMA 100 mL in a flask, the mixture was stirred under reflux at 220° C. for 5 hours. After completing the reaction, an organic layer was extracted with ethyl acetate, and the remaining moisture was removed using magnesium sulfate. The residue was dried and separated with column chromatography to obtain compound A-6 (5.8 g, 58%).

|     | MW     | UV     | PL     | M.P      |
| --- | ------ | ------ | ------ | -------- |
| A-6 | 623.73 | 354 nm | 557 nm | 269.3° C.|

EXAMPLE 7: PREPARATION OF COMPOUND A-3

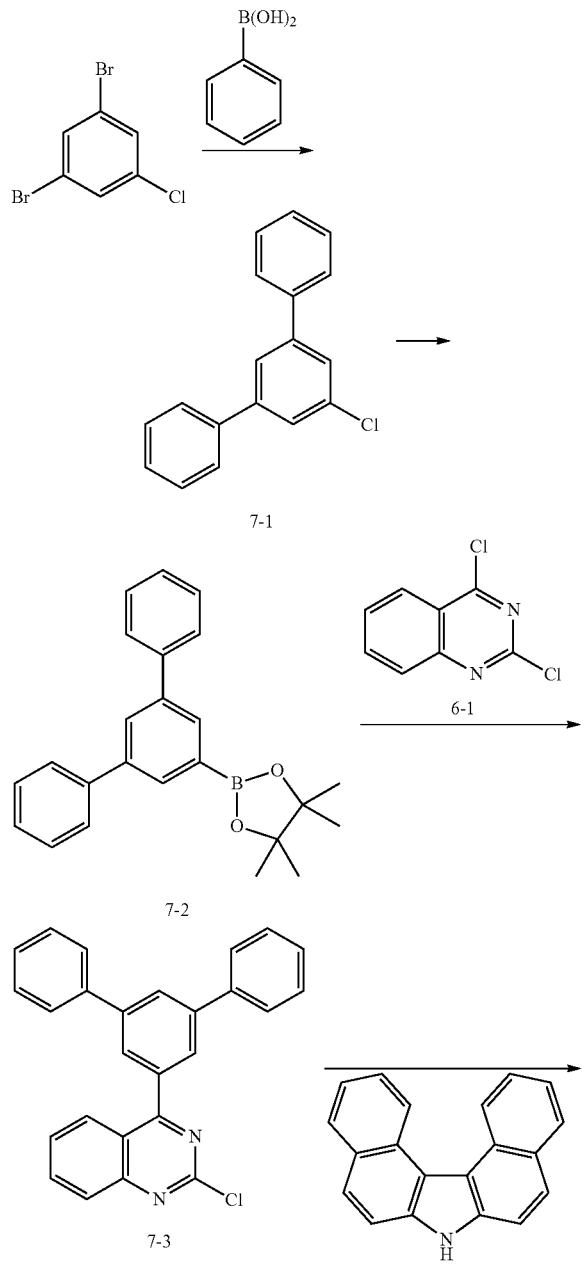

7-1

7-2

7-3

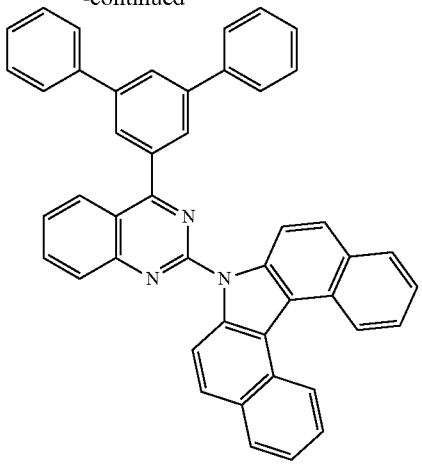

A-3

Preparation of Compound 7-1

After dissolving 1,3-dibromo-5-chlorobenzene (20 g, 73.98 mmol), phenyl boronic acid (22 g, 177.55 mmol), and Pd(PPh$_3$)$_4$ (4.3 g, 3.699 mmol) in a mixture solvent of 2 M K$_3$PO$_4$ aqueous solution 100 mL, toluene 400 mL, and 1,4-dioxane 100 mL in a flask, the mixture was stirred under reflux at 120° C. for 5 hours. After completing the reaction, an organic layer was extracted with ethyl acetate, and the remaining moisture was removed using magnesium sulfate. The residue was dried and separated with column chromatography to obtain compound 7-1 (23 g, 70%).

Preparation of Compound 7-2

After dissolving compound 7-1 (11 g, 44.89 mmol), diborane (33 g, 130.31 mmol), Pd$_2$(dba)$_3$ (2.4 g, 2.606 mmol), S-phos (3.6 g, 8.687 mmol), and KOAc (21.3 g, 271.17 mmol) in 1,4-dioxane 500 mL in a flask, the mixture was stirred under reflux at 120° C. for 5 hours. After completing the reaction, an organic layer was extracted with ethyl acetate, and the remaining moisture was removed using magnesium sulfate. The residue was dried and separated with column chromatography to obtain compound 7-2 (20 g, 67%).

Preparation of Compound 7-3

After dissolving compound 6-1 (5.6 g, 28.06 mmol), compound 7-2 (10 g, 28.06 mmol), and Pd(PPh$_3$)$_4$ (1.6 g, 1.403 mmol) in a mixture solvent of 2 M Na$_2$CO$_3$ aqueous solution 75 mL and toluene 150 mL in a flask, the mixture was stirred under reflux at 120° C. for 5 hours. After completing the reaction, an organic layer was extracted with ethyl acetate, and the remaining moisture was removed using magnesium sulfate. The residue was dried and separated with column chromatography to obtain compound 7-3 (10 g, 91%).

Preparation of Compound A-3

After dissolving compound 7-3 (7.5 g, 19.30 mmol), 7H-dibenzo[c,g]carbazole (4.3 g, 16.08 mmol), K$_2$CO$_3$ (2.2 g, 1.608 mmol), and DMAP (0.9 g, 1.608 mmol) in DMA 100 mL in a flask, the mixture was stirred under reflux at 220° C. for 5 hours. After completing the reaction, an organic layer was extracted with ethyl acetate, and the remaining moisture was removed using magnesium sulfate. The residue was dried and separated with column chromatography to obtain compound A-3 (5.3 g, 54%).

| | MW | UV | PL | M.P |
|---|---|---|---|---|
| A-3 | 623.73 | 344 nm | 560 nm | 244.8° C. |

EXAMPLE 8: PREPARATION OF COMPOUND A-287

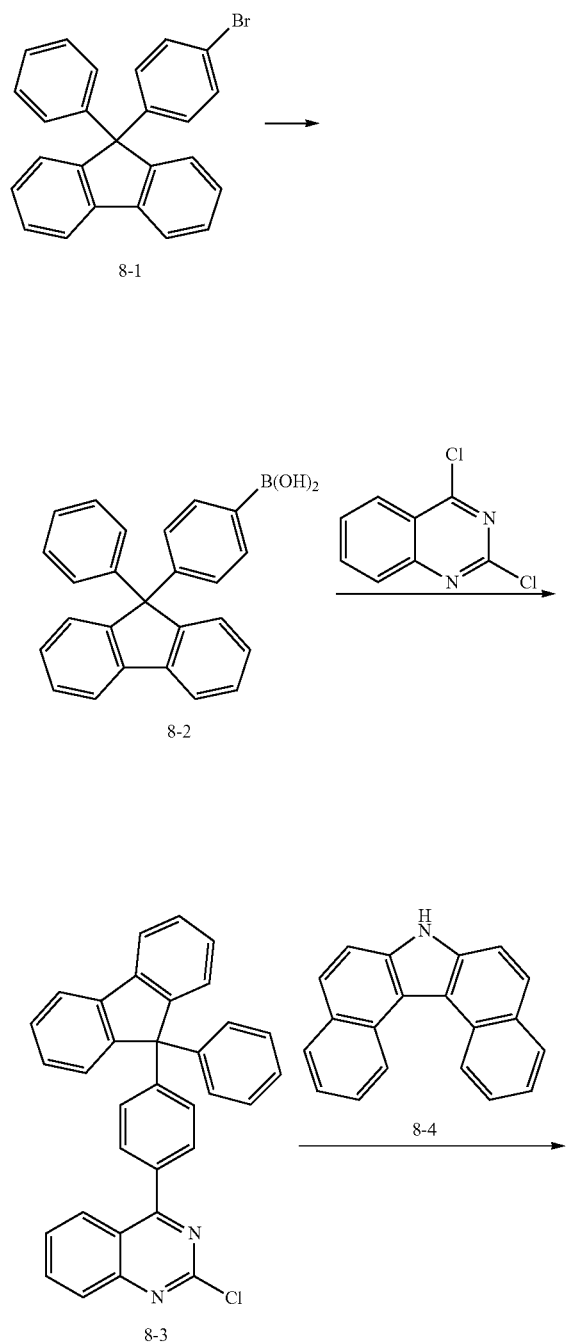

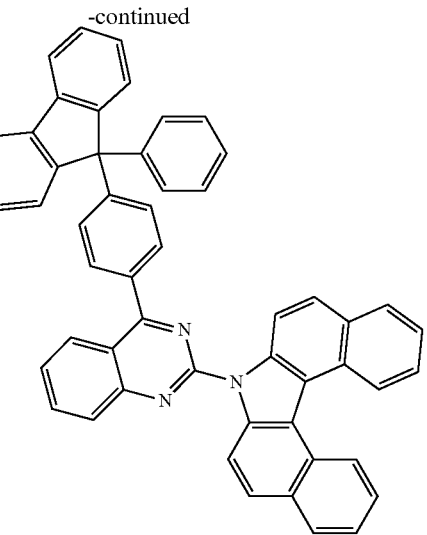

A-287

Preparation of Compound 8-2

After introducing compound 8-1 (20 g, 50.34 mmol) and tetrahydrofuran 250 mL in a reaction container, n-BuLi (30 mL, 75.51 mmol) was slowly added dropwise to the mixture at −78° C. After stirring the mixture for 1 hour, triisopropyl borate (8.5 mL, 75.51 mmol) was slowly added dropwise to the mixture. After completing the reaction, an organic layer was extracted with ethyl acetate, and the remaining moisture was removed using magnesium sulfate. The residue was dried and the solvent was removed using a rotary evaporator to obtain compound 8-2 (12.8 g, 70%).

Preparation of Compound 8-3

After introducing compound 8-2 (10 g, 27.61 mmol), 2,4-dichloroquinazoline (5.5 g, 27.61 mmol), tetrakistriphenylphosphine palladium (1 g, 0.83 mmol), sodium carbonate (7.3 g, 69.03 mmol), and a mixture solvent of toluene 160 mL, ethanol 40 mL, and distilled water 40 mL in a reaction container, the mixture was stirred at 120° C. for 4 hours. After completing the reaction, the mixture was washed with distilled water and extracted with ethyl acetate. The obtained organic layer was dried with magnesium sulfate, the solvent was removed using a rotary evaporator, and the residue was purified with column chromatography to obtain compound 8-3 (9.3 g, 70%).

Preparation of Compound A-287

After introducing compound 8-3 (9.3 g, 19.34 mmol), compound 8-4 (4.3 g, 16.11 mmol), potassium carbonate (2.2 g, 16.11 mmol), N,N-4-dimethylaminopyridine (1.0 g, 8.06 mmol), and N,N-dimethylformamide 81 mL in a reaction container, the mixture was stirred at 100° C. for 4 hours. After completing the reaction, the mixture was washed with distilled water and extracted with ethyl acetate. The obtained organic layer was dried with magnesium sulfate, the solvent was removed using a rotary evaporator, and the residue was purified with column chromatography to obtain compound A-287 (6 g, 52%).

| | MW | UV | PL | M.P |
|---|---|---|---|---|
| A-287 | 711.85 | 374 nm | 592 nm | 351° C. |

EXAMPLE 9: PREPARATION OF COMPOUND A-224

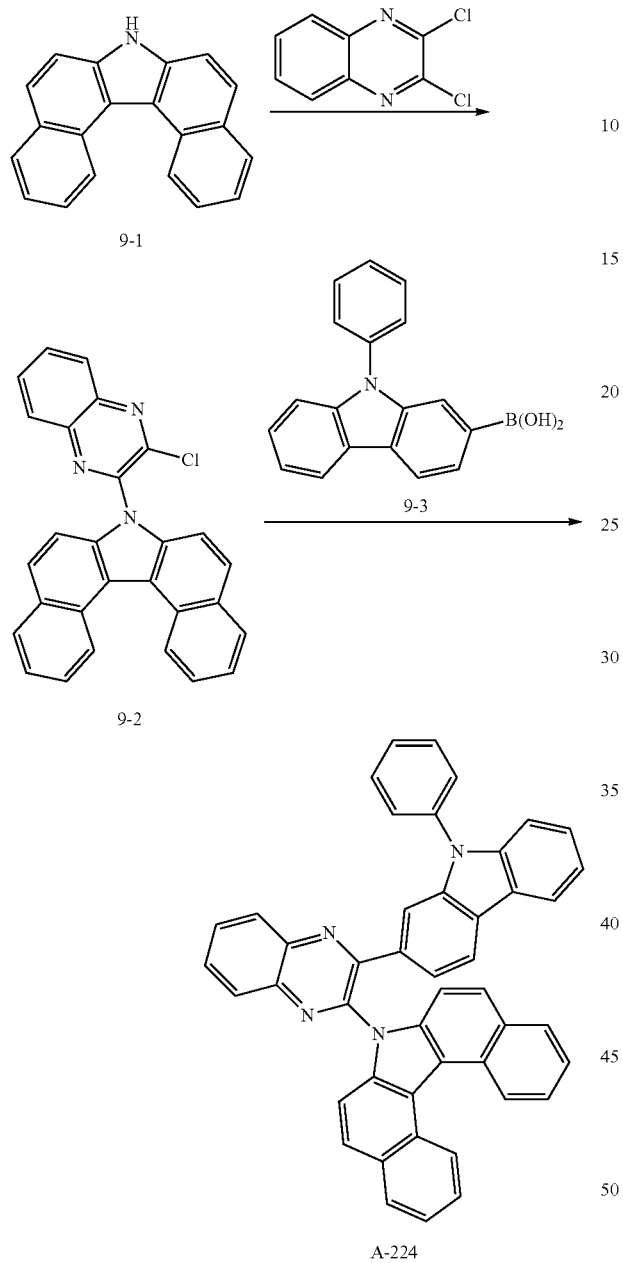

Preparation of Compound A-224

After introducing compound 9-2 (12.4 g, 28.84 mmol), compound 9-3 (10 g, 34.61 mmol), tetrakistriphenylphosphine palladium (1 g, 0.87 mmol), sodium carbonate (7.6 g, 72.10 mmol), and a mixture solvent of toluene 160 mL, ethanol 40 mL, and distilled water 40 mL in a reaction container, the mixture was stirred at 120° C. for 4 hours. After completing the reaction, the mixture was washed with distilled water and extracted with ethyl acetate. The obtained organic layer was dried with magnesium sulfate, the solvent was removed using a rotary evaporator, and the residue was purified with column chromatography to obtain compound A-224 (5 g, 27%).

|       | MW     | UV     | PL     | M.P     |
|-------|--------|--------|--------|---------|
| A-224 | 636.78 | 332 nm | 597 nm | 293° C. |

EXAMPLE 10: PREPARATION OF COMPOUND A-289

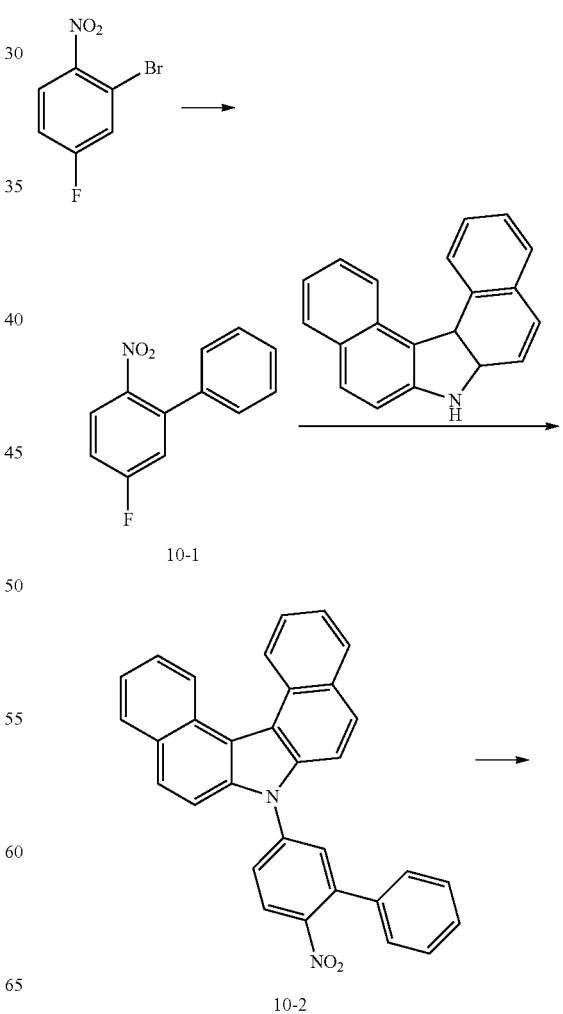

Preparation of Compound 9-2

After introducing compound 9-1 (11.5 g, 43.02 mmol) and DMF 220 mL in a reaction container, sodium hydride (2.6 g, 64.53 mmol) was slowly added dropwise to the mixture at 0° C. The mixture was stirred for 30 minutes, and 2,3-dichloroquinoxaline (10.3 g, 51.62 mmol) was then added dropwise to the mixture. The mixture was stirred for 3 hours at room temperature, and methanol and distilled water were then added to the mixture. The obtained solid was filtered under reduced pressure and separated with column chromatography to obtain compound 9-2 (12.4 g, 67%).

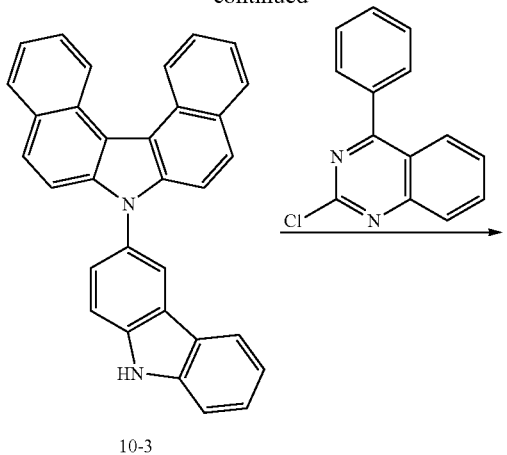

10-3

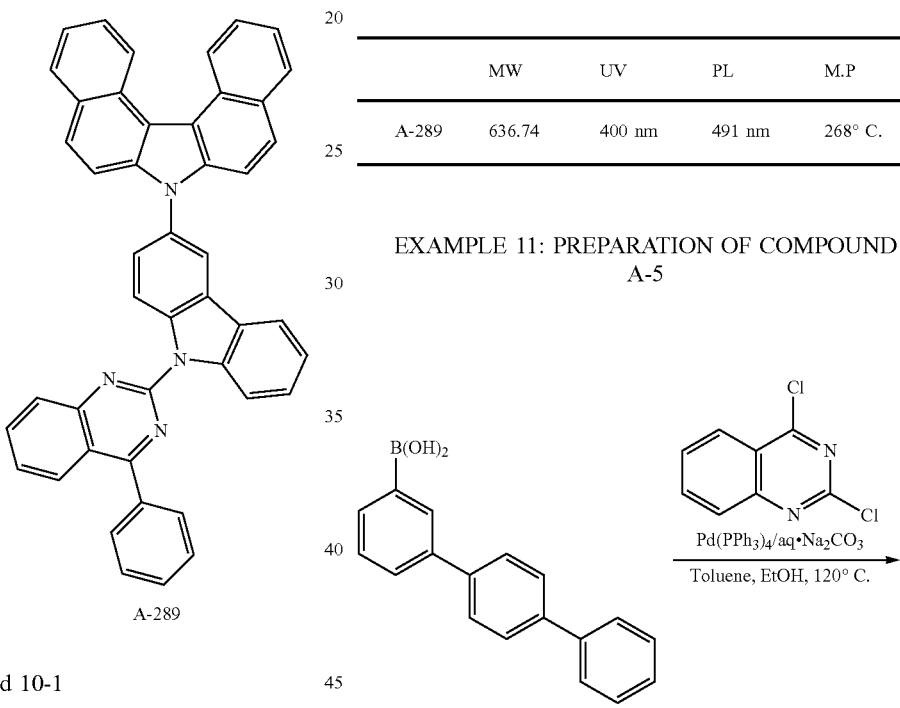

A-289

Preparation of Compound 10-1

After introducing 2-bromo-4-fluoro-1-nitrobenzene (50 g, 227.3 mmol), phenyl boronic acid (30.5 g, 250 mmol), Pd(PPh$_3$)$_4$ (13.1 g, 11.37 mmol), K$_2$CO$_3$ (62.8 g, 454.6 mmol), toluene 600 mL, EtOH 200 mL, and purified water 200 mL in a reaction container, the mixture was stirred under reflux for 6 hours. After cooling the mixture to room temperature, an organic layer was extracted with ethylacetate (EA) and distilled water. The obtained organic layer was distilled under reduced pressure, and the residue was separated with column chromatography to obtain compound 10-1 (49 g, 99%).

Preparation of Compound 10-2

After introducing 7H-dibenzo[c,g]carbazole (34.5 g, 128.9 mmol), compound 10-1 (28 g, 128.9 mmol), NaH (6.7 g, 167.6 mmol), and DMF 600 mL in a reaction container, the mixture was stirred at 75° C. for 2 hours. After cooling the mixture to room temperature, MeOH 1 L and purified water were added to the mixture and a solid was filtered. The filtrate was dried under reduced pressure to obtain compound 10-2 (52 g, 86.8%).

Preparation of Compound 10-3

After introducing compound 10-2 (52 g, 111.9 mmol), PPh$_3$ (88 g, 335.8 mmol), and 1,2-dichlorobenzene 500 mL in a reaction container, the mixture was stirred under reflux for 6 hours. 1,2-dichlorobenzene was then distilled, and the residue was separated with column chromatography to obtain compound 10-3 (39 g, 75.9%).

Preparation of Compound A-289

After introducing compound 10-3 (10 g, 23.12 mmol), 2-chloro-4-phenylquinazoline (6.1 g, 25.43 mmol), 4-dimethylaminopyridine (1.4 g, 11.56 mmol), K$_2$CO$_3$ (3.2 g, 23.12 mmol), and DMF 100 mL in a reaction container, the mixture was stirred under reflux for 3 hours, and cooled to room temperature. MeOH 200 mL and purified water were then added to the mixture and a solid was filtered. The dried solid was separated with column chromatography to obtain compound A-289 (5.5 g, 37.4%).

|  | MW | UV | PL | M.P |
|---|---|---|---|---|
| A-289 | 636.74 | 400 nm | 491 nm | 268° C. |

EXAMPLE 11: PREPARATION OF COMPOUND A-5

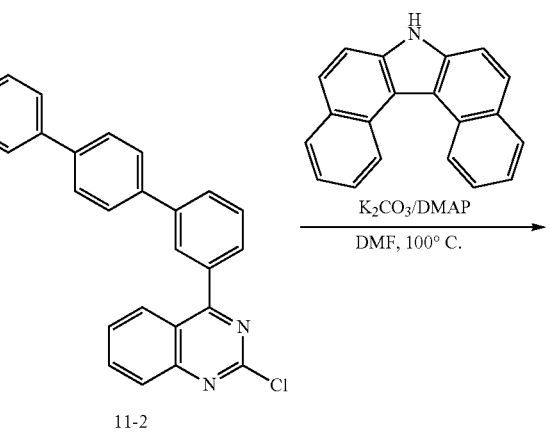

EXAMPLE 12: PREPARATION OF COMPOUND A-4

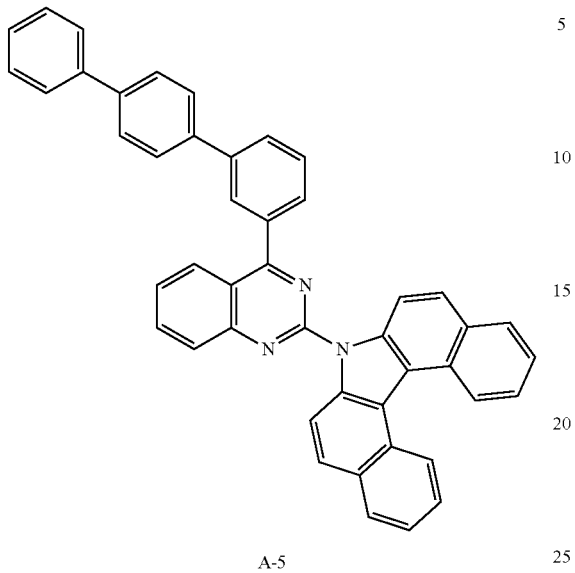

A-5

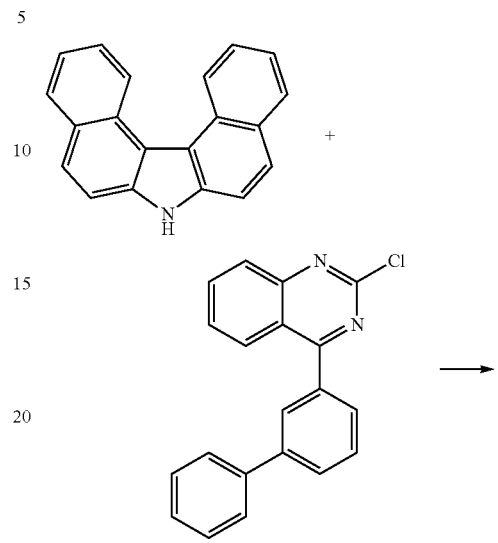

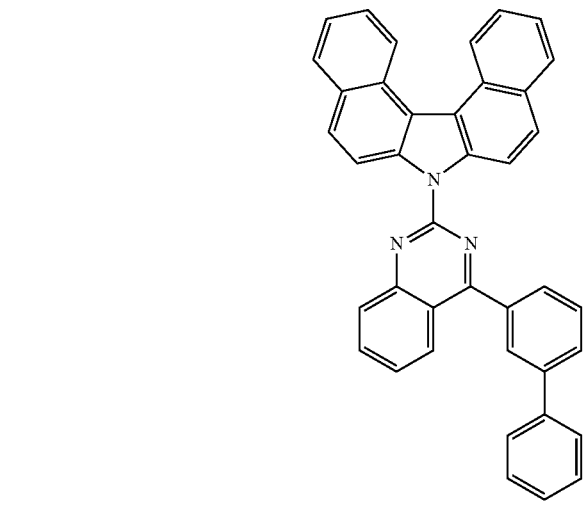

A-4

Preparation of Compound 11-2

After introducing compound 11-1 (7.6 g, 27.61 mmol), 2,4-dichloroquinazoline (5.5 g, 27.61 mmol), tetrakistriphenylphosphine palladium (1 g, 0.83 mmol), sodium carbonate (7.3 g, 69.03 mmol), toluene 160 mL, and ethanol 40 mL in a reaction container, distilled water 40 mL was added thereto, and the mixture was stirred at 120° C. for 4 hours. After completing the reaction, the mixture was washed with distilled water and extracted with ethyl acetate. The obtained organic layer was dried with magnesium sulfate, the solvent was removed using a rotary evaporator, and the residue was purified with column chromatography to obtain compound 11-2 (9.3 g, 86%).

Preparation of Compound A-5

After mixing compound 11-2 (2.6 g, 6.62 mmol), 7H-dibenzo[c,g]carbazole (1.7 g, 6.30 mmol), potassium carbonate (0.9 g, 6.30 mmol), and N,N-4-dimethylaminopyridine (0.4 g, 3.15 mmol) with N,N-dimethylformamide 32 mL, the mixture was stirred at 100° C. for 4 hours. After completing the reaction, the mixture was washed with distilled water and extracted with ethyl acetate. The obtained organic layer was dried with magnesium sulfate, the solvent was removed using a rotary evaporator, and the residue was purified with column chromatography to obtain compound A-5 (1.6 g, 41%).

After mixing 7H-dibenzo[c,g]carbazole (5.00 g, 18.70 mmol), 4-(biphenyl-3-yl)-2-chloroquinazoline (7.11 g, 22.45 mmol), $K_2CO_3$ (2.58 g, 18.70 mmol), and DMAP (1.14 g, 9.35 mmol) with DMF 100 mL, the mixture was stirred under reflux for 2 hours. The mixture was then cooled to room temperature, reversely added dropwise to MeOH 400 mL, and filtered under reduced pressure to obtain an ocherous solid. The dried solid was purified with column chromatography to obtain compound A-4 (7.2 g, 70%).

|     | MW | UV | PL | M.P |
| --- | --- | --- | --- | --- |
| A-5 | 623.74 | 392 nm | 557 nm | 198° C. |

|     | MW | UV | PL | M.P |
| --- | --- | --- | --- | --- |
| A-4 | 547.65 | 395 nm | 523 nm | 180° C. |

Device Example 1: Production of an OLED Device Using the Organic Electroluminescent Compound According to the Present Invention An OLED device was produced using the organic electroluminescent compound according to the present invention. A transparent electrode indium tin oxide (ITO) thin film (10 Ω/sq) on a glass substrate for an organic light-emitting diode (OLED) device (Geomatec, Japan) was subjected to an ultrasonic washing with trichloroethylene, acetone, ethanol, and distilled water, sequentially, and was then stored in isopropanol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby forming a first hole injection layer having a thickness of 80 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 10 nm on the second hole injection layer. Compound HT-2 was introduced into another cell of said vacuum vapor depositing apparatus, and was evaporated by applying an electric current to the cell, thereby forming a second hole transport layer having a thickness of 60 nm on the first hole transport layer. Thereafter, compound A-14 was introduced into one cell of the vacuum vapor depositing apparatus, as a host material, and compound D-96 was introduced into another cell as a dopant. The two materials were evaporated at different rates and were deposited in a doping amount of 3 wt % based on the total amount of the host and dopant to form a light-emitting layer having a thickness of 40 nm on the second hole transport layer. Compound ET-1 and compound EI-1 were then introduced into another two cells, evaporated at the rate of 1:1, and deposited in a doping amount of 50 wt % each to form an electron transport layer having a thickness of 30 nm on the light-emitting layer. Next, after depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced. All the materials used for producing the OLED device were purified by vacuum sublimation at $10^{-6}$ torr prior to use.

The produced OLED device showed a red emission having a luminance of 1800 cd/m² and a current density of 26.5 cd/A at 5.0 V. As for the lifespan characteristic, the time period for the luminance to decrease to 95% at 5,000 nit was 178 hours or more.

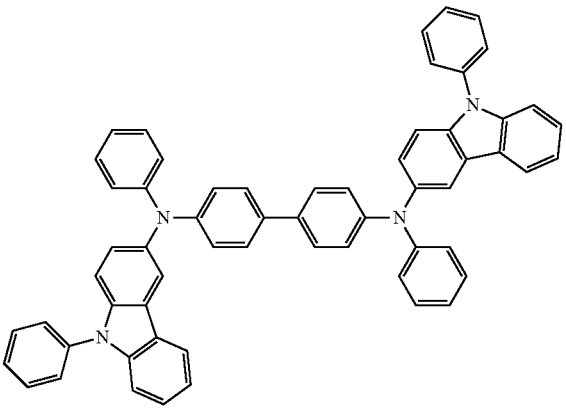

HI-1

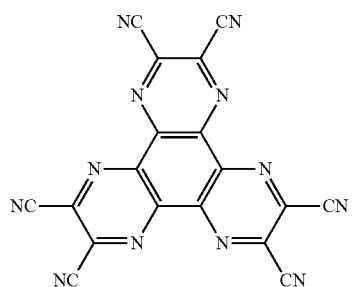

HI-2

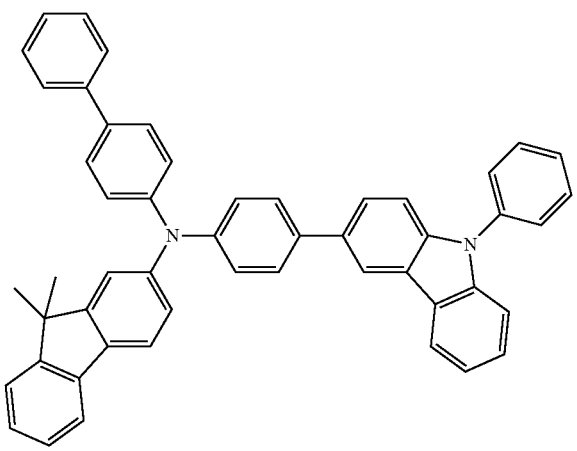

HT-1

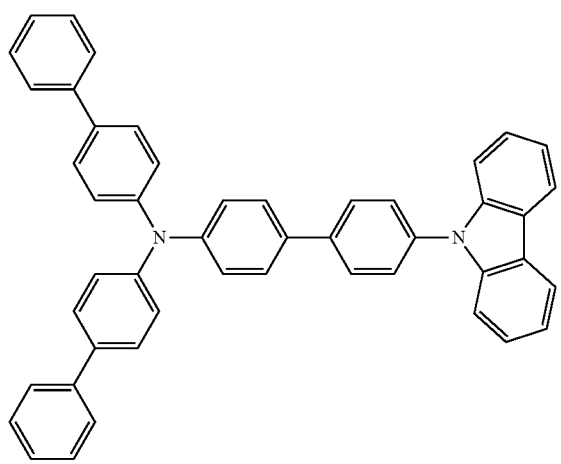

HT-2

-continued

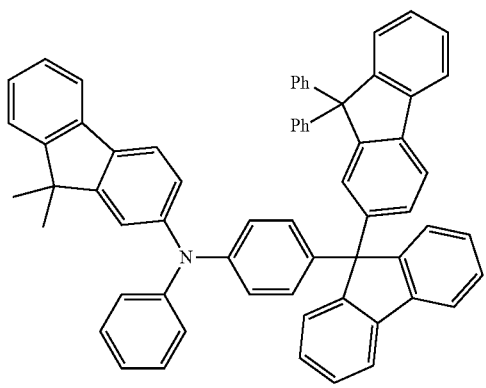

HT-3

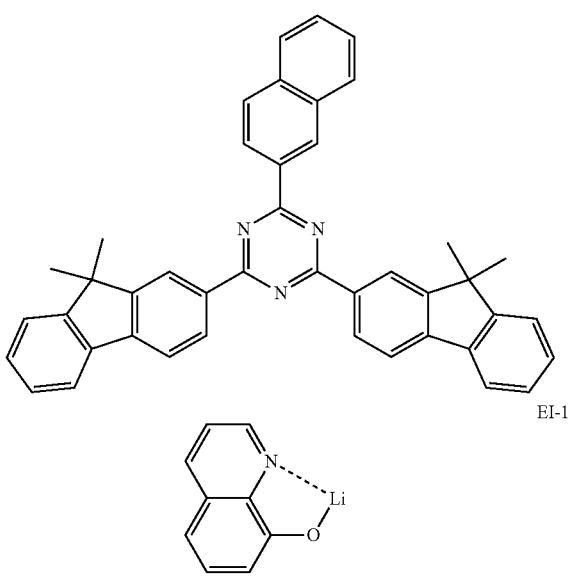

ET-1

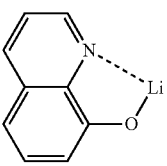

EI-1

Device Example 2: Production of an OLED Device Using the Organic Electroluminescent Compound According to the Present Invention An OLED device was produced in the same manner as in Device Example 1, except for using compound A-94 for the host as the light-emitting material.

The produced OLED device showed a red emission having a luminance of 1750 cd/m² and a current density of 25.5 cd/A at 6.0 V. As for the lifespan characteristic, the time period for the luminance to decrease to 95% at 5,000 nit was 153 hours or more.

Device Example 3: Production of an OLED Device Using the Organic Electroluminescent Compound According to the Present Invention An OLED device was produced in the same manner as in Device Example 1, except for using compound A-92 for the host as the light-emitting material.

The produced OLED device showed a red emission having a luminance of 1850 cd/m² and a current density of 25.8 cd/A at 4.6 V. As for the lifespan characteristic, the time period for the luminance to decrease to 95% at 5,000 nit was 170 hours or more.

Device Example 4: Production of an OLED Device Using the Organic Electroluminescent Compound According to the Present Invention An OLED device was produced in the same manner as in Device Example 1, except for using compound A-148 for the host as the light-emitting material.

The produced OLED device showed a red emission having a luminance of 1900 cd/m² and a current density of 28.6 cd/A at 5.4 V. As for the lifespan characteristic, the time period for the luminance to decrease to 95% at 5,000 nit was 68 hours or more.

Device Example 5: Production of an OLED Device Using the Organic Electroluminescent Compound According to the Present Invention An OLED device was produced in the same manner as in Device Example 1, except for using compound A-6 for the host as the light-emitting material.

The produced OLED device showed a red emission having a luminance of 1000 cd/m² and a current density of 27.5 cd/A at 5.0 V. As for the lifespan characteristic, the time period for the luminance to decrease to 95% at 5,000 nit was 170 hours or more.

Device Example 6: Production of an OLED Device Using the Organic Electroluminescent Compound According to the Present Invention An OLED device was produced in the same manner as in Device Example 1, except for using compound A-3 for the host as the light-emitting material.

The produced OLED device showed a red emission having a luminance of 1000 cd/m² and a current density of 26.3 cd/A at 4.1 V. As for the lifespan characteristic, the time period for the luminance to decrease to 95% at 5,000 nit was 236 hours or more.

Device Example 7: Production of an OLED Device Using the Organic Electroluminescent Compound According to the Present Invention An OLED device was produced in the same manner as in Device Example 1, except for using compound A-287 for the host as the light-emitting material.

The produced OLED device showed a red emission having a luminance of 1000 cd/m² and a current density of 26.4 cd/A at 5.1 V. As for the lifespan characteristic, the time period for the luminance to decrease to 95% at 5,000 nit was 66 hours or more.

Device Example 8: Production of an OLED Device Using the Organic Electroluminescent Compound According to the Present Invention An OLED device was produced in the same manner as in Device Example 1, except for using compound A-224 for the host as the light-emitting material.

The produced OLED device showed a red emission having a luminance of 1000 cd/m² and a current density of 28.4 cd/A at 4.2 V. As for the lifespan characteristic, the time period for the luminance to decrease to 95% at 5,000 nit was 74 hours or more.

Device Example 9: Production of an OLED Device Using the Organic Electroluminescent Compound According to the Present Invention An OLED device was produced in the same manner as in Device Example 1, except for using compound A-289 for the host as the light-emitting material, and compound HT-3 for the second hole transport layer.

The produced OLED device showed a red emission having a luminance of 1000 cd/m$^2$ and a current density of 28.9 cd/A at 4.1 V. As for the lifespan characteristic, the time period for the luminance to decrease to 95% at 5,000 nit was 53 hours or more.

Device Example 10: Production of an OLED Device Using the Organic Electroluminescent Compound According to the Present Invention An OLED device was produced in the same manner as in Device Example 1, except for using compound A-5 for the host as the light-emitting material, and compound HT-3 for the second hole transport layer.

The produced OLED device showed a red emission having a luminance of 1000 cd/m$^2$ and a current density of 30.3 cd/A at 4.9 V. As for the lifespan characteristic, the time period for the luminance to decrease to 95% at 5,000 nit was 306 hours or more.

Device Example 11: Production of an OLED Device Using the Organic Electroluminescent Compound According to the Present Invention An OLED device was produced in the same manner as in Device Example 1, except for using compound A-4 for the host as the light-emitting material, and compound HT-3 for the second hole transport layer.

The produced OLED device showed a red emission having a luminance of 1000 cd/m$^2$ and a current density of 29.9 cd/A at 4.4 V. As for the lifespan characteristic, the time period for the luminance to decrease to 95% at 5,000 nit was 300 hours or more.

Device Example 12: Production of an OLED Device Using the Organic Electroluminescent Compound According to the Present Invention An OLED device was produced in the same manner as in Device Example 1, except for using compound A-303 for the host as the light-emitting material, and compound HT-3 for the second hole transport layer.

The produced OLED device showed a red emission having a luminance of 1000 cd/m$^2$ and a current density of 29.4 cd/A at 4.6 V. As for the lifespan characteristic, the time period for the luminance to decrease to 95% at 5,000 nit was 323 hours or more.

Device Example 13: Production of an OLED Device Using the Organic Electroluminescent Compound According to the Present Invention An OLED device was produced in the same manner as in Device Example 1, except for using compound A-304 for the host as the light-emitting material, and compound HT-3 for the second hole transport layer.

The produced OLED device showed a red emission having a luminance of 1000 cd/m$^2$ and a current density of 29.4 cd/A at 5.1 V. As for the lifespan characteristic, the time period for the luminance to decrease to 95% at 5,000 nit was 320 hours or more.

Device Example 14: Production of an OLED Device Using the Organic Electroluminescent Compound According to the Present Invention An OLED device was produced in the same manner as in Device Example 1, except for using compound A-305 for the host as the light-emitting material, and compound HT-3 for the second hole transport layer.

The produced OLED device showed a red emission having a luminance of 1000 cd/m$^2$ and a current density of 28.5 cd/A at 3.9 V. As for the lifespan characteristic, the time period for the luminance to decrease to 95% at 5,000 nit was 172 hours or more.

Device Example 15: Production of an OLED Device Using the Organic Electroluminescent Compound According to the Present Invention An OLED device was produced in the same manner as in Device Example 1, except for using compound A-306 for the host as the light-emitting material, and compound HT-3 for the second hole transport layer.

The produced OLED device showed a red emission having a luminance of 1000 cd/m$^2$ and a current density of 30.5 cd/A at 4.5 V. As for the lifespan characteristic, the time period for the luminance to decrease to 95% at 5,000 nit was 294 hours or more.

Device Example 16: Production of an OLED Device Using the Organic Electroluminescent Compound According to the Present Invention An OLED device was produced in the same manner as in Device Example 1, except for using compound A-307 for the host as the light-emitting material, and compound HT-3 for the second hole transport layer.

The produced OLED device showed a red emission having a luminance of 1000 cd/m$^2$ and a current density of 29.0 cd/A at 4.2 V. As for the lifespan characteristic, the time period for the luminance to decrease to 95% at 5,000 nit was 319 hours or more.

Device Example 17: Production of an OLED Device Using the Organic Electroluminescent Compound According to the Present Invention An OLED device was produced in the same manner as in Device Example 1, except for using compound A-7 for the host as the light-emitting material, and compound HT-3 for the second hole transport layer.

The produced OLED device showed a red emission having a luminance of 1000 cd/m$^2$ and a current density of 29.8 cd/A at 4.5 V. As for the lifespan characteristic, the time period for the luminance to decrease to 95% at 5,000 nit was 328 hours or more.

Device Example 18: Production of an OLED Device Using the Organic Electroluminescent Compound According to the Present Invention An OLED device was produced in the same manner as in Device Example 1, except for using compound A-308 for the host as the light-emitting material, and compound HT-3 for the second hole transport layer.

The produced OLED device showed a red emission having a luminance of 1000 cd/m² and a current density of 29.9 cd/A at 4.9 V. As for the lifespan characteristic, the time period for the luminance to decrease to 95% at 5,000 nit was 93 hours or more.

Device Example 19: Production of an OLED Device Using the Organic Electroluminescent Compound According to the Present Invention An OLED device was produced in the same manner as in Device Example 1, except for using compound A-309 for the host as the light-emitting material, and compound HT-3 for the second hole transport layer.

The produced OLED device showed a red emission having a luminance of 1000 cd/m² and a current density of 29.8 cd/A at 5.3 V. As for the lifespan characteristic, the time period for the luminance to decrease to 95% at 5,000 nit was 52 hours or more.

Device Example 20: Production of an OLED Device Using the Organic Electroluminescent Compound According to the Present Invention An OLED device was produced in the same manner as in Device Example 1, except for using compound A-290 for the host as the light-emitting material, and compound HT-3 for the second hole transport layer.

The produced OLED device showed a red emission having a luminance of 1000 cd/m² and a current density of 30.7 cd/A at 4.0 V. As for the lifespan characteristic, the time period for the luminance to decrease to 95% at 5,000 nit was 99 hours or more.

Device Example 21: Production of an OLED Device Using the Organic Electroluminescent Compound According to the Present Invention An OLED device was produced in the same manner as in Device Example 1, except for using compound A-310 for the host as the light-emitting material, and compound HT-3 for the second hole transport layer.

The produced OLED device showed a red emission having a luminance of 1000 cd/m² and a current density of 29.6 cd/A at 4.4 V. As for the lifespan characteristic, the time period for the luminance to decrease to 95% at 5,000 nit was 51 hours or more.

Comparative Example 1: Production of an OLED Device Using a Conventional Organic Electroluminescent Compound An OLED device was produced in the same manner as in Device Example 1, except for using 4,4'-N,N'-dicarbazole-biphenyl for the host as the light-emitting material, and compound HT-3 for the second hole transport layer.

The produced OLED device showed a red emission having a luminance of 1000 cd/m² and a current density of 14.3 cd/A at 10 V. As for the lifespan characteristic, the time period for the luminance to decrease to 95% at 5,000 nit was less than 1 hour.

Comparative Example 2: Production of an OLED Device Using a Conventional Organic Electroluminescent Compound An OLED device was produced in the same manner as in Device Example 1, except for using the compound below for the host as the light-emitting material.

The produced OLED device showed a red emission having a luminance of 1500 cd/m² and a current density of 24.1 cd/A at 4.6 V. As for the lifespan characteristic, the time period for the luminance to decrease to 95% at 5,000 nit was less than 25 hours.

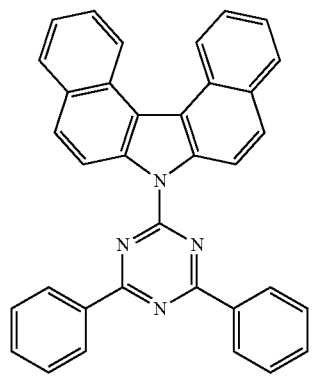 [SMILES: c1ccc(-c2nc(-c3ccccc3)nc(-n3c4ccc5ccccc5c4c4c5ccccc5ccc43)n2)cc1]

Comparative Example 3: Production of an OLED Device Using a Conventional Organic Electroluminescent Compound An OLED device was produced in the same manner as in Device Example 1, except for using the compound below for the host as the light-emitting material.

The produced OLED device showed a red emission having a luminance of 1500 cd/m² and a current density of 24.5 cd/A at 4.6 V. As for the lifespan characteristic, the time period for the luminance to decrease to 95% at 5,000 nit was less than 39 hours.

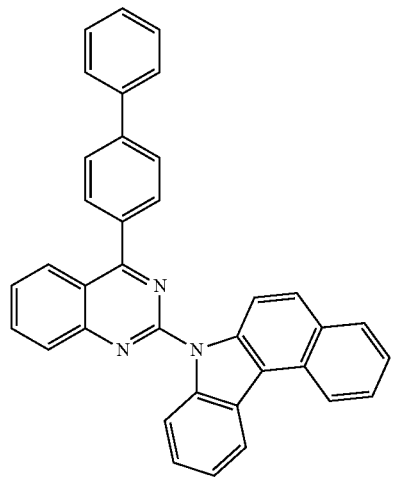 [SMILES: c1ccc(-c2ccc(-c3nc(-n4c5ccccc5c5c6ccccc6ccc54)nc4ccccc34)cc2)cc1]

As a result of using the compound according to the present invention and compounds which have similar structures as a phosphorescent red host material, it is verified that the compounds according to the present invention have higher efficiencies and better lifespan performances than the comparative compounds. The reason for this, i.e. the structure of the compound according to the present invention having more suitable HOMO (highest occupied molecular orbital) and LUMO (lowest unoccupied molecular orbital) energy levels for a phosphorescent red host material than the comparative compounds, is also confirmed by calculations.

It is verified that the luminous characteristics of the organic electroluminescent compound according to the present invention are superior to the conventional materials and provide longer operational lifespan. In addition, a device using the organic electroluminescent compound according to the present invention maintains luminous efficiency at high brightness when compared to that using a conventional organic electroluminescent compound so that it is trendier to the market requiring high resolution.

The invention claimed is:
1. An organic electroluminescent compound represented by the following formula 2:

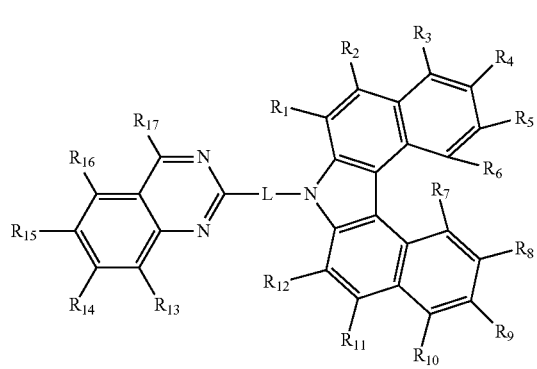

(2)

wherein

L represents a single bond, a substituted or unsubstituted (C6-C30)arylene, or a substituted or unsubstituted 3- to 30-membered heteroarylene;

$R_1$ to $R_{17}$ each independently represent hydrogen, deuterium, a substituted or unsubstituted (C6-C24)aryl, a substituted or unsubstituted 3- to 30-membered heteroaryl, a substituted or unsubstituted mono- or di-(C6-C30)arylamino, or a substituted or unsubstituted (C1-C30)alkyl(C6-C30)arylamino; or are linked to an adjacent substituent(s) to form a substituted or unsubstituted, mono- or polycyclic (C3-C30) alicyclic or aromatic ring, whose carbon atom(s) may be replaced with at least one hetero atom selected from nitrogen, oxygen, and sulfur; and the heteroaryl(ene) of the substituted or unsubstituted 3- to 30-membered heteroaryl(ene) contains at least one hetero atom selected from N, O, and S;

provided that where $R_1$ to $R_{16}$ is hydrogen and L is a single bond, $R_{17}$ is not 3-carbazole.

2. The organic electroluminescent compound according to claim 1, wherein the substituents of the substituted (C3-C30)cycloalkyl, the substituted (C6-C24) aryl(ene), the substituted 3- to 30-membered heteroaryl(ene), the substituted mono- or di-(C6-C30)arylamino, the substituted (C1-C30) alkyl(C6-C30)arylamino, and the substituted mono- or polycyclic (C3-C30) alicyclic or aromatic ring in L, and $R_1$ to $R_{17}$ each independently are at least one selected from the group consisting of deuterium, a halogen, a cyano, a carboxyl, a nitro, a hydroxyl, a (C1-C30)alkyl, a halo(C1-C30) alkyl, a (C2-C30)alkenyl, a (C2-C30)alkynyl, a (C1-C30) alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 5- to 30-membered heteroaryl unsubstituted or substituted with a (C6-C30)aryl, a (C6-C30)aryl unsubstituted or substituted with a 5- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, adi(C6-C30)arylboronyl, a di(C1-C30)alkylboronyl, a (C1-C30) alkyl(C6-C30)arylboronyl, a (C6-C30)aryl(C1-C30)alkyl, and a (C1-C30)alkyl(C6-C30)aryl.

3. The organic electroluminescent compound according to claim 1, wherein L represents a single bond, a substituted or unsubstituted (C6-C12)arylene, or a substituted or unsubstituted 3- to 20-membered heteroarylene;

$R_1$ to $R_{17}$ each independently represent hydrogen, a substituted or unsubstituted (C6-C)aryl, or a substituted or unsubstituted 3- to 20-membered heteroaryl; or are linked to an adjacent substituent(s) to form a substituted or unsubstituted, mono- or polycyclic (C3-C20) alicyclic or aromatic ring, whose carbon atom(s) may be replaced with at least one hetero atom selected from nitrogen, oxygen, and sulfur.

4. The organic electroluminescent compound according to claim 1, wherein L represents a single bond, an unsubstituted (C6-C12)arylene or a 3- to 20-membered heteroarylene unsubstituted or substituted with a (C6-C12)aryl;

$R_1$ to $R_{17}$ each independently represent hydrogen, a (C6-C)aryl unsubstituted or substituted with a (C6-C20)aryl (C1-C6)alkyl or a (C6-C)aryl, or a 3- to 20-membered heteroaryl unsubstituted or substituted with a (C6-C12) aryl; or are linked to an adjacent substituent(s) to form a mono- or polycyclic (C3-C20) aromatic ring unsubstituted or substituted with a (C6-C12)aryl, whose carbon atom(s) may be replaced with at least one hetero atom selected from nitrogen, oxygen, and sulfur.

5. The organic electroluminescent compound according to claim 1, wherein L represents a single bond, a substituted or unsubstituted phenyl, a substituted or unsubstituted biphenyl, a substituted or unsubstituted terphenyl, a substituted or unsubstituted naphthyl, a substituted or unsubstituted fluorenyl, a substituted or unsubstituted phenanthrenyl, a substituted or unsubstituted anthracenyl, a substituted or unsubstituted indenyl, a substituted or unsubstituted triphenylenyl, a substituted or unsubstituted pyrenyl, a substituted or unsubstituted tetracenyl, a substituted or unsubstituted perylenyl, a substituted or unsubstituted chrysenyl, a substituted or unsubstituted naphthacenyl, a substituted or unsubstituted fluoranthenyl, a substituted or unsubstituted carbazole, or a substituted or unsubstituted benzocarbazole.

6. The organic electroluminescent compound according to claim 1, wherein the compound represented by formula is selected from the group consisting of:

A-1
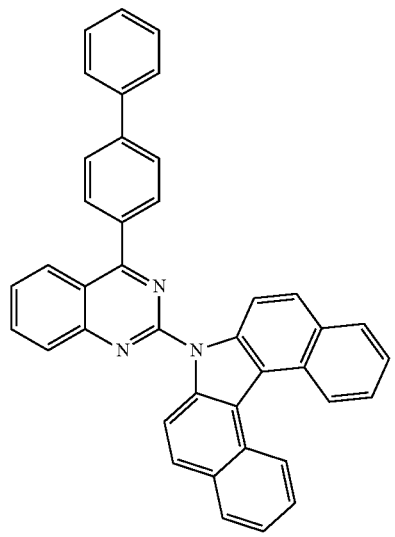
A-2
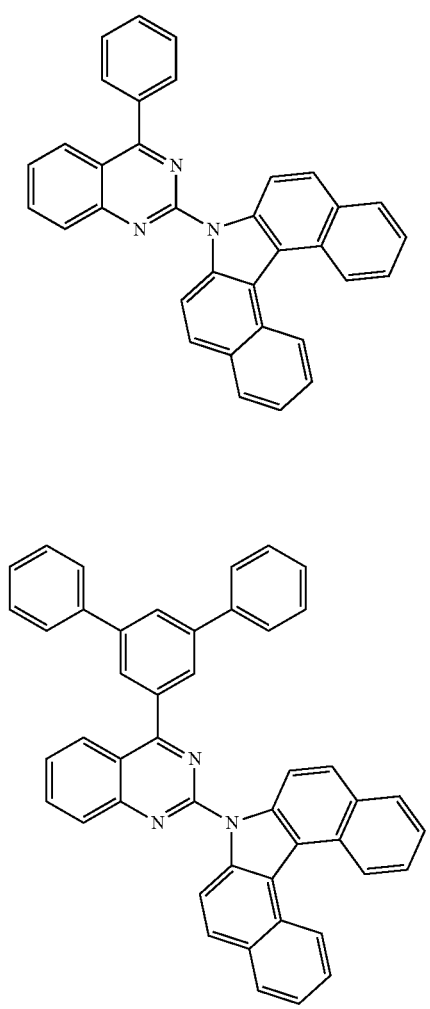
A-3
A-4
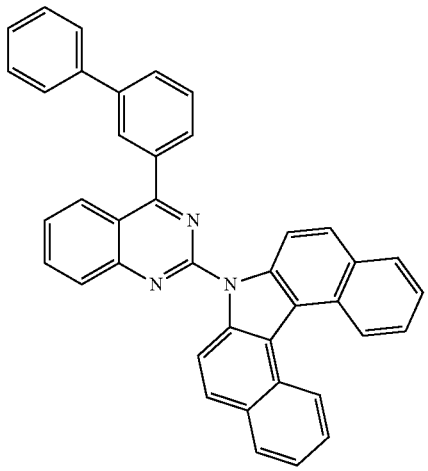
A-5
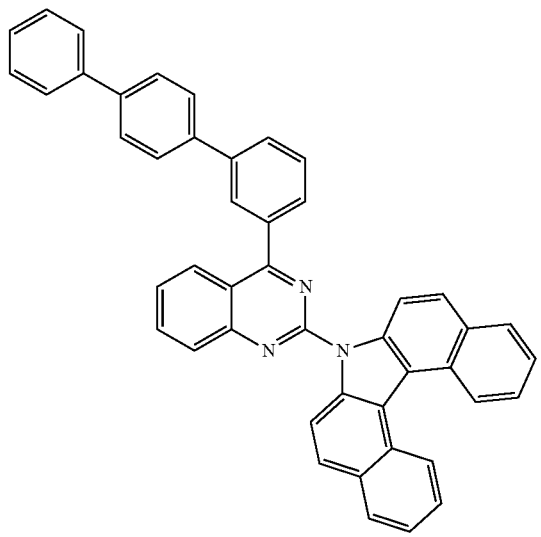
A-6
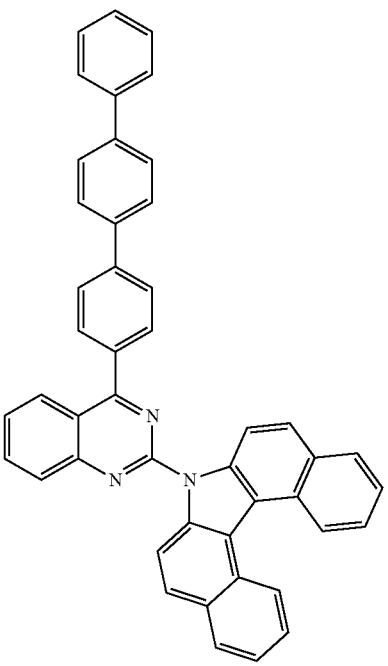

A-7
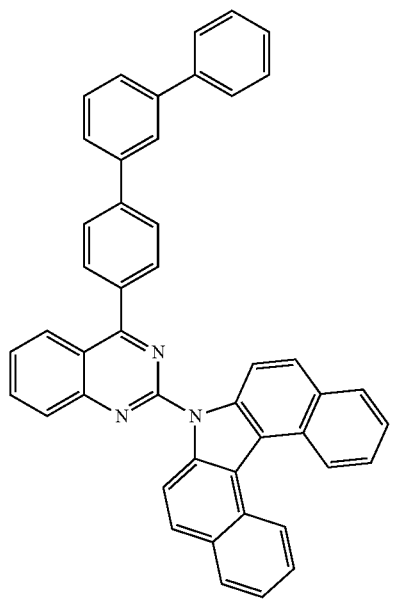
A-8
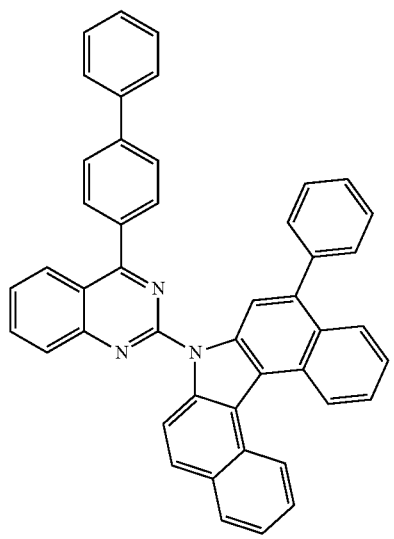
A-9
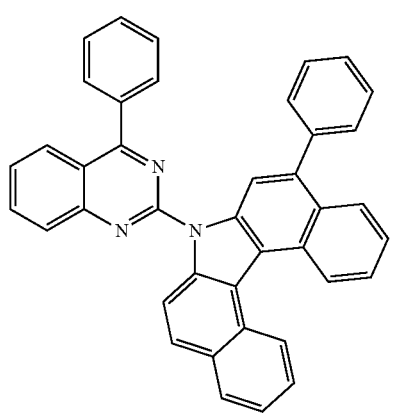
A-10
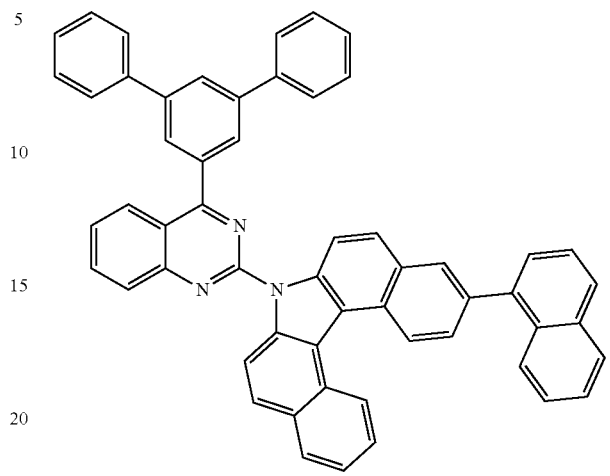
A-11
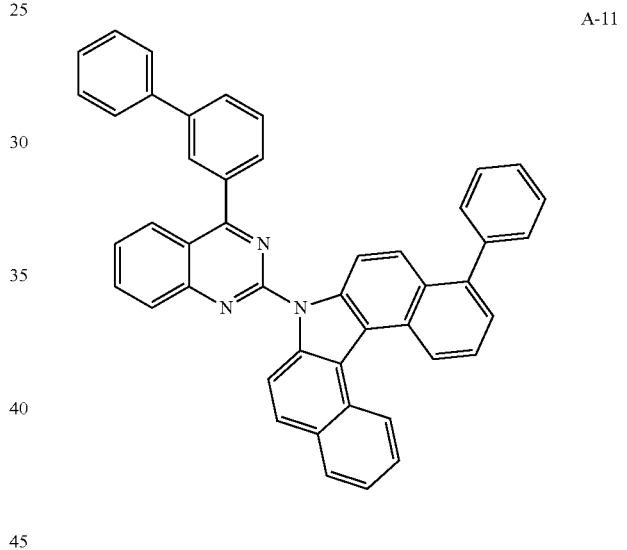
A-12
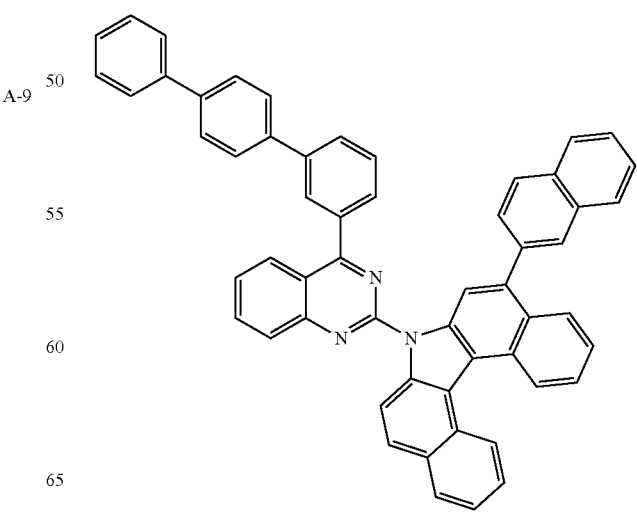

-continued
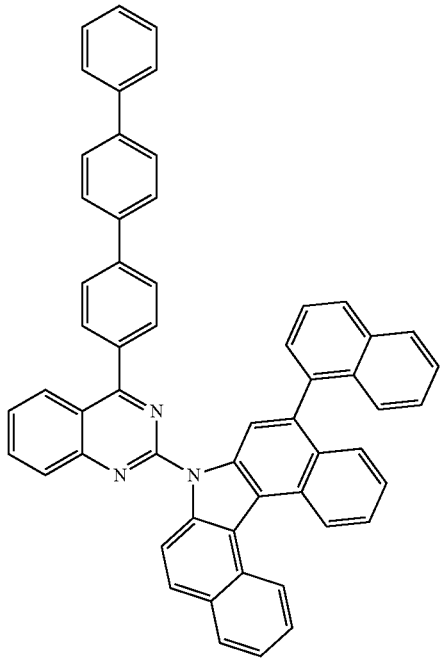
A-13
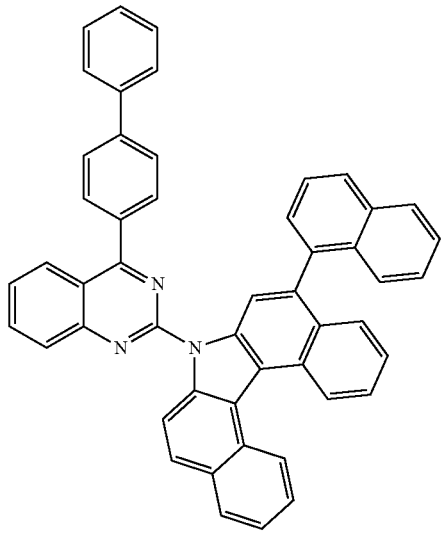
A-15
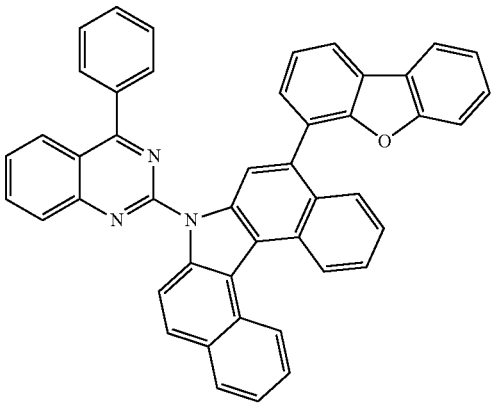
A-16
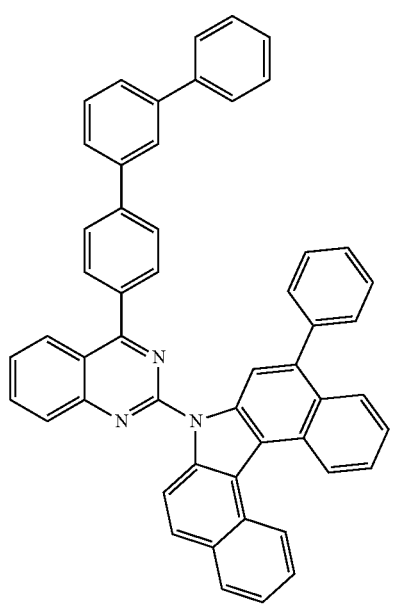
A-14
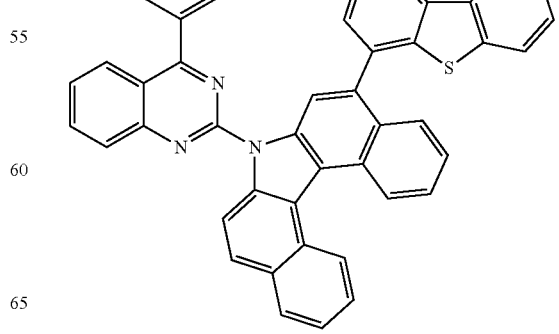
A-17

-continued
A-18
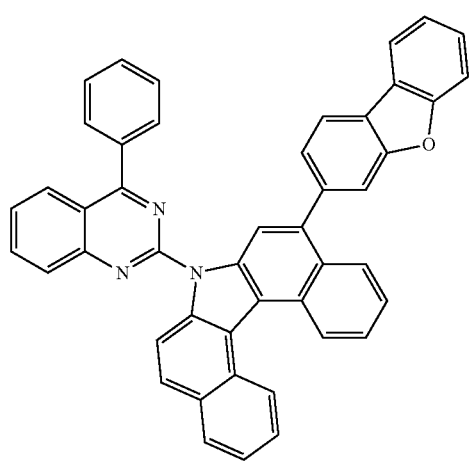
A-19
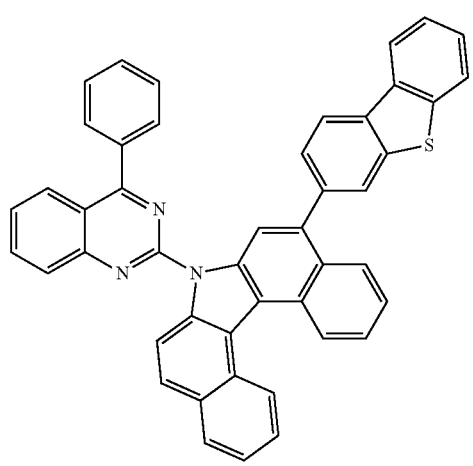
A-20
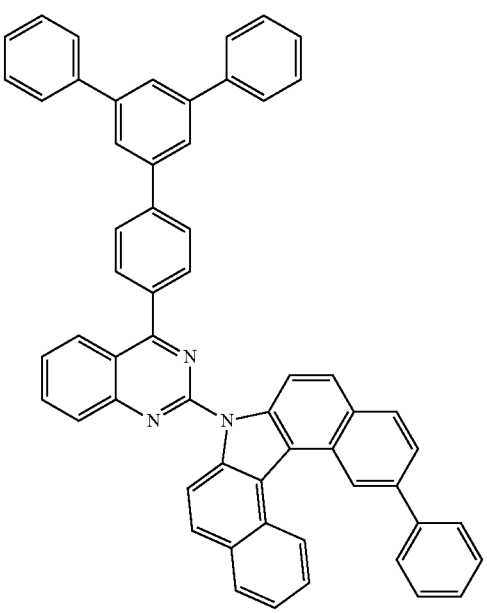
-continued
A-21
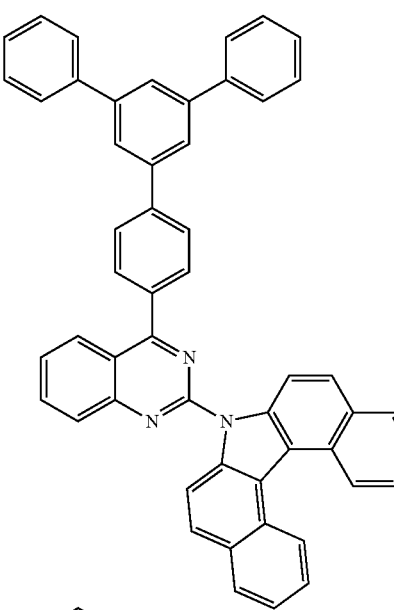
A-22
A-23
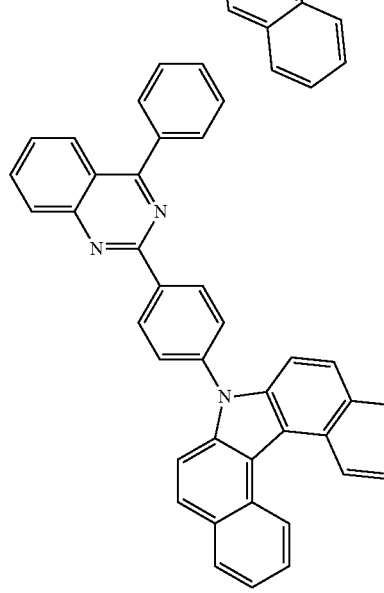

A-24
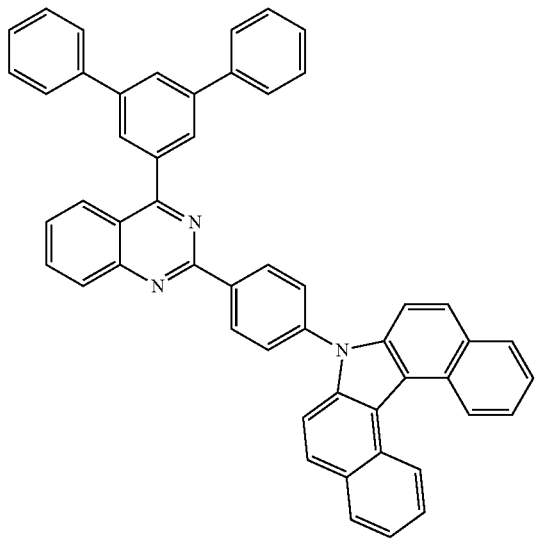
A-25
A-26
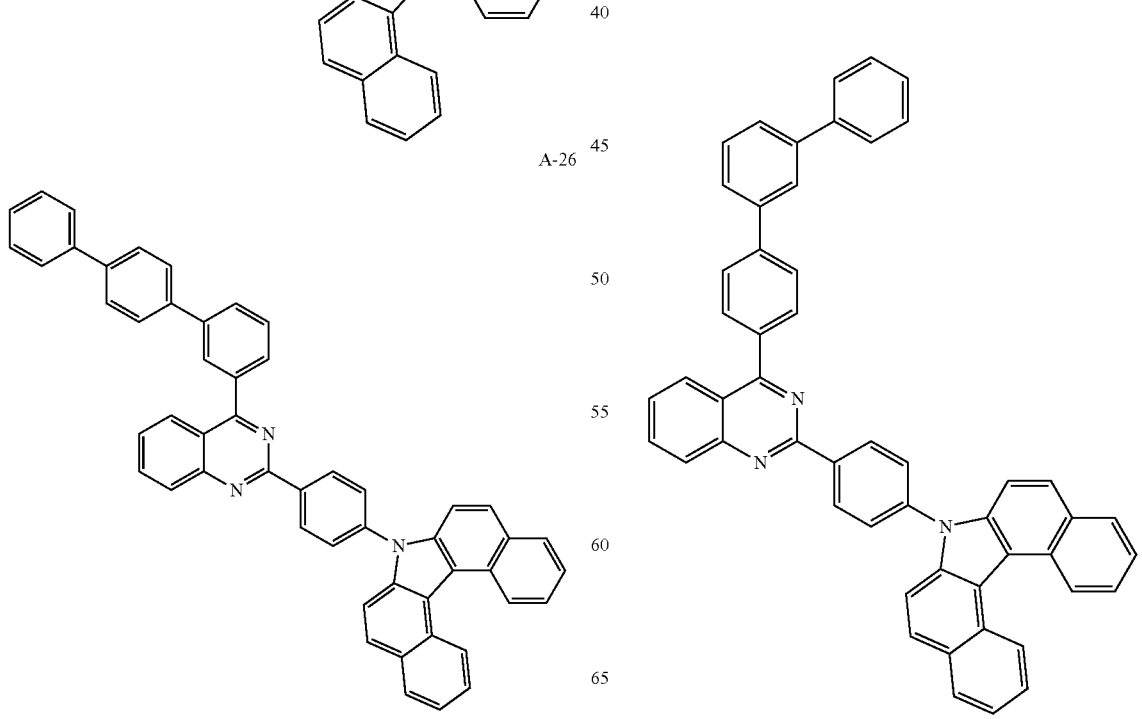
A-27
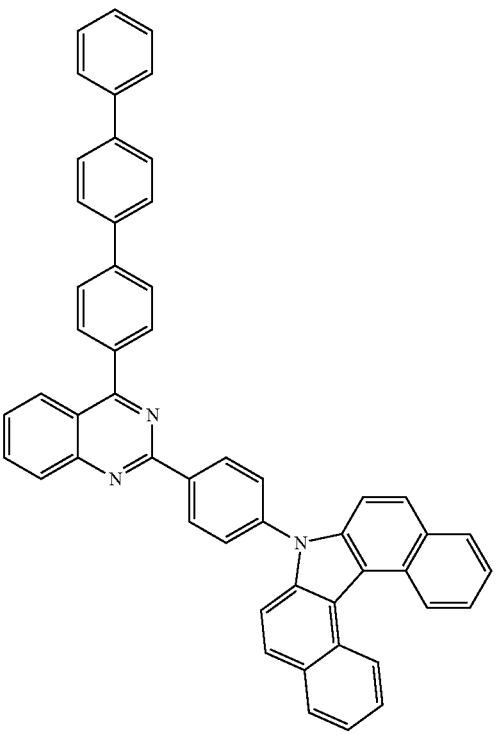
A-28

-continued
A-29
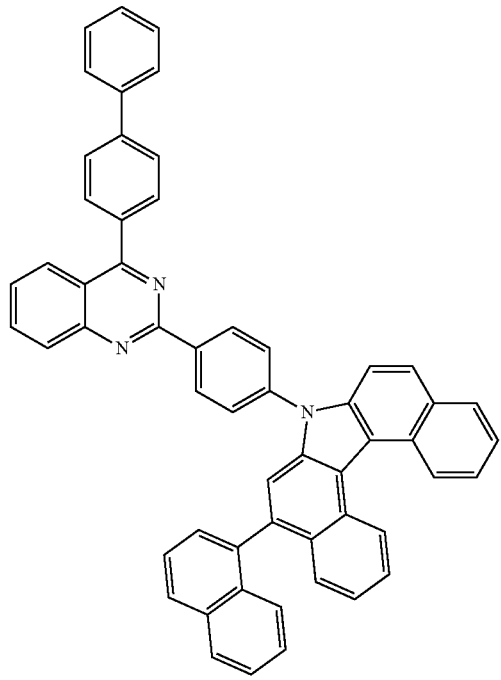
A-31
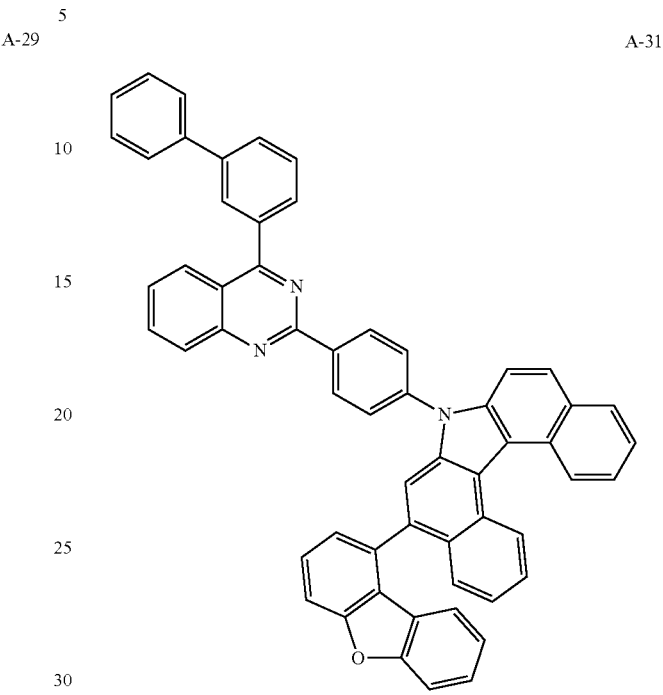
A-30
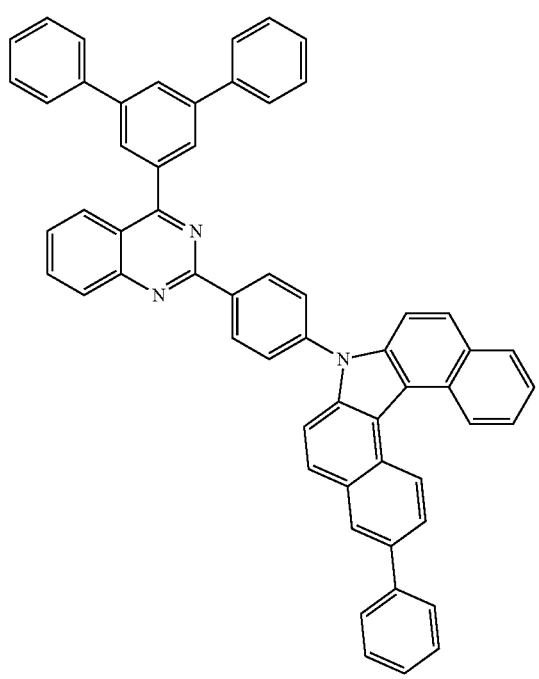
A-32

A-33
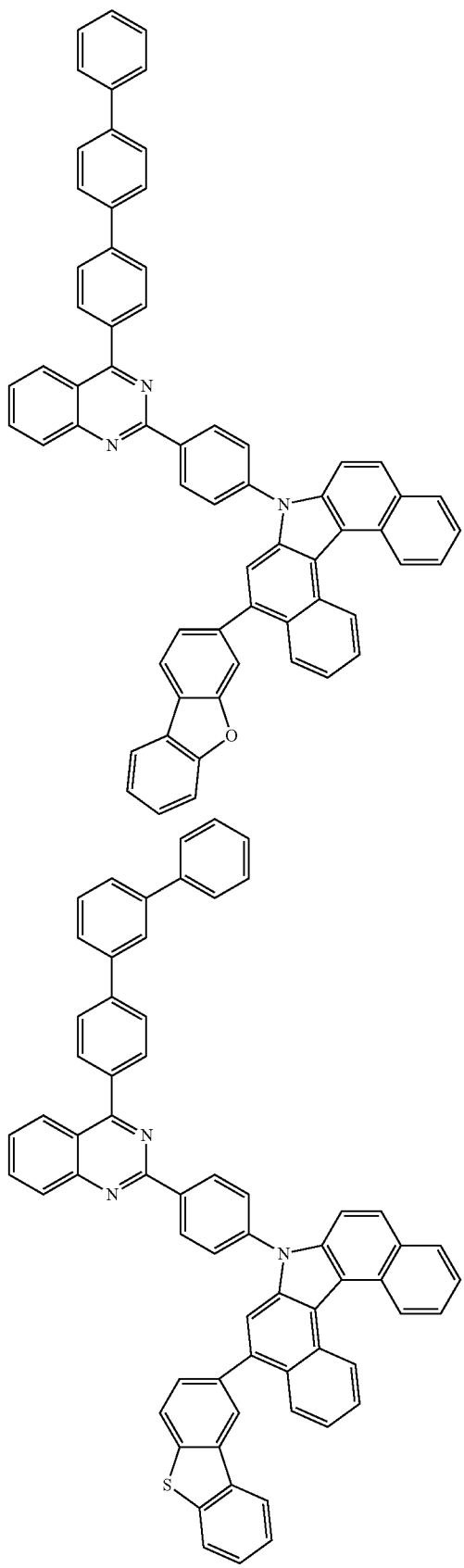
A-34
A-35
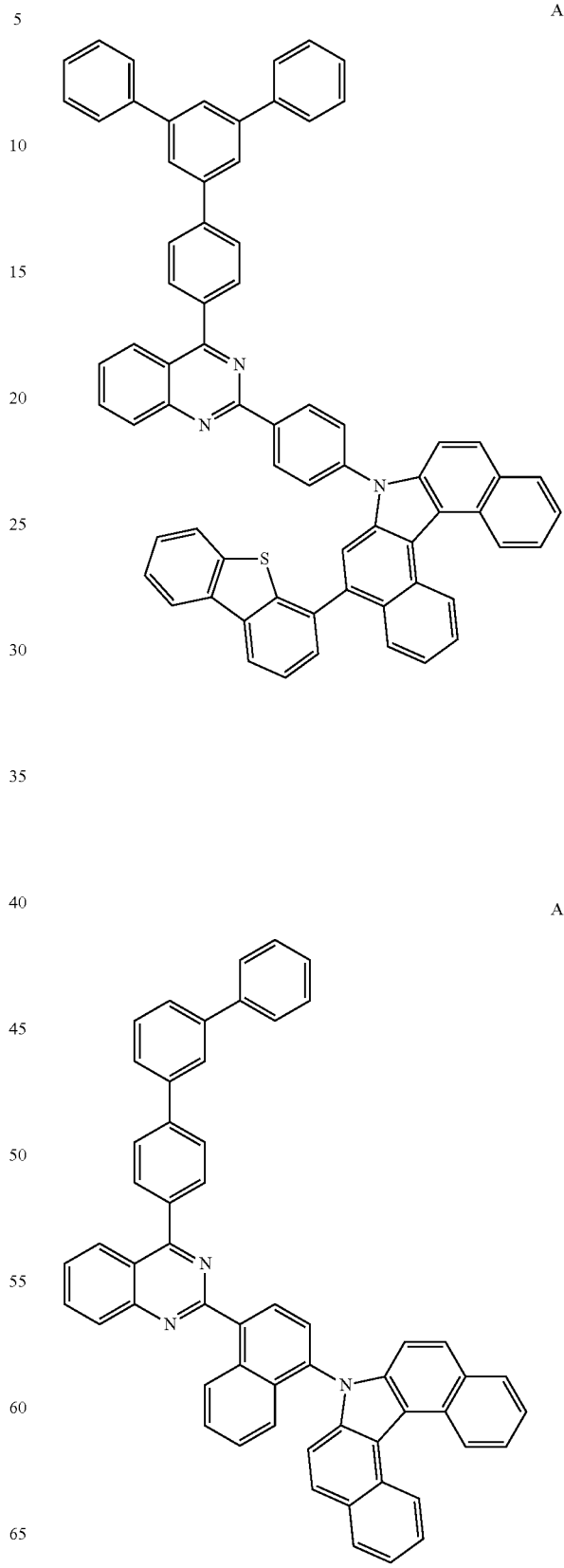
A-36

A-37
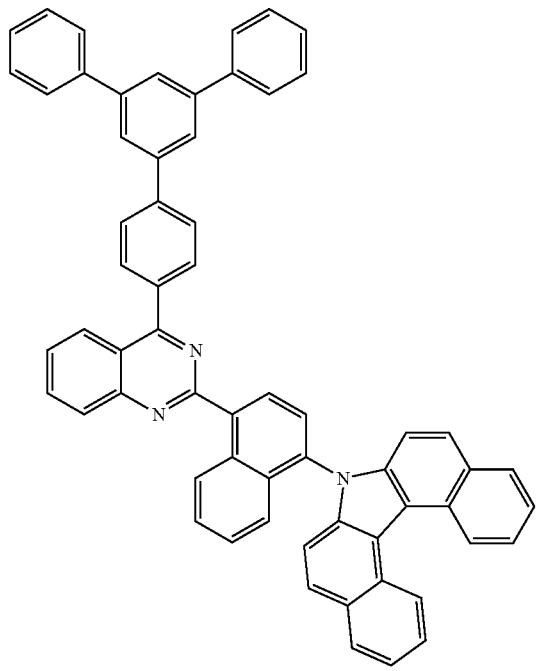
A-38
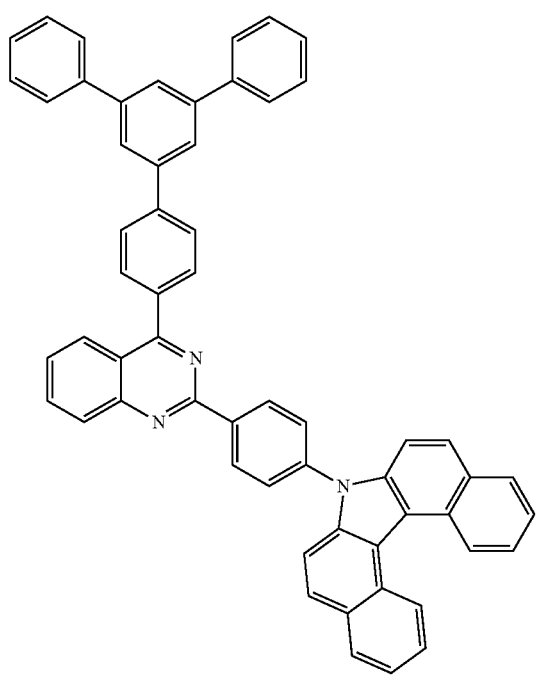
A-39
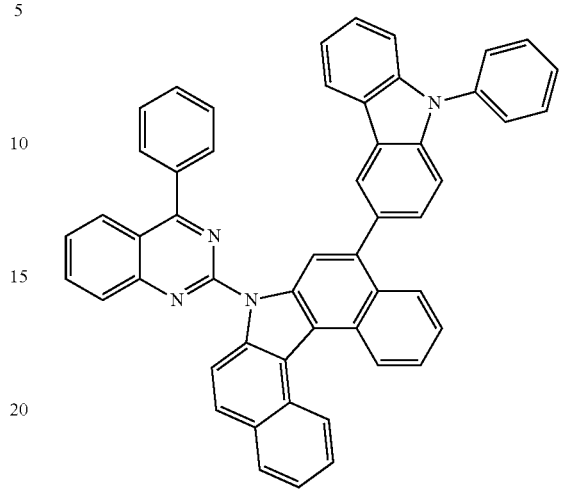
A-40
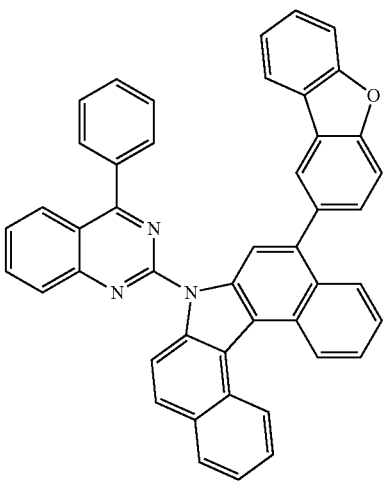
A-41
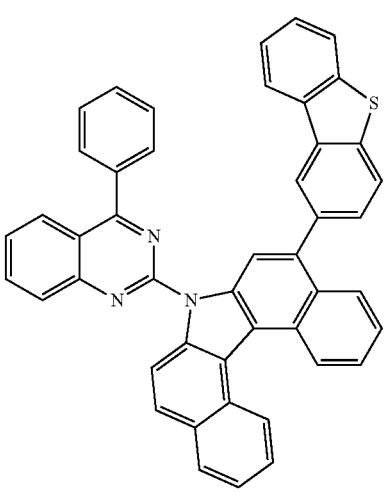

A-42
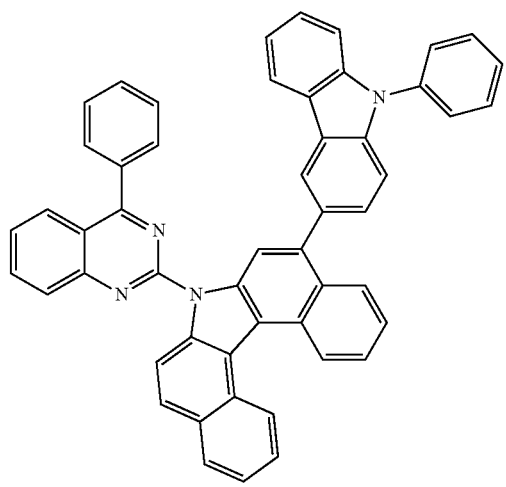
A-43
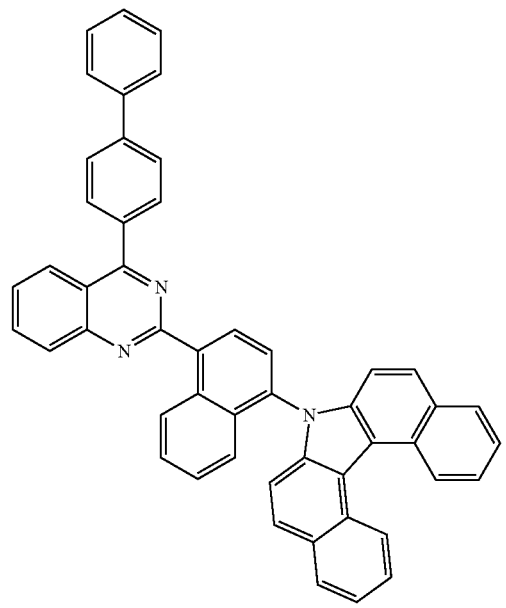
A-44
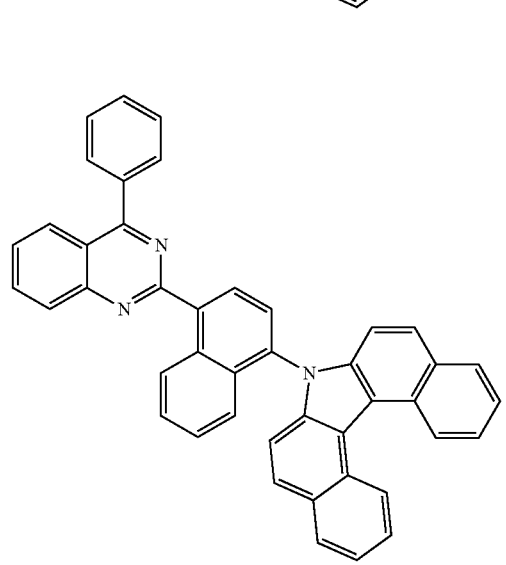
A-45
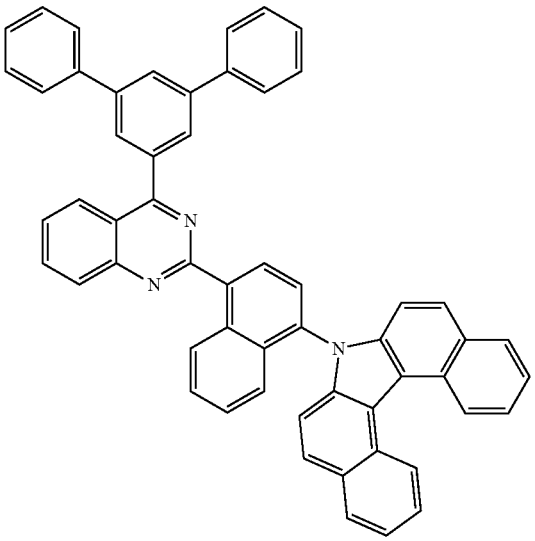
A-46
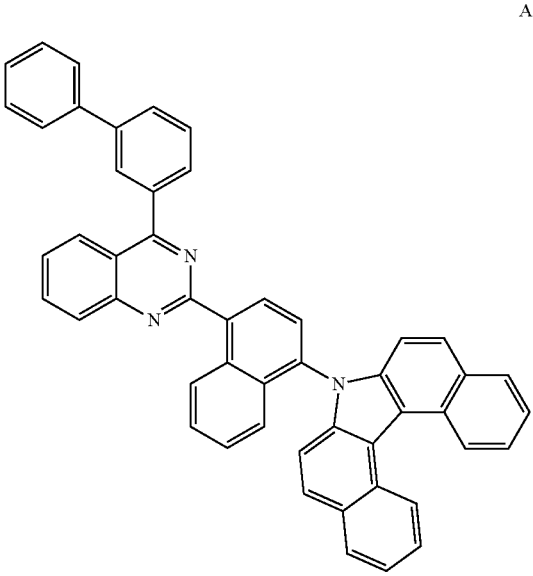
A-47
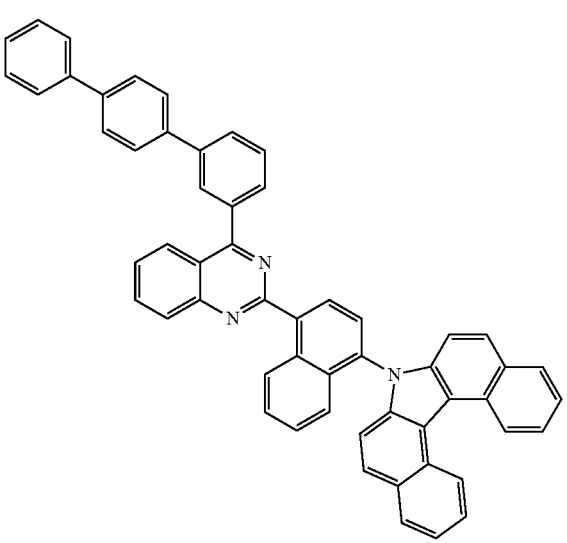

A-48
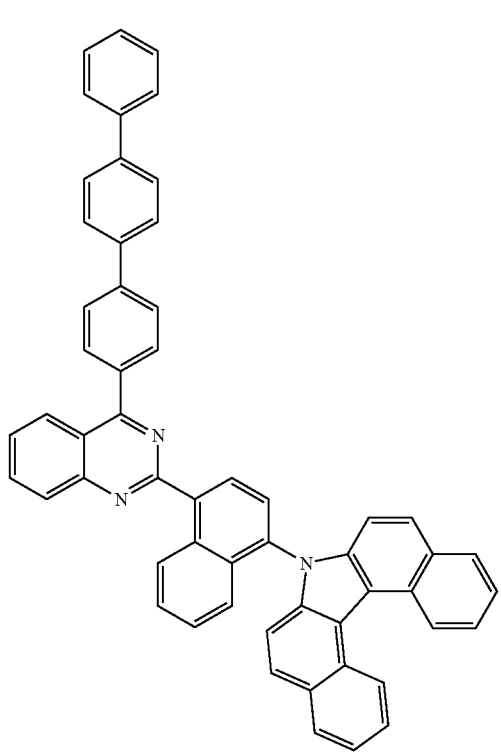
A-49
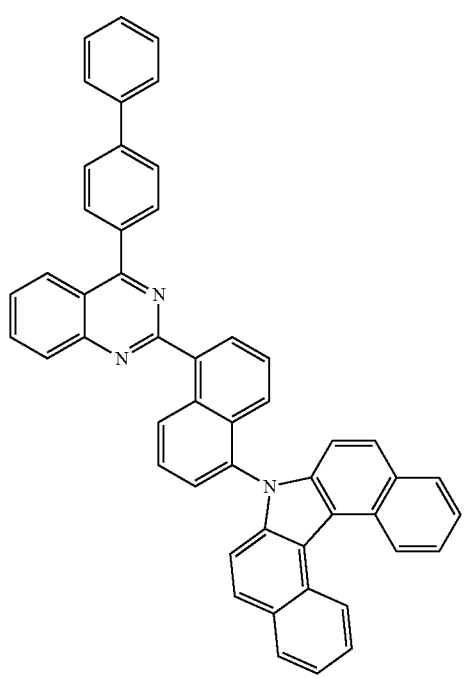
A-50
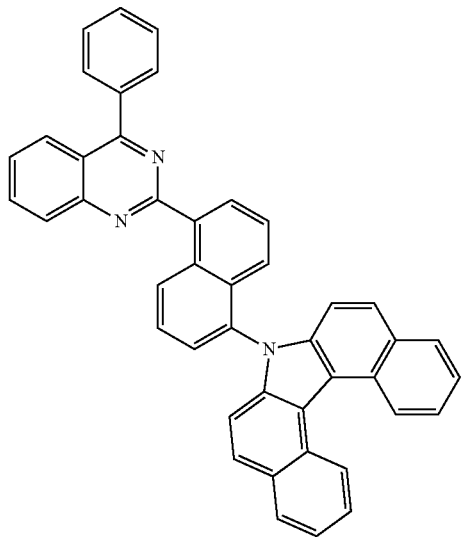
A-51
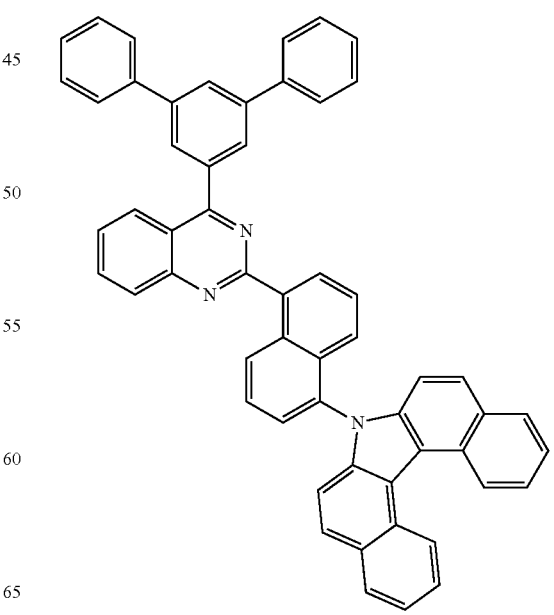

A-52
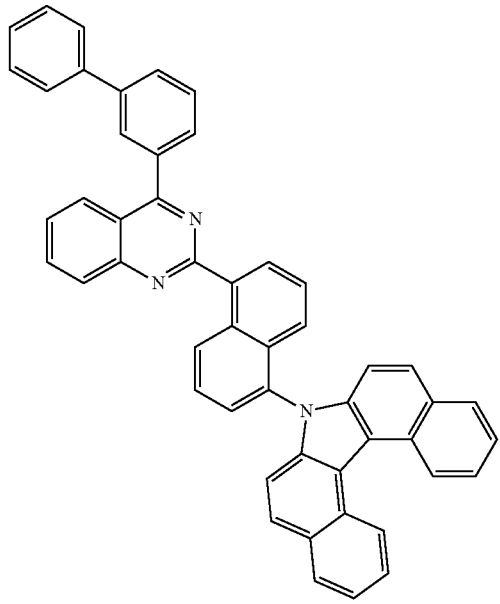
A-54
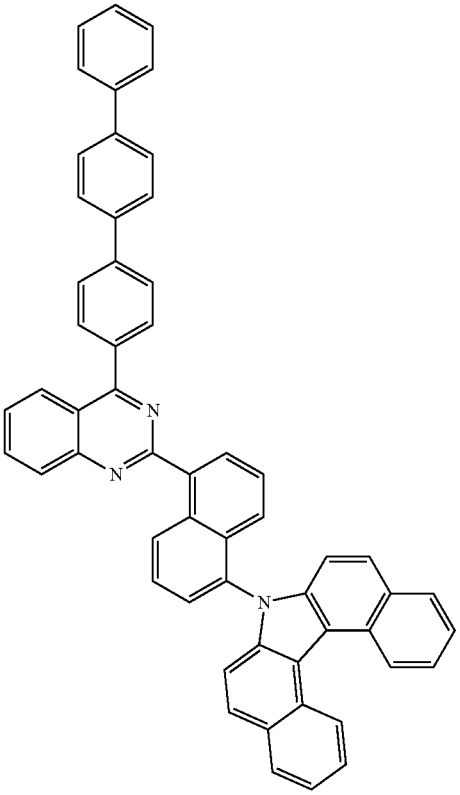
A-53
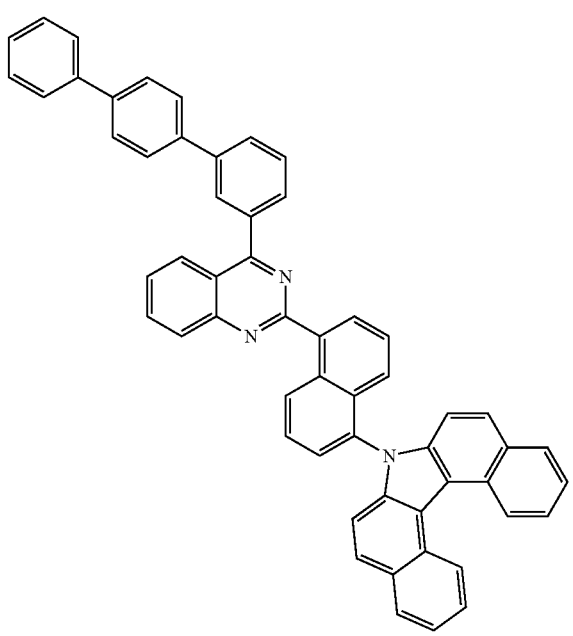
A-55
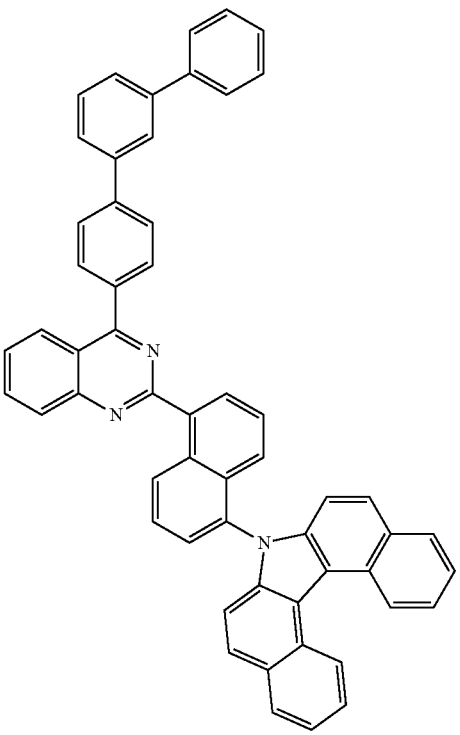

-continued
A-56
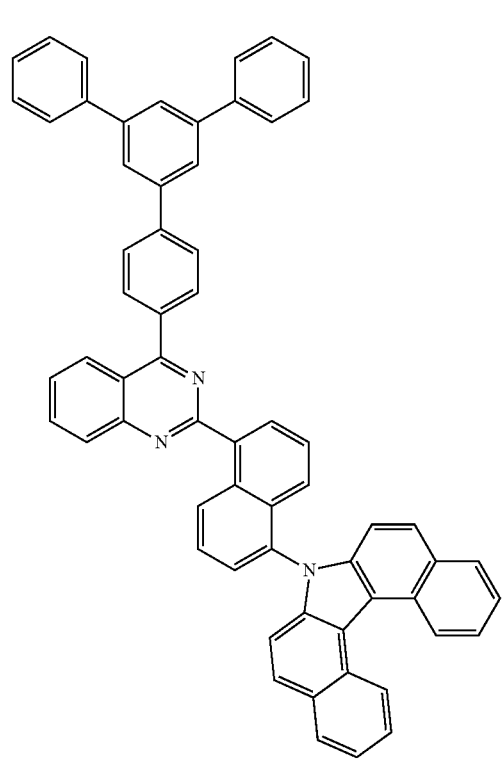
A-58
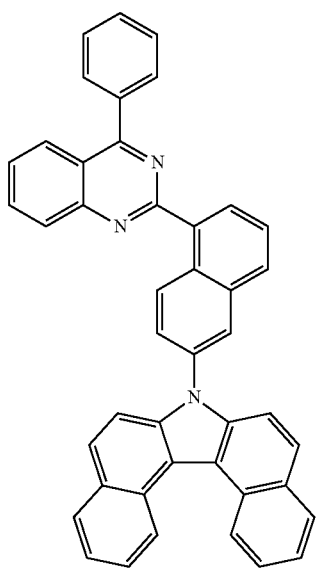
A-57
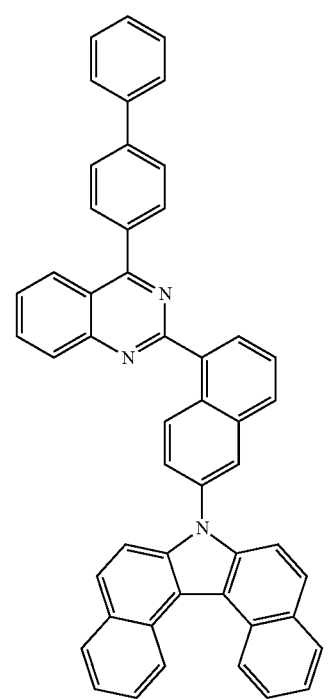
A-59
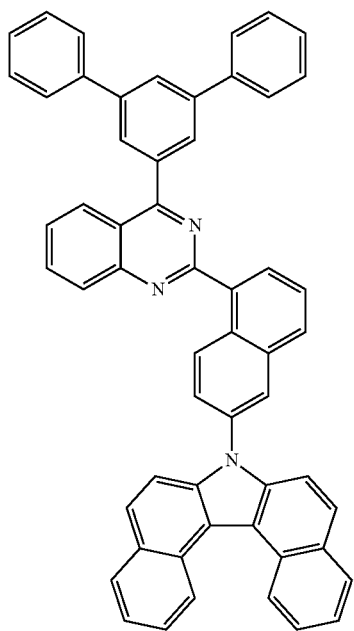

A-60
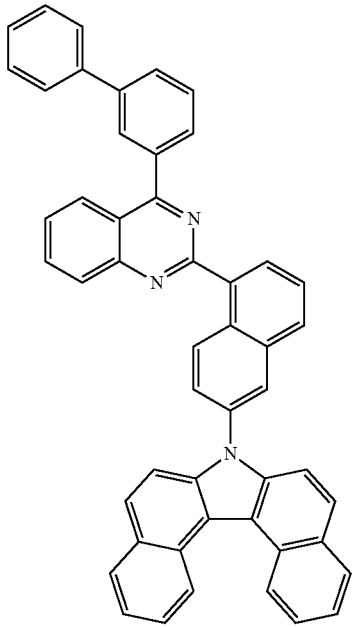
A-61
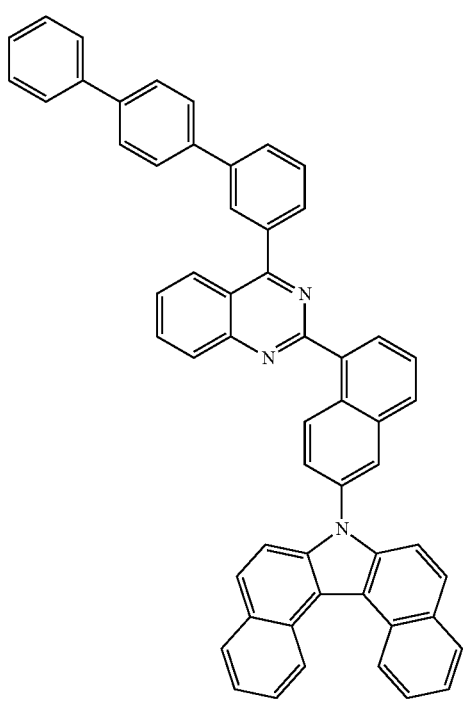
A-62
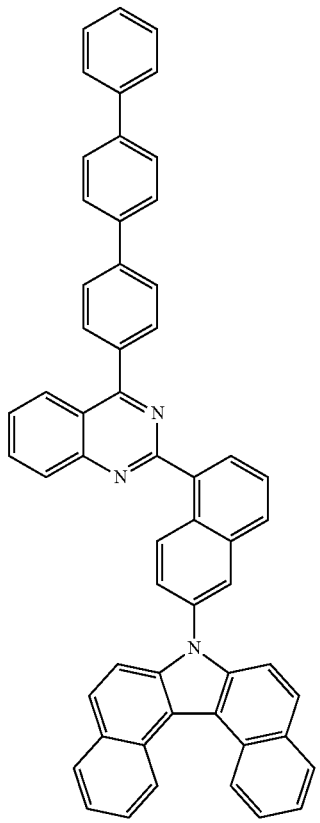
A-63
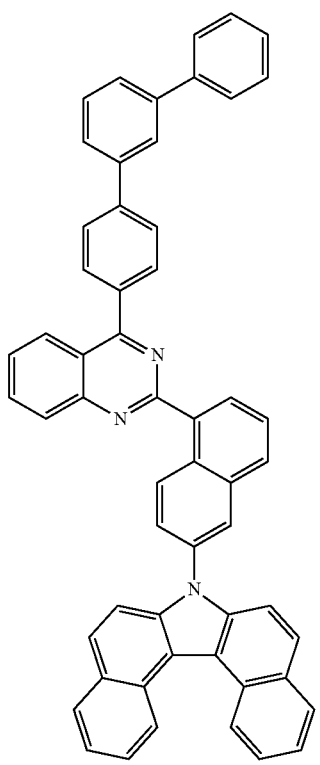

-continued
A-64
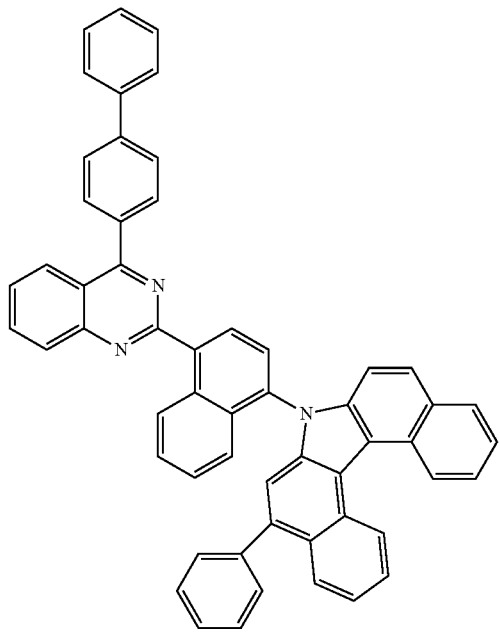
A-65
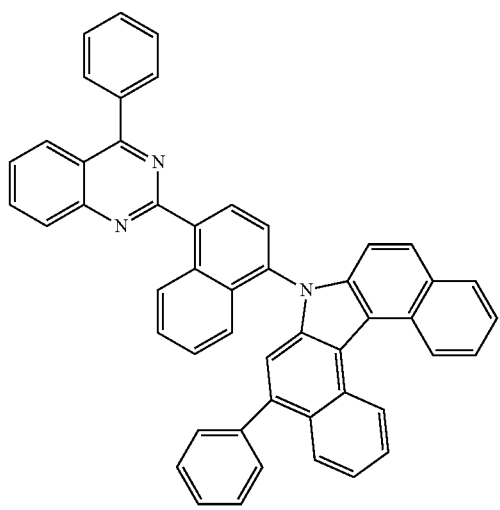
A-66
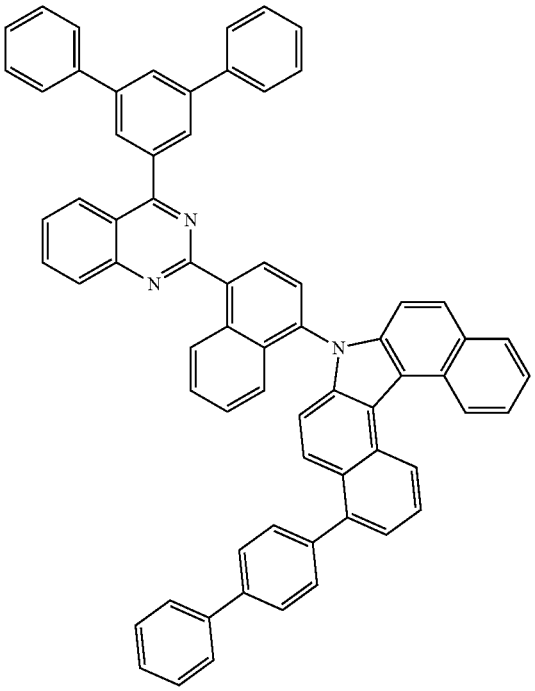
A-67
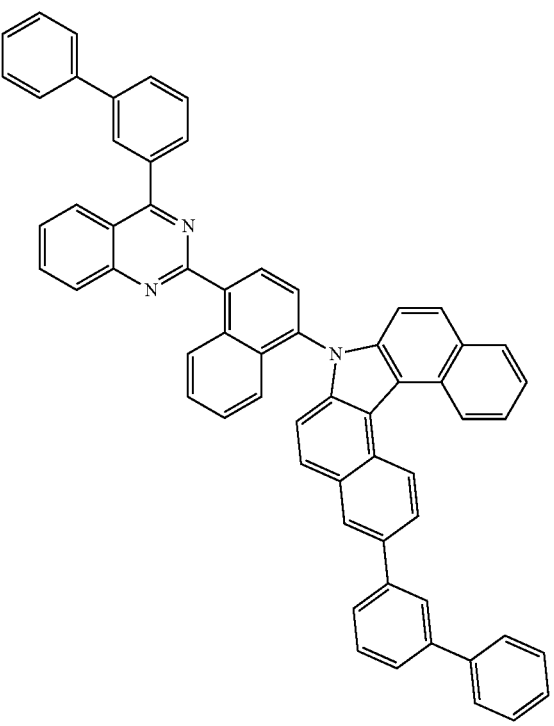

A-68
A-69
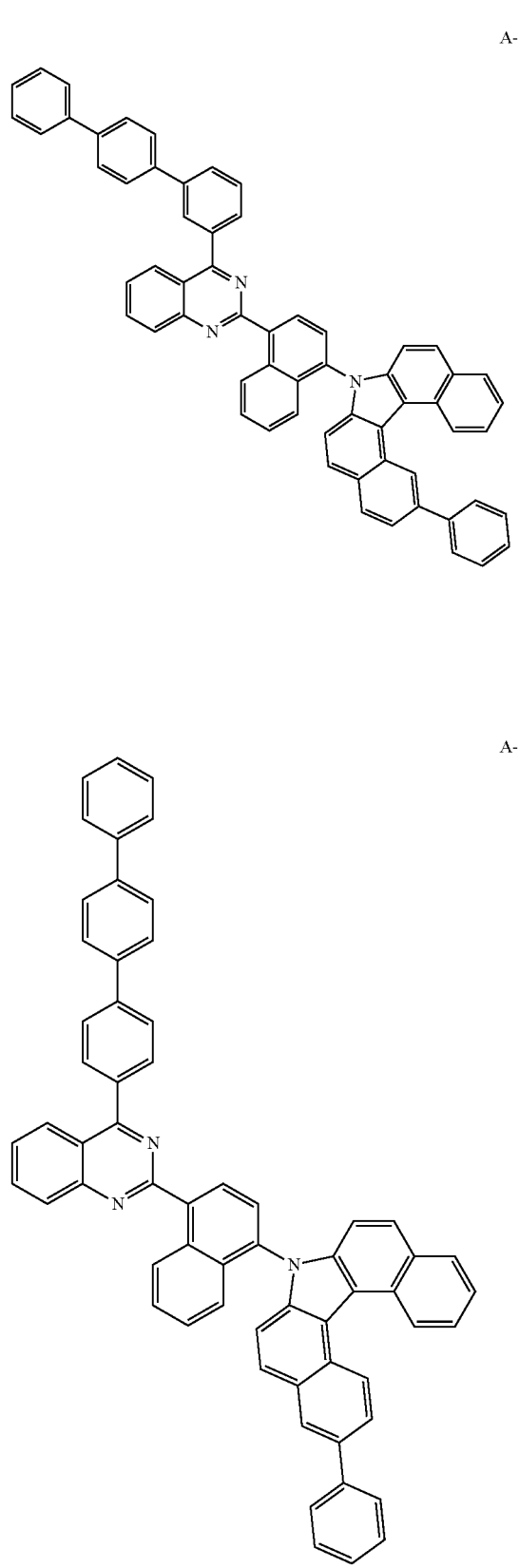
A-70
A-71
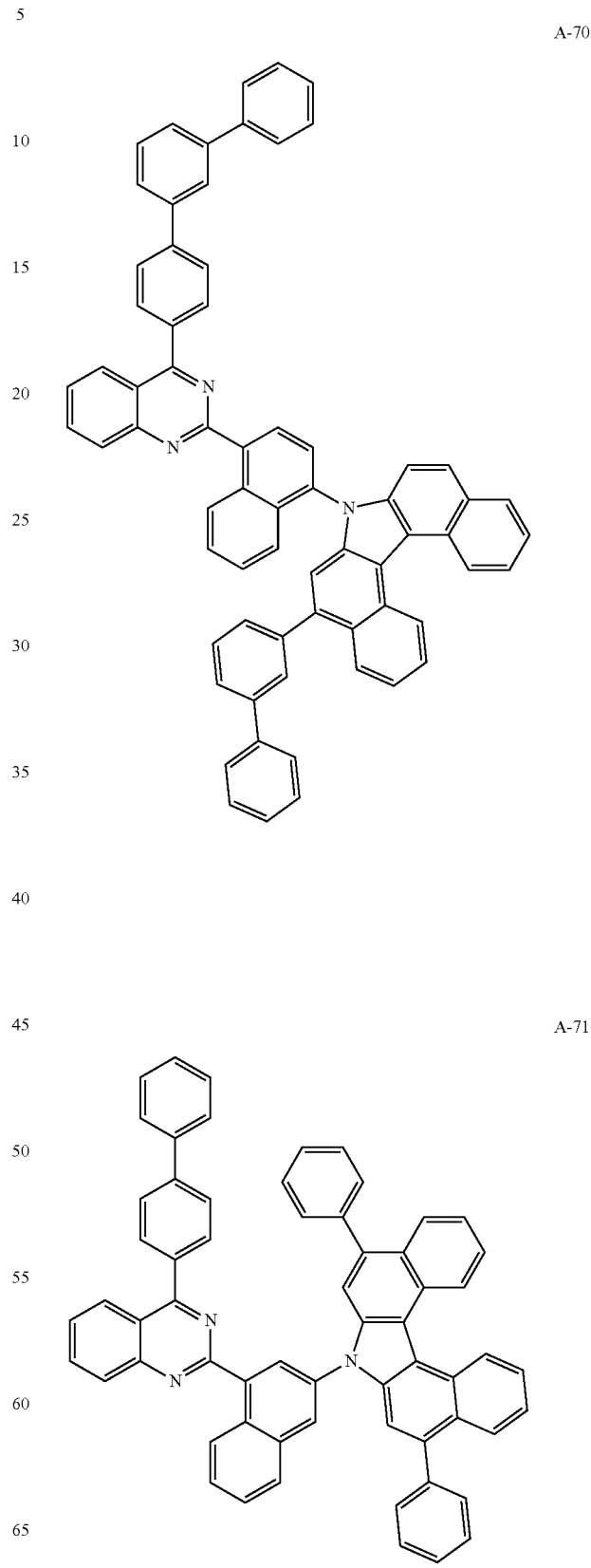

A-72
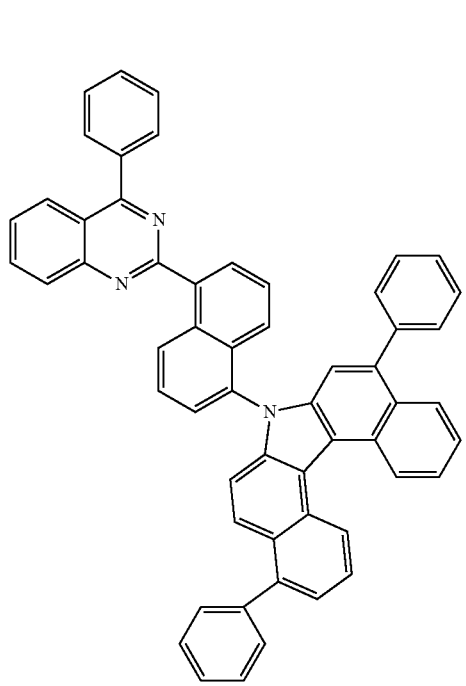
A-73
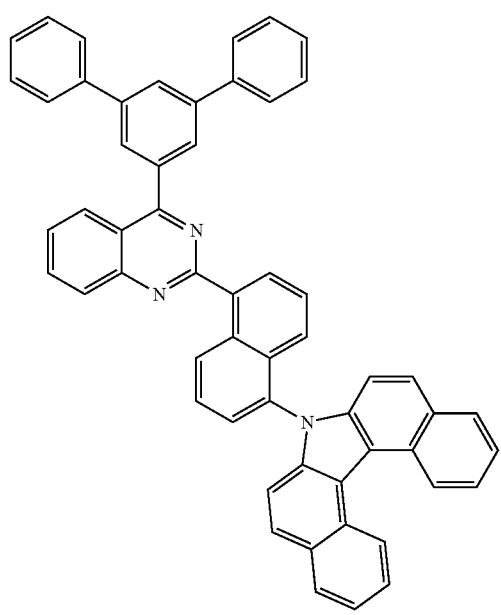
A-74
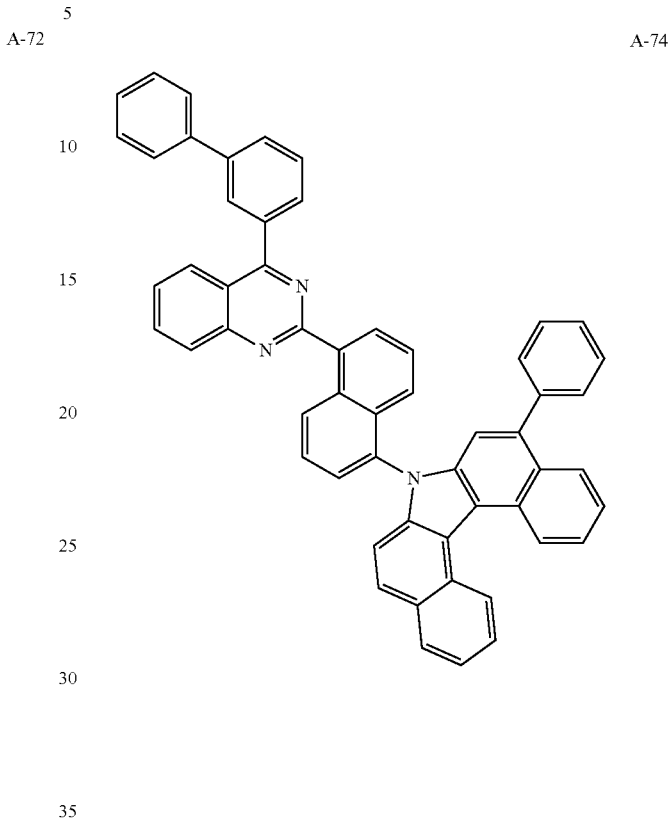
A-75
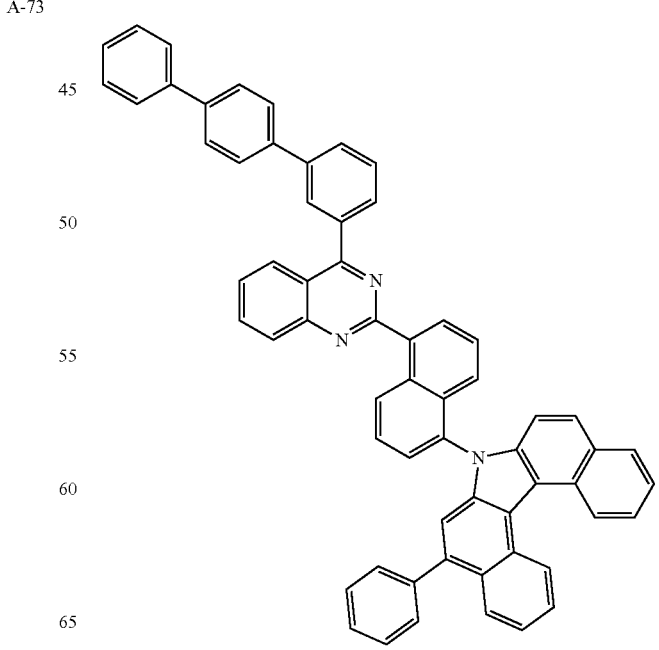

A-76
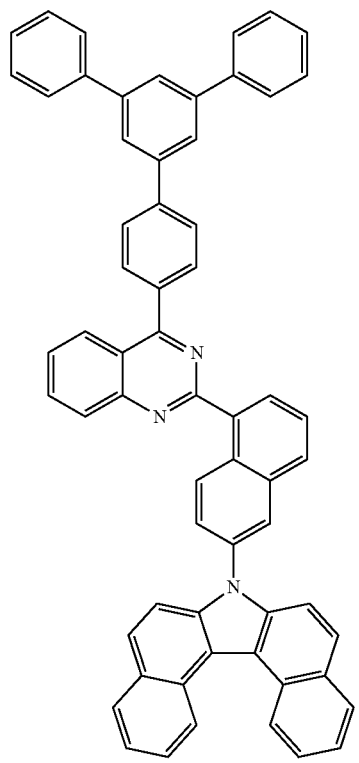
A-77
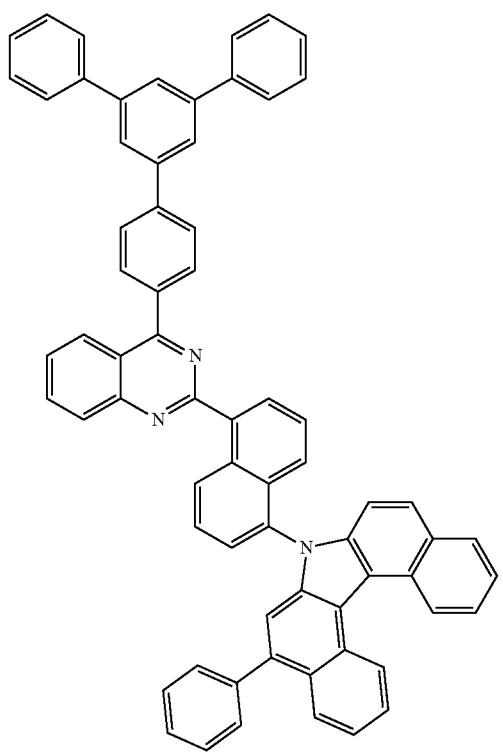
A-78
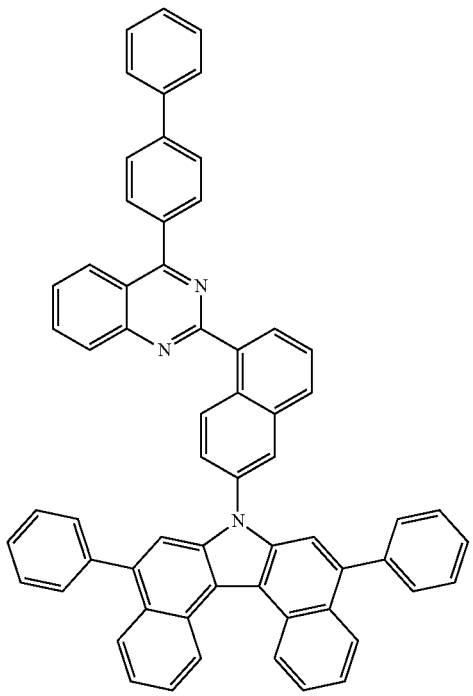
A-79
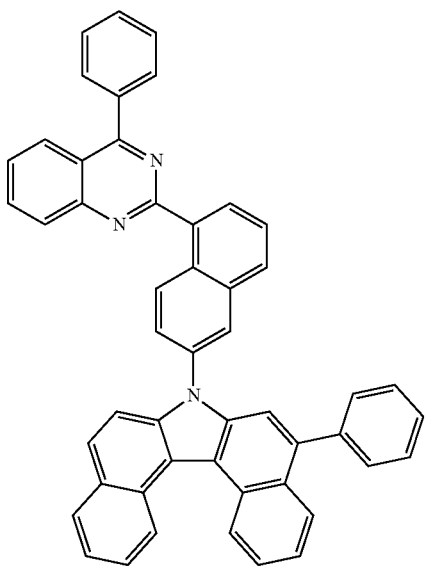

A-80
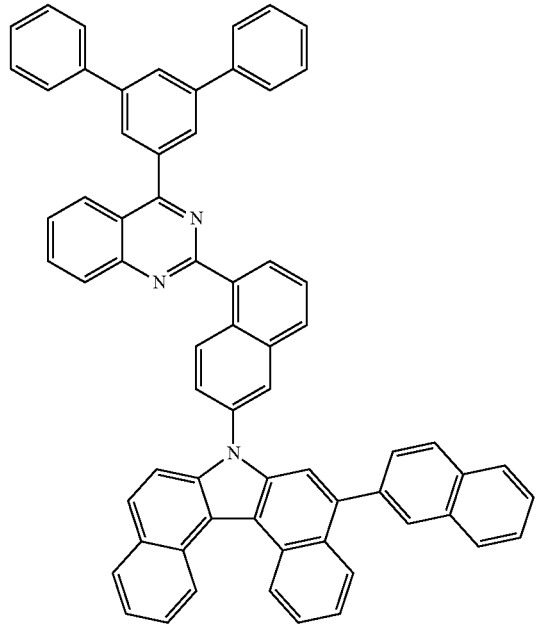
A-81
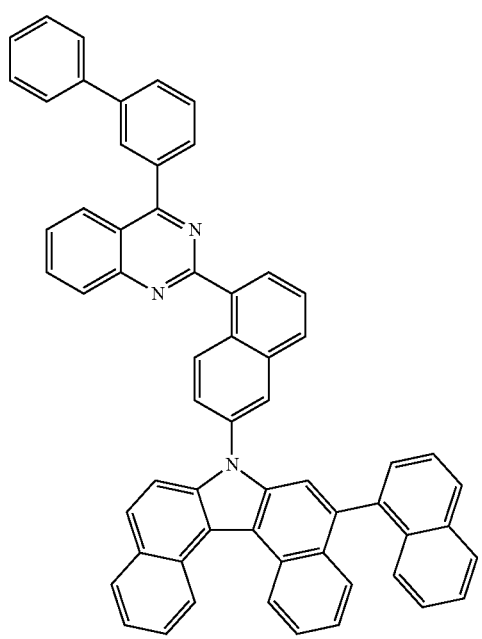
A-82
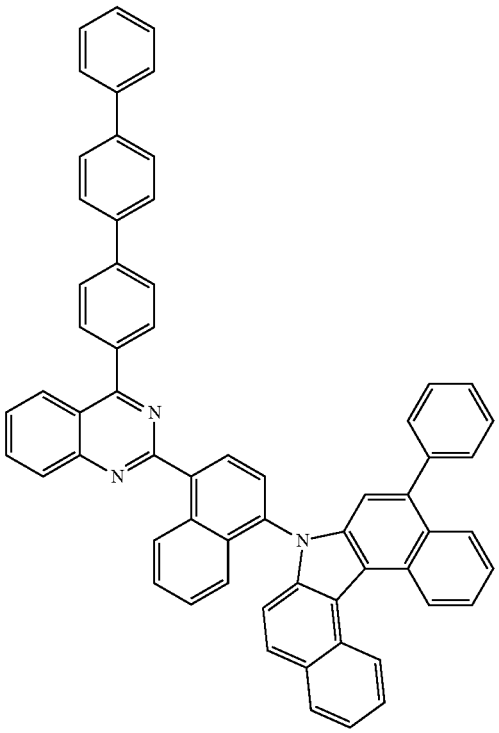
A-83
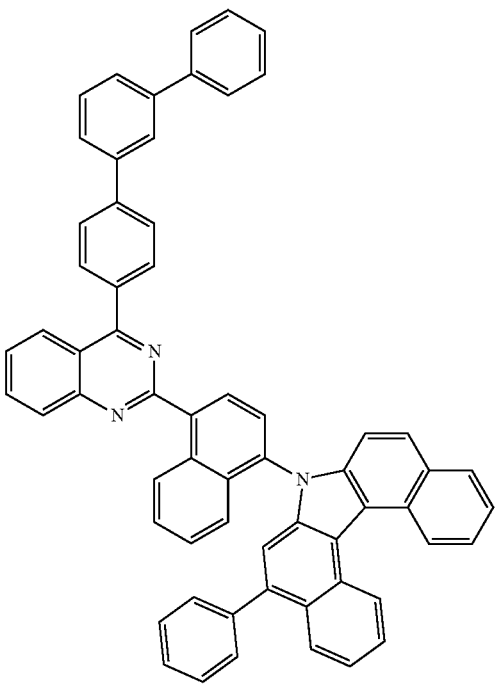

A-84
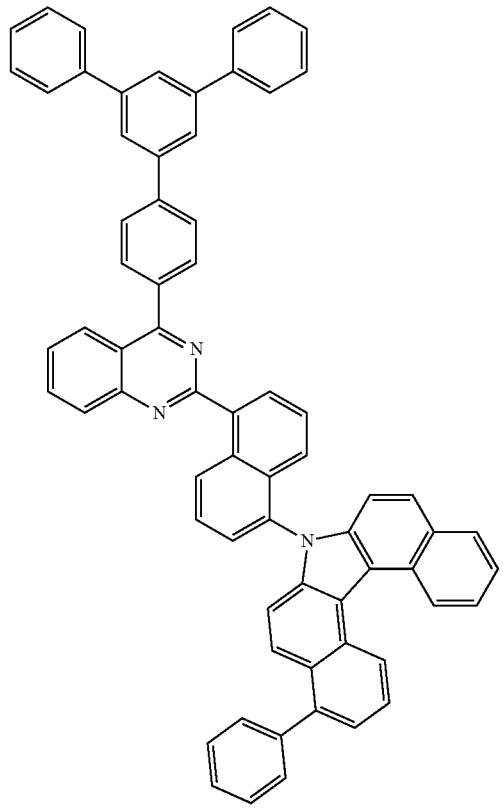
A-85
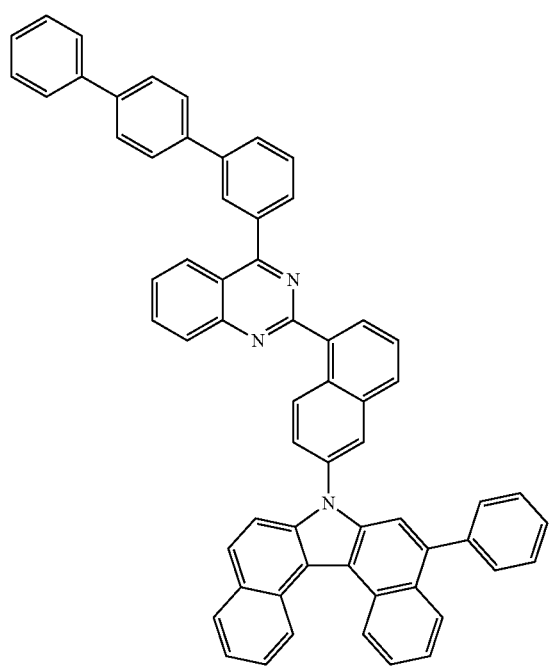
A-86
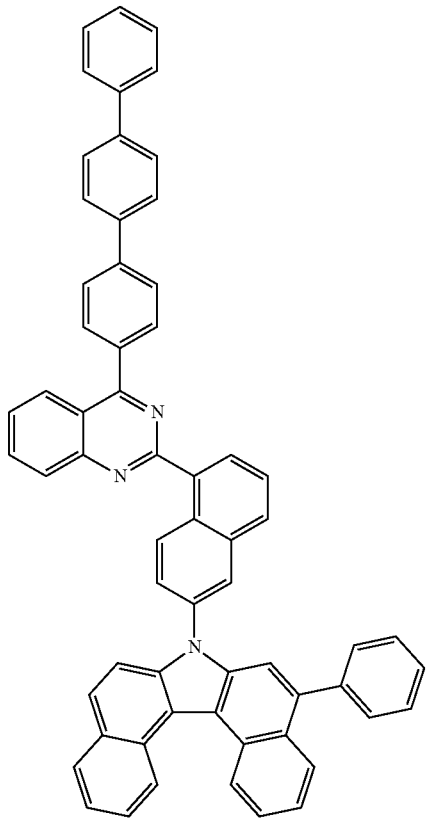
A-87
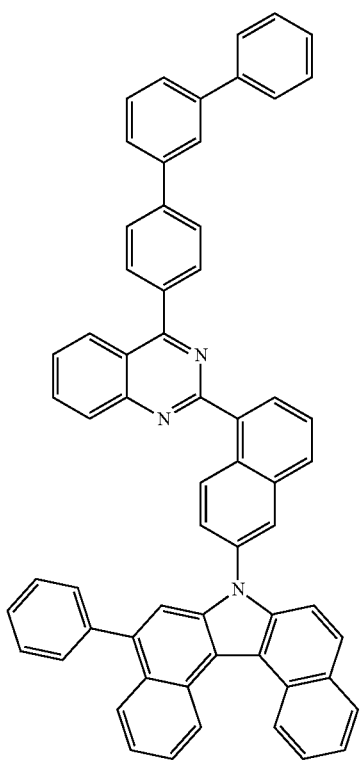

A-88 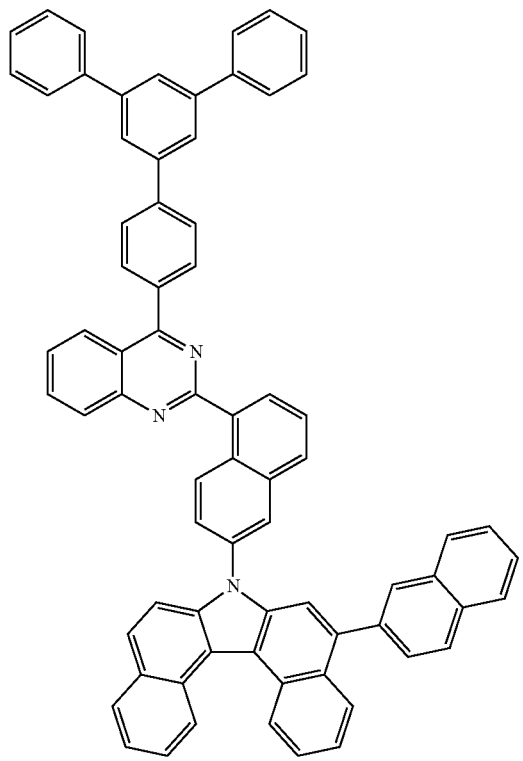
A-89 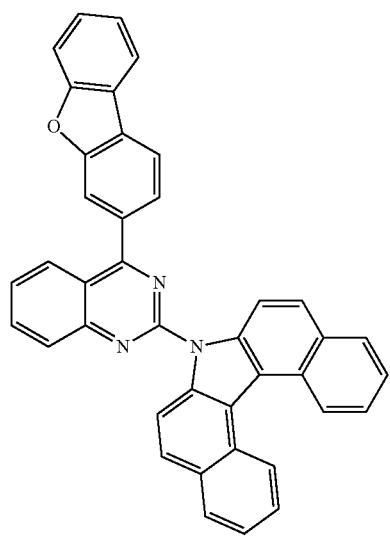
A-90 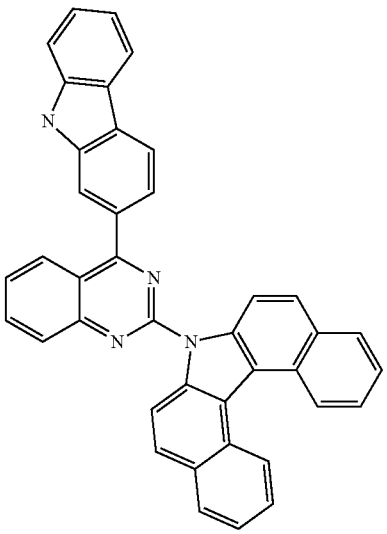
A-91 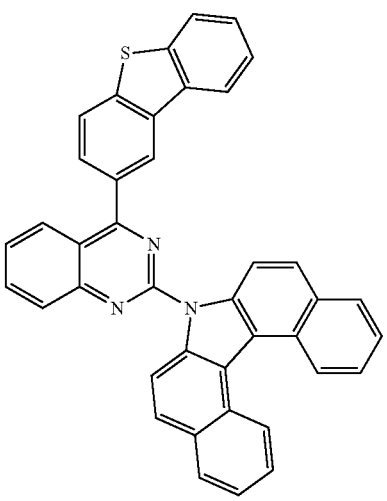
A-92 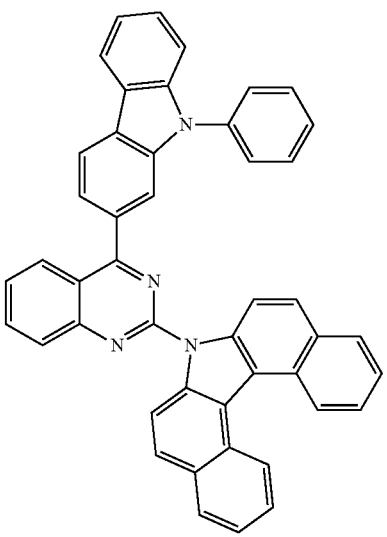

A-94
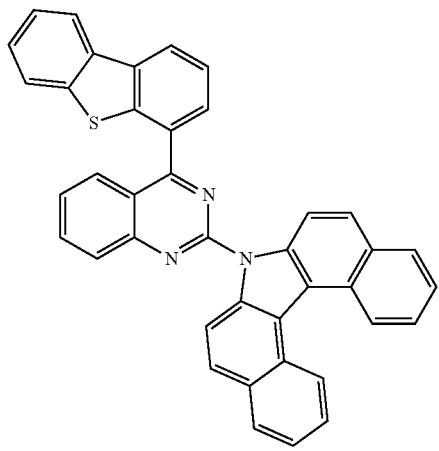
A-95
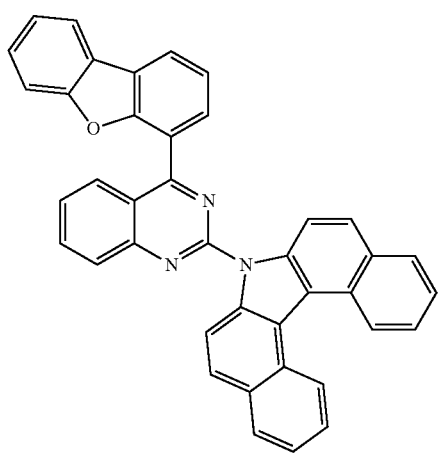
A-96
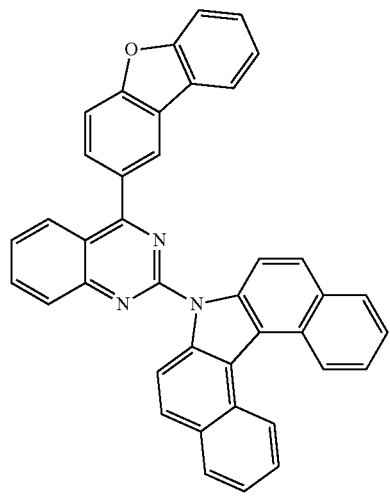
A-97
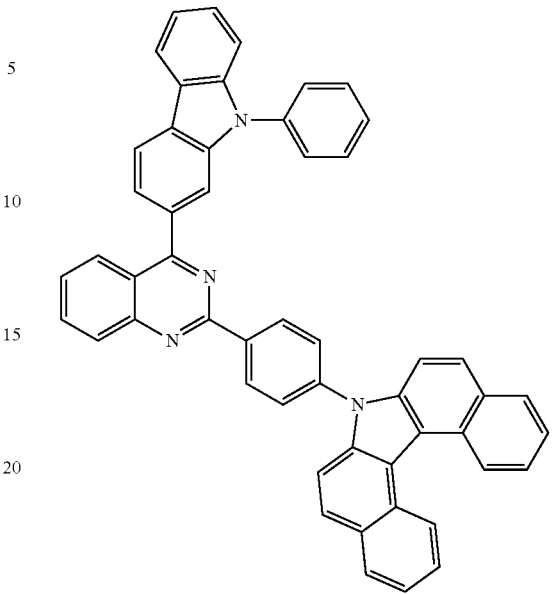
A-98
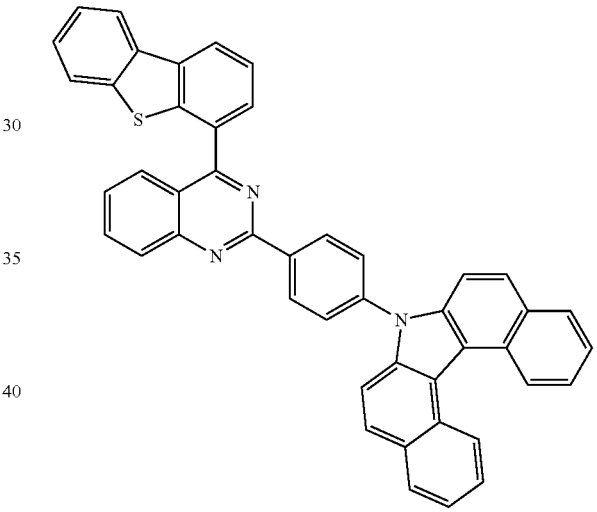
A-99
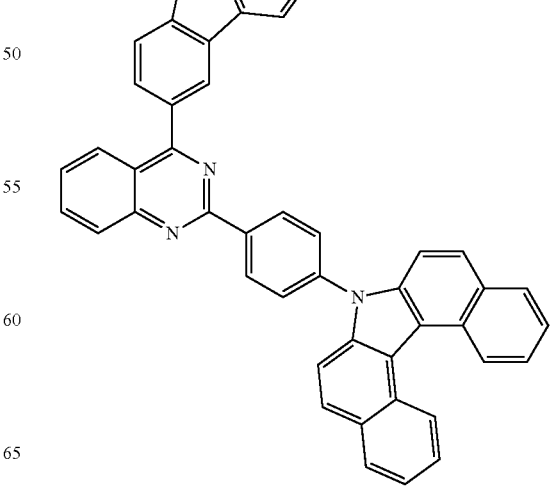

-continued
A-100
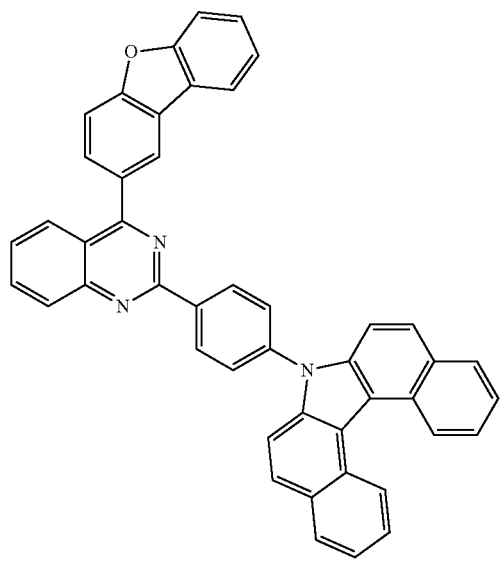
A-101
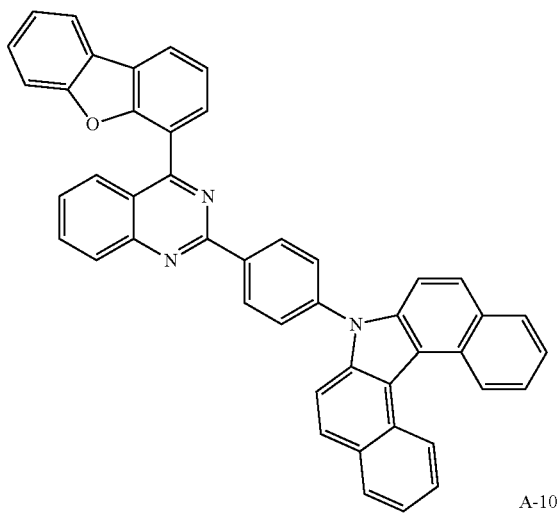
A-103
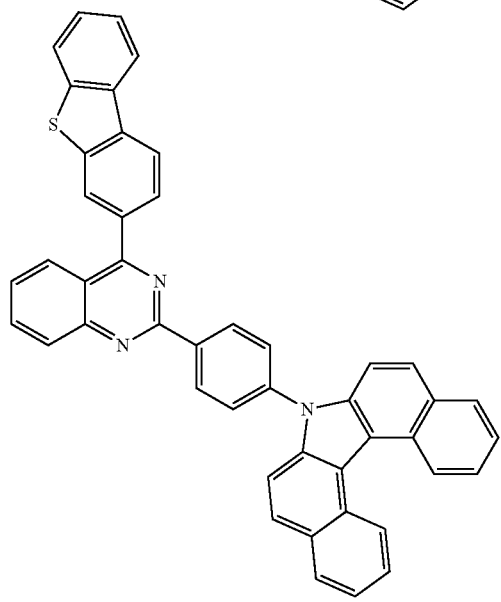
-continued
A-104
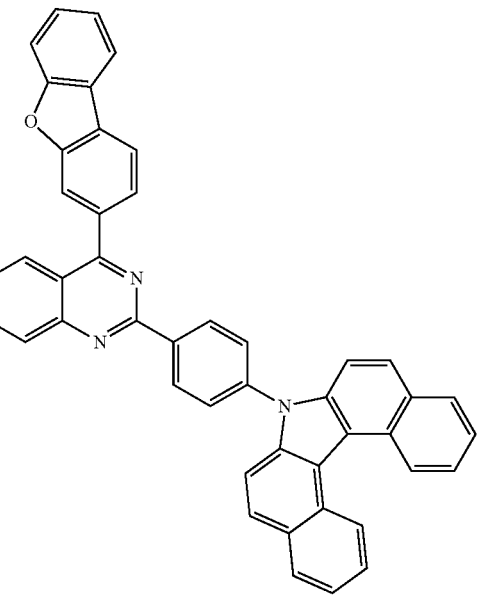
A-105
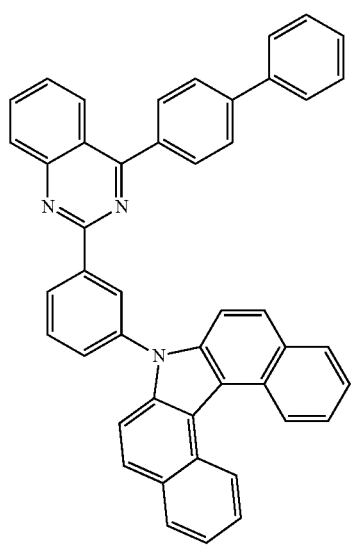
A-106
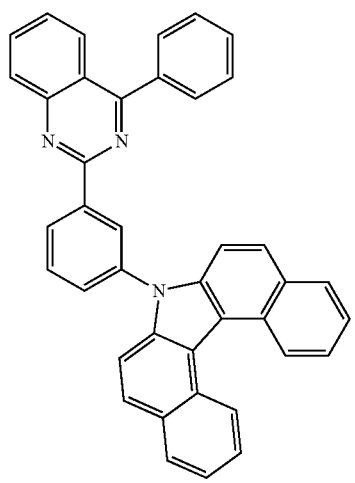

A-107
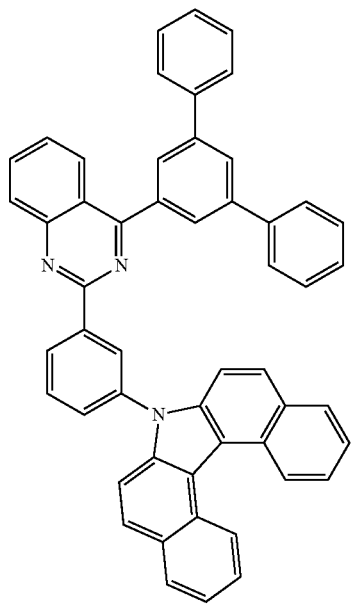
A-109
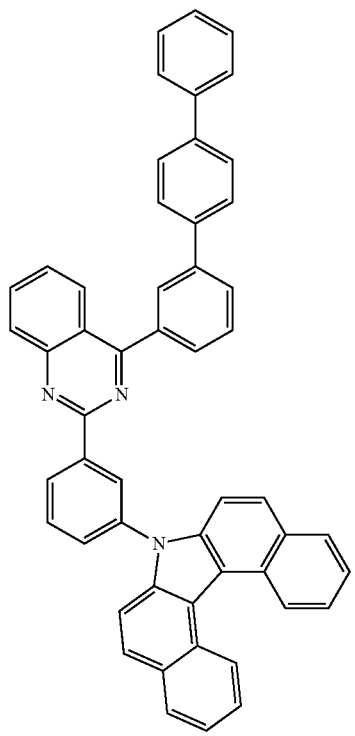
A-108
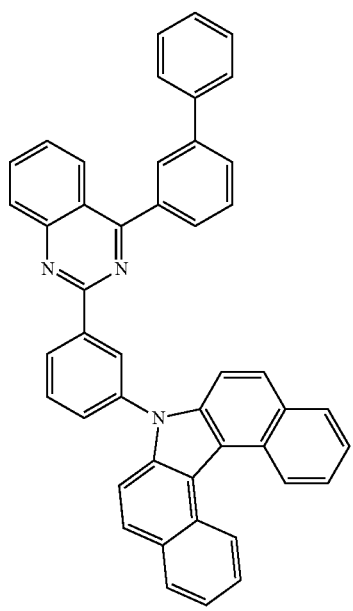
A-110
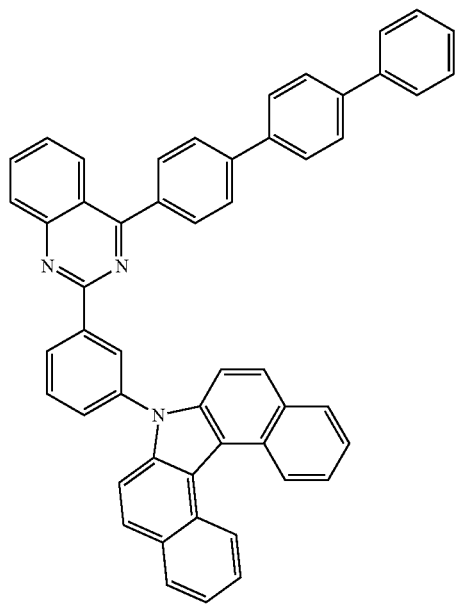

A-111
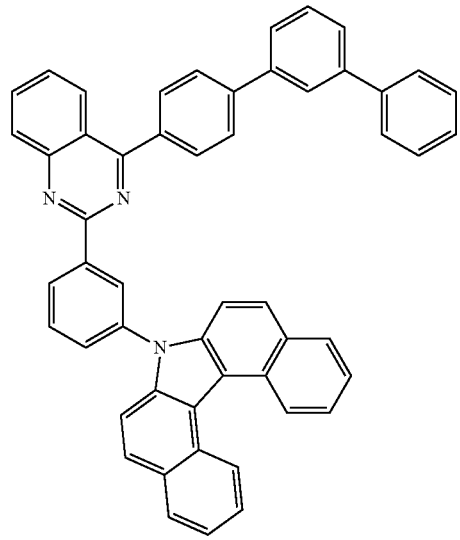
A-112
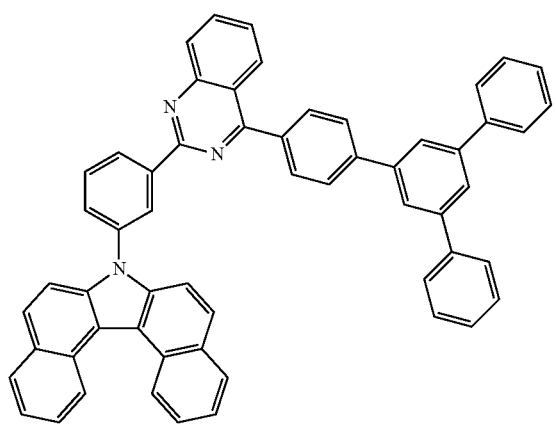
A-114
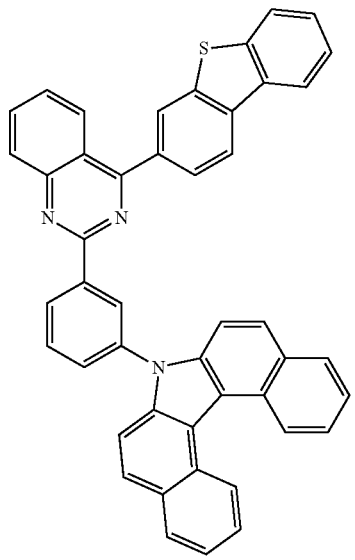
A-115
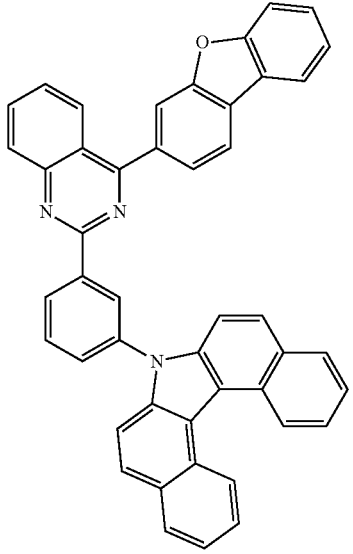
A-116
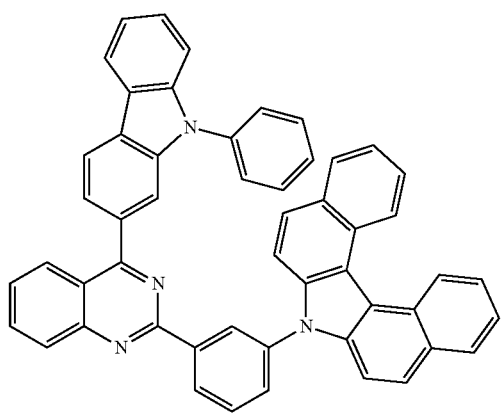
A-117
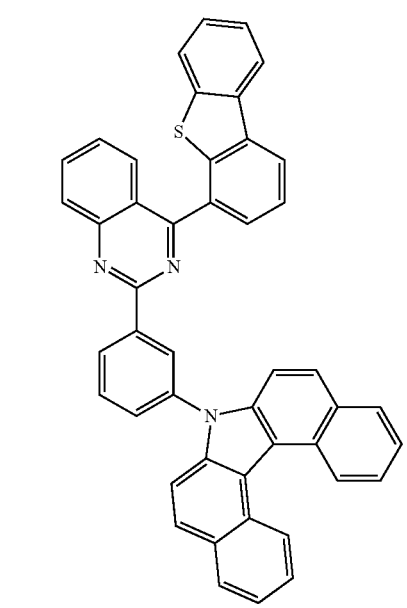

-continued
A-118
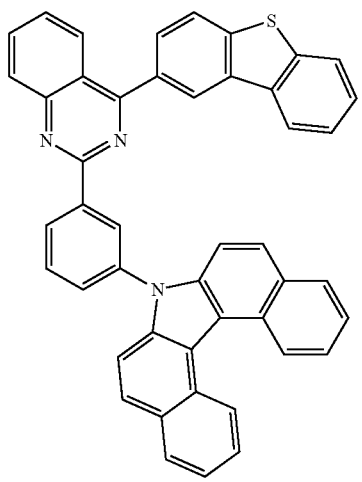
A-121
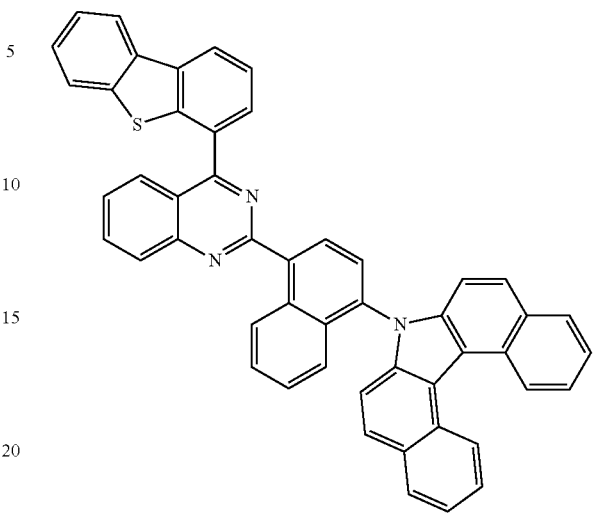
A-119
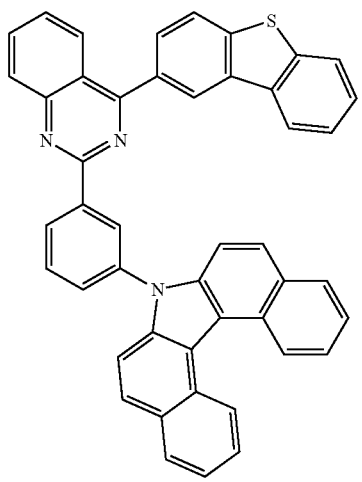
A-122
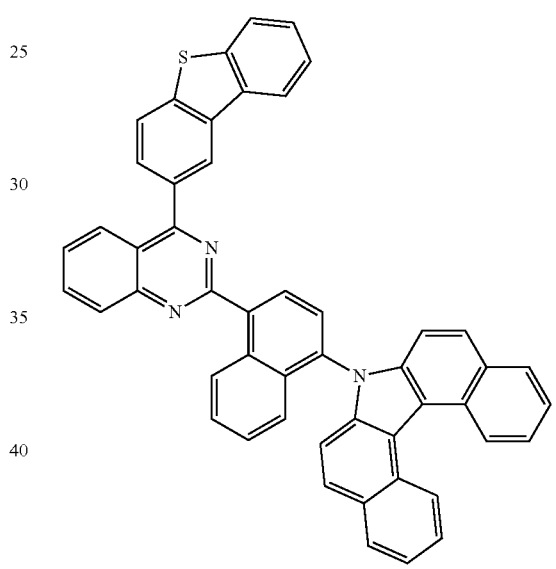
A-120
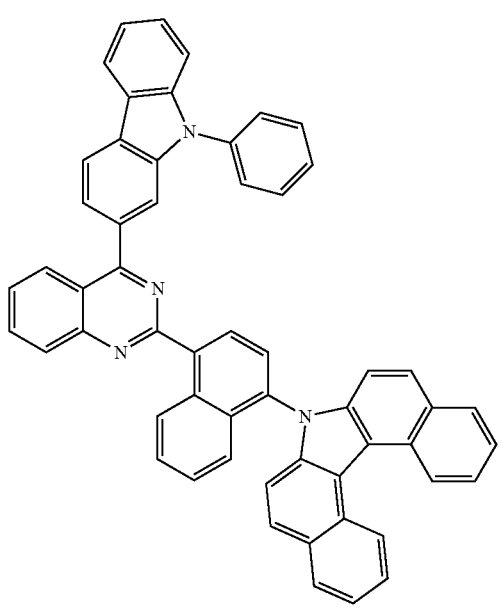
A-123
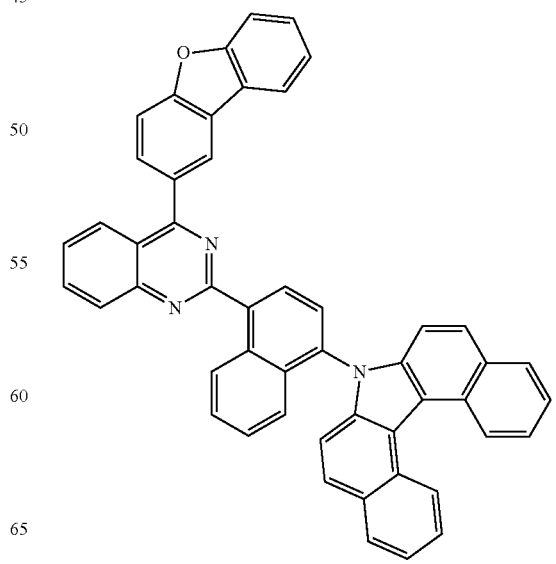

A-124
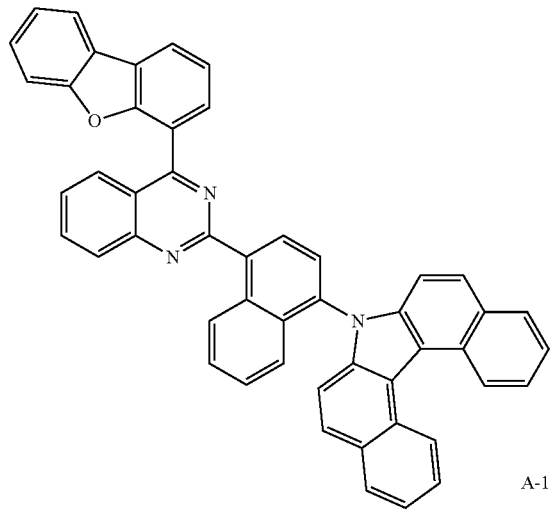
A-126
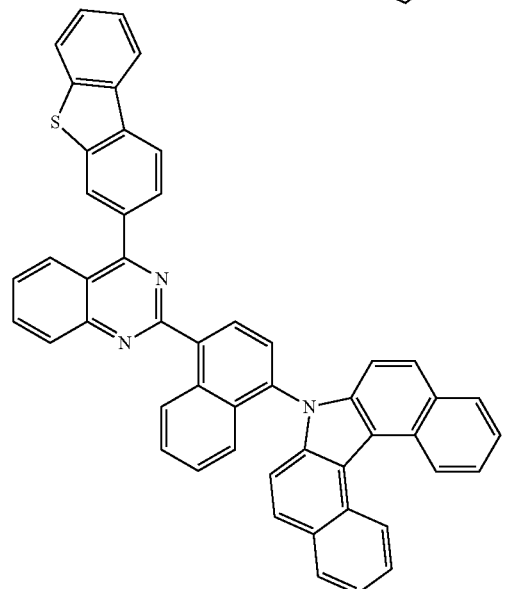
A-127
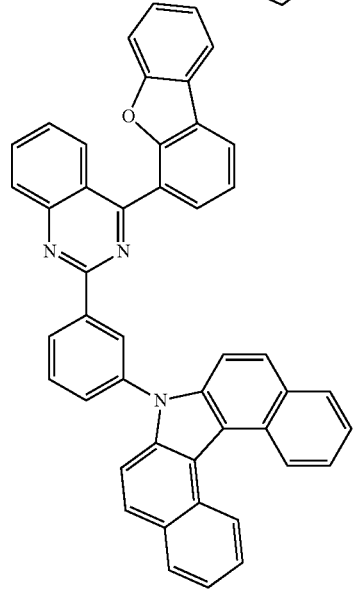
A-128
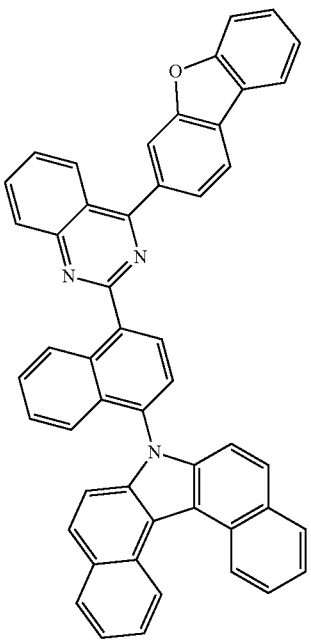
A-129
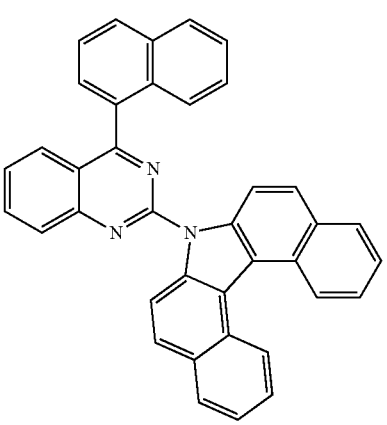
A-130
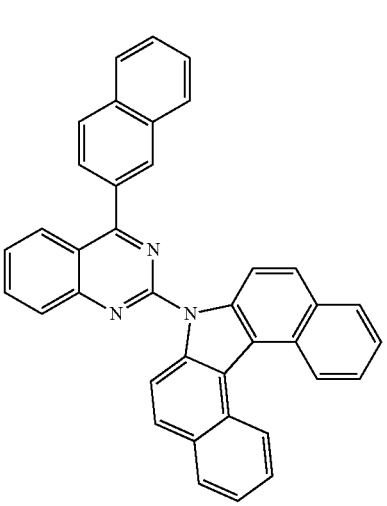

A-131
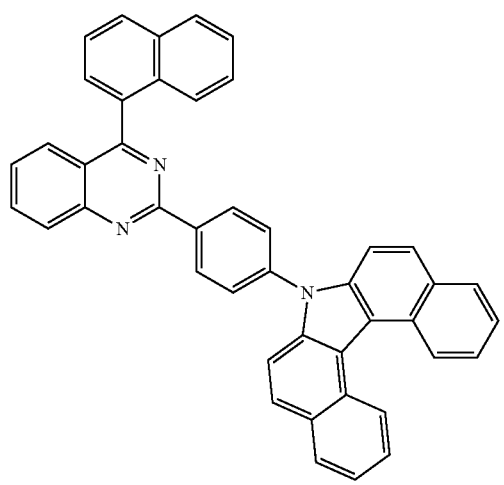
A-132
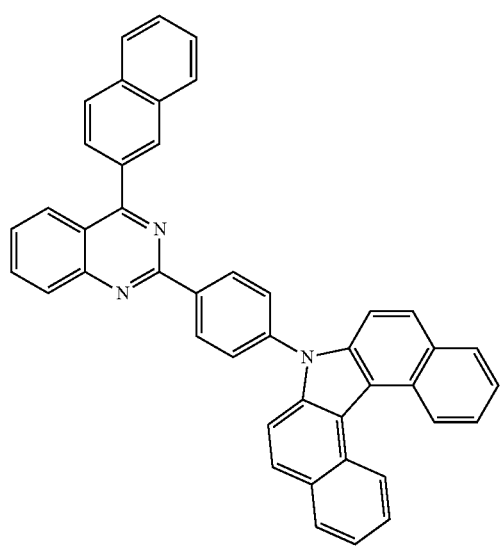
A-133
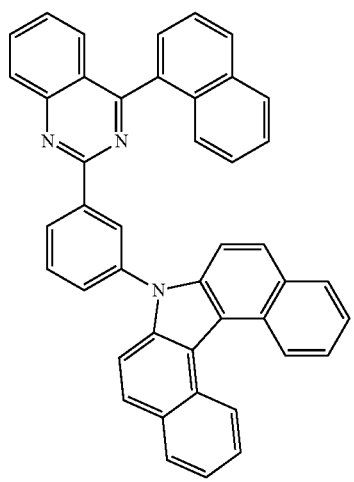
A-134
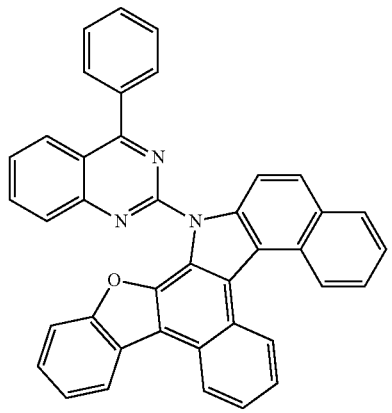
A-135
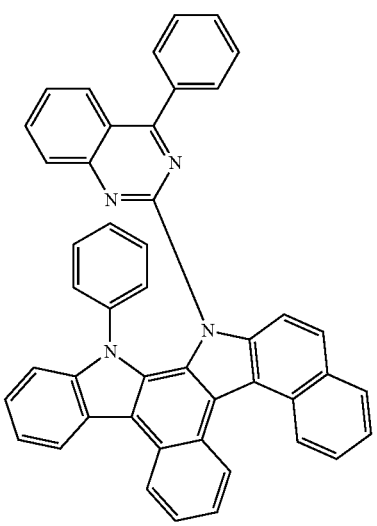
A-136
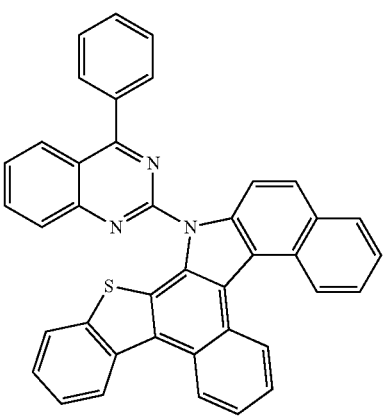

A-137
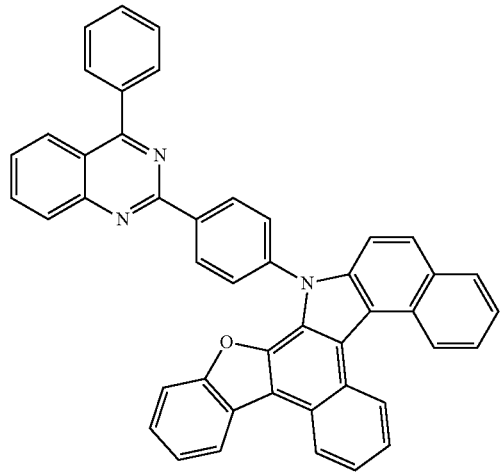
A-140
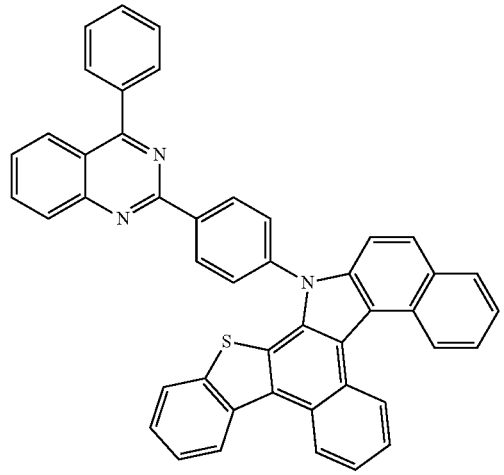
A-138
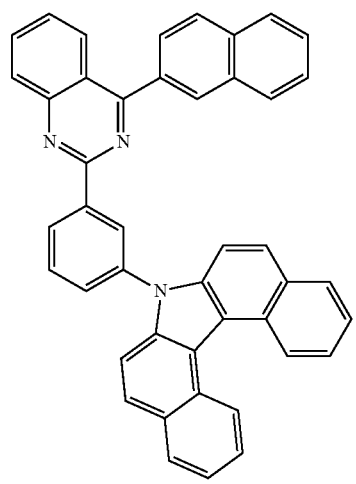
A-141
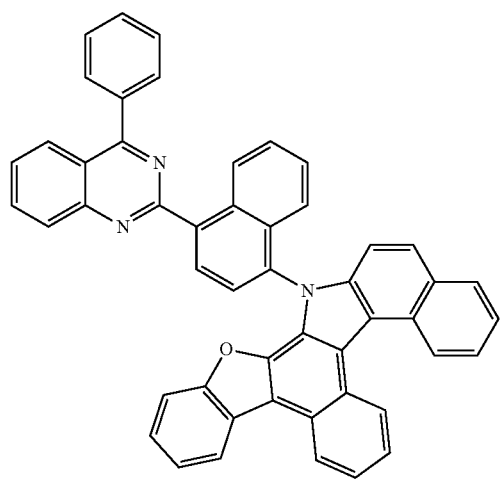
A-139
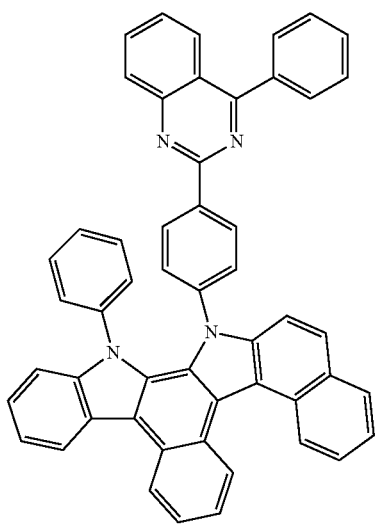
A-142
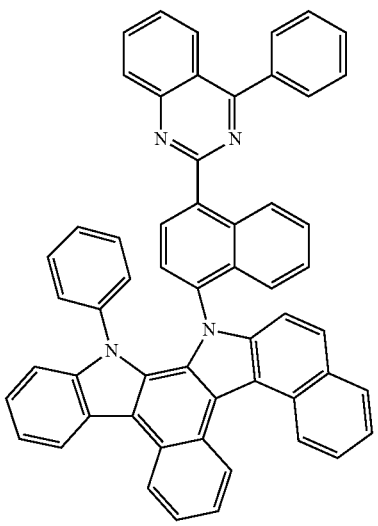

-continued
A-143
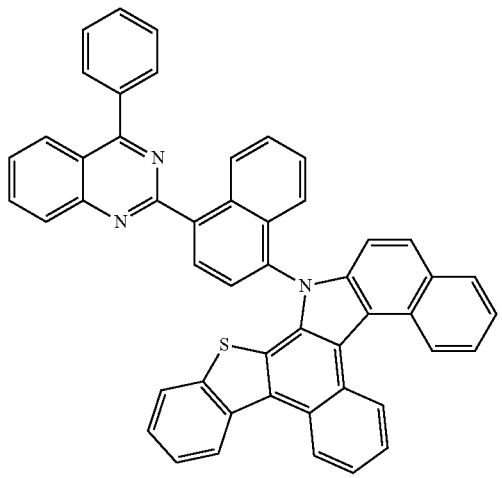
A-144
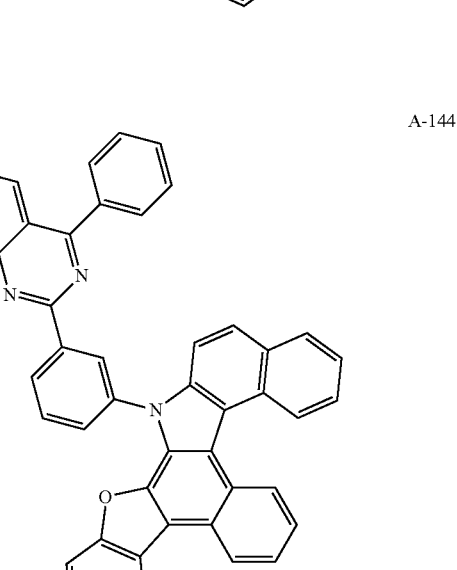
A-145
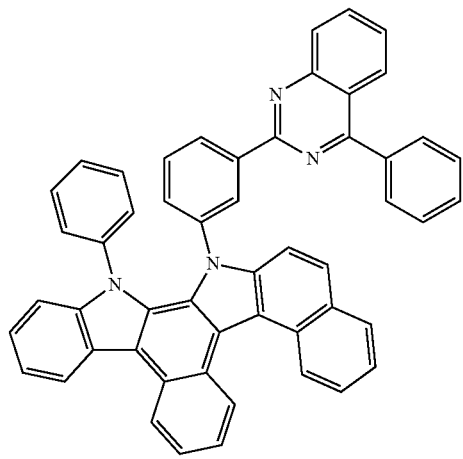
-continued
A-146
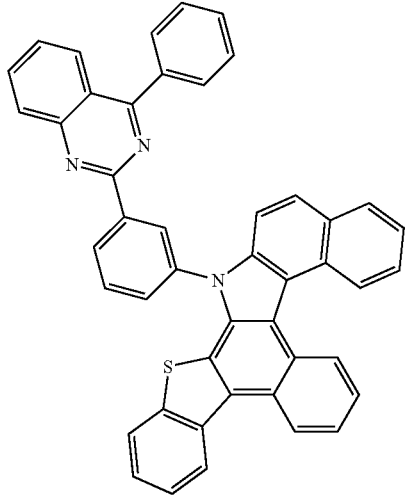
A-281
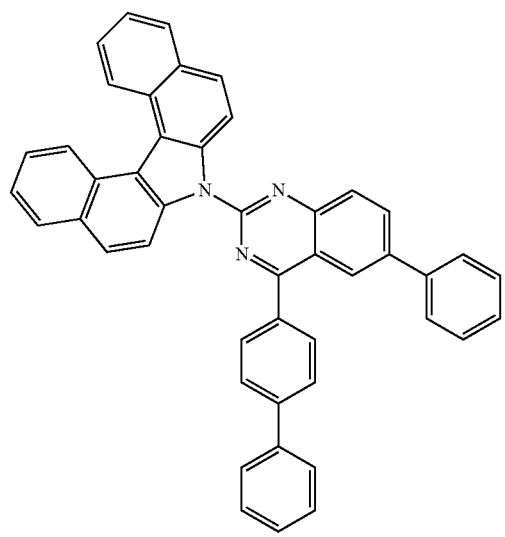
A-282
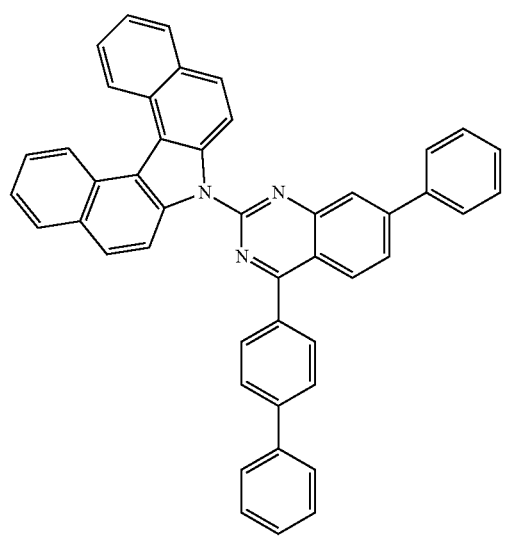

A-283
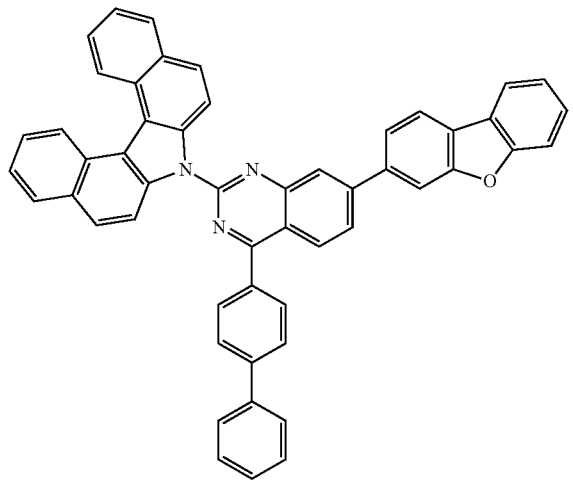
A-284
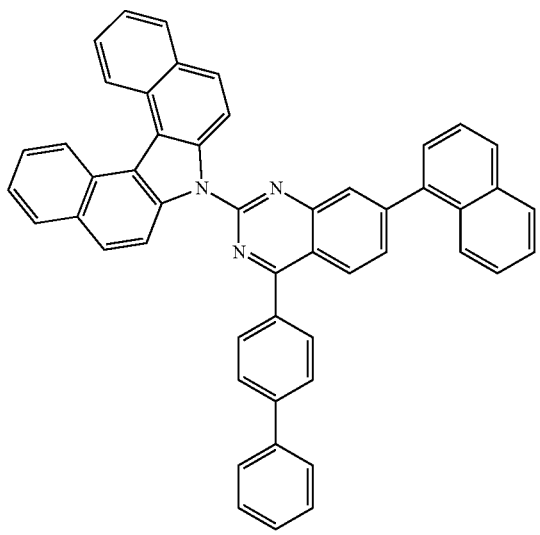
A-285
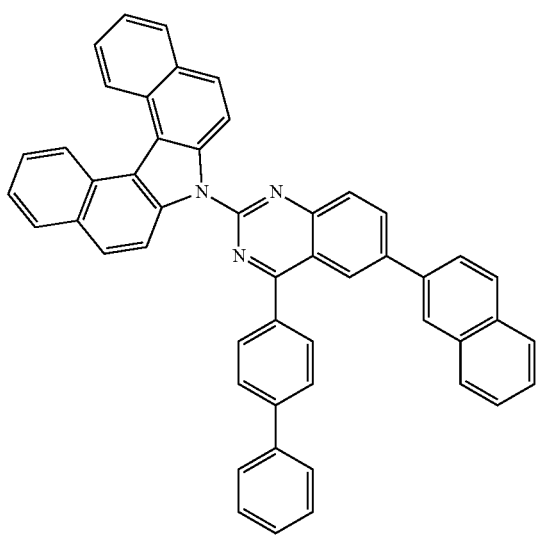
A-286
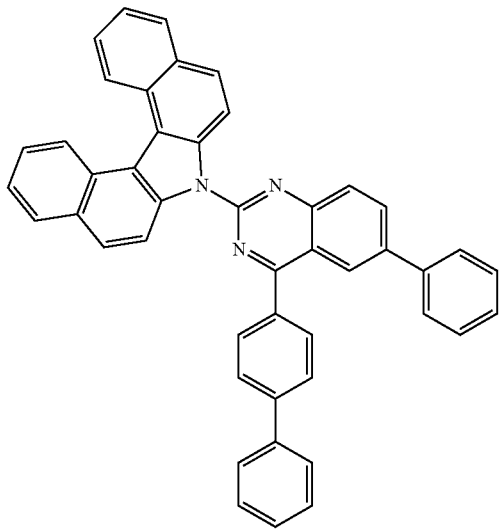
A-289
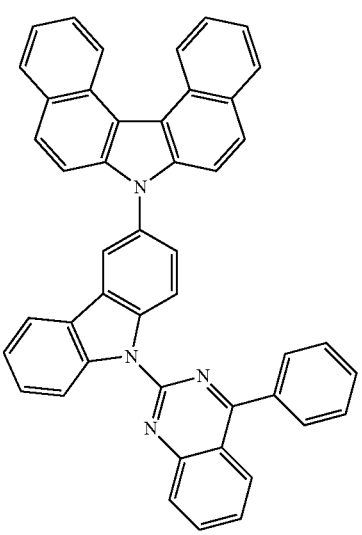
A-291
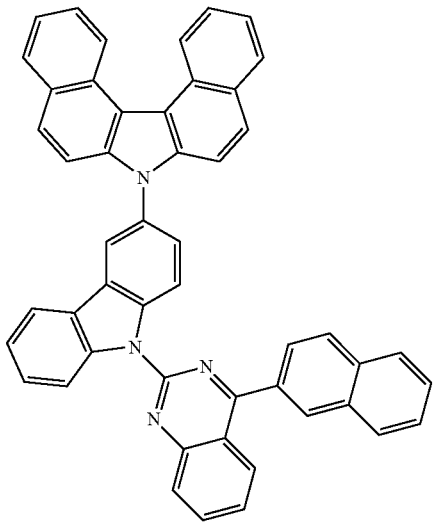

A-292
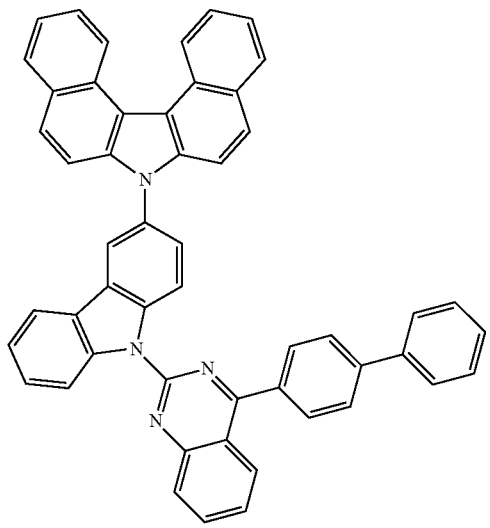
A-293
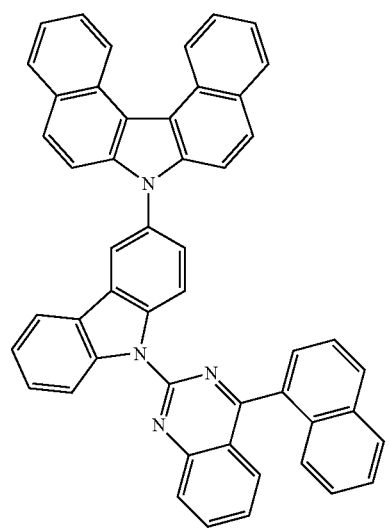
A-296
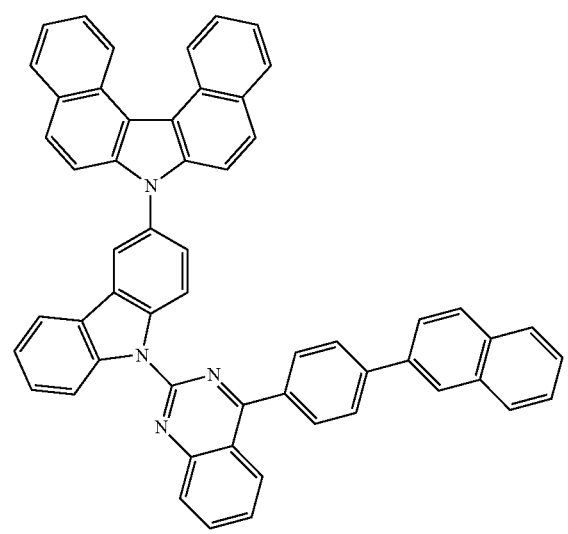
A-297
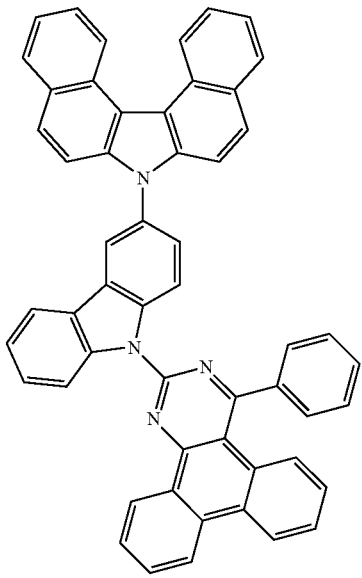
A-298
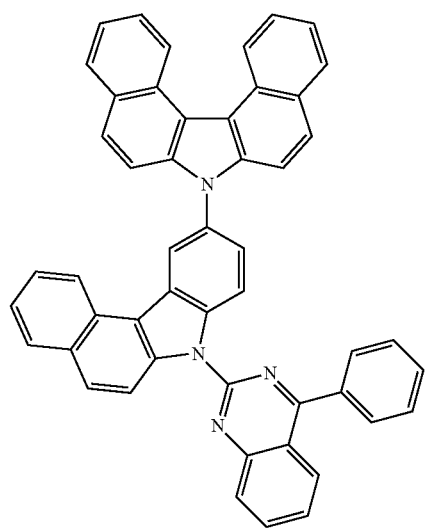
A-299
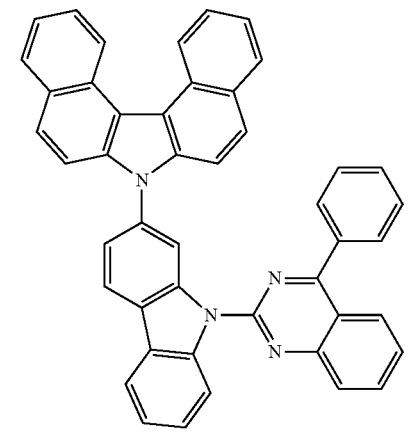

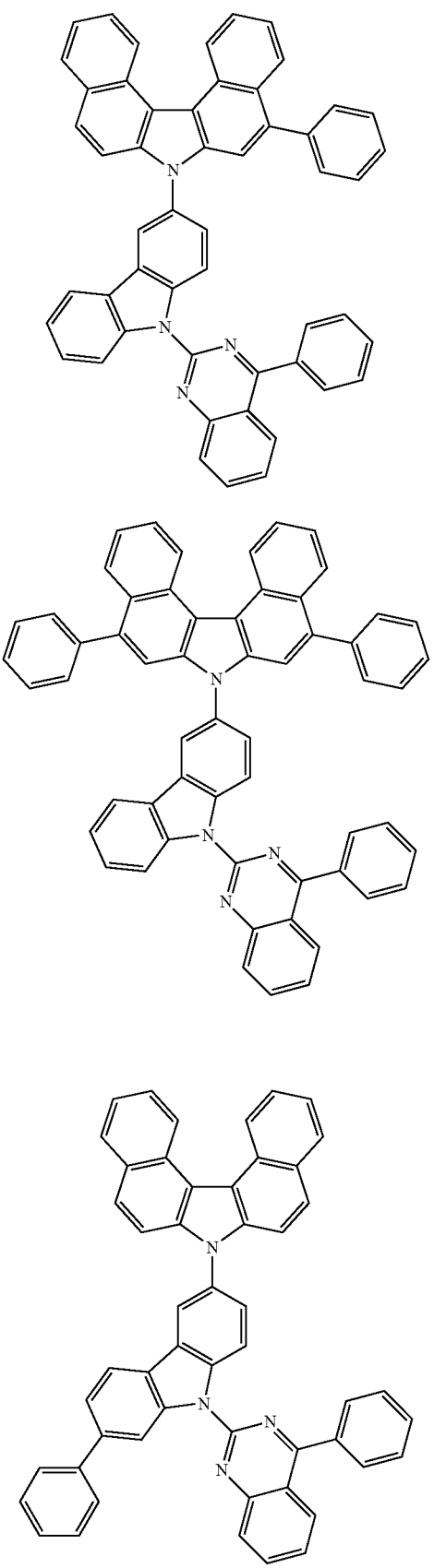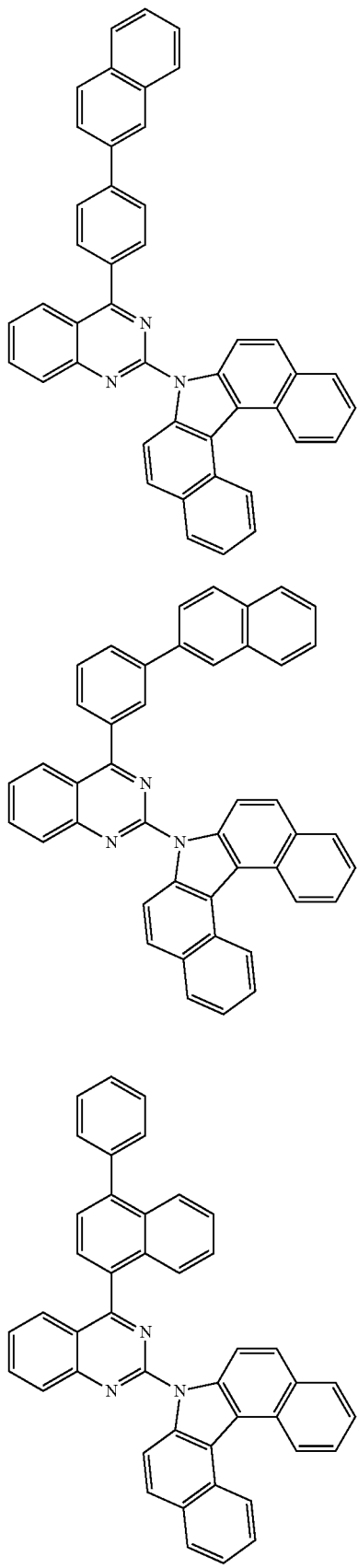

-continued
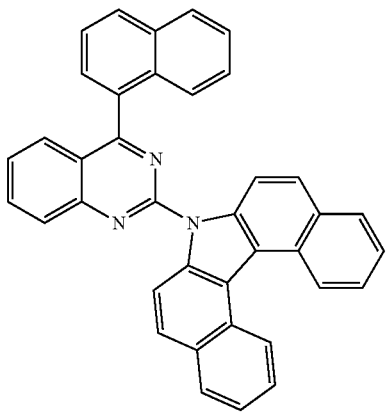
A-306
-continued
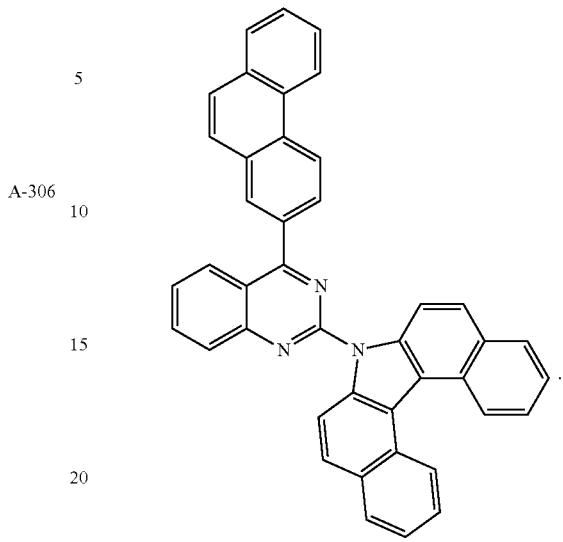
A-307
7. An organic electroluminescent device comprising the organic electroluminescent compound according to claim 1.
* * * * *